US011584781B2

(12) United States Patent
Fernandez Rodriguez et al.

(10) Patent No.: US 11,584,781 B2
(45) Date of Patent: Feb. 21, 2023

(54) CHIMERIC RECEPTOR BINDING PROTEINS RESISTANT TO PROTEOLYTIC DEGRADATION

(71) Applicant: Eligo Bioscience, Paris (FR)

(72) Inventors: Jesus Fernandez Rodriguez, Paris (FR); Xavier Duportet, Paris (FR)

(73) Assignee: ELIGO BIOSCIENCE, Paris (FR)

( * ) Notice: Subject to any disclaimer, the term of this patent is extended or adjusted under 35 U.S.C. 154(b) by 0 days.

(21) Appl. No.: 17/564,625

(22) Filed: Dec. 29, 2021

(65) Prior Publication Data

US 2022/0119458 A1    Apr. 21, 2022

Related U.S. Application Data

(63) Continuation-in-part of application No. PCT/EP2020/088043, filed on Dec. 30, 2020, and a continuation-in-part of application No. 17/138,084, filed on Dec. 30, 2020.

(60) Provisional application No. 63/132,190, filed on Dec. 30, 2020, provisional application No. 63/137,989, filed on Jan. 15, 2021, provisional application No. 62/955,278, filed on Dec. 30, 2019, provisional application No. 63/132,090, filed on Dec. 30, 2020.

(51) Int. Cl.
*C07K 14/005* (2006.01)
*A61K 47/42* (2017.01)
*A61K 31/713* (2006.01)

(52) U.S. Cl.
CPC .......... *C07K 14/005* (2013.01); *A61K 31/713* (2013.01); *A61K 47/42* (2013.01); *C07K 2319/00* (2013.01); *C12N 2795/00022* (2013.01)

(58) Field of Classification Search
None
See application file for complete search history.

(56) References Cited

U.S. PATENT DOCUMENTS

| | | | |
|---|---|---|---|
| 7,163,818 B2 | 1/2007 | Merril et al. | |
| 8,685,895 B2 * | 4/2014 | Enever | G01N 33/6845 506/18 |
| 10,113,163 B2 | 10/2018 | Liu et al. | |
| 10,676,721 B2 | 6/2020 | Collins et al. | |
| 11,236,133 B2 * | 2/2022 | Fernandez Rodriguez | A61K 38/465 |
| 2010/0261258 A1 * | 10/2010 | Scholl | C07K 14/21 435/252.33 |
| 2015/0064138 A1 | 3/2015 | Lu et al. | |
| 2015/0166980 A1 | 6/2015 | Liu et al. | |
| 2018/0155729 A1 | 6/2018 | Beisel et al. | |
| 2020/0199180 A1 | 6/2020 | Fernandez Rodriguez | |

FOREIGN PATENT DOCUMENTS

| | | |
|---|---|---|
| WO | 2014124226 A1 | 8/2014 |
| WO | 2017141173 A2 | 8/2017 |
| WO | 2018236548 A1 | 12/2018 |
| WO | 2020109339 A1 | 6/2020 |
| WO | 2020128108 A1 | 6/2020 |
| WO | 2020181178 A1 | 9/2020 |
| WO | 2020181180 A1 | 9/2020 |
| WO | 2020181193 A1 | 9/2020 |
| WO | 2020181195 A1 | 9/2020 |
| WO | 2020181202 A1 | 9/2020 |

OTHER PUBLICATIONS

Suttle et al., Nature 437: 356-361 (Year: 2005).*
Mobley et al., Structure 17: 489-98 (Year: 2009).*
Siponen et al., J of Bacteriology 191(10): 3220-3225 (Year: 2009).*
Papanikolopoulou et al., J Biological Chemistry 279(10): 6991-8998 (Year: 2004).*
Zhao et al., "New base editors change C to A in bacteria and C to G in mammalian cells," Nature Biotechnology, (2020); 11 pages.
Tanji et al., "Therapeutic Use of Phage Cocktail for Controlling *Escherichia coli* O157:H7 in Gastrointestinal Tract of Mice," Journal of Bioscience and Bioengineering, vol. 100, No. 3, (2005); pp. 280-287.
Li et al., "Targeted, random mutagenesis of plant genes with dual cytosine and adenine base editors," Nature Biotechnology, (2020); 12 pages.
Komor et al., "Programmable editing of a target base in genomic DNA without double-stranded DNA cleavage," Nature, Oct. 20, 2016, vol. 533 (7603); pp. 420-424.
Karberg et al., "Group II introns as controllable gene targeting vectors for genetic manipulation of bacteria," Nature Biotechnology, vol. 19, Dec. 2001; pp. 1162-1167.
Jamalludeen et al., "Evaluation of bacteriophages for prevention and treatment of diarrhea due to experimental enterotoxigenic *Escherichia coli* O149 infection of pigs," Veterinary Microbiology, vol. 136, (2009); pp. 135-141.
Grunewald et al., "A dual-deaminase CRISPR base editor enables concurrent adenine and cytosine editing," Nat. Biotechnol., Jul. 2020, vol. 38, No. 7; pp. 861-864.
Gaudelli et al., "Programmable base editing of A*T to G*C in genomic DNA without DNA cleavage," Nature, Nov. 23, 2017, vol. 551 (7681); pp. 464-471.

(Continued)

*Primary Examiner* — Phuong Huynh
(74) *Attorney, Agent, or Firm* — Carter, DeLuca & Farrell LLP; Carmella Stephens

(57) ABSTRACT

The present disclosure provides a chimeric receptor binding protein (RBP) resistant to proteolytic digestion wherein said RBP comprises a portion of a receptor binding protein derived from a bacteriophage fused through a designed linker region consisting of 1 to 70 amino acids, to a portion of a receptor binding protein derived from a different bacteriophage, wherein said linker region is designed to be resistant to proteolytic digestion.

17 Claims, 12 Drawing Sheets

Specification includes a Sequence Listing.

(56) References Cited

OTHER PUBLICATIONS

Thompson et al.,"The K5 Lyase KflA Combines a Viral Tail Spike Structure with a Bacterial Polysaccharide Lyase Mechanism," The Journal of Biological Chemistry, vol. 285, No. 31, Jul. 30, 2010; pp. 23963-23969.

Wang et al., "The C-Terminal Portion of the Tail Fiber Protein of Bacteriophage Lambda is Responsible for Binding to LamB, Its Receptor at the Surface of *Escherichia coli* K-12," Journal of Bacteriology, Jan. 2000, vol. 182, No. 2 pp. 508-512.

Northrop, "The Effect of Proteolytic Enzymes on *E. coli* Phages and on Native Proteins," The Journal of General Physiology, vol. 48, (1964); pp. 73-78.

Verthe et al., "Stability and activity of an Enterobacter aerogenes-specific bacteriophage under simulated gastro-intestinal conditions," Appl. Microbiol Biotechnol (2004), vol. 65; pp. 465-472.

Smith et al., "Factors Influencing the Survival and Multiplication of Bacteriophages in Calves and in Their Environment," Journal of General Microbiology (1987), vol. 133; pp. 1127-1135.

Dabrowska, "Phage therapy: What factors shape phage pharmacokinetics and bioavailability? Systematic and critical review," Med. Res. Rev., (2019), vol. 39; pp. 2000-2025.

Soding et al., "The HHpred interactive server for protein homology detection and structure prediction," Nucleic Acids Research, (2005), vol. 33, Web Server Issue; pp. W244-W248.

Jonezyk et al.,. "The influence of external factors on bacteriophages— review," Folia Microbiol, (2011), vol. 56; pp. 191-200.

Simon et al., "Retrons and their applications in genome engineering," Nucleic Acids Research, (2019), vol. 47, No. 21; pp. 11007-11019.

Wannier et al., "Improved bacterial recombineering by parallelized protein discovery," PNAS, Jun. 16, 2020, vol. 117, No. 24; pp. 13689-13698.

Anzalone et al., "Search-and-replace genome editing without double-strand breaks or donor DNA," Nature, Dec. 2019, vol. 576 (7785); pp. 149-157.

Farzadfard et al., "Genomicallly Encoded Analog Memory with Precise In vivo DNA Writing in Living Cell Populations," Science, Nov. 14, 2014, vol. 346 (6211); 1256272; pp. 1-18.

Sharon et al., "Functional genetic variants revealed by massively parallel precise genome editing," Cell, Oct. 4, 2018, vol. 175 (2); pp. 544-557.

Kurt et al., "CRISPR C-to-G base editors for inducing targeted DNA transversions in human cells," Nat Biotechnol., Jan. 2021, vol. 39 (1); pp. 41-46.

Chen et al., "Precise and Programmable C:G to G:C base editing in Genomic DNA," BioRxiv, Jul. 21, 2020; 19 pages.

Rees et al., "Base editing: precision chemistry on the genome and transcriptome of living cells," Nat. Rev. Genet., Dec. 2018, vol. 19 (12); pp. 770-788.

Koonin et al., "Diversity, classification and evolution of CRISPR-Cas systems," Curr Opin Microbiol., Jun. 2017, vol. 37; pp. 67-78.

Fonfara et al., "Phylogeny of Cas9 determines functional exchangeability of dual-RNA and Cas9 among orthologous type II Crispr-Cas systems," Nucleic Acids Research, (2014), vol. 42, No. 4; pp. 2577-2590.

Casjens et al., "Bacteriophage lambda: early pioneer and still relevant," Virology, May 2015, vol. 0; pp. 310-330.

Cotter et al., "Bacteriocins—a viable alternative to antibiotics?" Nature Reviews | Microbiology, vol. 11, Feb. 2013; pp. 95-105.

Abudayyeh et al., "RNA targeting with CRISPR-Cas13a," Nature, Oct. 12, 2017, vol. 550 (7675); pp. 280-284.

Henkel et al., "Toxins from Bacteria," EXS, (2010), vol. 100; pp. 1-29.

Chandra et al. "Properties of the cholera phage PL 163/10," Acta Virologica, May 1, 1975, vol. 19, No. 3; pp. 197-203 (Abstract Only).

International Search Report for related application No. PCT/EP2021/087775, dated May 12, 2022, 5 pages.

Shao, Yongping, et al. "Bacteriophage adsorption rate and optimal lysis time," Genetics, Sep. 2008, pp. 471-482, 180.1.

Montag, Dirk, et al. "A component of the side tail fiber of *Escherichia coli* bacteriophage lambda can functionally replace the receptor-recognizing part of a long tail fiber protein of the unrelated bacteriophage T4," Journal of bacteriology, Aug. 1989, pp. 4378-4384, 171.8.

Collins et al., "Cosmids: a type of plasmid gene-cloning vector that is packageable in vitro in bacteriophage lambda heads," Proc Natl Acad Sci USA, Sep. 1978, vol. 75, No. 9; pp. 4242-4246.

Cronan, "Cosmid-Based System for Transient Expression and Absolute Off-to-On Transcriptional Control of *Escherichia coli* Genes," Journal of Bacteriology, Nov. 2003, vol. 185; pp. 6522-6529.

Cronan, "Improved Plasmid-Based System for Fully Regulated Off-To-On Gene Expression in *Escherichia coli* Application to Production of Toxic Proteins," Plasmid, Jan. 2013, vol. 69, No. 1; pp. 81-89.

Haley, "Cosmid library construction," New Nucleic Acid Techniques, part of the Methods in Molecular Biology book series, Dec. 31, 1987, vol. 4; pp. 257-283 (Abstract Only).

Hendrix et al., "Bacteriophage lambda PaPa: not the mother of all lambda phages," Science, Nov. 13, 1992, vol. 258; pp. 1145-1148 (Abstract Only).

Rossmann et al., "The bacteriophage T4 DNA injection machine," Curr Opin Struct Biol., Apr. 2004, vol. 14, No. 2 pp. 171-180 (Abstract Only).

Zivanovic et al., "Insights into Bacteriophage T5 Structure from Analysis of Its Morphogenesis Genes and Protein Components,". Journal of Virology, (2014), vol. 88; pp. 1162-1174.

Speed et al., "Conformation of P22 tailspike folding and aggregation intermediates probed by monoclonal antibodies," Protein Science (1997), vol. 6; pp. 99-108.

Miwa et al., "Formation of oligomeric structures from plasmid DNA carrying cos lambda that is packaged into bacteriophage lambda heads," Journal of Bacteriology, Jan. 1983, vol. 153, No. 1; pp. 100-108.

Grayson et al., "The effect of genome length on ejection forces in bacteriophage lambda," Virology, May 10, 2006, vol. 348, No. 2; pp. 430-436.

Vimont et al., "The CTX-M-15-producing *Escherichia coli* clone O25b: H4-ST131 has high intestine colonization and urinary tract infection abilities," PloS One, Sep. 2012, vol. 7, Issue 9; 10 pages (e46547).

Myhal et al., "Relative colonizing abilities of human fecal and K 12 strains of *Escherichia coli* in the large intestines of streptomycin-treated mice," European Journal of Clinical Microbiology, Jun. 1982, vol. 1; pp. 186-192 (Abstract Only).

Chatterjee et al., "Interaction of Bacteriophage A with Its *E. coli* Receptor, LamB," Viruses (2012), vol. 4; pp. 3162-3178.

Charbit et al., :"Maltose transport and starch binding in phage-resistant point mutants of maltoporin. Functional and topological implications," Journal of Molecular Biology, Jun. 5, 1988, vol. 201, Issue 3; pp. 487-493 (Abstract Only).

Paepe et al., "Trade-Off between Bile Resistance and Nutritional Competence Drives *Escherichia coli* Diversification in the Mouse Gut," PLOS Genetics, Jun. 2011, vol. 7, Issue 6; 14 pages (e1002107).

Meyer et al., "Repeatability and Contingency in the Evolution of a Key Innovation in Phage Lambda," Science, Jan. 27, 2012, vol. 335; pp. 428-432.

Werts et al., "Adsorption of Bacteriophage Lambda on the LamB Protein of *Escherichia coli* K-12: Point Mutations in Gene J of Lambda Responsible for Extended Host Range," Journal of Bacteriology, Feb. 1994, vol. 176, No. 4 pp. 941-947.

Choi et al., "Protection from Hemolytic Uremic Syndrome by Eyedrop Vaccination with Modified Enterohemorrhagic *E. coli* Outer Membrane Vesicles," PLoS ONE, Jul. 2014, vol. 9, Issue 7; 9 pages (e100229).

Shifrin et al, "Transient Shielding of Intimin and the Type III Secretion System of Enterohemorrhagic and Enteropathogenic *Escherichia coli* by a Group 4 Capsule," Journal of Bacteriology, Jul. 2008, vol. 190, No. 14; pp. 5063-5074.

Roessner et al., "Proteinase Sensitivity of Bacteriophage Lambda Tail Proteins gpJ and pH* in Complexes with the Lambda Receptor," Journal of Bacteriology, Jan. 1984, vol. 157, No. 1; pp. 165-170.

(56) References Cited

OTHER PUBLICATIONS

Scandella et al., "Phage Lambda DNA injection into *Escherichia coli* pel—mutants is restored by mutations in phage genes V or H," Virology, Jan. 1976, vol. 69, No. 1, Jan. 1976; pp. 206-215 (Abstract Only).

Martin-Verstraete et al., "The Levanase Operon of Bacillus subtilis Expressed in *Escherichia coli* Can Substitute for the Mannose Permease in Mannose Uptake and Bacteriophage Lambda Infection," Journal of Bacteriology, Dec. 1996, vol. 178, No. 24; pp. 7112-7119.

De Vries et al., "Extension of bacteriophage lambda host range: Selection, cloning, and characterization of a constitutive lambda receptor gene," Proc. Natl. Acad. Sci. USA, Oct. 1984, vol. 81, pp. 6080-6084.

Francis et al., "Bacteriophage Lambda as a Delivery Vector for Tn10-Derived Transposons in Xenorhabdus bovienii," Applied and Environmental Microbiology, Sep. 1993, vol. 59, No. 9; pp. 3050-3055.

Ludwig, "Gene tandem-mediated selection of coliphage λ-receptive Agrobacterium, Pseudomonas, and Rhizobium strains," Proc. Natl. Acad Sci. USA, May 1987, vol. 84; pp. 3334-3338.

Hendrix et al., "Bacteriophage lambda PaPa: not the mother of all lambda phages," Science, Nov. 13, 1992, vol. 258; pp. 1145-1148.

Haley, "Cosmid Library Construction," New Nucleic Acid Techniques, part of the Methods in Molecular Biology book series, Chapter 18, Dec. 31, 1987, vol. 4; pp. 257-283.

Myhal et al., "Relative colonizing abilities of human fecal and K 12 strains of *Escherichia coli* in the large intestines of streptomycin-treated mice," European Journal of Clinical Microbiology, Jun. 1982, vol. 1, No. 3; pp. 186-192.

Scandella et al., "Phage Lambda DNA injection into *Escherichia coli* pel—mutants is restored by mutations in phage genes V or H," Virology, Jan. 1976, vol. 69, No. 1, Jan. 1976; pp. 206-215.

Charbit et al., :"Maltose transport and starch binding in phage-resistant point mutants of maltoporin. Functional and topological implications," Journal of Molecular Biology, Jun. 5, 1988, vol. 201, Issue 3; pp. 487-493.

Rossmann et al., "The bacteriophage T4 DNA injection machine," Curr Opin Struct BioL, Apr. 2004, vol. 14, No. 2 pp. 171-180.

International Search Report and Written Opinion of the International Searching Authority dated May 3, 2021, corresponding to International Application No. PCT/EP2020/088043; 16 total pages.

Bikard et al., "Exploiting CRISPR-Cas Nucleases to Produce Sequence-Specific Antimicrobials," Nature Biotechnology, vol. 32, No. 11, Oct. 5, 2014; pp. 1146-1150.

Citorik et al., "Sequence-Specific Antimicrobials Using Efficiently Delivered RNA-Guided Nucleases," Nature Biotechnology, vol. 32, No. 11, Sep. 21, 2014; pp. 1141-1145.

Office Action for related U.S. Appl. No. 17/138,048, filed Sep. 2, 2021, 44 pages.

Office Action for related U.S. Appl. No. 17/138,048, filed Jan. 6, 2022, 38 pages.

\* cited by examiner

CHIMERIC RECEPTOR BINDING PROTEINS RESISTANT TO PROTEOLYTIC DEGRADATION

CROSS-REFERENCE TO RELATED APPLICATIONS

This application is a continuation-in-part of International Application No. PCT/EP2020/088043, filed Dec. 30, 2020 and U.S. patent application Ser. No. 17/138,084, filed Dec. 30, 2020, both of which claim benefit and priority to U.S. Provisional Application No. 62/955,278, filed Dec. 30, 2019. This application also claims benefit and priority to U.S. Provisional Application No. 63/132,090, filed Dec. 30, 2020; U.S. Provisional Application No. 63/132,190, filed Dec. 30, 2020; and U.S. Provisional Application No. 63/137,989, filed Jan. 15, 2021 all of which are incorporated herein by reference in their entireties.

SEQUENCE LISTING

This application includes an electronically submitted sequence listing in .txt format. The .txt file contains a sequence listing entitled EB2020_08_Usreg_sequence_listing_ST25.txt and is 285,976 bytes in size. The sequence listing contained in this .txt file is part of the specification and is hereby incorporated by reference herein in its entirety.

TECHNICAL FIELD

The present disclosure relates to chimeric receptor binding proteins, in particular derived from bacteriophage receptor binding proteins, able to withstand proteolytic digestion, in particular gastrointestinal proteolytic digestion, bacterial delivery vehicles comprising said chimeric receptor binding proteins, and the use thereof in efficient transfer of a desired payload into a target bacterial cell population, in particular after oral administration.

BACKGROUND

One of the critical aspects to be addressed when considering protein-based DNA delivery vectors, such as packaged phagemids or Eligobiotics®, is their stability in in vivo conditions. Depending on the route of administration, packaged phagemids may be exposed to different factors that may affect their stability and functionality. For instance, orally administered packaged phagemids will have to traverse the gastrointestinal tract: harsh conditions, such as the low pH in the stomach and the presence of certain digestive enzymes, may have a negative effect on the structural stability of the particles.

Phages have evolved to be stable in a wide range of conditions [1]. From the evolutionary perspective, being able to resist these conditions is a clear advantage for any phage.

However, it is well known that many phages are not resistant to low pH values for a long period of time [1], [2], although this can be circumvented by the use of stomach acid neutralizers [3]-[6]. Similarly, some phages have evolved to be resistant to digestive enzymes, such as those found in pancreatic juices (trypsin, chymotrypsin, etc.), while some others are readily degraded [4], [7], [8] although the exact mechanisms of degradation have not been studied in detail.

From these facts, it can be concluded that for the development of a highly successful optimal phage-derived DNA delivery vector, such as an Eligobiotic®, it is useful to obtain a vector which is stable in in vivo conditions.

The present disclosure provides a solution to this need.

A powerful engineering pipeline has been developed to generate phage-derived DNA delivery vectors with improved or modified host ranges as disclosed in WO2020109339. To do this, the natural variability of phage parts has been exploited to generate functional protein chimeras in existing phage scaffolds: for instance, one was able to modify the tropism and injection efficiency of packaged phagemids by modifying the two main host range determinants of lambdoid phages such as the lambda phage, the gpJ and STF (Side Tail Fiber) proteins.

In the course of vector development, it was observed that one had to differentiate between functionality and stability. A given protein chimera (for instance, a STF fusion) can exhibit an ideal functionality, for example can contribute to a high injection efficiency into a target strain in in vitro conditions, but may be affected when exposed to pancreatin (i.e. still functional but less stable). This was an unpredictable aspect of the protein engineering process so far: starting from two different STFs that are not degraded in the presence of pancreatin could yield a protein chimera that was less resistant to proteolytic digestion.

Different direct (on the packaged phagemids itself) or indirect (on the environment of the packaged phagemids) approaches can be envisioned to protect these protein chimera from in vivo proteolytic digestion, e.g. a suitable formulation, such as controlled or delayed release formulations enabling the release of packaged phagemids displaying said protein chimera in the intestine or the colon. The present disclosure shows that another solution is to act directly on said protein chimera.

SUMMARY

The present disclosure is based on the unexpected finding that, by specifically designing a small fusion region (also called linker region) between two different STFs, it is possible to render a chimeric lambda based STF protein, which was initially engineered to be fully functional but was less stable in the presence of pancreatin, both functional and highly stable.

It is worth noting that in natural phage STFs, proteolytically degradable residues exist that due to conformation or interaction with other residues/proteins may not be accessible for degradation in normal conditions. However, such residues may become accessible for degradation when these STFs are used to produce chimeras. It has been specifically demonstrated that introducing point mutations in phenylalanine (F) and lysine (K) residues present in the linker region, corresponding to a region of about 10 to 12 amino acids adjacent to the insertion site of chimeric lambda STF-V10, rendered the chimeric lambda STF-V10 protein partially resistant to pancreatin hence with increased stability, while the original chimeric lambda STF-V10 protein was not resistant to pancreatin at all.

It has also been demonstrated that designing the linker region to include a short sequence which was initially present at the N-terminus end of the C-terminal region of V10 tail fiber used to produce the chimera, rendered the chimeric lambda STF-V10 protein highly resistant to pancreatin (without introducing further mutations in the linker region).

Further it has been demonstrated, in another chimeric receptor binding protein, namely a functional chimeric lambda STF-K5 protein, which was not very stable in the presence of pancreatin, that introducing, in the linker region, the same helix-forming sequence initially present at the N-terminus of the V10 tail fiber, rendered the chimeric STF-K5 protein highly resistant to pancreatin hence strongly stable.

Furthermore, it has been demonstrated, in another functional chimeric lambda STF-K5 protein, which was not very stable in the presence of pancreatin, that introducing, in the linker region another helix-forming sequence present within the STF protein of the *Escherichia* phage ZG49 (which has homology with the wild-type K5 protein), rendered the chimeric STF-K5 protein very highly resistant to pancreatin.

The present disclosure thus concerns a chimeric receptor binding protein (RBP) resistant to proteolytic digestion, in particular within the gastrointestinal tract, wherein said chimeric RBP comprises a portion of a receptor binding protein derived from a bacteriophage fused through a designed linker region consisting of 1 up to 70 amino acids, more particularly of 1 up to 30 amino acids, to a portion of a receptor binding protein derived from a different bacteriophage, wherein said linker region is designed to be resistant to proteolytic digestion, in particular within the gastrointestinal tract. In a particular embodiment, said chimeric RBP is resistant to proteolytic digestion by pancreatin, and said linker region is designed to be resistant to proteolytic digestion by pancreatin.

In a particular embodiment, said RBP is a side tail fiber (STF) protein, an L-shape fiber, a long tail fiber or a tailspike. In a particular embodiment, said chimeric RBP comprises a portion of a STF protein derived from a lambdoid bacteriophage fused through a designed linker region consisting of 1 up to 70 amino acids (more particularly of 1 up to 30 amino acids), to a portion of a RBP protein derived from a different bacteriophage. In a particular embodiment, said chimeric RBP comprises an N-terminal region of a STF protein derived from a lambdoid bacteriophage, fused through a designed linker region consisting of 1 up to 70 amino acids (more particularly of 1 up to 30 amino acids), to a C-terminal region of a RBP protein derived from a different bacteriophage, wherein said N-terminal region and C-terminal region are fused within a site of the N-terminal STF region, called insertion site, having at least 80% identity with a site selected from the group consisting of amino acids SAGDAS (SEQ ID NO: 1), ADAKKS (SEQ ID NO: 2), MDETNR (SEQ ID NO: 3), SASAAA (SEQ ID NO: 4), and GAGENS (SEQ ID NO: 5). In a particular embodiment, said insertion site has at least 80% identity with sequence GAGENS (SEQ ID NO: 5). In a particular embodiment, said designed linker region is at the C-terminal end of the insertion site. In a particular embodiment, said designed linker region is part of the N-terminal region or of the C-terminal region of the chimeric RBP.

In a particular embodiment, at least one amino acid of the designed linker region, corresponding to an amino acid of the wildtype domain sequence which is likely to be targeted by trypsin and/or chymotrypsin, is mutated compared to the wildtype domain sequence. In said particular embodiment, said designed linker region may be part of the C-terminal region of the chimeric RBP and said at least one amino acid may be located within the 15 amino acids following the insertion site. In still said particular embodiment, said at least one amino acid may be selected from the group consisting of lysin (K), arginine (R), phenylalanine (F), tryptophan (W), tyrosine (Y) leucine (L) and methionine (M).

In another particular embodiment, said N-terminal region or said C-terminal region comprises the sequence of the linker region, said sequence being identical to the corresponding sequence in the N-terminal region or C-terminal region of the RBP from which it is derived, and said sequence conferring resistance to proteolytic digestion to said chimeric RBP compared to the original chimeric RBP only differing by the absence of said linker region.

In another particular embodiment, said designed linker region comprises or consists of an heterologous amino acid sequence which is not derived from the N-terminal region or from the C-terminal region of the chimeric RBP. In said embodiment, said designed linker region may comprise or consist of an amino acid sequence which is derived from a RBP which is not one of the RBP from which the N-terminal region and the C-terminal region of the chimeric RBP are derived.

In a particular embodiment, said designed linker region may consist of 10 up to 20 amino acids. In said embodiment, said designed linker region may comprise or consist of an amino acid sequence GSATDVMIQL (SEQ ID NO: 6) or GSATDVMIQLA (SEQ ID NO: 7). In said embodiment, said sequence may be located directly after the insertion site.

In an alternative embodiment, said designed linker region may consist of 50 up to 65 amino acids. In said embodiment, said designed linker region may comprise or consist of an amino acid sequence SEQ ID NO: 34 or SEQ ID NO: 37. In said embodiment, said sequence may be located directly after the insertion site.

In a particular embodiment, the designed linker region comprises a helix or helical bundle.

In a particular embodiment, the N-terminal region of said STF protein derived from a lambdoid bacteriophage corresponds to amino acids 1 to 528 of the lambda STF protein of sequence SEQ ID NO: 8. In a particular embodiment, the C-terminal region of said STF protein derived from said different bacteriophage corresponds to amino acids 218 to 875 of the STF protein of sequence SEQ ID NO: 16. In said embodiment, said chimeric RBP may comprise or consist of the sequence SEQ ID NO: 9 or SEQ ID NO: 10. In another particular embodiment, the C-terminal region of said STF protein derived from said different bacteriophage corresponds to amino acids 208 to 875 of the STF protein of sequence SEQ ID NO: 16. In said embodiment, said chimeric RBP may comprise or consist of the sequence SEQ ID NO: 11. In a particular embodiment, the C-terminal region of said STF protein derived from said different bacteriophage corresponds to amino acids 28 to 632 of the STF protein of sequence SEQ ID NO: 12. In said embodiment, said chimeric RBP may comprise or consist of the sequence SEQ ID NO: 13 or SEQ ID NO: 14. In a particular embodiment, the C-terminal region of said STF protein derived from said different bacteriophage corresponds to amino acids 62 to 632 of the STF protein of sequence SEQ ID NO: 12. In said embodiment, said chimeric RBP may comprise or consist of the sequence SEQ ID NO: 38 or SEQ ID NO: 40.

The present disclosure also concerns a lambdoid bacterial delivery vehicle for use in in vivo delivery of a DNA payload of interest into a targeted bacterial cell, wherein said lambdoid delivery vehicle comprises the chimeric RBP provided herein. In a particular embodiment, said chimeric RBP is a chimeric STF protein as disclosed herein. In said embodiment, said chimeric STF protein may be a functional STF protein. In still said embodiment, the delivery vehicle may further comprise a functional lambdoid bacteriophage gpJ protein and/or a functional lambdoid bacteriophage gpH protein. In a particular embodiment, the chimeric STF protein has enzyme activity such as depolymerase activity and the bacterial cell population of interest comprises encapsulated bacteria. In a particular embodiment, one or more of the chimeric STF protein, the gpJ protein and/or the gpH protein are engineered to increase the efficiency of transfer of the DNA payload into a targeted bacterial cell population. In a particular embodiment, the delivery vehicle comprises the chimeric RBP comprising or consisting of the sequence SEQ ID NO: 11 and the gpJ chimeric protein 1A2 comprising or consisting of the sequence SEQ ID NO: 27.

In a particular embodiment, the bacterial cell population is selected from the group consisting of E. coli bacteria, K. pneumoniae and other species of interest.

In a particular embodiment, said bacterial delivery vehicle comprises said DNA payload of interest. In a particular embodiment, the DNA payload comprises a nucleic acid of interest selected from the group consisting of Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, and or any of their combination. In said embodiment, the nuclease may target cleavage of a host bacterial cell chromosome or a host bacterial cell plasmid. In said embodiment, the cleavage may occur in an antibiotic resistant gene. In a particular embodiment, the nucleic acid of interest encodes a therapeutic protein. In another particular embodiment, the nucleic acid of interest encodes an antisense nucleic acid molecule.

The present disclosure also relates to a pharmaceutical or veterinary composition comprising a bacterial delivery as disclosed herein and a pharmaceutically acceptable carrier. In a particular embodiment, said composition is for oral administration.

The present disclosure also provides a method for in vivo delivery of a DNA payload of interest into a subject comprising, administering to said subject the pharmaceutical or veterinary composition as provided herein.

Another object of the disclosure relates to providing a method for treating a disease or disorder caused by bacteria comprising administering to a subject having a disease or disorder in need of treatment a therapeutically efficient amount of a pharmaceutical or veterinary composition disclosed herein. In a particular embodiment, said disease or disorder is a bacterial infection, a metabolic disorder or a pathology involving bacteria of the human microbiome. In still a particular embodiment, said composition is administered orally.

The present disclosure also provides pharmaceutical or veterinary compositions for use in a method for treating a disease or disorder caused by bacteria. In a particular embodiment, said disease or disorder is a bacterial infection, a metabolic disorder or a pathology involving bacteria of the human microbiome. In still a particular embodiment, said composition is administered orally.

The present disclosure further concerns a method for reducing the amount of virulent and/or antibiotic resistant bacteria in a bacterial population comprising contacting the bacterial population with a bacterial delivery vehicle as provided herein. Another object concerns providing bacterial delivery vehicles for use in a method for reducing the amount of virulent and/or antibiotic resistant bacteria in a bacterial population.

DETAILED DESCRIPTION

Chimeric Receptor Binding Protein (RBP)

Figure 1:
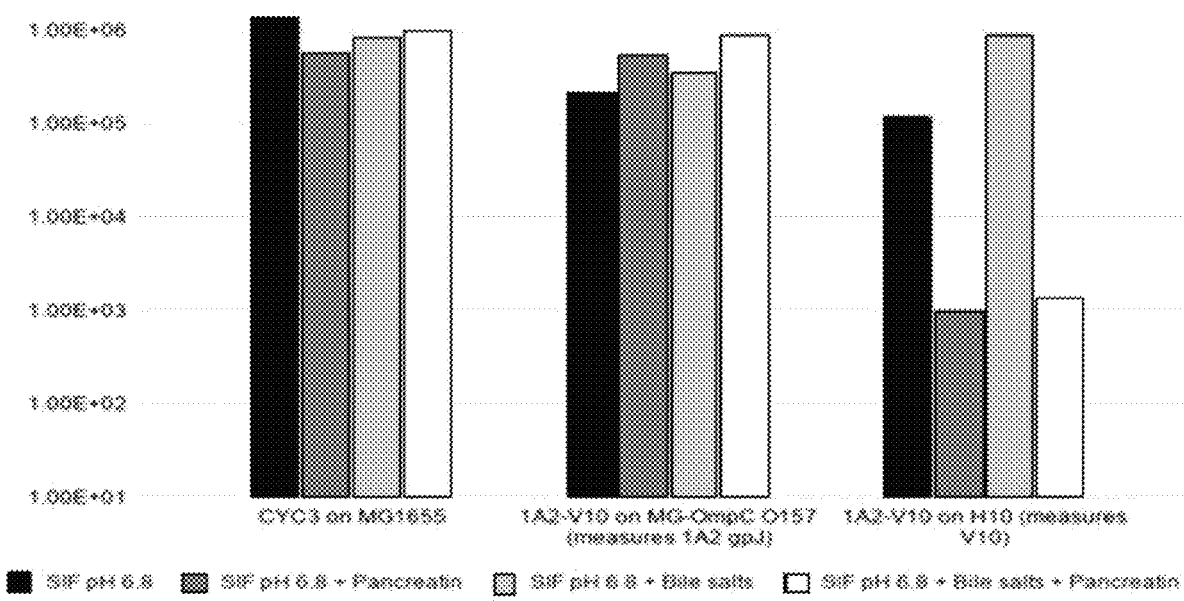
FIG. 1: Stability of lambda packaged phagemids in SIF (Simulated Intestinal Fluid). Left group of bars, wild-type lambda packaged phagemid produced from CYC3 in MG1655; central group of bars, lambda 1A2-V10 packaged phagemids in MG1656-OmpCO157; right group of bars, 1A2-V10 packaged phagemids on H10 (O157) strain. Y axis shows particle titer per µL.

The present disclosure relates to a chimeric receptor binding protein (RBP) resistant to proteolytic digestion, in particular within the gastrointestinal tract, wherein said RBP comprises a portion of a receptor binding protein derived from a bacteriophage fused through a designed linker region consisting of 1 to 70 amino acids, more particularly of 1 to 30 amino acids, to a portion of a corresponding receptor binding protein derived from a different bacteriophage, wherein said linker region is designed to be resistant to proteolytic digestion, in particular within the gastrointestinal tract.

Resistance to Proteolytic Digestion

By "proteolytic digestion" is meant herein proteolysis of a protein mediated by an enzyme having any protease activity. By "proteolytic digestion within the gastrointestinal tract" is meant herein proteolysis of a protein mediated by an enzyme having protease activity in any part of the gastrointestinal tract, such as in the mouth, the esophagus, the stomach, the small intestine or the large intestine. In a particular embodiment, said proteolytic digestion is within the small intestine. In a more particular embodiment, said proteolytic digestion is within the duodenum.

As well-known from the skilled person, proteolytic digestion within the duodenum is mainly affected by bile salts and pancreatin. In a particular embodiment, said proteolytic digestion is by pancreatin. By "pancreatin" is meant herein a mixture of pancreatic enzymes including trypsin and chymotrypsin, and optionally amylase and lipase. In another particular embodiment, said proteolytic digestion is by trypsin and/or chymotrypsin. By "trypsin" is meant herein an enzyme of the EC 3.4.21.4 category, which is a serine protease from the PA clan superfamily, found in the digestive system of many vertebrates, where it hydrolyzes proteins. Typically, trypsin cleaves peptides on the C-terminal side of lysine and arginine amino acid residues, but If a proline residue is on the carboxyl side of the cleavage site, the cleavage may not not occur, and if an acidic residue is on either side of the cleavage site, the rate of hydrolysis may be slower. By "chymotrypsin" is meant herein an enzyme of the EC 3.4.21.1 category, which is a serine protease from the PA clan superfamily, found in the digestive system of vertebrates, where it hydrolyzes proteins. Typically, chymotrypsin cleaves peptide bonds involving L-isomers of tyrosine, phenylalanine, and tryptophan.

By "resistant to proteolytic digestion" is meant herein that the chimeric RBP is not cleaved by said proteases and/or remains stable when contacted with said proteases and/or keeps its activity when contacted with said proteases. Techniques to determine if a protein is resistant to proteolytic digestion by pancreatin, in particular by trypsin and/or chymotrypsin, typically include exposing said protein to simulated intestinal fluid (SIF) in the presence or absence of pancreatin, typically at 2% w/v, for example at pH 6.8, typically for 3 h, in particular at 37° C., then determining the activity of said treated protein (for example by titration of the bacterial delivery vehicle comprising said chimeric RBP in bacteria which are specifically targeted by packaged phagemid comprising said RBPs) and comparing it with the activity of same but non-treated protein. In the context of the present disclosure, a chimeric RBP is preferably considered as resistant to proteolytic digestion if the titer of the bacterial delivery vehicle comprising said chimeric RBP in bacteria which are specifically targeted by said RBPs decreases of 1 log or less, after treatment with pancreatin, typically at 2% w/v, for example at pH 6.8, typically for 3 h, in particular at 37° C. compared to the titer of the same but non-treated bacterial delivery vehicle comprising the same chimeric RBP targeting the same bacteria.

Chimeric RBP

As used herein, a receptor binding protein or RBP is a polypeptide that recognizes, and optionally binds and/or modifies or degrades a substrate located on the bacterial outer envelope, such as, without limitation, bacterial outer membrane, LPS, capsule, protein receptor, channel, structure such as the flagellum, pili, secretion system. The substrate can be, without limitation, any carbohydrate or modified carbohydrate, any lipid or modified lipid, any protein or modified protein, any amino acid sequence, and any combination thereof.

Such bacteriophage RBPs, from which the RBP portions are derived, include, for example, "L-shape fibers", "side tail fibers (stfs)", "long tail fibers" or "tailspikes." In a preferred embodiment, the RBPs have a host range that is directed to specific bacterial cells of the host or subject microbiome. In one specific aspect, the different RBP of the chimeric RBP is derived from any bacteriophage or from any bacteriocin.

In an embodiment, said chimeric RBP is a chimeric side tail fiber (STF) protein.

In a particular embodiment, the chimeric STF comprises an N-terminal region of an STF derived from a lambdoid bacteriophage, preferably a lambda or lambda-like bacteriophage, fused through said designed linker region, to a C-terminal region of a STF protein derived from a different bacteriophage. Such chimeric RBPs include those having an altered host range and/or biological activity such as, for example, depolymerase activity.

As used herein, lambdoid bacteriophages comprise a group of related viruses that infect bacteria. The viruses are termed lambdoid because one of the first members to be described was lambda (λ). Lambdoid bacteriophages are members of the Caudovirus order (also known as tailed bacteriophages) and include those bacteriophages with similar lifestyles, including, for example, the ability to recombine when intercrossed, possession of identical pairs of cohesive ends, and prophages that are inducible by ultraviolet irradiation. Although members of the order may have genomes that vary at the nucleotide level, they carry regions of sufficient nucleotide sequence identity to guide recombination between themselves, typically giving rise to a fully functional phage that has all the necessary genes. (See, for example, Casjens and Hendrix (2015) Virology 479-480: 310-330). For purposes of the present disclosure, lambdoid bacteriophages for use as delivery vehicles, as well as lambdoid STF for use, would be understood generally by one skilled in the art.

Lambdoid phages can be defined as belonging to the lambda supercluster based on genomic analysis [9]. Within this supercluster, several clusters can be distinguished, each having a prototypical phage. The phage-like clusters and their members (between brackets) are: Lambda-like (lambda (λ), HK630, HK629), phi80-like (phi80, HK225, mEp237), N15-like (N15, PY54, phiKO2), HK97-like (HK97, HK022, HK75, HK106, HK140, HK446, HK542, HK544, HK633, mEpX1, mEpX2, mEp234, mEp235, mEp390, ENT39118), ES18-like (ES18, Oslo, SPN3UB), Gifsy-2-like (gifsy-2, gifsy-1, Fels-1, mEp043, mEp213, CP-1639, CTD-Iø, mEp640, FSL_SP-016), BP-4795-like (BP-4795, 2851, stx2-1717, YYZ-2008), SfV-like (SfV, SfII, SfIV, SfI, øP27, ST64B), P22-like (P22, L, SPN9CC, ST64T, ST104, ST160, epsilon34, g341, SE1, Emek, φ20, IME10, Sf6, HK620, CUS-3, SPC-P1), APSE-1-like (APSE-1, APSE-2), 933W-like (933W, stx1ø, stx2ø-I, stx2ø-II, stx2-86, min27, ø24B, P13374, TL-2011c, VT2-sakai, VT2ø_272), HK639-like (HK639), øES15-like (øES15), HS2-like (HS2), ENT47970-like (ENT47670), ZF40-like (ZF40), øEt88-like (øEt88). Lambdoid phages further encompass any bacteriophage encoding a RBP having amino acids sequence homology of around 35% identity for 45 amino acids or more, around 50% identify for 30 amino acids or more, or around 90% identity for 18 amino acids or more in one or more of three amino acids regions ranging from positions 1-150, 320-460, and 495-560 with reference to the lambda bacteriophage STF sequence SEQ ID NO: 8, independently of other amino acids sequences encoded by said bacteriophage.

In the present disclosure a lambdoïd STF protein includes, for example, a protein comprising or consisting of an amino acid sequence with at least 75% identity up to an amino acid corresponding to amino acid 130 of lambda STF (Uniprot P03764 SEQ ID NO: 8), in particular up to amino acid 130 of said lambda STF.

In one aspect, the STF protein includes a protein that comprises or consists of an amino acid sequence with 80, 85, 90, 95, 96, 97, 98, or 99% sequence identity with the wild type lambda STF protein amino acid sequence of SEQ ID NO: 8, or with any of the chimeric STF proteins disclosed herein.

As used herein, the percent homology between two sequences is equivalent to the percent identity between the two sequences. The percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

In the context of the present disclosure, said RBP derived from a bacteriophage (from which is derived the N-terminal region of the chimeric RBP) is resistant to proteolytic digestion as defined above, and said RBP derived from a different bacteriophage (from which is derived the C-terminal region of the chimeric RBP) is also resistant to proteolytic digestion as defined above. Indeed, as explained above, it is shown that, even if these "wild-type" RBPs are resistant to proteolytic digestion, using isolated regions from these stable RBPs to produce chimeras may lead to the production of a chimera which is not resistant to proteolytic digestion.

By "N-terminal region" of a STF protein from a bacteriophage is meant herein an amino acid region of said STF protein starting at the N-terminal end of said STF protein and ending at positions 80-150, 320-460 or 495-560 of said STF protein, said positions being with reference to the lambda bacteriophage STF sequence (SEQ ID NO: 8). By "C-terminal region" of a STF protein from a bacteriophage is meant herein an amino acid region of said STF protein starting at positions 25-150, 320-460 or 495-560 of said STF protein, said positions being with reference to the lambda bacteriophage STF sequence (SEQ ID NO: 8), and ending at the C-terminal end of said STF protein.

In a particular embodiment, the N-terminal region of a STF protein derived from a lambdoid bacteriophage corresponds to amino acids 1 to 528 of the lambda STF protein of sequence SEQ ID NO: 8.

In a particular embodiment, the C-terminal region of said STF protein derived from a different bacteriophage corresponds to amino acids 218 to 875 of the STF protein of sequence SEQ ID NO: 16.

In another particular embodiment, the C-terminal region of said STF protein derived from a different bacteriophage corresponds to amino acids 208 to 875 of the STF protein of sequence SEQ ID NO: 16.

In an alternative embodiment, the C-terminal region of said STF protein derived from a different bacteriophage corresponds to amino acids 28 to 632 of the STF protein of sequence SEQ ID NO: 12.

In an alternative embodiment, the C-terminal region of said STF protein derived from a different bacteriophage corresponds to amino acids 62 to 632 of the STF protein of sequence SEQ ID NO: 12.

In an embodiment, the chimeric STF protein comprises an N-terminal region of a STF protein derived from a lambdoid bacteriophage, preferably from a lambda or lambda-like bacteriophage, fused through said designed linker region to a C-terminal region of a different STF protein wherein said N-terminal region of the chimeric STF protein is fused to said C-terminal region of a different STF protein within one of the amino acids regions selected from positions 80-150, 320-460, or 495-560 of the N-terminal region with reference to the lambda bacteriophage STF sequence (SEQ ID NO: 8). In one aspect, the STF protein from the lambdoid bacteriophage, in particular from the lambda or lambda-like bacteriophage, and the STF protein derived from a different bacteriophage contain homology in one or more of three amino acids regions ranging from positions 80-150, 320-460, and 495-560 of the RBP with reference to the lambda bacteriophage STF sequence (SEQ ID NO: 8). In certain aspects, the homology is around 35% identity for 45 amino acids or more, around 50% identify for 30 amino acids or more, or around 90% identity for 18 amino acids or more within the one or more of three amino acids regions ranging from positions 80-150, 320-460, and 495-560 of the STF protein with reference to the lambda bacteriophage STF sequence. In one specific aspect, the C-terminal region of the chimeric STF protein is derived from a bacteriophage or a bacteriocin. In one aspect, the chimeric STF protein comprises an N-terminal region of a STF protein fused to a C-terminal region of a STF protein derived from a different bacteriophage within one of the amino acids regions selected from positions 80-150, 320-460, or 495-560 of the N-terminal STF region with reference to the lambda bacteriophage STF sequence (SEQ ID NO: 8).

In a particular embodiment, the chimeric RBP comprises an N-terminal region of a STF protein derived from a lambdoid bacteriophage, fused through a designed linker region consisting of 1 to 70 amino acids, more particularly of 1 to 30 amino acids, to a C-terminal region of a STF protein derived from a different bacteriophage, wherein said N-terminal region and C-terminal region are fused within a site of the N-terminal STF region, called insertion site, having at least 80%, 85%, 90%, 95%, 99% or 100% identity with a site selected from the group consisting of amino acids SAGDAS (SEQ ID NO: 1), ADAKKS (SEQ ID NO: 2), MDETNR (SEQ ID NO: 3), SASAAA (SEQ ID NO: 4), and GAGENS (SEQ ID NO: 5). In a particular embodiment, said insertion site has at least 80%, 85%, 90%, 95%, 99% or 100% identity with the site of sequence GAGENS (SEQ ID NO: 5).

In a particular embodiment, the chimeric RBP provided herein is an engineered branched receptor binding multi-subunit protein complex ("branched-RBP"). The engineered chimeric branched-RBP typically comprises two or more associated RBPs, derived from bacteriophages, which associate with one another based on the presence of interaction domains (IDs). The association of one subunit with another can be non-covalent or covalent. Each of the polypeptide subunits contain IDs that function as "anchors" for association of one subunit RBP with another. In specific embodiments, the chimeric branched-RBP may comprise multiple RBP subunits, including, for example, two, three, four, etc. subunits.

The individual RBP subunit may bring different biological functions to the overall engineered chimeric branched-RBP. Such functions include but are not limited to host recognition and enzymatic activity. Such enzymatic activity includes depolymerase activity. The two or more associated receptor binding proteins of the chimeric branched-RBP include, but are not limited to, chimeric RBPs described herein that comprise a fusion between the N-terminal region of a RBP derived from a lambdoid bacteriophage, in particular from a lambda or lambda-like bacteriophage, and the C-terminal region of a RBP derived from a different bacteriophage wherein said chimeric RBP further comprises an ID domain.

In an alternative embodiment, said chimeric RBP is a chimeric gpJ protein.

Designed Linker Region

By "designed linker region" is meant herein a region consisting of 1 to 70 amino acids, more particularly 1 to 65 amino acids, still particularly 1 to 60 amino acids, still particularly 1 to 55 amino acids, still particularly 1 to 50 amino acids, still particularly 1 to 45 amino acids, still particularly 1 to 40 amino acids, still particularly 1 to 35 amino acids, still particularly 1 to 30 amino acids, more particularly of 10 to 25 amino acids, or of 15 to 20 amino acids, in particular of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids, which links the N-terminal portion of the chimeric RBP and the C-terminal portion of the chimeric RBP.

In a particular embodiment, said designed linker region comprises the insertion site as defined above. In an alternative embodiment, said designed linker region is adjacent to the insertion site, as defined above. In a more particular embodiment, said designed linker region is at the C-terminal end of the insertion site as defined above. In other words, in that embodiment, the designed linker region starts at the amino acid directly following the last amino acid of the insertion site.

In a particular embodiment, said designed linker region is part of the N-terminal region or of the C-terminal region of the chimeric RBP. In a particular aspect of that embodiment, said N-terminal region or said C-terminal region of the chimeric RBP comprises the sequence of the linker region but said sequence has been specifically engineered (i.e. modified), compared to the corresponding wild-type sequence in the N-terminal region or C-terminal region of the RBP from which it is derived. Accordingly, in that particular aspect, when said designed linker region is part of the N-terminal region or of the C-terminal region of the chimeric RBP, the sequence of this designed linker region is not 100% identical to the sequence of the corresponding region in the N-terminal region of the RBP from which the N-terminal region of the chimeric RBP is derived or to the sequence of the corresponding region in the C-terminal region of the RBP from which the C-terminal region of the chimeric RBP is derived.

In a particular embodiment, said linker region is engineered in such a way as at least one amino acid of the linker region which is likely to be targeted by trypsin and/or chymotrypsin, as defined above, is mutated.

Accordingly, in a particular embodiment, at least one amino acid of the designed linker region, corresponding to an amino acid of the wildtype region sequence which is likely to be targeted by trypsin and/or chymotrypsin, is mutated compared to the wildtype region sequence.

In a particular embodiment said amino acid which is likely to be targeted to trypsin and/or chymotrypsin is selected from lysin (K), arginine (R), phenylalanine (F), tryptophan (W), tyrosine (Y) leucine (L) and methionine (M). In a particular embodiment, said amino acid is substituted by an alanine (A) or by any amino acid which is not lysin, arginine, phenylalanine, tryptophan, tyrosine, leucine or methionine, such as by an histidine (H).

In a particular embodiment, only one amino acid of the designed linker region is mutated. In an alternative embodiment, more than one amino acid of the designed linker region is mutated, in particular at least two or at least three amino acids of the designed linker region are mutated.

In a particular embodiment, said linker region is part of the C-terminal region of the chimeric RBP and said at least one amino acid is located within the 15 first amino acids of the linker region. In that embodiment, said at least one amino acid is in particular located within the 15 amino acids following the insertion site, as defined above.

In a particular embodiment, said chimeric RBP, typically including such designed linker region, comprises or consists of the sequence SEQ ID NO: 9 (herein called STF-V10-[FA]) or SEQ ID NO: 10 (herein called STF-V10-[AAH]).

In an alternative embodiment, said linker region is designed in such a way as it comprises a structure which is resistant to proteolytic digestion, and which thus typically restores the proteolytic digestion resistance of the chimeric RBP compared to a chimeric RBP which differs only by the absence of said linker region.

Therefore, In a particular aspect of the embodiment wherein said designed linker region is part of the N-terminal region or of the C-terminal region of the chimeric RBP, said N-terminal region or said C-terminal region of the chimeric RBP comprises the sequence of the linker region, preferably respectively at their C-terminal part or N-terminal part, said sequence being identical to the corresponding sequence in the N-terminal region or C-terminal region of the RBP from which it is derived, and said sequence restoring resistance to proteolytic digestion, as defined above, to said chimeric RBP compared to a chimeric RBP only differing by the absence of said linker region.

In other words, in that particular aspect, said designed linker region is part of the N-terminal region or of the C-terminal region of the chimeric RBP, and the sequence of this designed linker region has not been modified compared to the wild-type sequence in the N-terminal region or C-terminal region of the RBP from which it is derived, but has been specifically selected to be present, preferably at the C-terminal part of the N-terminal region or at the N-terminal part of the C-terminal region, compared to an N-terminal region or a C-terminal region not including it, because of its resistance to proteolytic digestion as defined above.

Alternatively, in a particular embodiment, said designed linker region comprises or consists of an heterologous amino acid sequence which is not derived from one of the RBP from which the N-terminal region and the C-terminal region of the chimeric RBP are derived. In a particular embodiment, said designed linker region comprises or consists of a sequence which is derived from a RBP which is not one of the RBP from which the N-terminal region and the C-terminal region of the chimeric RBP are derived.

In a particular embodiment, said designed linker region consists of 10 to 70 amino acids, in particular of 10 to 65 amino acids, of 10 to 64 amino acids, of 10 to 63 amino acids, of 10 to 62 amino acids, of 10 to 61 amino acids, of 10 to 60 amino acids, of 10 to 55 amino acids, of 10 to 50 amino acids, of 10 to 45 amino acids, of 10 to 40 amino acids, of 10 to 35 amino acids, of 10 to 30 amino acids, of 10 to 20 amino acids, in particular of 11 to 20 amino acids, or of 12 to 20 amino acids.

In a particular embodiment, said designed linker region comprises or consists of an amino acid sequence GSATDVMIQL (SEQ ID NO: 6) or GSATDVMIQLA (SEQ ID NO: 7), herein called helix sequence.

In a particular embodiment, said sequence is located within the 10 or 12 first amino acids of the designed linker region. In a more particular embodiment, said sequence is located directly after the insertion site, as defined above.

In a particular embodiment, said chimeric RBP, typically including such designed linker region, comprises or consists of the sequence SEQ ID NO: 11 (herein called STF-V10-[Helix]). In another embodiment, said chimeric RBP, typically including such designed linker region, comprises or consists of the sequence SEQ ID NO: 13 (herein called K5 5.0) or SEQ ID NO: 14 (herein called K5 5.1).

In a particular embodiment, said designed linker region comprises or consists of the amino acid sequence SEQ ID NO: 34 or SEQ ID NO: 36. In a particular embodiment, said sequence is located directly after the insertion site, as defined above. In a particular embodiment, said chimeric RBP, typically including such designed linker region, comprises or consists of the sequence SEQ ID NO: 38 (herein called K5 9.0) or SEQ ID NO: 40 (herein called K5 9.1).

In a particular embodiment, the designed linker region comprises a helix or helical bundle.

By "helical bundle" or "helix bundle" is meant herein a small protein fold composed of several alpha helices that are usually nearly parallel or antiparallel to each other.

By "helix" is meant herein a motif in the secondary structure of proteins.

The present disclosure also provides a nucleic acid encoding a chimeric RBP as defined above.

In a particular embodiment, said nucleic acid encodes a chimeric RBP comprising or consisting of the sequence SEQ ID NO: 9 and typically comprises or consists of the sequence SEQ ID NO: 17. In another particular embodiment, said nucleic acid encodes a chimeric RBP comprising or consisting of the sequence SEQ ID NO: 10 and typically comprises or consists of the sequence SEQ ID NO: 18. In another particular embodiment, said nucleic acid encodes a chimeric RBP comprising or consisting of the sequence SEQ ID NO: 11 and typically comprises or consists of the sequence SEQ ID NO: 19. In another particular embodiment, said nucleic acid encodes a chimeric RBP comprising or consisting of the sequence SEQ ID NO: 13 and typically comprises or consists of the sequence SEQ ID NO: 20. In another particular embodiment, said nucleic acid encodes a chimeric RBP comprising or consisting of the sequence SEQ ID NO: 14 and typically comprises or consists of the sequence SEQ ID NO: 21. In another particular embodiment, said nucleic acid encodes a chimeric RBP comprising or consisting of the sequence SEQ ID NO: 38 and typically comprises or consists of the sequence SEQ ID NO: 39. In another particular embodiment, said nucleic acid encodes a chimeric RBP comprising or consisting of the sequence SEQ ID NO: 40 and typically comprises or consists of the sequence SEQ ID NO: 41.

Such nucleic acids may be included in vectors such as bacteriophages, plasmids, phagemids, phage-plasmids, viruses, and other vehicles which enable transfer and expression of the chimeric RBP encoding nucleic acids. The present disclosure thus also provides such a vector comprising a nucleic acid encoding a chimeric RBP as defined above, in particular comprising a nucleic acid encoding a chimeric RBP comprising or consisting of the sequence SEQ ID NO: 11 which typically comprises or consists of the sequence SEQ ID NO: 19.

Lambdoid Bacterial Delivery Vehicle

The present disclosure relates to a lambdoid bacterial delivery vehicle, typically for use in in vivo delivery of a DNA payload of interest into a targeted bacterial cell, wherein said lambdoid delivery vehicle comprises a chimeric RBP resistant to proteolytic digestion, in particular within the gastrointestinal tract, as defined in the section "Chimeric RBP" above.

The bacterial delivery vehicles provided herein enable transfer of a nucleic acid payload, encoding a protein or nucleic acid of interest, into a desired target bacterial host cell.

Delivery Vehicle

As used herein, the term "delivery vehicle" refers to any means that allows the transfer of a payload into a bacterium.

There are several types of delivery vehicles encompassed by the present disclosure including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation). Any combination of delivery vehicles is also encompassed by the present disclosure. The delivery vehicle can refer to a bacteriophage derived scaffold and can be obtained from a natural, evolved or engineered capsid.

The bacterial delivery vehicles provided herein which enable transfer of a nucleic acid payload, encoding a protein or nucleic acid of interest, into a desired target bacterial host cell are characterized by having a chimeric RBP resistant to proteolytic digestion, in particular within the gastrointestinal tract, as defined in the section "Chimeric RBP" above.

In a particular embodiment, said chimeric RBP is a chimeric STF protein as defined in the section "Chimeric RBP" above. In a particular embodiment, said chimeric STF protein is a functional STF protein.

As used herein, a functional protein means in general a protein with a biological activity; more specifically a functional chimeric protein relates to a chimeric protein contributing to the efficient delivery of a DNA payload into a target strain. The efficiency threshold depends on a number of factors such as the type of protein, type of target strain and type of environment. For instance, STF and gpJ proteins allow for recognition, binding (and in some cases also degradation) of an extracellular epitope such as LPS, capsules and outer membrane proteins; gpH proteins allow for an efficient injection and hence successful passage of the DNA payload through the periplasm.

In some embodiments, the bacterial delivery vehicles disclosed herein further comprise the corresponding natural chaperone proteins (designated "accessory proteins" or "AP") of the chimeric RBPs. Such AP proteins assist in the folding of the chimeric RBPs.

In a particular embodiment, the chimeric STF protein has enzyme activity such as depolymerase activity and the bacterial cell population of interest comprises encapsulated bacteria.

Bacterial delivery vehicles are also provided that further comprise recombinant gpJ proteins. Such gpJ proteins include recombinant gpJ proteins, including chimeric proteins as defined in the section "Chimeric RBP" above, that permit recognition of a bacterial cell receptor other than the LamB OMP receptor. It is known that receptor-recognition activity of gpJ lies in the C-terminal part of the protein, with a fragment as small as 249 amino acids conferring capability of binding to the LamB receptor [10]. In a particular embodiment, such chimeric gpJ protein may comprise a fusion between the N-terminal region of a gpJ protein from a lambdoid bacteriophage, in particular from a lambda or lambda-like bacteriophage, and the C-terminal region of a different gpJ protein.

By "N-terminal region" of a gpJ protein from a bacteriophage is meant herein an amino acid region of said gpJ protein starting at the N-terminal end of said gpJ protein and ending at positions 810-825 or 950-970 of said gpJ protein, said positions being with reference to the lambda bacteriophage gpJ protein sequence (SEQ ID NO: 22). By "C-terminal region" of a gpJ protein from a bacteriophage is meant herein an amino acid region of said gpJ protein starting at positions 810-825 or 950-970 of said gpJ protein, said positions being with reference to the lambda bacteriophage gpJ protein sequence (SEQ ID NO: 22), and ending at the C-terminal end of said gpJ protein.

For production of chimeric gpJ proteins, two insertion points, located respectively at positions corresponding to amino acids 814-821 and 958-966 of the lambda bacteriophage gpJ protein sequence (SEQ ID NO: 22) have previously been identified by the inventors. In non-limiting aspects, such insertion sites may be utilized for production of chimeric proteins. Both insertion points yield functional gpJ chimeras with altered receptor binding. In an embodiment, the bacterial delivery vehicles contain a chimeric gpJ protein comprising a fusion between an N-terminal region of a gpJ protein derived from a lambdoid bacteriophage, in particular from a lambda or lambda-like bacteriophage, and a C-terminal region of a different gpJ protein wherein said N-terminal region of the chimeric gpJ protein is fused to said C-terminal region of a different gpJ protein within one of the amino acids regions selected from positions 810-825, or 950-970 of the N-terminal region with reference to the lambda bacteriophage gpJ protein sequence (SEQ ID NO: 22).

In a specific embodiment, the chimeric gpJ protein comprises a fusion between the N-terminal region of a lambda bacteriophage gpJ protein and the C-terminal region of a gpJ protein from a different bacteriophage, which typically recognizes and binds OmpC, said N-terminal region being in particular fused to said C-terminal region within the amino acid region 950-970 of the N-terminal region with reference to the lambda bacteriophage gpJ protein sequence (SEQ ID NO: 22). In said embodiment, the chimeric gpJ variant may be H591 comprising or consisting of the amino acid sequence SEQ ID NO: 23 and typically encoded by the nucleotide sequence SEQ ID NO: 24, said H591 chimeric gpJ variant typically recognizing and binding OmpC. In another embodiment, the chimeric gpJ protein comprises a fusion between the N-terminal region of a lambda bacteriophage gpJ protein and the C-terminal region of a gpJ protein from a different bacteriophage, which typically recognizes a receptor present in O157 strains, said N-terminal region being in particular fused to said C-terminal region within the amino acid region 810-825 of the N-terminal region with reference to the lambda bacteriophage gpJ protein sequence (SEQ ID NO: 22). In said embodiment, the chimeric gpJ variant may be Z2145 comprising or consisting of the amino acid sequence SEQ ID NO: 25 and typically encoded by the nucleotide sequence SEQ ID NO: 26, said Z2145 chimeric gpJ variant typically recognizing a receptor present in O157 strains. In still another embodiment, the chimeric gpJ protein comprises a fusion between the N-terminal region of a lambda bacteriophage gpJ protein and the C-terminal region of a gpJ protein from a different bacteriophage, which typically recognizes the OmpC receptor present in O157 strains, said N-terminal region being in particular fused to said C-terminal region within the amino acid region 950-970 of the N-terminal region with reference to the lambda bacteriophage gpJ protein sequence (SEQ ID NO: 22). In said embodiment, the chimeric gpJ variant may be the "1A2" variant comprising or consisting of the of amino acid sequence SEQ ID NO: 27 and typically encoded by the nucleotide sequence SEQ ID NO: 28, said 1A2 chimeric gpJ variant typically recognizing the OmpC receptor present in O157 strains. In still another embodiment, the chimeric gpJ protein comprises a fusion between the N-terminal region of a lambda bacteriophage gpJ protein and the C-terminal region of a gpJ protein from a different bacteriophage, which typically recognizes the OmpC receptor present in both O157 and MG1655 strains, said N-terminal region being in particular fused to said C-terminal region within the amino acid region 950-970 of the N-terminal region with reference to the lambda bacteriophage gpJ protein sequence (SEQ ID NO: 22). In said embodiment, the chimeric gpJ variant may be the "A8" variant comprising or consisting of the amino acid sequence SEQ ID NO: 29 and typically encoded by the nucleotide sequence SEQ ID NO: 30, said A8 chimeric gpJ variant typically recognizing the OmpC receptor in both O157 and MG1655 strains.

Bacterial delivery vehicles are also provided that further comprise recombinant gpH proteins. Such gpH proteins include recombinant gpH proteins that permit or allow improved entry of bacterial vectors in cells having deficiencies or alterations in permease complexes. One such variant is the "gpH-IAI" variant of amino acid sequence SEQ ID NO: 31.

In a particular embodiment, said bacterial delivery vehicle comprises chimeric STF of sequence SEQ ID NO: 11 and chimeric gpJ variant of sequence SEQ ID NO: 27.

In a particular embodiment, the lambdoid delivery vehicle as disclosed above further comprises a functional lambdoid bacteriophage gpJ protein, as defined above, and/or a functional lambdoid bacteriophage gpH protein, as defined above.

In aspects, the bacterial delivery vehicles provided herein, are vehicles wherein the one or more of the chimeric STF protein, the gpJ protein and/or the gpH protein are further engineered to increase the efficiency of transfer of the DNA payload into the targeted bacterial cell population. Such bacterial cell populations include for example E. coli. and other bacterial species of interest.

In a particular embodiment, the delivery vehicle is incapable of self-reproduction.

In the context of the present invention, "self-reproduction" is different from "self-replication", "self-replication" referring to the capability of replicating a nucleic acid, whereas "self-reproduction" refers to the capability of having a progeny, in particular of producing new delivery vehicles, said delivery vehicles being either produced empty or with a nucleic acid of interest packaged.

By "delivery vehicle incapable of self-reproduction" is meant herein that at least one, several or all functional gene(s) necessary to produce said delivery vehicle is(are) absent from said delivery vehicle (and from said vector included in said delivery vehicle). In a preferred embodiment, said at least one, several or all functional gene(s) necessary to produce said delivery vehicle is(are) present in the donor cell as defined above, preferably in a plasmid, in the chromosome or in a helper phage present in the donor cell as defined below, enabling the production of said delivery vehicle in said donor cell.

In the context of the invention, said functional gene(s) necessary to produce said delivery vehicle may be absent through (i) the absence of the corresponding gene or (ii) the presence of the corresponding gene but in a non-functional form.

In an embodiment, the sequence of said gene necessary to produce said delivery vehicle is absent from said delivery vehicle. In a preferred embodiment, the sequence of said gene necessary to produce said delivery vehicle has been replaced by a nucleic acid sequence of interest.

Alternatively, said gene necessary to produce said delivery vehicle is present in said delivery vehicle in a non-functional form, for example in a mutant non-functional form, or in a non-expressible form, for example with deleted or mutated non-functional regulators. In a preferred embodiment, said gene necessary to produce said delivery vehicle is present in said delivery vehicle in a mutated form which renders it non-functional in the target cell, while remaining functional in the donor cell.

In the context of the invention, genes necessary to produce said delivery vehicle encompass any coding or non-coding nucleic acid required for the production of said delivery vehicle.

Examples of genes necessary to produce said delivery vehicle include genes encoding phage structural proteins; phage genes involved in the control of genetic expression; phage genes involved in transcription and/or translation regulation; phage genes involved in phage DNA replication; phage genes involved in production of phage proteins; phage genes involved in phage proteins folding; phage genes involved in phage DNA packaging; and phage genes encoding proteins involved in bacterial cell lysis.

Packaged Phagemids

Delivery vehicles include packaged phagemids, as well as bacteriophage, as disclosed herein. An Eligobiotic® is a packaged phagemid, i.e a payload encapsidated in a phage-derived capsid. The engineering of such delivery vehicles is well known to those skilled in the art. Such engineering techniques may employ production cell lines engineered to express the STF, gpJ and gpH proteins disclosed herein. The present disclosure thus also provides a production cell line expressing the chimeric RBPs provided herein.

In one aspect, bacterial delivery vehicles with desired target host ranges are provided for use in transfer of a payload to the microbiome of a host. The bacterial delivery vehicles may be characterized by combinations of chimeric STF, and wild-type and engineered gpJ and gpH proteins.

Generation of packaged phagemids and bacteriophage particles are routine techniques well-known to one skilled in the art. In an embodiment, a satellite phage and/or helper phage may be used to promote the packaging of the payload in the delivery vehicles disclosed herein. Helper phages provide functions in trans and are well known to the man skilled in the art. The helper phage comprises all the genes coding for the structural and functional proteins that are indispensable for the payload to be packaged, (i.e. the helper phage provides all the necessary gene products for the assembly of the delivery vehicle). The helper phage may contain a defective origin of replication or packaging signal, or completely lack the latter, and hence it is incapable of self-packaging, thus only bacterial delivery particles carrying the payload or plasmid will be produced. Helper phages may be chosen so that they cannot induce lysis of the host used for the delivery particle production. One skilled in the art would understand that some bacteriophages are defective and need a helper phage for payload packaging. Thus, depending on the bacteriophage chosen to prepare the bacterial delivery particles, the person skilled in the art would know if a helper phage is required. Sequences coding for one or more proteins or regulatory processes necessary for the assembly or production of packaged payloads may be supplied in trans. For example, the STF, gpJ and gpH proteins of the present disclosure may be provided in a plasmid under the control of an inducible promoter or expressed constitutively. In this case, the phage wild-type sequence may or not contain a deletion of the gene or sequence supplied in trans. Additionally, chimeric or modified phage sequences encoding a new function, like an engineered STF, gpJ or gpH protein, may be directly inserted into the desired position in the genome of the helper phage, hence bypassing the necessity of providing the modified sequence in trans. Methods for both supplying a sequence or protein in trans in the form of a plasmid, as well as methods to generate direct genomic insertions, modifications and mutations are well known to those skilled in the art.

In a particular embodiment, said helper phage comprises a nucleic acid sequence encoding the chimeric RBP comprising or consisting of the sequence SEQ ID NO: 11, said nucleic acid sequence typically comprising or consisting of the sequence SEQ ID NO: 19, and said helper phage optionally further comprises a nucleic acid sequence encoding the chimeric gpJ variant comprising or consisting of the sequence SEQ ID NO: 27, said nucleic acid sequence typically comprising or consisting of the sequence SEQ ID NO: 28.

In a particular embodiment, said helper phage is a lambda prophage wherein (i) the nucleic acid encoding a wild-type STF protein has been replaced by a nucleic acid sequence encoding the chimeric RBP comprising or consisting of the sequence SEQ ID NO: 11, said nucleic acid sequence typically comprising or consisting of the sequence SEQ ID NO: 19, (ii) the nucleic acid encoding a wild-type gpJ protein has been replaced by a nucleic acid sequence encoding the chimeric gpJ variant comprising or consisting of the sequence SEQ ID NO: 27, said nucleic acid sequence typically comprising or consisting of the sequence SEQ ID NO: 28, and (iii) the Cos site has been removed, and wherein optionally (iv) the helper prophage contains a mutation which prevents spontaneous cell lysis, such as the Sam7 mutation and (v) the helper prophage contains a thermosensitive version of the master cI repressor, such as the c1857 version.

Another object of the disclosure thus also concerns providing a production cell line, as defined above, comprising a helper phage as defined above.

In a particular embodiment, said bacterial delivery vehicle comprises said DNA payload of interest.

Payload

As used herein, the term "payload" refers to any nucleic acid sequence or amino acid sequence, or a combination of both (such as, without limitation, peptide nucleic acid or peptide-oligonucleotide conjugate) transferred into a bacterium with a delivery vehicle. The term "payload" may also refer to a plasmid, a vector or a cargo. The payload can be a phagemid or phasmid obtained from natural, evolved or engineered bacteriophage genome. The payload can also be composed only in part of phagemid or phasmid obtained from natural, evolved or engineered bacteriophage genome.

In a particular embodiment, the payload has a size superior or equal to 4 kbp, and preferably inferior or equal to 51 kb.

In said embodiment, the payload may have a size, an integer multiple of which is between 36 kb and 51 kb. In other words, in that embodiment, there is at least an integer n, such as 36 kb≤n×size of the payload ≤51 kb.

As described herein it is more particularly demonstrated that it is possible to produce a more uniform population of bacterial delivery vehicles comprising an almost unique number of payload copies when said payload has a size of a specific range.

In a particular embodiment, the payload has a size strictly superior to 10.000 kb and strictly inferior to 12.000 kb. In an alternative embodiment, the payload has a size strictly superior to 12.500 kb and strictly inferior to 16.667 kb, in particular a size strictly superior to 12.500 kb and inferior to 13.000 kb.

In another particular embodiment, the payload has a size superior or equal to 18.000 kb and inferior or equal to 25.000 kb, in particular inferior or equal to 24.000 kb.

In a particular embodiment, said payload has a size of 11.6 kb.

The payload may be a nucleic acid plasmid that is able to circularize upon transfer into the target cell and then either replicate or integrate inside the chromosome. Replication of the vector DNA is dependent on the presence of a bacterial origin of replication. Once replicated, inheritance of the plasmid into each of the daughter cells can be mediated by the presence of an active partitioning mechanism and a plasmid addiction system such as toxin/anti-toxin system.

As used herein, the term "nucleic acid" refers to a sequence of at least two nucleotides covalently linked together which can be single-stranded or double-stranded or contains portion(s) of both single-stranded and double-stranded sequence. Nucleic acids can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphosphoroamidite linkage and/or deoxyribonucleotides and ribonucleotides nucleic acids. Any combination of the above features of a nucleic acid is also encompassed by the present disclosure.

Origins of replication known in the art have been identified from species-specific plasmid DNAs (e.g. ColE1, R1, pT181, pSC101, pMB1, R6K, RK2, p15a and the like), from bacterial virus (e.g. φX174, M13, F1 and P4) and from bacterial chromosomal origins of replication (e.g. oriC). In one embodiment, the phagemid according to the disclosure comprises a bacterial origin of replication that is functional in the targeted bacteria.

Alternatively, the plasmid according to the disclosure does not comprise any functional bacterial origin of replication or contain an origin of replication that is inactive in the targeted bacteria. Thus, the plasmid of the disclosure cannot replicate by itself once it has been introduced into a bacterium by the bacterial virus particle.

In one embodiment, the origin of replication on the plasmid to be packaged is inactive in the targeted bacteria, meaning that this origin of replication is not functional in the bacteria targeted by the bacterial virus particles, thus preventing unwanted plasmid replication.

In one embodiment, the plasmid comprises a bacterial origin of replication that is functional in the bacteria used for the production of the bacterial virus particles.

Plasmid replication depends on host enzymes and on plasmid-controlled cis and trans determinants. For example, some plasmids have determinants that are recognized in almost all gram-negative bacteria and act correctly in each host during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microbio and Molec Biol. Rev 62:434-464) that start at the origin of replication. These replication origins contain sites that are required for interactions of plasmid and/or host encoded proteins.

Origins of replication used on the plasmid of the disclosure may be of moderate copy number, such as colE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

In an embodiment, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5 and pPS10.

In an embodiment, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

In an embodiment, the bacterial origin of replication is ColE1.

The delivered nucleic acid sequence according to the disclosure may comprise a phage replication origin which can initiate, with complementation of a complete phage genome, the replication of the delivered nucleic acid sequence for later encapsulation into the different capsids.

A phage origin of replication comprised in the delivered nucleic acid sequence of the disclosure can be any origin of replication found in a phage.

In an embodiment, the phage origin of replication can be the wild-type or non-wildtype sequence of the M13, f1, φX174, P4, lambda, P2, lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22, P22-like, N15 and N15-like bacteriophages.

In an embodiment, the phage origin of replication is selected in the group consisting of phage origins of replication of M13, f1, φX174, P4, and lambda.

In a particular embodiment, the phage origin of replication is the lambda or P4 origin of replication. In a particular embodiment, the phage origin of replication is from *Propionibacterium* phages: BW-like phages such as Doucette, B22, E6, G4, BV-like phages such as Anatole, E1, B3, BX-like phages such as PFR1 and PFR2, filamentous B5 phage, BU-like phages (*Cutibacterium acnes* phages).

In a particular embodiment, the payload or vector comprises a conditional origin of replication which is inactive in the targeted bacteria but is active in a donor bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication of said origin of replication may further depend on a process, such as transcription, to activate said replication.

In the context of the invention, said conditional origin of replication is inactive in the targeted bacteria because of the absence of said given protein, peptid, RNA, nucleic acid, molecule or any combination thereof in said targeted bacteria.

In a particular embodiment, said conditional origin of replication is active in said donor bacterial cell because said donor bacterial cell expresses said given protein, peptid, RNA, nucleic acid, molecule or any combination thereof. In a particular embodiment, said protein, peptid, RNA nucleic acid, molecule or any combination thereof is expressed in trans in said donor bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a vector, in particular a plasmid. In a particular embodiment, said vector comprises an antibiotic resistance marker. In an alternative embodiment, said vector is devoid of antibiotic resistance marker.

Since said conditional origin of replication is inactive in the targeted bacteria because of the absence of said given protein, peptid, RNA, nucleic acid, molecule or any combination thereof in said targeted bacteria, said conditional origin of replication may be selected depending on the specific bacteria to be targeted.

The conditional origin of replication disclosed herein may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, P4, lambda, phi82, phi80.

In a particular embodiment, said conditional origin of replication is selected from the group consisting of the R6λ, DNA replication origin and derivatives thereof, the IncPα oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host microbiome, in particular of the bacteria representing more than 50%, more particularly more than 60%, more than 70%, more than 80%, more than 90% or more than 95% of the host microbiome.

As used herein, the term "phage-inducible chromosomal islands" or "PICIs" refers to mobile genetic elements having a conserved gene organization, and encode a pair of divergent regulatory genes, including a PICI master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

A particular conditional origin of replication has indeed been derived from PICIs.

It was shown that it is possible to derive novel conditionally replicative vectors or payloads, in particular based on the primase-helicase and origin of replication from PICIs. These origins may be relatively rare in target strains, and more advantageously the primase-ori pair may be unique for each PICI, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) The ISME Journal 12:2114-2128.

In a particular embodiment, said conditional origin of replication is the primase ori from the PICI of the *Escherichia coli* strain CFT073, typically of sequence SEQ ID NO: 46.

In another particular embodiment, said conditional origin of replication is the primase ori from the PICI of the *Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNTGG (SEQ ID NO: 47), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase ori from the PICI of the *Escherichia coli* strain CFT073, devoid of the restriction site GAAABCC.

Preferably, said conditional origin of replication is of sequence SEQ ID NO: 48.

In another particular embodiment, said conditional origin of replication is the primase ori from the PICI of the *Escherichia coli* strain CFT073 devoid of the restriction sites GAAABCC, GCCGGC, RCCGGY, GCNGC, TWCANNNNNTGG (SEQ ID NO: 47), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 49.

In a particular embodiment, wherein said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 50, typically encoded by a nucleic acid comprising or consisting of the sequence SEQ ID NO: 51.

It was demonstrated that these specific conditional origins of replication were particularly compatible with lambda-based packaging, leading to sufficiently high titers ($>10^{10}$/mL) required for microbiota-related applications.

In a particular embodiment, when said payload or vector is a phagemid, said origin of replication may be derived from a microorganism which is different from the one that is used to encode the structural elements of the capsid packaging said phagemid.

By "donor bacterial cell" is meant herein a bacterium that is capable of hosting a payload or vector as defined above, of producing a payload or vector as defined above and/or which is capable of transferring said payload or vector as defined above to another bacterium. In a particular embodiment, said payload or vector may be a phagemid, and said donor bacterial cell may then be a bacterial cell able to produce said phagemid, more particularly in the form of a packaged phagemid.

Preferably, said donor bacterial cell stably comprises said payload or vector and is able to replicate said payload or vector.

In a particular embodiment, when the conditional origin of replication of said payload or vector is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof.

Preferably, said protein, peptid, nucleic acid, RNA, molecule or any combination thereof is expressed in trans, as defined above.

In a particular embodiment, said donor bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 50.

In a particular embodiment, said donor bacterial cell stably comprises a nucleic acid encoding said rep protein, in particular said primase-helicase, said nucleic acid typically comprising or consisting of the sequence SEQ ID NO: 51.

In a particular embodiment, said donor bacterial cell is a production cell line, in particular a cell line producing packaged phagemids including the payload or vector of the invention.

The delivered nucleic acid of interest preferably comprises a nucleic acid sequence under the control of a promoter. In certain embodiments, the nucleic acid of interest is selected from the group consisting of a Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, and any of their combination. In an embodiment, the nucleic acid payload encodes a therapeutic protein. In another embodiment, the nucleic acid payload encodes an antisense nucleic acid molecule.

In one embodiment, the sequence of interest is a programmable nuclease circuit to be delivered to the targeted bacteria. This programmable nuclease circuit is able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed nuclease circuits provided herein may be used to selectively cleave DNA encoding a gene of interest such as, for example, a toxin gene, a virulence factor gene, an antibiotic resistance gene, a remodeling gene or a modulatory gene (cf. WO2014124226).

Other sequences of interest, such as programmable sequences, can be added to the delivered nucleic acid sequence so as to be delivered to targeted bacteria. In an embodiment, the sequence of interest added to the delivered nucleic acid sequence leads to cell death of the targeted bacteria. For example, the nucleic acid sequence of interest added to the plasmid may encode holins or toxins.

Alternatively, the sequence of interest circuit added to the delivered nucleic acid sequence does not lead to bacteria death. For example, the sequence of interest may encode reporter genes leading to a luminescence or fluorescence signal. Alternatively, the sequence of interest may comprise proteins and enzymes achieving a useful function such as modifying the metabolism of the bacteria or the composition of its environment.

In a particular embodiment, the nucleic acid of interest is selected from the group consisting of Cas9, a single guide RNA (sgRNA), a CRISPR locus, a gene expressing an enzyme such as a nuclease or a kinase, a TALEN, a ZFN, a meganuclease, a recombinase, a bacterial receptor, a membrane protein, a structural protein, a secreted protein, resistance to an antibiotic or to a drug in general, a gene expressing a toxic protein or a toxic factor and a gene expressing a virulence protein or a virulence factor and any of their combination.

In a particular embodiment, the nucleic acid of interest is a gene expressing a nuclease. More particularly, the nuclease may target cleavage of a host bacterial cell chromosome or a host bacterial cell plasmid. In a more particular embodiment, the cleavage may occur in an antibiotic resistant gene.

In a particular embodiment, the delivered nucleic acid sequence according to the disclosure comprises a nucleic acid sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocin had been described from gram negative bacteria (e.g. microcins, colicin-like bacteriocins and tailocins) and from gram positive bacteria (e.g. Class I, Class II, Class III or Class IV bacteriocins).

In one embodiment, the delivered nucleic acid sequence according to the disclosure further comprises a sequence of interest encoding a toxin selected in the group consisting of microcins, colicin-like bacteriocins, tailocins, Class I, Class II, Class III and Class IV bacteriocins.

In a particular embodiment, the corresponding immunity polypeptide (i.e. anti-toxin) may be used to protect bacterial cells (see review by Cotter et al., Nature Reviews Microbiology 11: 95, 2013, which is hereby incorporated by reference in its entirety) for delivered nucleic acid sequence production and encapsidation purpose but is absent in the pharmaceutical composition and in the targeted bacteria in which the delivered nucleic acid sequence of the disclosure is delivered.

In one aspect of the disclosure, the CRISPR system is included in the delivered nucleic acid sequence. The CRISPR system contains two distinct elements, i.e. i) an endonuclease, in this case the CRISPR associated nuclease (Cas or "CRISPR associated protein") and ii) a guide RNA. The guide RNA is in the form of a chimeric RNA which consists of the combination of a CRISPR (RNAcr) bacterial RNA and a RNAtracr (trans-activating RNA CRISPR) (Jinek et al., Science 2012). The guide RNA combines the targeting specificity of the RNAcr corresponding to the "spacing sequences" that serve as guides to the Cas proteins, and the conformational properties of the RNAtracr in a single transcript. When the guide RNA and the Cas protein are expressed simultaneously in the cell, the target genomic sequence can be permanently modified or interrupted. The modification is advantageously guided by a repair matrix. In general, the CRISPR system includes two main classes depending on the nuclease mechanism of action. Class 1 is made of multi-subunit effector complexes and includes type I, III and IV. Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D).

The sequence of interest according to the present disclosure comprises a nucleic acid sequence encoding Cas protein. A variety of CRISPR enzymes are available for use as a sequence of interest on the plasmid. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a sgRNA. In certain embodiments, the sgRNA targets a gene selected in the group consisting of an antibiotic resistance gene, virulence protein or factor gene, toxin protein or factor gene, a bacterial receptor gene, a membrane protein gene, a structural protein gene, a secreted protein gene and a gene expressing resistance to a drug in general.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csxl, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site. In a particular embodiment, said Cas protein is Cas12a (Cpf1).

In a particular embodiment, the CRISPR enzyme is any Cas9 protein, for instance any naturally occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA(s).

The sequence encoding Cas9 (the entire protein or a fragment thereof) as used in the context of the disclosure can be obtained from any known Cas9 protein (Fonfara et al., Nucleic Acids Res 42 (4), 2014; Koonin et al., Nat Rev Microbiol 15(3), 2017). Examples of Cas9 proteins useful in the present disclosure include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the disclosure can be obtained from any known Cpf1 (Cas12a) protein (Koonin et al., 2017). Examples of Cpf1(Cas12a) proteins useful in the present disclosure include, but are not limited to, Cpf1(Cas12a) proteins of *Acidaminococcus* sp, Lachnospiraceae bacteriu and *Francisella novicida*.

The sequence encoding Cas13a (the entire protein or a fragment thereof) can be obtained from any known Cas13a (C2c2) protein (Abudayyeh et al., 2017). Examples of Cas13a (C2c2) proteins useful in the present disclosure include, but are not limited to, Cas13a (C2c2) proteins of *Leptotrichia wadei* (LwaCas13a).

The sequence encoding Cas13d (the entire protein or a fragment thereof) can be obtained from any known Cas13d protein (Yan et al., 2018). Examples of Cas13d proteins useful in the present disclosure include, but are not limited to, Cas13d proteins of *Eubacterium siraeum* and *Ruminococcus* sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In a particular embodiment, the nucleic sequence of interest is a CRISPR/cas, in particular a CRISPR/Cas9, system for the reduction of gene expression or inactivation a gene selected in the group consisting of an antibiotic resistance gene, virulence factor or protein gene, toxin factor or protein gene, a gene expressing a bacterial receptor, a membrane protein, a structural protein, a secreted protein, and a gene expressing resistance to a drug in general.

In one embodiment, the CRISPR system is used to target and inactivate a virulence factor. A virulence factor can be any substance produced by a pathogen that alters host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2 h (VT2 h), fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft.

In another embodiment, the CRISPR/Cas system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecRI) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-TolC, MsbA, MsrA,VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR/Cas system is used to target and inactivate a bacterial toxin gene. Bacterial toxins can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, *Staphylococcus* toxins, *Diphtheria* toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29). In a particular embodiment, said toxin is Shiga toxin.

In another embodiment, the nucleic acid of interest encodes a gene or group of genes encoding one or more exogenous enzyme(s) which result(s) in a genetic modification.

In a particular embodiment, said nucleic acid of interest is a gene encoding a base-editor or a prime-editor.

In some embodiments, the genetic modification is made with one or more of the following enzymes and systems.

Cytosine base editors (CBE) and Adenosine base editors (ABE), as described in Rees et al. (2018) *Nat Rev Genet* 19:770-788, which is hereby incorporated by reference.

So far there is seven types of DNA base editors described:
Cytosine Base Editor (CBE) that convert C:G into T:A (Komor et al. (2016) *Nature* 533:420-424)
Adenine Base Editor (ABE) that convert A:T into G:C (Gaudelli et al. (2017) *Nature* 551:464-471)
Cytosine Guanine Base Editor (CGBE) that convert C:G into G:C (Chen et al. (2020) *Biorxiv* "Precise and programmable C:G to G:C base editing in genomic DNA"; Kurt et al. (2020) Nat. *Biotechnol.* "CRISPR C-to-G base editors for inducing targeted DNA transversions in human cells")
Cytosine Adenine Base Editor (CABE) that convert C:G into A:T (Zhao et al. (2020) *Nature Biotechnol.* "New base editors change C to A in bacteria and C to G in mammalian cells")
Adenine Cytosine Base Editor (ACBE) that convert A:T into C:G (WO2020181180)
Adenine Thymine Base Editor (ATBE) that convert A:T into T:A (WO2020181202)
Thymine Adenine Base Editor (TABE) that convert T:A into A:T (WO2020181193, WO2020181178, WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA.TadA* include TadA-8a-e and TadA-7.10.

Except from base modification enzyme there has been also modifications implemented to base editor to increase editing efficacy, precision and modularity:
the addition of one or two uracil DNA glycosylase inhibitor domain (UGI) to prevent base excision repair mechanism to revert base edition
the addition of Mu-GAM that decrease insertion-deletion rate by inhibiting Non-homologous end joining mechanism in the cell (NHEJ)
the use of nickase active Cas9 (nCas9 D10A) that, by creating nicks on the non-edited strand favor its repair and consequently the fixation of the edited base
the use of diverse Cas proteins from for example different organisms, mutants with different PAM motifs or different fidelity or different family (e.g. Cas12a).

Non-limiting examples of DNA based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:
[a] A cytosine deaminase (rAPOBEC) and base excision repair proteins (e.g. rXRCC1) (Chen et al. (2020) Biorxiv "Precise and programmable C:G to G:C base editing in genomic DNA").
[b] A rat APOBEC1 variant (R33A) protein and an *E. coli*-derived uracil DNA N-glycosylase (eUNG) (Kurt et al. (2020) Nat. *Biotechnol.* "CRISPR C-to-G base editors for inducing targeted DNA transversions in human cells").

Cytosine Adenine Base Editors (CABE) consist of a Cas9 nickase, a cytidine deaminase (e.g. AID), and a uracil-DNA glycosylase (Ung) (Zhao et al. (2020) *Nature Biotechnol.* "New base editors change C to A in bacteria and C to G in mammalian cells").

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193, WO2020181178, WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald et al. (2020) *Nature Biotechnol.* "A dual-deaminase CRISPR base editor enables concurrent adenine and cytosine editing"; Li et al. (2020) *Nature Biotechnol.* "Targeted, random mutagenesis of plant genes with dual cytosine and adenine base editors").

Prime editors (PE), as described in Anzalone et al. (2019) *Nature* 576:149-157, which is hereby incorporated by reference, consist of nCas9 fused to a reverse transcriptase used in combination with a prime editing RNA (pegRNA, a guide RNA that includes a template region for reverse transcription).

Prime Editing allows introduction of insertions, deletions (indels) and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
a prime editing guide RNA (pegRNA)

To favor editing the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PEI-M1, PE1-M2, PE1-M3, PE1-M6, PE1-M15, PE1-M3inv, PE2, PE3, PE3b.

Cas9 Retron precISe Parallel Editing via homologY ('CRISPEY'), a retron RNA fused to the sgRNA and expressed together with Cas9 and the retron proteins including at least the reverse transcriptase (Sharon et al. (2018) *Cell* 175:544-557.e16).

The SCRIBE strategy: a retron system expressed in combination with a recombinase promoting the recombination of single stranded DNA, also known as single stranded annealing proteins (SSAPs) (Farzadfard & Lu (2014) *Science* 346:1256272). Such recombinases include but are not limited to phage recombinases such as lambda red, recET, Sak, Sak4, and newly described SSAPs described in Wannier et al. (2020) *Proc Natl Acad Sci USA* 117(24):13689-13698 which is hereby incorporated by reference.

The targetron system based on group II introns described in Karberg et al. (2001) *Nat Biotechnol* 19:1162-7, which is hereby incorporated by reference, and which has been adapted to many bacterial species.

Other retron based gene targeting approaches are described in Simon et al. (2019) *Nucleic Acids Res* 47:11007-11019, which is hereby incorporated by reference.

In various embodiments, the nucleic acid of interest encodes fusion proteins comprising a Cas, in particular Cas9 (e.g., a Cas9 nickase), domain and a deaminase domain. In some embodiments, the fusion protein comprises a Cas, in particular Cas9, and a cytosine deaminase enzyme, such as APOBEC enzymes, or adenosine deaminase enzymes, such as ADAT enzymes, for example as disclosed in U.S. Patent Publ. 2015/0166980, which is hereby incorporated by reference. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163, which is hereby incorporated by reference. In some embodiments, the fusion proteins further comprise an inhibitor of base repair, such as, a nuclease dead inosine specific nuclease (dISN), for example as disclosed in U.S. Pat. No. 10,113,163. In various embodiments, the nucleic acid of interest encodes fusion proteins comprising a catalytically impaired Cas, in particular Cas9, endonuclease fused to an engineered reverse transcriptase, programmed with a prime editing guide RNA (pegRNA) that both specifies the target site and encodes the desired edit, for example as described in Anzalone et al. (2019) *Nature* 576:149-157, which is hereby incorporated by reference.

In some embodiments, the genetic modification is made at the RNA level. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain ($ADAR_{DD}$) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain (ADAR2DD-E488Q for REPAIRv1 and $ADAR2_{DD}$-E488Q-T375G for REPAIRv2) Cox et al improved specificity and efficiency compare to previous RNA editing strategies. Non-limiting examples of RNA based editor proteins include REPAIRv1, REPAIRv2.

In some embodiments, the nucleic acid of interest encodes other programmable nucleases. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a gene of interest such as, for example, a toxin gene, a virulence factor gene, an antibiotic resistance gene, a remodeling gene or a modulatory gene (cf. WO2014124226 and US2015/0064138).

In a particular embodiment, said payload comprises or consists of the nucleic acid sequence SEQ ID NO: 33. In an alternative embodiment, said payload comprises or consists of the nucleic acid sequence SEQ ID NO: 42.

In an alternative embodiment, the nucleic acid of interest encodes a therapeutic protein. In another embodiment, the nucleic acid of interest encodes an antisense nucleic acid molecule.

The present disclosure thus also provides a production cell line, as defined above, comprising a helper prophage as defined above, and further comprising a phagemid comprising or consisting of the payload as defined above, in particular of the nucleic acid sequence SEQ ID NO: 33 or of the nucleic acid sequence SEQ ID NO: 42.

In a particular embodiment, the bacterial delivery vehicle provided herein comprises chimeric STF of sequence SEQ ID NO: 11 and chimeric gpJ variant of sequence SEQ ID NO: 27, and further comprises a payload which comprises or consists of the nucleic acid sequence SEQ ID NO: 33.

In another particular embodiment, the bacterial delivery vehicle provided herein comprises chimeric STF of sequence SEQ ID NO: 11 and chimeric gpJ variant of sequence SEQ ID NO: 27, and further comprises a payload which comprises or consists of the nucleic acid sequence SEQ ID NO: 42.

Targeted Bacteria

The bacteria targeted by bacterial delivery vehicles disclosed herein can be any bacteria present in a mammal organism. In a certain aspect, the bacteria are targeted through interaction of the chimeric RBPs of the delivery vehicles with the bacterial cell. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the type of bacteriophages being used for preparing the bacterial delivery vehicles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucelia* spp., *Campylobacter* spp., *Chlamydophilia* spp., *Cutibacterium* (formerly *Propionibacterium*) spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., and *Lactobacillus* spp, and a mixture thereof.

Thus, bacterial delivery vehicles may target (e.g., specifically target) a bacterial cell from any one or more of the foregoing genus of bacteria to specifically deliver the payload of interest according to the disclosure.

In an embodiment, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., and *Listeria* spp.

In some embodiments, targeted bacterial cells of the present disclosure are anaerobic bacterial cells (e.g., cells that do not require oxygen for growth). Anaerobic bacterial cells include facultative anaerobic cells such as but not limited to *Escherichia coli*, *Shewanella oneidensis* and *Listeria*. Anaerobic bacterial cells also include obligate anaerobic cells such as, for example, *Bacteroides* and *Clostridium* species. In humans, anaerobic bacteria are most commonly found in the gastrointestinal tract. In some particular embodiment, the targeted bacteria are thus bacteria most commonly found in the gastrointestinal tract. Bacteriophages used for preparing the bacterial virus particles, and then the bacterial virus particles, may target (e.g., to specifically target) anaerobic bacterial cells according to their specific spectra known by the person skilled in the art to specifically deliver the plasmid.

In some embodiments, the targeted bacterial cells are, without limitation, *Bacteroides* thetaiotaomicron, *Bacteroides fragilis*, *Bacteroides distasonis*, *Bacteroides vulgatus*, *Clostridium leptum*, *Clostridium coccoides*, *Staphylococcus aureus*, *Bacillus subtilis*, *Clostridium butyricum*, *Brevibacterium lactofermentum*, *Streptococcus agalactiae*, *Lactococcus lactis*, *Leuconostoc lactis*, *Actinobacillus actinomycetemcomitans*, cyanobacteria, *Escherichia coli*, *Helicobacter pylori*, *Selenomonas ruminatium*, *Shigella sonnei*, *Zymomonas mobilis*, *Mycoplasma mycoides*, *Treponema denticola*, *Bacillus thuringiensis*, *Staphylococcus lugdunensis*, *Leuconostoc oenos*, *Corynebacterium xerosis*, *Lactobacillus plantarum*, *Lactobacillus rhamnosus*, *Lactobacillus casei*, *Lactobacillus acidophilus*, *Enterococcus faecalis*, *Bacillus coagulans*, *Bacillus cereus*, *Bacillus popillae*, *Synechocystis* strain PCC6803, *Bacillus liquefaciens*, *Pyrococcus abyssi*, *Selenomonas nominantium*, *Lactobacillus hilgardii*, *Streptococcus ferus*, *Lactobacillus pentosus*, *Bacteroides fragilis*, *Staphylococcus epidermidis*, *Streptomyces phaechromogenes*, *Streptomyces ghanaenis*, *Klebsiella pneumoniae*, *Enterobacter cloacae*, *Enterobacter aerogenes*, *Serratia marcescens*, *Morganella morganii*, *Citrobacter freundii*, *Pseudomonas aeruginosa*, *Parvimonas micra*, *Prevotella intermedia*, *Fusobacterium nucleatum*, *Prevotella nigrescens*, *Actinomyces israelii*, *Porphyromonas endodontalis*, *Porphyromonas gingivalis* *Micrococcus luteus*, *Bacillus megaterium*, *Aeromonas hydrophila*, *Aeromonas caviae*, *Bacillus anthracis*, *Bartonella henselae*, *Bartonella Quintana*, *Bordetella pertussis*, *Borrelia burgdorferi*, *Borrelia garinii*, *Borrelia afzelii*, *Borrelia recurrentis*, *Brucella abortus*, *Brucella canis*, *Brucella melitensis*, *Brucella suis*, *Campylobacter jejuni*, *Campylobacter coli*, *Campylobacter fetus*, *Chlamydia pneumoniae*, *Chlamydia trachomatis*, *Chlamydophila psittaci*, *Clostridium botulinum*, *Clostridium dfficile*, *Clostridium perfringens*, *Clostridium tetani*, *Corynebacterium diphtheria*, *Cutibacterium acnes* (formerly *Propionibacterium acnes*), *Ehrlichia canis*, *Ehrli-* chia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexneri, Shigella dysenteriae, Staphylococcus saprophyticus, Streptococcus pneumoniae, Streptococcus pyogenes, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aeruginosa, and a mixture thereof. In an embodiment the targeted bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof.

In some embodiments, the targeted bacterial cells are, without limitation, *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter, Weisella, Clostridium, Bacteroides, Ruminococcus, Faecalibacterium, Treponema, Phascolarctobacterium, Megasphaera, Faecalibacterium, Bifidobacterium, Lactobacillus, Sutterella,* and/or *Prevotella*.

In other embodiments, the targeted bacteria cells are, without limitation, *Achromobacter xylosoxidans, Acidaminococcus fermentans, Acidaminococcus intestini, Acidaminococcus sp., Acinetobacter baumannii, Acinetobacter junii, Acinetobacter lwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes finegoldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogenmformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus lichenmformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides sp., Bacteroides stercoris, Bacteroides thetaiotaomicron, Bacteroides uniformis, Bacteroides vulgatus, Bacteroides xylanisolvens, Bacteroides pectinophilus ATCC, Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii, Blautia hydrogenotrophica, Blautia luti, Blautia obeum, Blautia producta, Blautia wexlerae, Brachymonas chironomi, Brevibacterium senegalense, Brvantella formatexigens*, butyrate-producing bacterium, *Butyricicoccus pullicaecorum, Butyricimonas virosa, Butyrivibrio crossotus, Butyrivibriofibrisolvens, Caldicoprobacter faecalis, Campylobacter concisus, Campylobacter jejuni, Campylobacter upsaliensis, Catenibacterium mitsuokai, Cedecea davisae, Cellulomonas massiliensis, Cetobacterium somerae, Citrobacter braakii, Citrobacter freundii, Citrobacter pasteurii, Citrobacter sp., Citrobacter youngae, Cloacibacillus evryensis, Clostridiales bacterium, Clostridioides difficile, Clostridium asparagiforme, Clostridium bartlettii, Clostridium boliviensis, Clostridium bolteae, Clostridium hathewayi, Clostridium hiranonis, Clostridium hylemonae, Clostridium leptum, Clostridium methylpentosum, Clostridium nexile, Clostridium orbiscindens, Clostridium ramosum, Clostridium scindens, Clostridium sp, Clostridium sp., Clostridium spiroforme, Clostridium sporogenes, Clostridium symbiosum, Collinsella aerofaciens, Collinsella intestinalis, Collinsella stercoris, Collinsella tanakaei, Coprobacillus cateniformis, Coprobacter fastidiosus, Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella tarda, Eggerthella lenta, Eisenbergiella tayi, Enorma massiliensis, Enterobacter aerogenes, Enterobacter asburiae, Enterobacter cancerogenus, Enterobacter cloacae, Enterobacter massiliensis, Enterococcus casseliavus, Enterococcus durans, Enterococcus faecalis, Enterococcus faecium, Enterococcus flavescens, Enterococcus gallinarum, Enterococcus sp., Enterovibrio nigricans, Erysipelatoclostridium ramosum, Escherichia coli, Escherichia sp., Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium* cf *Faecalibacterium prausnitzii, Faecalitalea cylindroides, Ferrimonas balearica, Finegoldia magna, Flavobacterium daejeonense, Flavonifractor plautii, Fusicatenibacter saccharivorans, Fusobacterium gonidiaformans, Fusobacterium mortiferum, Fusobacterium necrophorum, Fusobacterium nucleatum, Fusobacterium periodonticum, Fusobacterium sp., Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis,*

*Herbaspirillum massiliense, Holdemanella biformis, Holdemania fdiformis, Holdemania filiformis, Holdemania massiliensis, Holdemania filiformis, Hungatella hathewayi, Intestinibacter bartlettii, Intestinimonas butyriciproducens, Klebsiella oxytoca, Klebsiella pneumoniae, Kurthia massiliensis, Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis, Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillus plantarum subsp., Leuconostoc mesenteroides, Leuconostoc pseudomesenteroides, Listeria grayi, Listeria innocua, Mannheimia granulomatis, Marvinbryantia formatexigens, Megamonas funmformis, Megamonas hypermegale, Methanobrevibacter smithii, Methanobrevibacter smithii, Micrococcus luteus, Microvirgula aerodenitrificans, Mitsuokella jalaludinii, Mitsuokella multacida, Mollicutes bacterium, Murimonas intestini, Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides nerdae, Paraprevotella xylaniphila, Parasutterella excrementihominis, Parvimonas micra, Pediococcus acidilactici, Peptoclostridium difficile, Peptoniphilus harei, Peptoniphilus obesi, Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oralis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteus penneri ATCC, Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina, Romboutsia lituseburensis, Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus sp, Ruminococcus sp., Ruminococcus torques, Sarcina ventriculi, Sellimonas intestinalis, Senegalimassilia anaerobia, Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oralis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus, Subdoligranulum variabile, Succinatimonas hippei, Sutterella parvirubra, Sutterella wadsworthensis, Terrisporobacter glycolicus, Terrisporobacter mayombei, Thalassobacillus devorans, Timonella senegalensis, Turicibacter sanguinis, unknown sp, unknown sp., Varibaculum cambriense, Veillonella atypica, Veillonella dispar, Veillonella parvula, Vibrio cincinnatiensis, Virgibacillus salexigens* or *Weissella paramesenteroides*.

In other embodiments, the targeted bacteria cells are those commonly found on the skin microbiota and are without limitation *Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans* subsp. *xylosoxidans, Acidovorax konjaci, Acidovorax radicis, Acinetobacter johnsonii, Actinomadura citrea, Actinomadura coerulea, Actinomadura fibrosa, Actinomadura fidvescens, Actinomadura jiaoheensis, Actinomadura luteofluorescens, Actinomadura mexicana, Actinomadura nitritigenes, Actinomadura verrucosospora, Actinomadura yumaensis, Actinomyces odontolyticus, Actinomycetospora atypica, Actinomycetospora corticicola, Actinomycetospora rhizophila, Actinomycetospora rishiriensis, Aeromonas australiensis, Aeromonas bestiarum, Aeromonas bivalvium, Aeromonas encheleia, Aeromonas eucrenophila, Aeromonas hydrophila* subsp. *hydrophila, Aeromonas piscicola, Aeromonas popoffli, Aeromonas rivuli, Aeromonas salmonicida* subsp. *pectinolytica, Aeromonas salmonicida* subsp. *smithia, Amaricoccus kaplicensis, Amaricoccus veronensis, Aminobacter aganoensis, Aminobacter ciceronei, Aminobacter lissarensis, Aminobacter niigataensis, Ancylobacter polymorphus, Anoxybacillus flavithermus* subsp. *yunnanensis, Aquamicrobium aerolatum, Archangium gephyra, Archangium gephyra, Archangium minus, Archangium violaceum, Arthrobacter viscosus, Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium afermentans* subsp. *lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens, Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacter halotolerans, Flavobacterium arau-*

*cananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense* subsp. *putei, Herbaspirillum lusitanum, Herminiimonas fonticola, Hydrogenophaga intermedia, Hydrogenophaga pseudoflava, Klebsiella oxytoca, Kosakonia sacchari, Lactobacillus delbrueckii* subsp. *bulgaricus, Lactobacillus modestisalitolerans, Lactobacillus plantarum* subsp. *argentoratensis, Lactobacillus xiangfangensis, Lechevalieria roselyniae, Lentzea albida, Lentzea californiensis, Leuconostoc carnosum, Leuconostoc citreum, Leuconostoc gelidum* subsp. *gasicomitatum, Leuconostoc mesenteroides* subsp. *suionicum, Luteimonas aestuarii, Lysobacter antibioticus, Lysobacter koreensis, Lysobacter oryzae, Magnetospirillum moscoviense, Marinomonas alcarazii, Marinomonas primoryensis, Massilia aurea, Massilia jejuensis, Massilia kyonggiensis, Massilia timonae, Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydan, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogene, Micromonospora rhizosphaerae, Micromonospora saelicesensis, Microvirga subterranea, Microvirga zambiensis, Mycobacterium alvei, Mycobacterium avium* subsp. *silvaticum, Mycobacterium colombiense, Mycobacterium conceptionense, Mycobacterium conceptionense, Mycobacterium farcinogenes, Mycobacterium fortuitum* subsp. *fortuitum, Mycobacterium goodii, Mycobacterium insubricum, Mycobacterium llatzerense, Mycobacterium neoaurum, Mycobacterium neworleansense, Mycobacterium obuense, Mycobacterium peregrinum, Mycobacterium saopaulense, Mycobacterium septicum, Mycobacterium setense, Mycobacterium smegmatis, Neisseria subflava, Nocardia ljiangensis, Nocardia thailandica, Novosphingobium barchaimii, Novosphingobium lindaniclasticum, Novosphingobium lindaniclasticum, Novosphingobium mathurense, Ochrobactrum pseudogrignonense, Oxalicibacterium solurbis, Paraburkholderia glathei, Paraburkholderia humi, Paraburkholderia phenazinium, Paraburkholderia phytofirmans, Paraburkholderia sordidicola, Paraburkholderia terricola, Paraburkholderia xenovorans, Paracoccus laeviglucosivorans, Patulibacter ginsengiterrae, Polymorphospora rubra, Porphyrobacter colymbi, Prevotella jejuni, Prevotella melaninogenica, Propionibacterium acnes* subsp. *elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis, Pseudonocardia alaniniphila, Pseudonocardia ammonioxydans, Pseudonocardia autotrophica, Pseudonocardia kongjuensis, Pseudonocardia yunnanensis, Pseudorhodoferax soli, Pseudoxanthomonas daejeonensis, Pseudoxanthomonas indica, Pseudoxanthomonas kaohsiungensis, Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis, Ramlibacter ginsenosidimutans, Rheinheimera japonica, Rheinheimera muenzenbergensis, Rheinheimera soli, Rheinheimera tangshanensis, Rheinheimera texasensis, Rheinheimera tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium vallis, Rhizobium vignae, Rhizobium vignae, Rhizobium yanglingense, Rhodococcus baikonurensis, Rhodococcus enclensis, Rhodoferax saidenbachensis, Rickettsia canadensis, Rickettsia heilongjiangensis, Rickettsia honei, Rickettsia raoultii, Roseateles aquatilis, Roseateles aquatilis, Salmonella enterica* subsp. *salamae, Serratiaficaria, Serratia myotis, Serratia vespertilionis, Shewanella aestuarii, Shewanella decolorationis, Sphingobium amiense, Sphingobium baderi, Sphingobium barthaii, Sphingobium chlorophenolicum, Sphingobium cupriresistens, Sphingobium czechense, Sphingobium fuliginis, Sphingobium indicum, Sphingobium indicum, Sphingobium japonicum, Sphingobium lactosutens, Sphingomonas dokdonensis, Sphingomonas pseudosanguinis, Sphingopyxis chilensis, Sphingopyxis fribergensis, Sphingopyxis granuli, Sphingopyxis indica, Sphingopyxis witfiariensis, Staphylococcus agnetis, Staphylococcus aureus* subsp. *aureus, Staphylococcus epidermidis, Staphylococcus hominis* subsp. *novobiosepticus, Staphylococcus nepalensis, Staphylococcus saprophyticus* subsp. *bovis, Staphylococcus sciuri* subsp. *carnaticus, Streptomyces caeruleatus, Streptomyces canarius, Streptomyces capoamus, Streptomyces ciscaucasicus, Streptomyces griseorubiginosus, Streptomyces olivaceoviridis, Streptomyces panaciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces neuii* subsp. *anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibacter segnis, Agrococcus baldri, Albibacter methylovorans, Alcaligenes faecalis* subsp. *faecalis, Algoriphagus ratkowskyi, Alkalibacterium* olivapovliticus, Alkalibacterium pelagium, Alkalibacterium pelagium, Alloprevotella rava, Alsobacter metallidurans, Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter venerupis, Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides unmformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans subsp. lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus subsp. caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertbacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas sulfidaeris, Herpetosiphon aurantiacus, Hydrocarboniphaga effusa, Idiomarina maris, Janibacter anophelis, Janibacter hoylei, Janibacter indicus, Janibacter limosus, Janibacter melonis, Jeotgalicoccus halophihus, Jonquetella anthropi, Kaistia geumhonensis, Kingella denitrificans, Kingella oralis, Klebsiella oxytoca, Knoellia aerolata, Knoellia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevanmformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agariphilus, Nocardioides dilutus, Nocardioides ganghwensis, Nocardioides hwasunensis, Nocardioides nanhaiensis, Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacter terrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multilagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimanifer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacter uvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes subsp. acnes, Propionibacterium acnes subsp. acnes, Propionibacterium acnes subsp. elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida, Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis, Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides, Staphylococcus auricularis, Staphylococcus epidermidis, Staphylococcus epidermidis, Staphylococcus hominis subsp. novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oralis, Streptococcus sanguinis, Streptomyces iconiensis, Streptomyces yanglinensis, Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibactersanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus arseniciresistens, Yimella lutea, Zimmermannella alba, Zimmermannella bifida or Zoogloea caeni.

In other embodiments, the targeted bacteria cells are those commonly found in the vaginal microbiota and are, without limitation, Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyonggiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis,

*Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum subsp. infantis, Bifidobacterium longum, Bifdobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fumgorum, Burkholderia phenoliruptix, Caldicelhulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudogenitalium, Corynebacterium pyruviciproducens, Corynebacterium singulare, Corynebacterium striatum, Corynebacterium tuberculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister micraerophilus, Dialister pneumosintes, Dialister propionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotolerans, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odoribacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylli, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans,*

*Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstoniapickettii, Ralstoniasolanacearum, Raoultellaplanticola, Rhizobacterdauci, Rhizobium etli, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atvpica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae* or *Zoogloea ramigera*.

In one embodiment, the targeted bacteria are *Escherichia coli*.

Thus, bacteriophages used for preparing the bacterial delivery vehicles, and then the bacterial delivery vehicles, may target (e.g., specifically target) a bacterial cell from any one or more of the foregoing genus and/or species of bacteria to specifically deliver the payload of interest.

In one embodiment, the targeted bacteria are pathogenic bacteria. The targeted bacteria can be virulent bacteria.

The targeted bacteria can be antibacterial resistance bacteria, including those selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. The targeted bacteria can be selected from the group consisting of extended-spectrum beta-lactamase-producing (ESBL) *Escherichia coli* strains. In a particular embodiment, said targeted bacteria are ESBL *Escherichia coli* and/or ESBL *Klebsiella pneumoniae*.

Alternatively, the targeted bacterium can be a bacterium of the microbiome of a given species, including a bacterium of the human microbiota.

The present disclosure is directed to a bacterial delivery vehicle containing the payload as described herein. The bacterial delivery vehicles are typically prepared from bacterial virus. The bacterial delivery vehicles are typically chosen in order to be able to introduce the payload into the targeted bacteria.

Bacterial viruses, from which the bacterial delivery vehicles disclosed herein may be derived, include bacteriophages. Optionally, the bacteriophage is selected from the Order Caudovirales consisting of, based on the taxonomy of Krupovic et al, Arch Virol, 2015, the family Myoviridae, the family Podoviridae, the family Siphoviridae, and the family Ackermannviridae.

Bacteriophages may be selected from the family Myoviridae (such as, without limitation, genus Cp220virus, Cp8virus, Ea214virus, Felixolvirus, Mooglevirus, Suspvirus, Hplvirus, P2virus, Kayvirus, P100virus, Silviavirus, Spolvirus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Selvirus, V5virus, Abouovirus, Agatevirus, Agrican357virus, Ap22virus, Arvlvirus, B4virus, Bastillevirus, Bc431virus, Bcep78virus, Bcepmuvirus, Biquartavirus, Bxzl virus, Cd119virus, Cp51virus, Cvm10virus, Eah2virus, E1virus, Hapunavirus, Jimmervirus, Kpp10virus, M12virus, Machinavirus, Marthavirus, Msw3virus, Muvirus, Myohalovirus, Nit1virus, Plvirus, Pakpunavirus, Pbunavirus, Phikzvirus, Rheph4virus, Rs12virus, Rslunavirus, Secunda5virus, Seplvirus, Spn3virus, Svunavirus, Tg1virus, Vhmlvirus and Wphvirus).

Bacteriophages may be selected from the family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, T12011virus, Bcep22virus, Bpplvirus, Cba41virus, Df112virus, Ea92virus, Epsilon15virus, F116virus, G7cvirus, Jwalphavirus, Kf1 virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus).

Bacteriophages may be selected from the family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, Klgvirus, Sp31virus, Lmdlvirus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Roguelvirus, Rtpvirus, T1virus, T1svirus, Ab18virus, Amigovirus, Anatolevirus, Andromedavirus, Attisvirus, Barnyardvirus, Bemal13virus, Biseptimavirus, Bronvirus, C2virus, C5virus, Cba181virus, Cbastvirus, Cecivirus, Che8virus, Chivirus, Cjwlvirus, Comdogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phife1virus, Phijl1virus, Pis4avirus, Psavirus, Psimunavirus, Rdj1virus, Rer2virus, Sap6virus, Send513virus, Septima3virus, Seuratvirus, Sextaecvirus, Sfi11virus, Sfi21dt1virus, Sitaravirus, Sklvirus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus).

Bacteriophages may be selected from the family Ackermannviridae (such as, without limitation, genus Ag3virus, Limestonevirus, Cba120virus and Vi1virus).

Optionally, the bacteriophage is not part of the order Caudovirales but from families with unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

Optionally, the bacteriophage is targeting Archea not part of the Order Caudovirales but from families with unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. The chimeric RBPs and/or the recombinant gpJ proteins and/or the recombinant gpH proteins, and the bacterial delivery vehicles disclosed herein may be engineered, as non-limiting examples, from the following phages. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CT1, CT2, CT3, CT4, CT6, CT7, CT8 and 1281.

Bacteria of the genus *Aeromonas* can be infected by the following phages: AA-I, Aeh2, N, PM1, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-1, Col1, Cor1, CP-53, CS-1, CSi, D, D, D, D5, ent1, FP8, FP9, FSi, FS2, FS3, FS5, FS8, FS9, G, GH8, GT8, GV-I, GV-2, GT-4, g3, g12, g13, g14, g16, g17, g21, g23, g24, g29, H2, ken1, KK-88, Kum1, Kyu1, J7W-1, LP52, (syn=LP-52), L7, Mex1, MJ-I, mor2, MP-7, MP1O, MP12, MP14, MP15, Neo1, No 2, N5, N6P, PBCI, PBLA, PBPI, P2, S-a, SF2, SF6, Sha1, Si11, SP02, (syn=ΦSPP1), SPβ, STI, STi, SU-I1, t, TbI, Tb2, Tb5, TIO, Tb26, Tb51, Tb53, Tb55, Tb77, Tb97, Tb99, Tb560, Tb595, Td8, Td6, Td15, Tg1, Tg4, Tg6, Tg7, Tg9, TgIO, Tgl1, Tg13, Tg15, Tg21, Tin1, Tin7, Tin8, Tin13, Tm3, Toc1, Tog1, to11, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, pl 1, φmed-2, φT, φμ-4, φ3T, φ75, φ1O5, (syn=φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, darl, denl, DP-7, enti, FoSi, FoS2, FS4, FS6, FS7, G, gall, gamma, GEl, GF-2, GSi, GT-1, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBSl, PKl, PMBI, PMB12, PMJI, S, SPOI, SP3, SP5, SP6, SP7, SP8, SP9, SPlO, SP-15, SP50, (syn=SP-50), SP82, SST, subl, SW, Tg8, Tg12, Tg13, Tg14, thu1, thuA, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, B1, B2, GA-I, GP-IO, GV-3, GV-5, g8, MP20, MP27, MP49, Nf, PP5, PP6, SF5, Tg18, TP-I, Versailles, φ15, φ29, 1-97, 837/IV, mi-*Bacillus* (1), BatlO, BSLlO, BSLI1, BS6, BSI 1, BS16, BS23, BSlOl, BS102, g18, mor1, PBL1, SN45, thu2, thu3, TmI, Tm2, TP-20, TP21, TP52, type F, type G, type IV, HN-BacMus (3), BLE, (syn=θc), BS2, BS4, BS5, BS7, B1O, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: ad I2, Baf-44, Baf-48B, Baf-64, Bf-I, Bf-52, B40-8, F1, β1, φA1, BrO1, φBrO2, 11, 67.1, 67.3, 68.1, mt-*Bacteroides* (3), Bf42, Bf7, HN-Bdellovibrio (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FO1), (syn=FQ1), D, FP2, (syn=FP2), (syn=FD2), Fz, (syn=Fz75/13), (syn=Firenze 75/13), (syn=Fi), Fi, (syn=F1), Fim, (syn=FIm), (syn=Fim), FiU, (syn=FlU), (syn=FiU), F2, (syn=F2), F3, (syn=F3), F4, (syn=F4), F5, (syn=F5), F6, F7, (syn=F7), F25, (syn=F25), (syn=25), F25U, (syn=F25u), (syn=F25U), (syn=F25V), F44, (syn=F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=FiO), (syn=F10), 371/XXIX, (syn=371), (syn=Fn), (syn=F11) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phages: Chp1.

Bacteria of the genus *Clostridium* can be infected by the following phages: CAK1, CA5, Ca7, CEβ, (syn=IC), CEγ, Cld1, c-n71, c-203 Tox-, DEβ, (syn=ID), (syn=IDt0X+), HM3, KMl, KT, Ms, NA1, (syn=Naltox+), PA1350e, Pf6, PL73, PL78, PL81, P1, P50, P5771, P19402, ICtOX+, 2CtOX\, 2D3 (syn=2Dt0X+), 3C, (syn=3Ctox+), 4C, (syn=4CtOX+), 56, III-1, NN-*Clostridium* (61), NBltOX+, α1, CA1, HMT, HM2, PF15 P-23, P-46, Q-05, Q-oe, Q-16, Q-21, Q-26, Q-40, Q-46, S11, SA02, WA01, WA03, Wm, W523, 80, C, CA2, CA3, CPT1, CPT4, c1, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, α2, 41, 12ZS23, 214/S23, 233/Ai, 234/S23, 235/S23, II-1, II-2, II-3, NN-*Clostridium* (12), CA1, F1, K, S2, 1, 5 and NN-*Clostridium* (8).

Bacteria of the genus *Corynebacterium* can be infected by the following phages: CGKI (defective), A, A2, A3, AlO1, A128, A133, A137, A139, A155, A182, B, BF, B17, B18, B51, B271, B275, B276, B277, B279, B282, C, capi, CC1, CG1, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, p, (syn=ptox+), βhv64, βvir, γ, (syn=γtoχ-), γl9, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* can be infected by the following phages: DF78, F1, F2, 1, 2, 4, 14, 41, 867, D1, SB24, 2BV, 182, 225, C2, C2F, E3, E62, DS96, H24, M35, P3, P9, SBIO1, S2, 2BII, 5, 182a, 705, 873, 881, 940, 1051, 1057, 21096C, NN-*Enterococcus* (1), PE1, F1, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, E1, E24, E41, FI-2, FI-4, FI-5, HI8A, Ff18B, i, MM, Mu, (syn=mu), (syn=MuI), (syn=Mu-I), (syn=MU-I), (syn=MuI), (syn=μ), 025, PhI-5, Pk, PSP3, P1, P1D, P2, P4 (defective), S1, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, F13, H, H1, H3, H8, K3, M, N, ND-2, ND-3, ND4, ND-5, ND6, ND-7, Ox-I (syn=OX1), (syn=HF), Ox-2 (syn=0×2), (syn=0×2), Ox-3, Ox-4, Ox-5, (syn=0×5), Ox-6, (syn=66F), (syn=φ66t), (syn=φ66t-)5 0111, PhI-I, RB42, RB43, RB49, RB69, S, Sal-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, α1, 1, IA, 3, (syn=Ac3), 3A, 3T+, (syn=3), (syn=M1), 5φ, (syn=φ5), 9266Q, CFO103, HK620, J, K, KLF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φ1, φ1.2, φ20, φ95, φ263, φlO92, φl, φll, (syn=φW), Ω28, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, (syn=(DHK97), HK139, HK253, HK256, K7, ND-I, no.D, PA-2, q, S2, T1, (syn=α), (syn=P28), (syn=T-I), (syn=Tx), T3C, T5, (syn=T-5), (syn=T5), UC-I, w, β4, γ2, λ (syn=lambda), (syn=φλ), φD326, φγ, Φ06, Φ7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-J and 933H.

Bacteria of the genus *Fusobacterium* can be infected by the following phages: NN-*Fusobacterium* (2), fv83-554/3, fv88-531/2, 227, fv2377, fv2527 and fv8501.

Bacteria of the genus *Haemophilus* can be infected by the following phages: HP1, S2 and N3.

Bacteria of the genus *Helicobacter* can be infected by the following phages: HP1 and ^^-*Helicobacter* (1).

Bacteria of the genus *Klebsiella* can be infected by the following phages: AIO-2, KI4B, K16B, K19, (syn=K19), K114, K115, K121, K128, K129, K132, K133, K135, K1106B, K1171B, K1181B, K1832B, AIO-I, AO-I, AO-2, AO-3, FC3-10, K, K11, (syn=KII), K12, (syn=K12), K13, (syn=K13), (syn=K1 70/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-I, K14B, K18, K111, K112, K113, K116, K117, K118, K120, K122, K123, K124, K126, K130, K134, K1106B, KIi65B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=KII 81), (syn=K181B), K1765/!, (syn=K1765/1), K1842B, (syn=K1832B), K1937B, (syn=K1937B), L1, φ28, 7, 231, 483, 490, 632 and 864/100.

Bacteria of the genus Lepitospira can be infected by the following phages: LE1, LE3, LE4 and ~NN-*Leptospira* (1).

Bacteria of the genus *Listeria* can be infected by the following phages: A511, 01761, 4211, 4286, (syn=B054), A005, A006, A020, A500, A502, A511, A118, A620, A640, B012, B021, B024, B025, B035, B051, B053, B054, B055, B056, B101, BI 10, B545, B604, B653, C707, D441, HS047, HlOG, H8/73, H19, H21, H43, H46, H107, H108, HI 10, H163/84, H312, H340, H387, H391/73, H684/74, H924A, PSA, U153, pMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* can be infected by the following phage: 47.

Bacteria of the genus *Mycobacterium* can be infected by the following phages: 13, AG1, ALi, ATCC 11759, A2, B.C3, BG2, BK1, BK5, *butyricum*, B-I, B5, B7, B30, B35, Clark, C1, C2, DNAIII, DSP1, D4, D29, GS4E, (syn=GS4E), GS7, (syn=GS-7), (syn=GS7), IPa, lacticola, Legendre, Leo, L5, (syn=ΦL-5), MC-I, MC-3, MC-4, minetti, MTPHI 1, Mx4, MyF3P/59a, phlei, (syn=phlei 1), phlei 4, Polonus II, rabinovitschi, smegmatis, TM4, TM9, TMlO, TM20, Y7, YlO, φ630, IB, IF, IH, 1/1, 67, 106, 1430, B1, (syn=Bol), B24, D, D29, F-K, F-S, HP, Polonus I, Roy, R1, (syn=RL-Myb), (syn=Ri), 11, 31, 40, 50, 103a, 103b, 128, 3111-D, 3215-D and NN-*Mycobacterium* (1).

Bacteria of the genus *Neisseria* can be infected by the following phages: Group I, group II and NPI.

Bacteria of the genus *Nocardia* can be infected by the following phages: MNP8, NJ-L, NS-8, N5 and TtiN-*Nocardia*.

Bacteria of the genus *Proteus* can be infected by the following phages: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI 1, Pv2, π1, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* can be infected by the following phages: PL25, PL26, PL37, 9211/9295, 9213/9211b, 9248, 7/R49, 7476/322, 7478/325, 7479, 7480, 9000/9402 and 9213/921 Ia.

Bacteria of the genus *Pseudomonas* can be infected by the following phages: PfI, (syn=Pf-I), Pf2, Pf3, PP7, PRR1, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PB1), pfl6, PMN17, PP1, PP8, Psa1, PsP1, PsP2, PsP3, PsP4, PsP5, PS3, PS17, PTB80, PX4, PX7, PYO1, PYO2, PYO5, PYO6, PYO9, PYOlO, PYO13, PYO14, PYO16, PYO18, PYO19, PY020, PY029, PY032, PY033, PY035, PY036, PY037, PY038, PY039, PYO41, PY042, PY045, PY047, PY048, PY064, PY069, PYO003, PIK, SLP1, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, F1 16, HF, H90, K5, K6, K1 04, K109, K166, K267, N4, N5, O6N-25P, PE69, Pf, PPN25, PPN35, PPN89, PPN91, PP2, PP3, PP4, PP6, PP7, PP8, PP56, PP87, PPL 14, PP206, PP207, PP306, PP651, Psp231a, Pssy401, Pssy9220, psi, PTB2, PTB20, PTB42, PX1, PX3, PX10, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F10, g, gd, ge, gξ Hw12, Jb 19, KFI, L°, OXN-32P, 06N-52P, PCH-I, PC13-1, PC35-1, PH2, PH51, PH93, PH132, PMW, PM13, PM57, PM61, PM62, PM63, PM69, PM105, PMl 13, PM681, PM682, P04, PPl, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-10, Pz, SD1, SL1, SL3, SL5, SM, φC5, φC1 1, φC11-1, φC13, φC15, φMO, φX, φO4, φ1 1, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), GlO1, M6, M6a, L1, PB2, Pssyl5, Pssy4210, Pssy4220, PYO12, PY034, PY049, PYO50, PYO51, PYO52, PYO53, PYO57, PYO59, PYO200, PX2, PX5, SL4, φO3, φO6 and 1214.

Bacteria of the genus *Rickettsia* can be infected by the following phage: NN-*Rickettsia*.

Bacteria of the genus *Salmonella* can be infected by the following phages: b, Beccles, CT, d, Dundee, f, Fels 2, GI, GUI, GVI, GVIII, k, K, i, j, L, 01, (syn=0-1), (syn=O1), (syn=O-I), (syn=7), 02, 03, P3, P9a, PlO, Sab3, Sab5, SanlS, Sanl7, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22a1, P22-4, P22-7, P22-11, SNT-I, SNT-2, SP6, Villi, ViIV, ViV, ViVI, ViVII, Worksop, Sj5, ε34, 1, 37, 1(40), (syn=φ1[40]), 1, 422, 2, 2.5, 3b, 4, 5, 6, 14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, ViII, φ1, 1, 2, 3a, 3a1, 1010, Ym-*Salmonella* (1), N-4, SasL6 and 27.

Bacteria of the genus *Serratia* can be infected by the following phages: A2P, PS20, SMB3, SMP, SMP5, SM2, V40, V56, ic, ΦCP-3, ΦDCP-6, 3M, 10/1a, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWI, ΦCP6-1, ΦCP6-2, ΦCP6-5, 3T, 5, 8, 9F, 10/1, 2OE, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/1Oa, L.359 and SMB1.

Bacteria of the genus *Shigella* can be infected by the following phages: Fsa, (syn=a), FSD2d, (syn=D2d), (syn=W2d), FSD2E, (syn=W2e), fv, F6, f7.8, H-Sh, PE5, P90, SfII, Sh, SHm, SHrv, (syn=HIV), SHvi, (syn=HVI), SHVvm, (syn=HVIII), SKγ66, (syn=gamma 66), (syn=γββ), (syn=γ66b), SKm, (syn=SIIIb)5 (syn=UI), SKw, (syn=Siva), (syn=IV), SIC™, (syn=SIVA), (syn=IVA), SKvi, (syn=KVI), (syn=Svi), (syn=VI), SKvm, (syn=Svm), (syn=VIII), SKVIIIA, (syn=SvmA), (syn=VIIIA), STvi, STK, STx1, STxn, S66, W2, (syn=D2c), (syn=D20), φ1, φIVb 3-SO-R, 8368-SO-R, F7, (syn=FS7), (syn=K29), FlO, (syn=FSlO), (syn=K31), I1, (syn=alfa), (syn=FSa), (syn=K1 8), (syn=α), I2, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO-S-R), W1, (syn=D8), (syn=FSD8), W2a, (syn=D2A), (syn=FS2a), DD-2, Sf6, FSi, (syn=F1), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BI1, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI 1, P2-SO-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=SsI), SKVII, (syn=KVII), (syn=Svn), (syn=SsVII), SKIX, (syn=KIX), (syn=S1x), (syn=SsIX), SKXII, (syn=KXII), (syn=Sxn), (syn=SsXII), STi, STffl, STrv, STVi, STvπ, S70, S206, U2-SO-S, 3210-SO-S, 3859-SO-S, 4020-SO-S, φ3, φ5, φ7, φ8, φ9, φlO, φ1 1, φ13, φ14, φ18, SHm, (syn=Hπi), SHχi, (syn=HXt) and SKxI, (syn=KXI), (syn=Sχi), (syn=SsXI), (syn=XI).

Bacteria of the genus *Staphylococcus* can be infected by the following phages: A, EW, K, Pb5, Ph9, PhIO, Ph13, P1, P2, P3, P4, P8, P9, PlO, RG, SB-i, (syn=Sb-I), S3K, Twort, ΦSK311, φ812, 06, 40, 58, 119, 130, 131, 200, 1623, STC1, (syn=stc1), STC2, (syn=stc2), 44AHJD, 68, AC1, AC2, A6"C", A9"C", b581, CA-I, CA-2, CA-3, CA-4, CA-5, DI 1, L39x35, L54a, M42, N1, N2, N3, N4, N5, N7, N8, NIO, Ni 1, N12, N13, N14, N16, Ph6, Ph12, Ph14, UC-18, U4, U15, S1, S2, S3, S4, S5, X2, Z1, φB5-2, φD, ω,, 11, (syn=φ1 1), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AlO, A13, b594n, D, HK2, N9, N15, P52, P87, S1, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* can be infected by the following phages: EJ-I, NN-Streptococais (1), a, C1, FLOThs, H39, Cp-I, Cp-5, Cp-7, Cp-9, Cp-IO, AT298, A5, alO/J1, alO/J2, alO/J5, alO/J9, A25, BTI 1, b6, CA1, c20-1, c20-2, DP-I, Dp-4, DT1, ET42, elO, FA101, FEThs, Fx, FKKIOI, FKLIO, FKP74, FKH, FLOThs, FyIO1, fl, F10, F20140/76, g, GT-234, HB3, (syn=HB-3), HB-623, HB-746, M102, O1205, φO1205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfII 1, (syn=SFiI1), (syn=φSFil1), (syn=ΦSfil 1), (syn=φSfil 1), sfi19, (syn=SFil9), (syn=φSFil9), (syn=φSfil9), Sfi21, (syn=SFi21), (syn=φSFi21), (syn=φSfi21), STO, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φ1OO, φ1O1, p1O2, φ227, Φ7201, ω1, ω2, ω3, ω4, ω5, ω6, ω8, ωlO, 1, 6, 9, 1OF, 12/12, 14, 17SR, 19S, 24, 50/33, 50/34, 55/14, 55/15, 70/35, 70/36, 71/STI5, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* can be infected by the following phage: NN-*Treponema* (1).

Bacteria of the genus *Vibrio* can be infected by the following phages: CTXΦ, fs, (syn=si), fs2, Ivpf5, Vf12, Vf33, VPIΦ, VSK, v6, 493, CP-T1, ET25, kappa, K139, Labol, XN-69P, OXN-86, O6N-21P, PB-I, P147, rp-1, SE3, VA-I, (syn=VcA-I), VcA-2, VP1, VP2, VP4, VP7, VP8, VP9, VPIO, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHC1-1, ΦHC1-2, ΦHC1-3, ΦHC1-4, ΦHC2-1, >HC2-2, ΦHC2-3, ΦHC2-4, ΦHC3-1, ΦHC3-2, ΦHC3-3, ΦHD1S-1, ΦHDIS-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φ138, 1-II, 5, 13, 14, 16, 24, 32, 493, 6214, 7050, 7227, II, (syn=group II), (syn=p2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pA1, 7, 7-8, 70A-2, 71A-6, 72A-5, 72A-8, 108A-10, 109A-6, 109A-8, 110A-1, 110A-5, 110A-7, hv-1, OXN-52P, P13, P38, P53, P65, P108, Pill, TP13 VP3, VP6, VP12, VP13, 70A-3, 70A-4, 70A-10, 72A-1, 108A-3, 109-B1, 110A-2, 149, (syn=9149), IV, (syn=group IV), NN-*Vibrio* (22), VP5, VPI1, VP15, VP16, α1, α2, α3a, α3b, 353B and HN-*Vibrio* (7).

Bacteria of the genus *Yersinia* can be infected by the following phages: H, H-I, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

In an embodiment, the bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus PhaxI, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus ViI, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaEl, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiOI8P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA 11, *Staphylococcus* virus Stau2, *Bacillus* virus Camphawk, *Bacillus* virus SPOI, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phil, *Escherichia* virus RB49, *Escherichia* virus HX01, *Escherichia* virus JSO9, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HYO1, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, Cronobacter virus CR3, Cronobacter virus CR8, Cronobacter virus CR9, Cronobacter virus PBESO2, *Pectobacterium* virus phiTE, Cronobacter virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcepl, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, Edwardsiella virus MSW3, Edwardsiella virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLACIC, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, Microcystis virus Ma-LMMO1, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kpl, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, Xyella virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvpl, *Pseudomonas* virus gh1, *Prochlorococcus* virus PSSP7, *Synechococcus* virus P60, *Synechococcus* virus Syn5, *Streptococcus* virus Cp1, *Streptococcus* virus Cp7, *Staphylococcus* virus 44AHJD, *Streptococcus* virus C1, *Bacillus* virus B103, *Bacillus* virus GA1, *Bacillus* virus phi29, Kurthia virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepi102, *Burkholderia* virus Bcepmig1, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, Roseobacter virus SIO1, *Vibrio* virus VpV262, *Vibrio* virus VC8, *Vibrio* virus VP2, *Vibrio* virus VP5, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wks13, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LNO3, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, Cronobacter virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphy*lococcus virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus L1ij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus SO1, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC 117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, Nonlabens virus P12024L, Nonlabens virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus PL.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHLOO9M11, *Propionibacterium* virus PHL025MOO, *Propionibacterium* virus PHL037MO2, *Propionibacterium* virus PHL041M10, *Propionibacterium* virus PHL060LOO, *Propionibacterium* virus PHL067MO1, *Propionibacterium* virus PHL070NOO, *Propionibacterium* virus PHL071N05, *Propionibacterium* virus PHL082MO3, *Propionibacterium* virus PHL092MOO, *Propionibacterium* virus PHL095NOO, *Propionibacterium* virus PHL111MO1, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308MOO, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, Roseobacter virus RDJL1, Roseobacter virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lacto-* coccus virus sk1, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sa12, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phi17, *Xanthomonas* virus Xop411, *Xanthomonas* virus Xp10, *Streptomyces* virus TP1604, *Streptomyces* virus YDN12, Alphaproteobacteria virus phiJ1001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, Acholeplasma virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, Spiroplasma virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, Spiroplasma virus C74, Spiroplasma virus R8A2B, Spiroplasma virus SkV1CR23x, *Escherichia* virus F1, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus ID52, *Escherichia* virus Talmos, *Escherichia* virus phiX174, Bdellovibrio virus MAC1, Bdellovibrio virus MH2K, *Chlamydia* virus Chp1, *Chlamydia* virus Chp2, *Chlamydia* virus CPAR39, *Chlamydia* virus CPG1, Spiroplasma virus SpV4, Acholeplasma virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stx1phi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus EC026_P06, *Escherichia* virus ECO103_P15, *Escherichia* virus ECO103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Sp5.

In one embodiment, the bacterial virus particles typically target *E. coli* and include the capsid of a bacteriophage selected in the group consisting of BW73, B278, D6, D108, E, E1, E24, E41, FI-2, FI-4, FI-5, HI8A, Ff18B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, DD-VI, E4, E7, E28, FI1, F13, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sal-2, Sal-3, Sal-4, Sal-5, Sal-6, TC23, TC45, TuII*-6, TuIP-24, TuII*46, TuIP-60, T2, T4, T6, T35, α1, 1, IA, 3, 3A, 3T+, 5φ, 9266Q, CFO103, HK620, J, K, KiF, m59, no. A, no. E, no. 3, no. 9, N4, sd, T3, T7, WPK, W31, ΔH, TC3888, φK3, φK7, φK12, φV-1, Φ04-CF, Φ05, 006, Φ07, φ1, φ1.2, φ20, φ95, φ263, φlO92, φl, φll, Ω28, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1, ), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, KlO, ZG/3A, 5, 5A, 21EL, H19-J and 933H.

Pharmaceutical or Veterinary Composition

The present disclosure also provides a pharmaceutical or veterinary composition comprising the bacterial delivery vehicle as defined in the section "Bacterial delivery vehicle" above and a pharmaceutically acceptable carrier.

Generally, for pharmaceutical use, the bacterial delivery vehicles may be formulated as a pharmaceutical preparation or composition comprising at least one bacterial delivery vehicle and at least one pharmaceutically acceptable carrier, diluent or excipient, and optionally one or more further pharmaceutically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. In a particular embodiment, said composition is for oral administration. Such administration forms may be solid, semi-solid or liquid, depending on the manner and route of administration. For example, formulations for oral administration may be provided with an enteric coating that will allow the synthetic bacterial delivery vehicles in the formulation to resist the gastric environment and pass into the intestines. More generally, synthetic bacterial delivery vehicle formulations for oral administration may be suitably formulated for delivery into any desired part of the gastrointestinal tract. In addition, suitable suppositories may be used for delivery into the gastrointestinal tract. Various pharmaceutically acceptable carriers, diluents and excipients useful in bacterial delivery vehicle compositions are known to the skilled person The pharmaceutical or veterinary composition according to the disclosure may further comprise a pharmaceutically acceptable vehicle. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidone, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions disclosed herein may be administered orally in the form of a sterile solution or suspension containing other solutes or suspending agents (for example, enough saline or glucose to make the solution isotonic), bile salts, acacia, gelatin, sorbitan monoleate, polysorbate 8o (oleate esters of sorbitol and its anhydrides copolymerized with ethylene oxide) and the like. The particles according to the disclosure can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial delivery vehicles disclosed herein may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmoregulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

In another particular embodiment, the present disclosure provides a pharmaceutical or veterinary composition as defined above for use to improve the effectiveness of drugs. Indeed, some bacteria of the microbiome, without being pathogenic by themselves, are known to be able to metabolize drugs and to modify them in ineffective or harmful molecules.

In another particular embodiment, the disclosure provides a composition that may further comprise at least one additional active ingredient, for instance a prebiotic and/or a probiotic and/or an antibiotic, and/or another antibacterial or antibiofilm agent, and/or any agent enhancing the targeting of the bacterial delivery vehicle to a bacteria and/or the delivery of the payload into a bacteria.

As used herein, a "prebiotic" refers to an ingredient that allows specific changes, both in the composition and/or activity in the gastrointestinal microbiota that may confer benefits upon the host. A prebiotic can be a comestible food or beverage or ingredient thereof. A prebiotic may be a selectively fermented ingredient. Prebiotics may include complex carbohydrates, amino acids, peptides, minerals, or other essential nutritional components for the survival of the bacterial composition. Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

As used herein, a "probiotic" refers to a dietary supplement based on living microbes which, when taken in adequate quantities, has a beneficial effect on the host organism by strengthening the intestinal ecosystem. Probiotic can comprise a non-pathogenic bacterial or fungal population, e.g., an immunomodulatory bacterial population, such as an anti-inflammatory bacterial population, with or without one or more prebiotics. They contain a sufficiently high number of living and active probiotic microorganisms that can exert a balancing action on gut flora by direct colonisation. It must be noted that, for the purposes of the present description, the term "probiotic" is taken to mean any biologically active form of probiotic, preferably including but not limited to lactobacilli, bifidobacteria, streptococci, enterococci, propionibacteria or saccharomycetes but even other microorganisms making up the normal gut flora, or also fragments of the bacterial wall or of the DNA of these microorganisms. These compositions are advantageous in being suitable for safe administration to humans and other mammalian subjects and are efficacious for the treatment, prevention, of a disease or disorder caused by bacteria such as bacterial infection. Probiotics include, but are not limited to lactobacilli, bifidobacteria, streptococci, enterococci, propionibacteria, saccharomycetes, lactobacilli, bifidobacteria, or proteobacteria.

The antibiotic can be selected from the group consisting of penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cephaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefininox, cefotetan, cefoxitin, cefotiam, cefcapene, cefdaloxime, cefdinir, cefditoren, cefetamet, cefixime, cefienoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; fluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomicin, nalidixic acid, rifampin, derivatives and combination thereof.

Applications

The present disclosure provides a method for in vivo delivery of a DNA payload of interest into a subject comprising, administering to said subject a pharmaceutical or veterinary composition as disclosed herein.

Also provided are methods for treating a disease or disorder caused by bacteria such as bacterial infection using the bacterial delivery vehicles or compositions disclosed herein. The methods include administering a therapeutically efficient amount of bacterial delivery vehicles or compositions disclosed herein to a subject having a bacterial infection in need of treatment.

The present disclosure also provides the pharmaceutical or veterinary compositions disclosed herein or the bacterial delivery vehicles disclosed herein for use in a method for treating a disease or disorder caused by bacteria.

Another object of the disclosure concerns providing the use of a bacterial delivery vehicle as described herein for the manufacture of a medicament intended for the treatment of a disease or disorder caused by bacteria.

In some embodiments, the subject is a mammal. In some embodiments, the subject is a human.

Said disease or disorder may be a bacterial infection, a metabolic disorder or a pathology involving bacteria of the human microbiome.

The diseases or disorders caused by bacteria may be selected from the group consisting of abdominal cramps, acne vulgaris, acute epiglottitis, arthritis, bacteraemia, bloody diarrhea, botulism, Brucellosis, brain abscess, chancroid venereal disease, *Chlamydia*, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Windermere syndrome, Legionaire's disease, meningitis, mucopurulent conjunctivitis, multi-drug resistant bacterial infections, multi-drug resistant bacterial carriage, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough.

The disease or disorder caused by bacteria may be a bacterial infection selected from the group consisting of skin infections such as acne, intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, and a combination thereof. In an embodiment, the infection according to the disclosure is caused by a bacterium presenting an antibiotic resistance. In a particular embodiment, the infection is caused by a bacterium as listed above in the targeted bacteria.

The disease or disorder caused by bacteria may also be a metabolic disorder, for example, obesity and/or diabetes. The disclosure thus also concerns a pharmaceutical or veterinary composition as disclosed herein for use in the treatment of a metabolic disorder including, for example, obesity and/or diabetes. It further concerns a method for treating a metabolic disorder comprising administering a therapeutically efficient amount of the pharmaceutical or veterinary composition as disclosed herein, and the use of a pharmaceutical or veterinary composition as disclosed herein for the manufacture of a medicament for treating a metabolic disorder.

The disease or disorder caused by bacteria may also be a pathology involving bacteria of the human microbiome. Thus, in a particular embodiment, the disclosure concerns a pharmaceutical or veterinary composition as disclosed herein for use in the treatment of pathologies involving bacteria of the human microbiome, such as inflammatory and auto-immune diseases, cancers, infections or brain disorders. It further concerns a method for treating a pathology involving bacteria of the human microbiome comprising administering a therapeutically efficient amount of the pharmaceutical or veterinary composition as disclosed herein, and the use of a pharmaceutical or veterinary composition as disclosed herein for the manufacture of a medicament for treating a pathology involving bacteria of the human microbiome. Indeed, some bacteria of the microbiome, without triggering any infection, can secrete molecules that will induce and/or enhance inflammatory or auto-immune diseases or cancer development. More specifically, the present disclosure relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

In certain embodiments, the disease to be treated is cancer or a proliferative disorder, including but not limited to, breast cancer (e.g., triple negative breast cancer, ER+ breast cancer, or ER– breast cancer), basal cell carcinoma, skin cancer, lung cancer, small cell lung cancer, non-small cell lung cancer, brain cancer, medulloblastoma, glioma (including glioblastoma, oligodendroglioma, astrocytoma, ependymoma), neuroblastoma, colorectal cancer, ovarian cancer, liver cancer, pancreatic cancer (e.g., carcinoma, angiosarcoma, adenosarcoma), gastric cancer, gastroesophageal junction cancer, prostate cancer, cervical cancer, bladder cancer, head and neck cancer, lymphoma (e.g., mantle cell lymphoma, diffuse large B-cell lymphoma), removable solid tumors or solid tumors that cannot be removed by surgery, locally advanced solid tumors, metastatic solid tumors, leukemia (e.g., acute myeloid leukemia (AML), acute lymphoblastic leukemia (ALL), or chronic myeloid leukemia (CML)), or recurrent or refractory tumors.

In one embodiment, the diseases to be treated include, but are not limited to, inflammatory or allergic diseases, including systemic anaphylaxis and hypersensitivity disorders, atopic dermatitis, urticaria, drug allergies, insect sting allergies, food allergies (including celiac disease and the like), and mastocytosis; inflammatory bowel diseases, including Crohn's disease, ulcerative colitis, ileitis, and enteritis; vasculitis, and Behcet's syndrome; psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; asthma and respiratory allergic diseases, including allergic asthma, exercise induced asthma, allergic rhinitis, otitis media, allergic conjunctivitis, hypersensitivity lung diseases, and chronic obstructive pulmonary disease; autoimmune diseases, including arthritis (including rheumatoid and psoriatic), systemic lupus erythematosus, type I diabetes, myasthenia gravis, multiple sclerosis, Graves' disease, and glomerulonephritis; graft rejection (including allograft rejection and graft-v-host disease), e.g., skin graft rejection, solid organ transplant rejection, bone marrow transplant rejection; fever; cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; cerebrovascular disorders, including traumatic brain injury, stroke, ischemic reperfusion injury and aneurysm; fibrosis, connective tissue disease, and sarcoidosis, genital and reproductive conditions, including erectile dysfunction; gastrointestinal disorders, including gastritis, ulcers, nausea, pancreatitis, and vomiting; neurologic disorders, including Alzheimer's disease; sleep disorders, including insomnia, narcolepsy, sleep apnea syndrome, and Pickwick Syndrome; pain; renal disorders; ocular disorders, including glaucoma; and non-bacterial infectious diseases, including HIV.

In some aspects, the disease to be treated may be an autoimmune disease such as autoimmune hemolytic anemia, autoimmune neonatal thrombocytopenia, autoimmune neutropenia, autoimmunocytopenia, antiphospholipid syndrome, dermatitis, gluten-sensitive enteropathy, allergic encephalomyelitis, myocarditis, relapsing polychondritis, rheumatic heart disease, glomerulonephritis, Multiple Sclerosis, Neuritis, Uveitis Ophthalmia, Polyendo-crinopathies, Purpura, Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitis, autoimmune inflammatory eye, autoimmune thyroiditis, hypothyroidism, systemic lupus erythematosus, discoid lupus, Goodpasture's syndrome, Pemphigus, Graves' Disease, Myasthenia Gravis, and insulin resistance, autoimmune hemolytic anemia, autoimmune thrombocytopenic purpura, rheumatoid arthritis, scleroderma with anti-collagen antibodies, mixed connective tissue disease, polymyositis/dermatomyositis, pernicious anemia, idiopathic Addison's disease, infertility, glomerulonephritis, bullous pemphigoid, Sjogren's syndrome, diabetes mellitus, adrenergic drug resistance with asthma or cystic fibrosis, chronic active hepatitis, primary biliary cirrhosis, endocrine gland failure, vitiligo, vasculitis, post-MI, cardiotomy syndrome, urticaria, atopic dermatitis, asthma, inflammatory myopathies, an inflammatory disorder, a granulomatous disorder, an atrophic disorder, or an alloimmune disease.

The subject to be treated may have been diagnosed with, or may be at risk of developing an infection, a disorder and/or a disease preferably due to a bacterium. Diagnostic methods of such infection, disorder and/or disease are well known by the man skilled in the art.

In a particular embodiment, the infection, disorder and/or disease presents a resistance to treatment, preferably the infection, disorder or disease presents an antibiotic resistance.

In a particular embodiment, the subject has never received any treatment prior to the administration of the delivery vehicles according to the invention or of the pharmaceutical or veterinary composition according to the invention.

In a particular embodiment, the subject has already received at least one line of treatment, preferably several lines of treatment, prior to the administration of the delivery vehicles according to the invention or of the pharmaceutical or veterinary composition according to the invention.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with delivery vehicles according to the invention or with the pharmaceutical or veterinary composition according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of or about 1 week. Alternatively, the treatment may last as long as the infection, disorder and/or disease persists.

The form of the pharmaceutical or veterinary compositions, the route of administration and the dose of administration of delivery vehicles according to the invention or of pharmaceutical or veterinary composition according to the invention can be adjusted by the man skilled in the art according to the type and severity of the infection (e.g. depending on the bacteria species involved in the disease, disorder and/or infection and its localization in the patient's or subject's body), and to the patient or subject, in particular its age, weight, sex, and general physical condition.

Particularly, the amount of delivery vehicles according to the invention or of pharmaceutical or veterinary composition according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of delivery vehicles according to the invention for each administration is between $10^4$ and $10^{15}$ delivery vehicles.

In a particular embodiment, in the treatment methods or uses, said composition or bacterial delivery vehicle is administered orally.

Some bacteria of the microbiome can also secrete molecules that will affect the brain, such as serotonin and melatonin for use in the treatment of depression, dementia or sleep disorder.

Therefore, a further object of the disclosure is a method for controlling the microbiome of a subject, comprising administering an effective amount of the pharmaceutical or veterinary composition as disclosed herein in said subject.

In a particular embodiment, the disclosure also relates to a method for personalized treatment for an individual in need of treatment for a disease or disorder such as bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical or veterinary composition according to the disclosure capable of recognizing each pathogenic bacterial strain or species identified in the sample and to deliver the packaged payload.

In an embodiment, the biological sample comprises pathological and non-pathological bacterial species, and subsequent to administering the pharmaceutical or veterinary composition according to the disclosure to the individual, the amount of pathogenic bacteria on or in the individual are reduced, but the amount of non-pathogenic bacteria is not reduced.

In another particular embodiment, the disclosure concerns a pharmaceutical or veterinary composition according to the disclosure for use to improve the effectiveness of drugs. Indeed, some bacteria of the microbiome, without being pathogenic by themselves, are known to be able to metabolize drugs and to modify them in ineffective or harmful molecules.

In another aspect, the methods and compositions described herein provide long term stable expression of a gene of interest in the microbiome of a host. In such an instance, the delivery vehicle comprises a nucleic acid molecule encoding the gene of interest wherein the nucleic acid is engineered to either integrate into the bacterial chromosome or, alternatively, stably replicate within the targeted microbiome of the host. Once delivered into the bacteria of interest, i.e., the microbiome, the gene of interest will typically be expressed. In a particular embodiment, the disclosure concerns the in-situ bacterial production of any compound of interest, including therapeutic compound such as prophylactic and therapeutic vaccine for mammals. The compound of interest can be produced inside the targeted bacteria, secreted from the targeted bacteria or expressed on the surface of the targeted bacteria. In a more particular embodiment, an antigen is expressed on the surface of the targeted bacteria for prophylactic and/or therapeutic vaccination.

The present disclosure also provides a method for reducing the amount of virulent and/or antibiotic resistant bacteria in a bacterial population comprising contacting the bacterial population with an efficient amount of the bacterial delivery vehicle as defined in the section "Bacterial delivery vehicle" above. The present disclosure further provides the bacterial delivery vehicles as defined in the section "Bacterial delivery vehicle" above, for use in a method for reducing the amount of virulent and/or antibiotic resistant bacteria in a bacterial population, in particular in the treatment of a bacterial infection typically due to virulent and/or antibiotic resistant bacteria. Another object of the disclosure provides the use of the bacterial delivery vehicle as defined in the section "Bacterial delivery vehicle" above for the manufacture of a medicament intended for reducing the amount of virulent and/or antibiotic resistant bacteria in a bacterial population, in particular for the treatment of bacterial infection typically due to virulent and/or antibiotic resistant bacteria.

The present disclosure also relates to a non-therapeutic use of the bacterial delivery particles. For instance, the non-therapeutic use can be a cosmetic use or a use for improving the well-being of a subject, in particular a subject who does not suffer from a disease. Accordingly, the present disclosure also relates to a cosmetic composition or a non-therapeutic composition comprising the bacterial delivery particles of the disclosure.

The present invention further concerns the following embodiments:

1. A chimeric receptor binding protein (RBP) resistant to proteolytic digestion, wherein said RBP comprises a portion of a receptor binding protein derived from a bacteriophage fused through a designed linker region consisting of 1 to 70 amino acids, to a portion of a receptor binding protein derived from a different bacteriophage, wherein said linker region is designed to be resistant to proteolytic digestion.

2. The chimeric RBP according to embodiment 1, wherein the designed linker region consists of 1 to 30 amino acids.

3. The chimeric RBP according to embodiment 1 or 2, wherein said chimeric RBP is resistant to proteolytic digestion by pancreatin, and said linker region is designed to be resistant to proteolytic digestion by pancreatin.

4. The chimeric RBP according to any one of embodiments 1 to 3, wherein said RBP is a side tail fiber (STF) protein, an L-shape fiber, a long tail fiber or a tailspike.

5. The chimeric RBP according to embodiment 4, wherein said chimeric RBP comprises a portion of a STF protein derived from a lambdoid bacteriophage fused through a designed linker region consisting of 1 to 70 amino acids or of 1 to 30 amino acids, to a portion of a RBP protein derived from a different bacteriophage.

6. The chimeric RBP according to embodiment 4 or 5, wherein said chimeric RBP comprises an N-terminal region of a STF protein derived from a lambdoid bacteriophage, fused through a designed linker region consisting of 1 to 70 amino acids or 1 to 30 amino acids, to a C-terminal region of a RBP protein derived from a different bacteriophage, wherein said N-terminal region and C-terminal region are fused within a site of the N-terminal STF region, called insertion site, having at least 80% identity with a site selected from the group consisting of amino acids SAGDAS (SEQ ID NO: 1), ADAKKS (SEQ ID NO: 2), MDETNR (SEQ ID NO: 3), SASAAA (SEQ ID NO: 4), and GAGENS (SEQ ID NO: 5).

7. The chimeric RBP according to embodiment 6, wherein said insertion site has at least 80% identity with sequence GAGENS (SEQ ID NO: 5).

8. The chimeric RBP according to embodiment 6 or 7, wherein said designed linker region is at the C-terminal end of the insertion site.

9. The chimeric RBP according to any one of embodiments 6 to 8, wherein said designed linker region is part of the N-terminal region or of the C-terminal region of the chimeric RBP.

10. The chimeric RBP according to embodiment 9, wherein at least one amino acid of the designed linker region, corresponding to an amino acid of the wildtype domain sequence which is likely to be targeted by trypsin and/or chymotrypsin, is mutated compared to the wildtype domain sequence.

11. The chimeric RBP according to embodiment 10, wherein said designed linker region is part of the C-terminal region of the chimeric RBP and said at least one amino acid is located within the 15 amino acids following the insertion site.

12. The chimeric RBP according to embodiment 10 or 11, wherein said amino acid is selected from the group consisting of lysin (K), arginine (R), phenylalanine (F), tryptophan (W), tyrosine (Y) leucine (L) and methionine (M).

13. The chimeric RBP according to embodiment 9, wherein said N-terminal region or said C-terminal region comprises the sequence of the linker region, said sequence being identical to the corresponding sequence in the N-terminal region or C-terminal region of the RBP from which it is derived, and said sequence restoring resistance to proteolytic digestion to said chimeric RBP compared to a chimeric RBP only differing by the absence of said linker region.

14. The chimeric RBP according to any one of embodiments 6 to 8, wherein said engineered linker region comprises or consists of an heterologous amino acid sequence which is not derived from one of the RBP from which the N-terminal region and the C-terminal region of the chimeric RBP are derived.

15. The chimeric RBP according to embodiment 13 or 14, wherein said designed linker region comprises a helix or helical bundle.

16. The chimeric RBP according to any one of embodiments 13 to 15, wherein said designed linker region consists of 10 to 20 amino acids.

17. The chimeric RBP according to any one of embodiments 13 to 16, wherein said designed linker region comprises or consists of an amino acid sequence GSATDVMIQL (SEQ ID NO: 6) or GSATDVMIQLA (SEQ ID NO: 7).

18. The chimeric RBP according to any one of embodiments 13 to 15, wherein said designed linker region consists of 50 to 65 amino acids.

19. The chimeric RBP according to embodiment 18, wherein said designed linker region comprises or consists of the amino acid sequence SEQ ID NO: 34 or SEQ ID NO: 36.

20. The chimeric RBP according to embodiment 17 or 19, wherein said sequence is located directly after the insertion site.

21. The chimeric RBP according to any one of embodiments 6 to 20, wherein the N-terminal region of said STF protein derived from said lambdoid bacteriophage corresponds to amino acids 1 to 528 of the lambda STF protein of sequence SEQ ID NO: 8.

22. The chimeric RBP according to any one of embodiments 6 to 21, wherein the C-terminal region of said STF protein derived from said different bacteriophage corresponds to amino acids 208 to 875 of the STF protein of sequence SEQ ID NO: 16 or to amino acids 218 to 875 of the STF protein of sequence SEQ ID NO: 16.

23. The chimeric RBP according to embodiment 22, wherein said chimeric RBP comprises or consists of the sequence SEQ ID NO: 9, SEQ ID NO: 10 or SEQ ID NO: 11.

24. The chimeric RBP according to any one of embodiments 6 to 21, wherein the C-terminal region of said STF protein derived from said different bacteriophage corresponds to amino acids 28 to 632 of the STF protein of sequence SEQ ID NO: 12 or amino acids 62 to 632 of the STF protein of sequence SEQ ID NO: 12.

25. The chimeric RBP according to embodiment 24, wherein said chimeric RBP comprises or consists of the sequence SEQ ID NO: 13, SEQ ID NO: 14, SEQ ID NO: 38 or SEQ ID NO: 40.

26. A nucleic acid encoding a chimeric RBP according to any one of embodiments 1 to 25.

27. A vector comprising the nucleic acid encoding a chimeric RBP according to embodiment 26.

28. A lambdoid bacterial delivery vehicle for use in in vivo delivery of a DNA payload of interest into a targeted bacterial cell, wherein said lambdoid delivery vehicle comprises the chimeric RBP according to any one of embodiments 1 to 25.

29. The lambdoid delivery vehicle according to embodiment 28, wherein said chimeric RBP is a chimeric STF protein as defined in any one of embodiments 4 to 25.

30. The lambdoid delivery vehicle according to embodiment 29, wherein said chimeric STF protein is a functional STF protein.

31. The lambdoid delivery vehicle according to embodiment 30, further comprising a functional lambdoid bacteriophage gpJ protein and/or a functional lambdoid bacteriophage gpH protein.

32. The bacterial delivery vehicle according to any one of embodiments 29 to 31, wherein the chimeric STF protein has enzyme activity such as depolymerase activity and the bacterial cell population of interest comprises encapsulated bacteria.

33. The bacterial delivery vehicle according to any one of embodiments 29 to 32, said bacterial delivery vehicle comprising a chimeric STF of sequence SEQ ID NO: 11 and a chimeric gpJ variant of sequence SEQ ID NO: 27.

34. The bacterial delivery vehicle according to any one of embodiments 31 to 32, wherein one or more of the chimeric STF protein, the gpJ protein and/or the gpH protein are engineered to increase the efficiency of transfer of the DNA payload into a targeted bacterial cell population.

35. The bacterial delivery vehicle according to any one of embodiments 28 to 34, wherein the bacterial cell population is selected from the group consisting of *E. coli* bacteria, *K. pneumoniae* and other species of interest.

36. The bacterial delivery vehicle according to any one of embodiments 28 to 35, wherein said bacterial delivery vehicle comprises said DNA payload of interest.

37. The bacterial delivery vehicle according to any one of embodiments 28 to 36, wherein the DNA payload comprises a nucleic acid of interest selected from the group consisting of Cas nuclease gene, a Cas9 nuclease gene, a guide RNA, a CRISPR locus, a toxin gene, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor, and a gene expressing a virulence protein or a virulence factor, and or any of their combination.

38. The bacterial delivery vehicle according to embodiment 37, wherein the nuclease targets cleavage of a host bacterial cell chromosome or a host bacterial cell plasmid.

39. The bacterial delivery vehicle according to embodiment 38, wherein the cleavage occurs in an antibiotic resistant gene.

40. The bacterial delivery vehicle according to any one of embodiments 28 to 39, wherein said payload comprises or consists of the nucleic acid sequence SEQ ID NO: 33 or of the nucleic acid sequence SEQ ID NO: 42.

41. The bacterial delivery vehicle according to embodiment 37, wherein the nucleic acid of interest encodes a therapeutic protein.

42. The bacterial delivery vehicle according to embodiment 37, wherein the nucleic acid of interest encodes an antisense nucleic acid molecule.

43. A pharmaceutical or veterinary composition comprising the bacterial delivery vehicle according to any one of embodiments 28 to 42 and a pharmaceutically acceptable carrier.

44. The pharmaceutical or veterinary composition according to embodiment 43, wherein said composition is for oral administration.

45. A method for in vivo delivery of a DNA payload of interest into a subject comprising, administering to said subject the pharmaceutical or veterinary composition of embodiment 43 or 44.

46. A method for treating a disease or disorder caused by bacteria comprising administering to a subject having a disease or disorder in need of treatment the pharmaceutical or veterinary composition of embodiment 43 or 44.

47. The method according to embodiment 46, wherein said disease or disorder is a bacterial infection, a metabolic disorder or a pathology involving bacteria of the human microbiome.

48. The method according to embodiment 46 or 47, wherein said composition is administered orally.

49. The pharmaceutical or veterinary composition according to embodiment 43 or 44 for use in a method for treating a disease or disorder caused by bacteria.

50. The pharmaceutical or veterinary composition for its use according to embodiment 49, wherein said disease or disorder is a bacterial infection, a metabolic disorder or a pathology involving bacteria of the human microbiome.

51. The pharmaceutical or veterinary composition for its use according to embodiment 49 or 50, wherein said composition is administered orally.

52. A method for reducing the amount of virulent and/or antibiotic resistant bacteria in a bacterial population comprising contacting the bacterial population with the bacterial delivery vehicle of any one of embodiments 28 to 42.

53. The bacterial delivery vehicle according to any one of embodiments 28 to 42 for use in a method for reducing the amount of virulent and/or antibiotic resistant bacteria in a bacterial population.

54. A production cell line expressing the chimeric RBP according to any one of embodiments 1 to 25.

55. The production cell line according to embodiment 54, comprising the nucleic acid according to embodiment 26 and/or the vector according to embodiment 27.

56. The production cell line according to embodiment 54 or 55, producing the bacterial delivery vehicle according to any one of embodiments 28 to 42.

57. The production cell line according to any one of embodiments 54 to 56, comprising a helper phage which is a lambda prophage wherein (i) the nucleic acid sequence encoding a wild-type STF protein has been replaced by a nucleic acid sequence encoding the chimeric RBP comprising or consisting of the sequence SEQ ID NO: 11, (ii) the nucleic acid sequence encoding a wild-type gpJ protein has been replaced by a nucleic acid sequence encoding the chimeric gpJ variant comprising or consisting of the sequence SEQ ID NO: 27, and (iii) the Cos site has been removed, and wherein optionally (iv) the helper prophage contains a mutation which prevents spontaneous cell lysis, such as the Sam7 mutation and (v) the helper prophage contains a thermosensitive version of the master cI repressor, such as the cI857 version.

Unless defined otherwise, all technical and scientific terms used herein have the same meaning as commonly understood by one of ordinary skill in the art to which this invention belongs.

All publications mentioned herein are incorporated herein by reference. It is understood that the present disclosure supersedes any disclosure of an incorporated publication to the extent there is a contradiction.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

The present invention will be further illustrated by the examples below.

| BRIEF DESCRIPTION OF THE SEQUENCES | |
|---|---|
| SEQ ID NO: | Description |
| 1 | Insertion site sequence SAGDAS |
| 2 | Insertion site sequence ADAKKS |
| 3 | Insertion site sequence MDETNR |
| 4 | Insertion site sequence SASAAA |
| 5 | Insertion site sequence GAGENS |
| 6 | GSATDVMIQL sequence |
| 7 | GSATDVMIQLA sequence |
| 8 | Lambda STF amino acid sequence |
| 9 | STF-V10-[FA] amino acid sequence |
| 10 | STF-V10-[AAH] amino acid sequence |
| 11 | STF-V10-[Helix] amino acid sequence |
| 12 | K5 amino acid sequence |
| 13 | K5 5.0 amino acid sequence |

-continued

BRIEF DESCRIPTION OF THE SEQUENCES

SEQ ID NO: Description

| | |
|---|---|
| 14 | K5 5.1 amino acid sequence |
| 15 | STF-V10 amino acid sequence |
| 16 | V10 amino acid sequence |
| 17 | STF-V10-[FA] DNA sequence |
| 18 | STF-V10-[AAH] DNA sequence |
| 19 | STF-V10-[Helix] DNA sequence |
| 20 | K5 5.0 DNA sequence |
| 21 | K5 5.1 DNA sequence |
| 22 | Lambda gpJ amino acid sequence |
| 23 | H591 amino acid sequence |
| 24 | H591 DNA sequence |
| 25 | Z2145 amino acid sequence |
| 26 | Z2145 DNA sequence |
| 27 | 1A2 amino acid sequence |
| 28 | 1A2 DNA sequence |
| 29 | A8 amino acid sequence |
| 30 | A8 DNA sequence |
| 31 | gpH IAI amino acid sequence |
| 32 | Lambda-K5 amino acid sequence |
| 33 | Payload p1392 plasmid sequence |
| 34 | helical bundle 1 and linker from STF protein from *Escherichia* phage ZG49 amino acid sequence |
| 35 | recoded helical bundle 1 and linker from STF protein from *Escherichia* phage ZG49 DNA sequence |
| 36 | helical bundle 2 and linker from STF protein from *Escherichia* phage ZG49 amino acid sequence |
| 37 | recoded helical bundle 2 and linker from STF protein from *Escherichia* phage ZG49 DNA sequence |
| 38 | K5 9.0 amino acid sequence |
| 39 | K5 9.0 DNA sequence |
| 40 | K5 9.1 amino acid sequence |
| 41 | K5 9.1 DNA sequence |
| 42 | payload p1900 plasmid sequence |
| 43 | candidate STF protein from *Escherichia* phage ZG49 amino acid sequence |
| 44 | candidate STF protein from *Escherichia* phage ZG49 DNA sequence |
| 45 | payload p775 plasmid sequence |
| 46 | primase ori from the PICI of the *Escherichia coli* strain CFT073 |
| 47 | restriction site |
| 48 | Primase ori deltaGAAABCC |
| 49 | Primase ori devoid of restriction sites |
| 50 | PICI primase-helicase amino acid sequence |
| 51 | PICI primase-helicase DNA sequence |

EXAMPLES

Example 1

It has been shown that a chimera between lambda STF and V10 STF (originating from a prophage found in O157 strains), said chimera being of sequence SEQ ID NO: 15, is able to target O157 strains with high efficiency in vitro by recognizing and degrading the O157 antigen group IV capsule. However, initial in vivo experiments showed that lambda packaged phagemids containing the V10 chimeric STF did not deliver with high efficiency into O157 strains colonizing the mouse gut. Efficiencies of delivery in this mouse model were, on average, 20% and the delivery was not improved by increasing the dosage given to the mouse (MOI).

One possible reason for this observation was that the chimeric lambda particles containing V10 fusions were stable in in vitro conditions, where delivery and killing experiments were done in the presence of known reagents (for instance, LB), but lost part of their activity once they passed through the mouse gut.

It had been observed that wild-type lambda particles are able to pass and replicate in the gut suggesting that some part of the engineering process to generate the lambda-V10 fusion had rendered it at least less stable and partly susceptible to degradation in in vivo conditions. Apart from the lambda STF-V10 fusion, the lambda particles used in these experiments have also been engineered at the gpJ level to modify its primary receptor, and contain the 1A2 gpJ variant (and are thus called herein 1A2-V10 particles). Thus, it was possible that either the 1A2 gpJ variant and/or the STF-V10 fusion were the sources of reduced stability in in vivo conditions.

In vitro assays were set up to differentiate between 1A2 gpJ activity and STF-V10 activity based on the fact that, for some strains, the presence of a functional STF is dispensable for injection, as is the case for the MG1655 K-12 strain. Since the 1A2 gpJ variant recognizes the OmpC receptor of O157 strains, but not that of MG1655, an MG1655 variant was engineered in which the OmpC receptor was replaced to encode that of the O157 variant. This strain was called MG1656-OmpCO157. On the other hand, efficient delivery in O157 strains is completely dependent on the presence of a functional STF containing V10. Hence, by exposing the 1A2-V10 packaged phagemids to different conditions and evaluating the gpJ versus STF-V10 activity in vitro, it was possible to determine which part of the packaged phagemid was unstable.

The 1A2-V10 packaged phagemids were then exposed to simulated intestinal fluid (SIF) in the presence or absence of pancreatin (which contains the digestive enzymes trypsin and chymotrypsin) and bile salts. Specifically, packaged phagemids were produced, diluted 1:100 in the buffer of choice and incubated at 37° C. for 3 hours. After that, the packaged phagemids were directly titrated on MG1656-OmpCO157 and H10 (O157)-delta-stx strains. As a control, the wild-type lambda packaged phagemid produced with CYC3 strains was also exposed to the same conditions. H10-delta-stx is a variant of O157 strain for which the stx gene has been deleted. Briefly, the wild-type H10 strain was transduced with packaged lambda phagemids containing a lambda-V10 STF chimera and a packaged circuit encoding a Cpf1 nuclease programmed to target the stx2 gene. After transduction, survivor colonies were checked by PCR to verify the presence or absence of the stx gene and only colonies with stx gene deleted were kept.

As can be seen in FIG. 1, the wild-type lambda particle produced with CYC3 strains was stable under any conditions, as the titers remained the same across all experiments. However, for the 1A2-V10 variant, a constant gpJ activity (central bars in FIG. 1) was observed, which indicates that this gpJ variant was not degraded in the presence of pancreatin. Finally, the titers of the 1A2-V10 dropped by a factor of 2 log when titrated in H10-delta-stx (O157) strains only in the presence of pancreatin. Bile salts by themselves did not affect the activity of the packaged phagemids. These results clearly demonstrate that the STF-V10 chimera is at least partially degraded in the presence of pancreatin.

Figure 2:
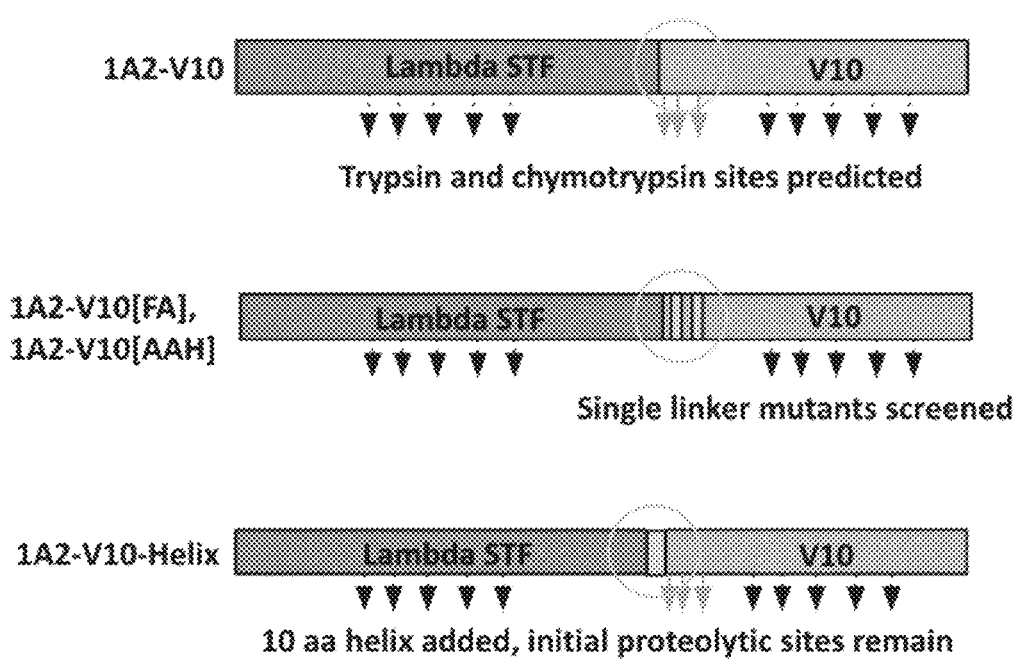
FIG. 2: Lambda STF-V10 engineered variants. Arrows depict predicted trypsin and chymotrypsin sites (not all sites shown for clarity reasons)
Figure 3:
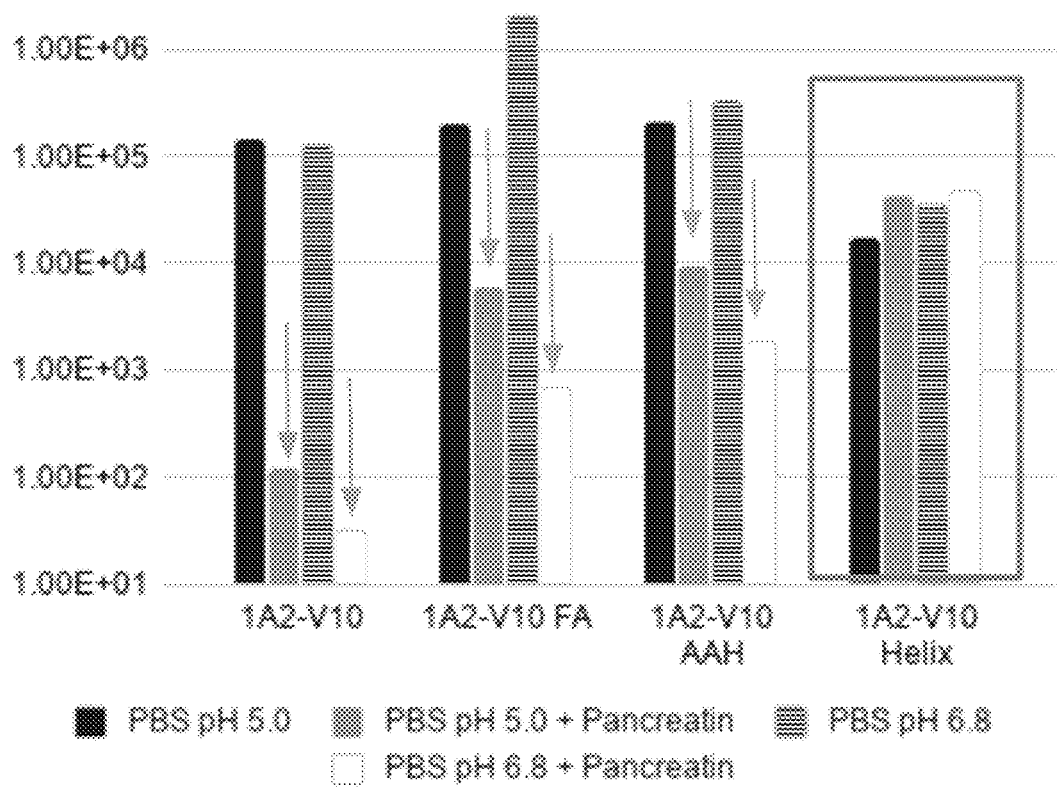
FIG. 3: Stability of lambda STF-V10 variants in different conditions. Left group of bars, original lambda STF-V10 variant (SEQ ID NO: 15); second group of bars, STF-V10-[FA] variant (SEQ ID NO: 9); third group of bars, STF-V10-[AAH] variant (SEQ ID NO: 10); fourth group of bars, STF-V10-Helix variant (SEQ ID NO: 11). The Y axis shows CFU count per µL.
Figure 4:
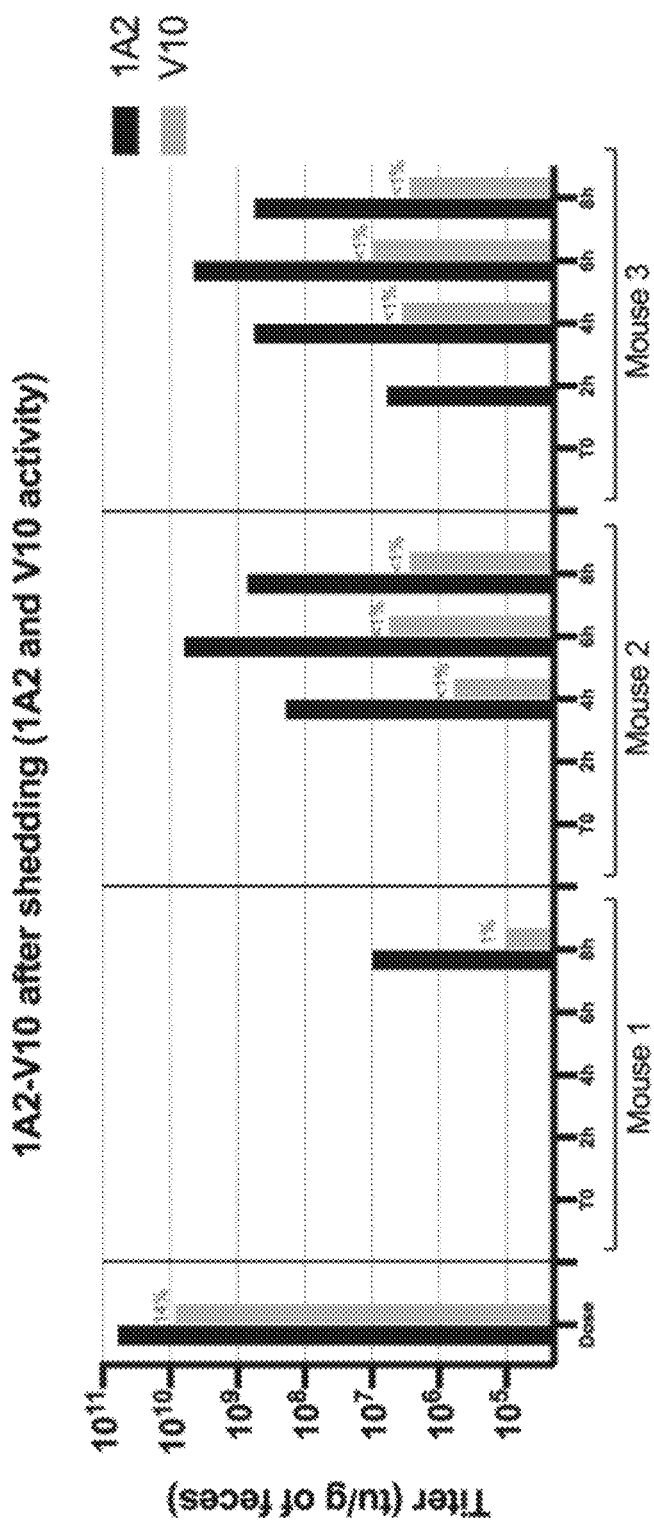
FIG. 4: Shedding of lambda packaged phagemids 1A2 gpJ-STF-V10 (1A2-V10) over time in un-colonized mice (n=3). The dose bars on the left correspond to the titration after production of the packaged phagemids. "black bars": 1A2 activity; "grey bars": V10 activity.
Figure 5:
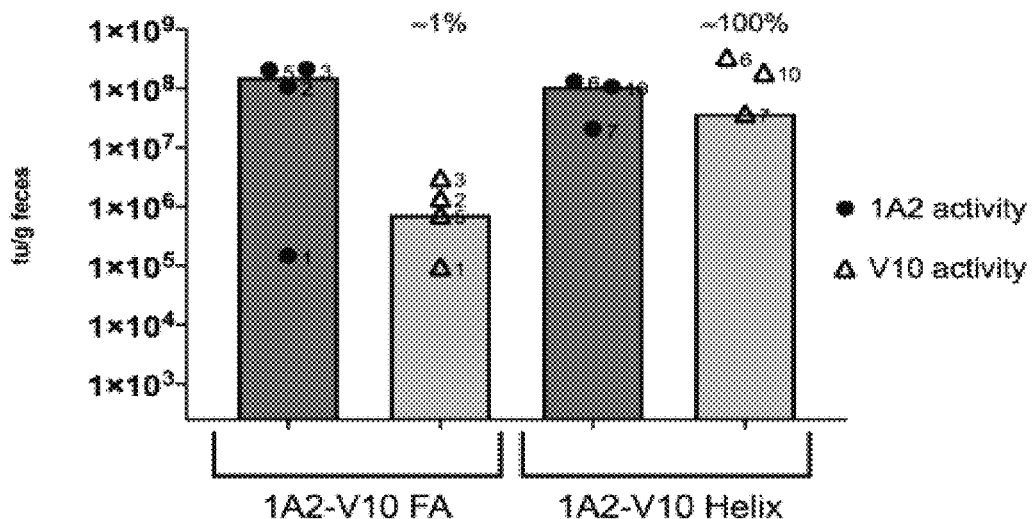
FIG. 5: Shedding of lambda packaged phagemids 1A2-STF-V10-[FA] (n=4) and 1A2-STF-V10-[Helix] (n=3) at t=6 h after administration in un-colonized mice. "black circles", 1A2 activity; "white triangle", V10 activity.
Figure 6:
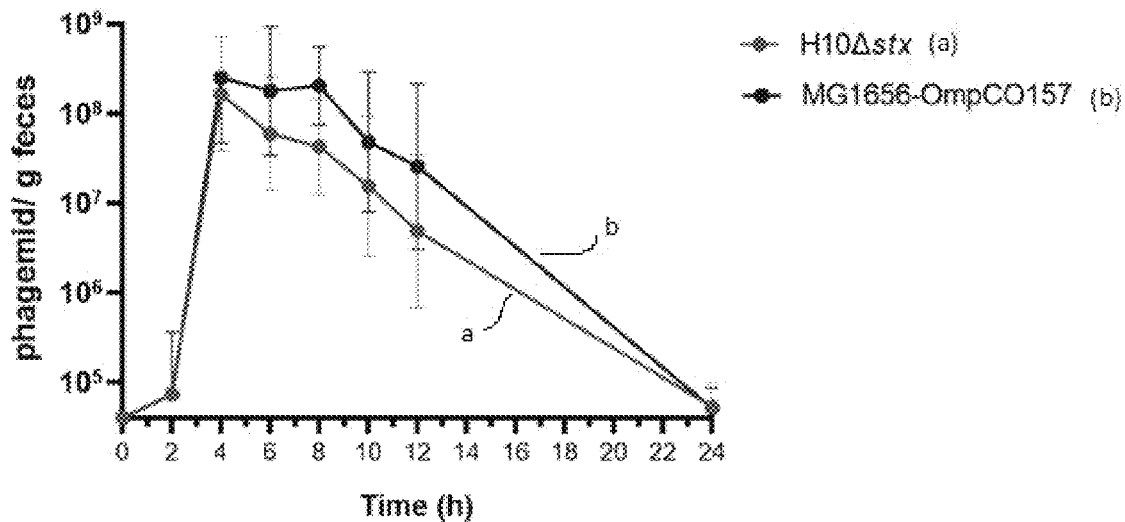
FIG. 6. Shedding of lambda packaged phagemids 1A2-STF-V10-[Helix] overtime (n=5 mice) following a single oral administration of these packaged phagemids. Legend: H10Δstx=V10 activity; MG1656-OmpCO157=1A2 activity.
Figure 7:
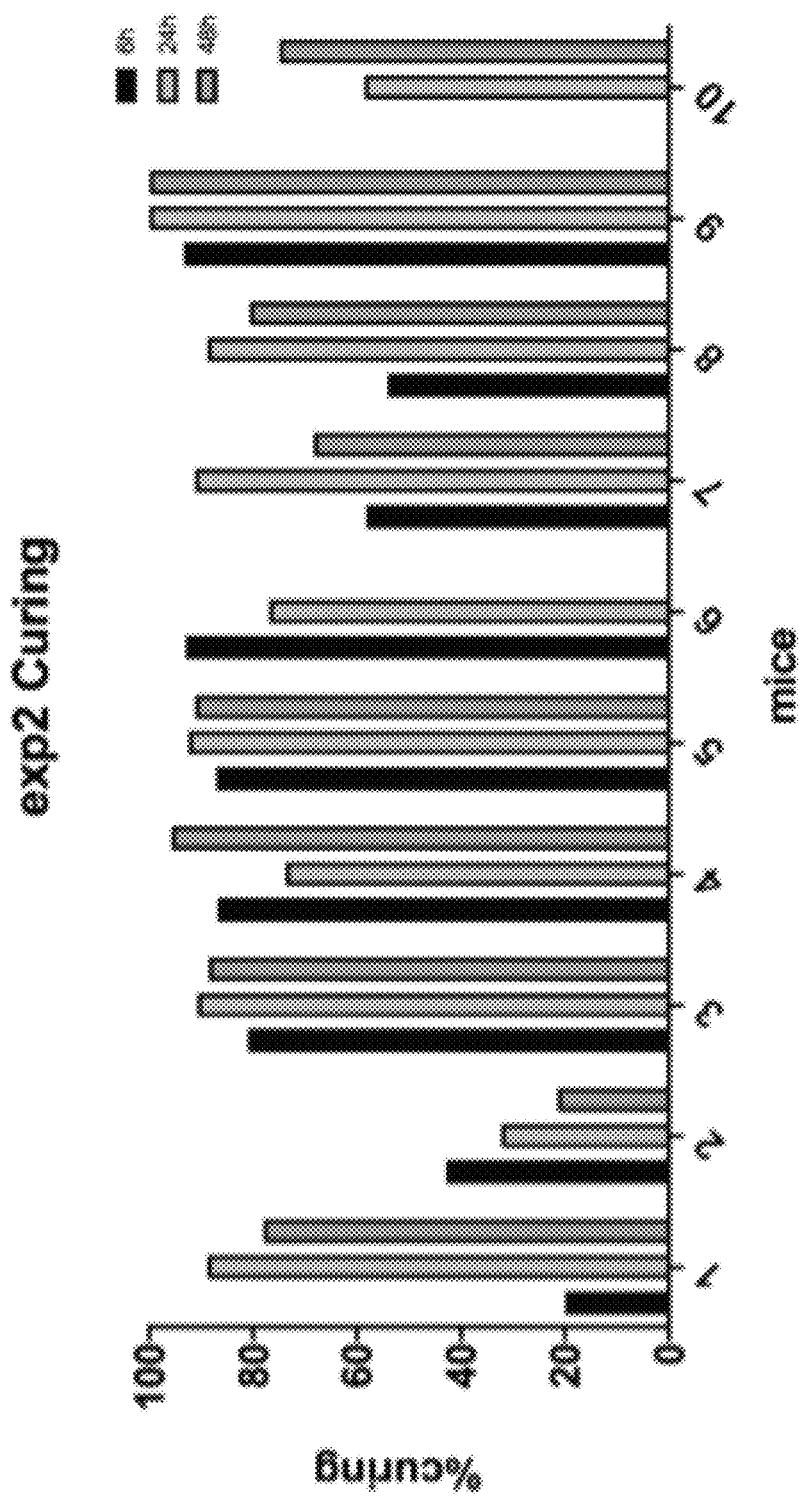
FIG. 7: Percentage of pRFP curing from H10Δstx/pRFP in vivo (n=10 mice) at three different time points after the first dose of the cocktail (1A2-STF-V10-[FA] and 1A2-STF-V10-[Helix]): t=6 h, black; t=24 h, light grey; t=48 h, dark grey.

It was hypothesized that the source of reduced stability was not in the V10 moiety itself, but in the way the fusion with the lambda STF was generated. Further, it was hypothesized that although no linker amino acids were inserted in the initial lambda STF-V10 chimera, the context of the fusion was not natural, and hence, had not been selected for stability in the presence of proteolytic enzymes. To test this hypothesis, two types of lambda STF-V10 chimeras were generated: the first type contains point mutations in phenylalanine (F) and lysine (K) residues present in the fusion point between lambda STF and V10 STF (FIG. 2); for the second type, a more detailed structural analysis was performed. Structural homology analyses with the original V10 fusion showed a crystallized STF with high identity to the V10 moiety (PDB ID: 5W6S): this STF contains a short helix at its N-terminus which has a homolog in V10, but that was not included in the original lambda STF-V10 chimera. The helix forms a very tight bundle that "fastens" the domain right after it in the crystal structure. Based on the delivery efficiency results that were obtained with the original lambda STF-V10 version, this helix may not be important for activity but it may be important for stability since it may confer a proper folding where exposed trypsin- and chymotrypsin-accessible residues are buried (FIG. 2).

Accordingly, three lambda-STF-V10 fusion variants were constructed: V10-[FA] (SEQ ID NO: 9), where a lysine (K) residue was exchanged by an alanine (A); V10-[AAH] (SEQ ID NO: 10), where an FKF tripeptide was exchanged to AAH tripeptide; and V10-Helix (SEQ ID NO: 11), where the short 10-amino acid helix bundle GSATDVMIQLA (SEQ ID NO: 7) was included as part of the chimeric protein just after the insertion site. The insertion site with the lambda STF, GAGENS (SEQ ID NO: 5), was not changed for any of the variants.

The three variants were then exposed to buffer at different pH values (5.0 and 6.8) in the presence or absence of pancreatin as detailed for the original lambda STF-V10 fusion above. As can be seen in FIG. 3, all variants showed some degree of resistance to pancreatin treatment: the V10-[FA] and V10-[AAH] variants showed between 1 and 1.5 log higher particle levels than the original V10 counterpart, although the stability was not complete and was dependent on pH. However, the V10-Helix variant showed an apparent complete resistance to digestive proteases at any pH tested. Taken together, the results showed that one can engineer lambda STF-V10 variants that are resistant to digestive proteases by only engineering the linker region, and that are good candidates for in vivo use, with V10-Helix showing highly positive results in vitro.

In vivo studies were next conducted. It was difficult to deliver O157 strains in vivo at a decent efficiency (max 40%, but typically under 20%) and interestingly, the delivery was not improved by increasing the MOI administered to the mouse. However, delivery was observed with the same vector while using a strain deleted for the O157 antigen (ΔwaaJ mutants). Based on this result, it was possible that the V10 activity somehow may not survive the transit through the GIT.

In vivo assays were conducted to measure the kinetics of shedding of packaged phagemids with 1A2 gpJ and chimeric lambda STF-V10 after oral administration to streptomycin-treated, uncolonized BALB/c mice as well as the residual V10 activity. The specific V10 activity was evaluated by comparing transduction efficiencies on H10Δstx, where 1A2 and V10 are both needed and MG-ompC_O157 where only 1A2 is required. Packaged phagemids were produced at high titer and given to 3 mice in sucrose-bicarbonate buffer to reduce the stomach acidity and to help packaged phagemids to reach the intestine. Stool samples were collected at T0, T2 h, T4 h, T6 h and T8 h, and resuspended in PBS. After centrifugation, supernatants containing shed packaged phagemids were used in transduction assays against H10Δstx and MG-ompC_O157.

Interestingly, as can be seen in FIG. 4, the initial dose of packaged phagemid contained approximately 10% of the particles with V10 activity. Most of the 1A2 activity could be recovered between 6 to 8 hours after oral gavage, which indicates that this gpJ variant is not degraded after transit through the entire Gastrointestinal Tract (GIT). However, the estimated titers measuring the V10 activity were very low. Less than 1% of the recovered packaged phagemids kept their V10 functionality. This result indicates that at least 90% of the packaged phagemid with 1A2 gpJ and chimeric lambda STF-V10 lose their V10 activity in the GIT. The presence of numerous proteolytic enzymes (trypsin and chymotrypsin) secreted by the pancreas in the gut may be responsible for this degradation. This experiment finally demonstrates that 1A2-V10 can survive through the GI tract but loses an important part of its V1O activity which would explain why one cannot deliver in O157 strains at high efficiency.

Following on from this experiment and the result of in vitro stability testing of 3 new lambda-STF-V10 fusion variants, 2 variants that seemed to better resist the digestive proteases were used: lambda-STF-V10-[FA] and lambda-STF-V10-[Helix], disclosed above. Indeed, in vitro experiments have shown that these packaged phagemids (also called eligobiotics or EB) seemed able to resist in pancreatin-containing medium at least 1 h without losing their capacity to deliver into strains where V10 activity is required. This was especially true for the lambda-STF-V10-[Helix] variant. Then, in the exact same conditions as with the original 1A2-V10, the inventors assessed the residual activity of V10 after passage through the entire GI tract of uncolonized BALB/c mice.

As can be seen on FIG. 5, V10 activity of the variant 1A2-V10-[FA] was approximately at 1% after passage through the gut. As opposed to this observation, the new 1A2-V10-[Helix] showed a V10 activity approximately similar to the total activity of this packaged phagemid after passage through the GIT. These data indicate that 1A2-V10-[Helix] could perform optimally in vivo due to the high stability of its V10 activity (as opposed to the original version of 1A2-V10). To further confirm this stability, a simplified pharmacokinetics study was conducted in mice, where the shedding of the 1A2-V10-[Helix] over time was observed, following oral gavage of uncolonized BALB/c mice with a single dose of this packaged phagemid (administered as a 1:1 mixture with a sucrose/bicarbonate buffer).

As shown in FIG. 6, the STF activity (required to enter into H10 but not into MG1656) was just as stable over time as the Tip/overall capside functionality, as indicated by the identical pattern of shedding in the stool.

In another experiment, the in vivo delivery of the two new versions through plasmid curing was studied. The lambda-STF-V10-[Helix] and lambda-STF-V10-[FA] packaged phagemids were administered (2 doses, 6 h apart) targeting one part of the pRFP plasmid into mice colonized with H10Δstx/pRFP. Assuming that the payload is fully effective (100% cutting efficacy once expressed in the cell), the delivery can be calculated as the ratio of bacteria that lost the target plasmid over the total number of bacteria. Practically, the plasmid carries a kanamycin resistance gene; this makes it easier to check for colonies that kept versus lost the plasmid by simply patching streptomycin-resistant bacteria onto Kan plates.

As can be seen on FIG. 7, the curing efficiency was great with this mixture of packaged phagemids as most of the mice displayed a curing percentage of 80% or more (9 mice out of 10). Even though a great peak was observed after a single administration at t=6 h, the peak of curing efficacy was higher at 24 hours post-treatment likely reflecting the interest of a second administration, although this may be due to transit time variations between animals. Another interesting observation is that pRFP curing (i.e., sensitivity to kanamycin) was still visible at T24 h and T48 h whereas payload delivery (i.e., resistance to chloramphenicol) had strongly decreased. This indicates that the curing method could give a more stable view of delivery/nuclease efficacy over time. The results clearly demonstrate that the mixture of new packaged phagemids tested is much more capable of targeting strains of interest in the mouse intestine.

In order to optimize for phagemids, PCRs were conducted on several clones from the feces to discriminate between lambda-STF-V10-[Helix] and lambda-STF-V10-[FA]: out of 38 tested clones, 71% had received the payload from lambda-STF-V10-[Helix], indicating that this version was significantly efficient under in vivo conditions.

According to previous results, a decolonization experiment in vivo of the STEC strain H10WT with the new mutant 1A2-V10-[Helix] was conducted. In order to avoid colonization rebound immediately after treatment with packaged phagemids, it was decided to remove the antibiotic pressure (streptomycin) that was used to clear and maintain a niche for Enterobacteriaceae in the gut of mice with conventional specific-pathogen-free flora. Mice were treated with 5 doses of the packaged phagemid, 2 days apart, and compared with a control group treated with 5 doses of buffer (sucrose Bicarbonate).

Figure 8:
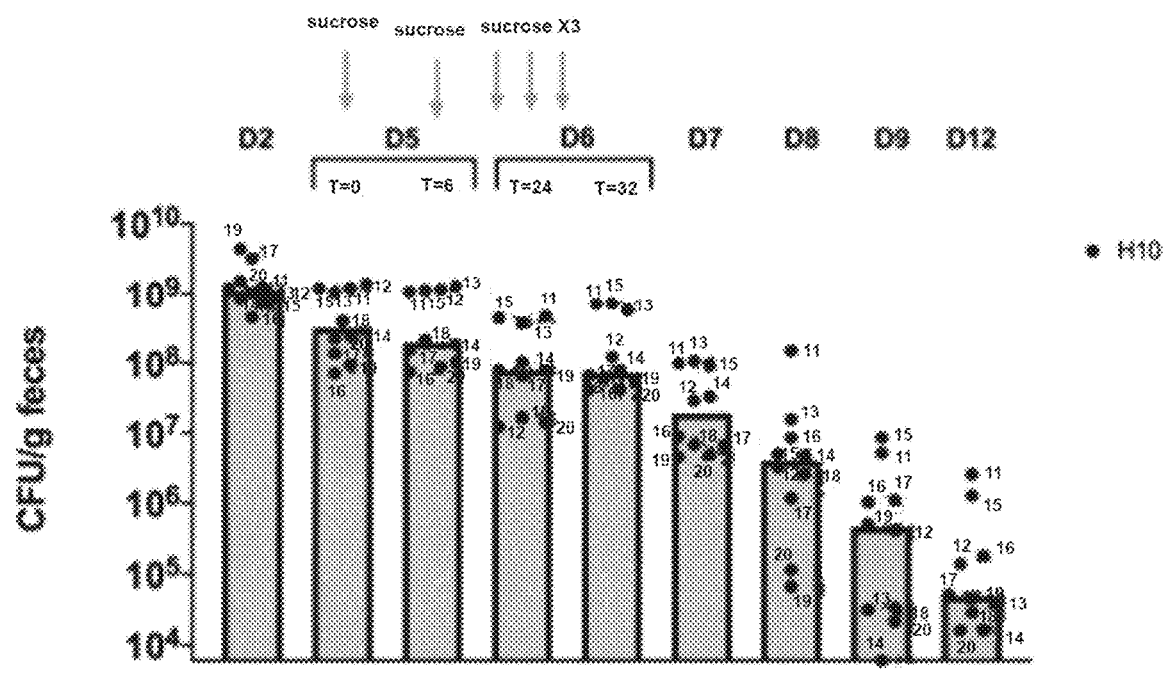
FIG. 8: Intestinal decolonization of the STEC strain H10WT overtime after 5 doses of packaged phagemids: colonization overtime of the control group gavaged with buffer (sucrose bicarbonate).
Figure 9:
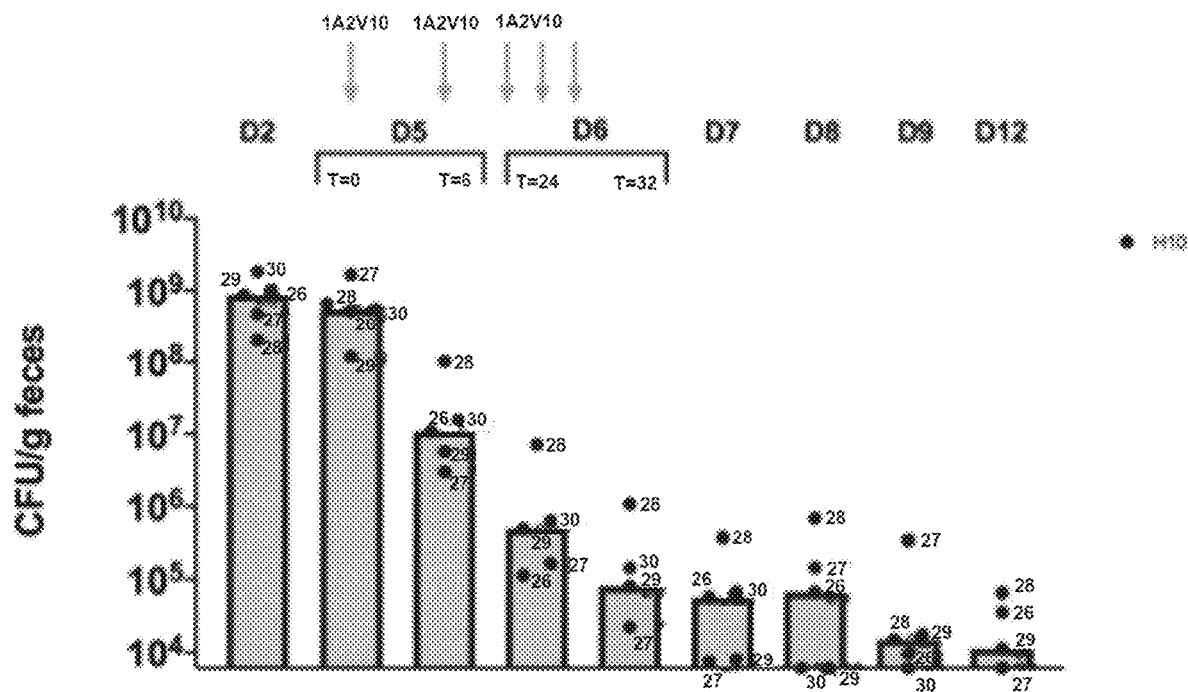
FIG. 9: Intestinal decolonization of the STEC strain H10WT overtime after 5 doses of packaged phagemids: colonization overtime of the test group treated with lambda packaged phagemids 1A2-STF-V10-[Helix].

As can be observed in FIGS. 8 and 9 on the control group, the colonization was not totally stable overtime. A slow decrease day after day can be seen from D6 to D12, However, the buffer did not seem to have an impact on the colonization level. In contrast, the colonization level of the STEC strains presented a great response to treatment. Indeed, a 2 logs reduction was observed after the first dose and more than 3 logs after the second for 4 mice out of 5. After the full 5-dose regimen (D7), a total of 4 logs of killing was obtained. Interestingly, no rebound of the colonization was observed after the last treatment.

To check for a potential resistant population to the packaged phagemids (natural or acquired) at the end of the experiment, surviving colonies on D7/D8 were patched and a transduction experiment was carried out. Interestingly, no resistance (entry or nuclease) was observed in this experiment. Taken together, the results described herein show an increased efficacy of variants, such as the variant 1A2-V10-[Helix] to decolonize STEC strains from the mouse gut.

Example 2

To test if the approach followed with the lambda-STF-V10 chimeric STF in Example 1 above was generalizable to other STF chimeras, a second set of experiments was performed. In this case, a functional chimeric STF was engineered between lambda STF and the K5 tailspike, called lambda-K5 (SEQ ID NO: 37) which has been described in the literature to infect K5-encapsulated *E. coli* strains and for which a crystal structure is available [11]. The same approach as for lambda-V10 chimera was followed, including the insertion point in the lambda STF protein (GAGENS (SEQ ID NO: 5)). In this case, the readout strain for K5 STF activity was LMR_503 and the readout for gpJ activity was MG1656-OmpCO157, as explained before. Packaged phagemids harboring the 1A2 gpJ (SEQ ID: 27) and the lambda-K5 STF were produced and titrated in both LMR_503 or MG1656-OmpCO157 after treatment with or without pancreatin at pH 6.8.

Figure 10:
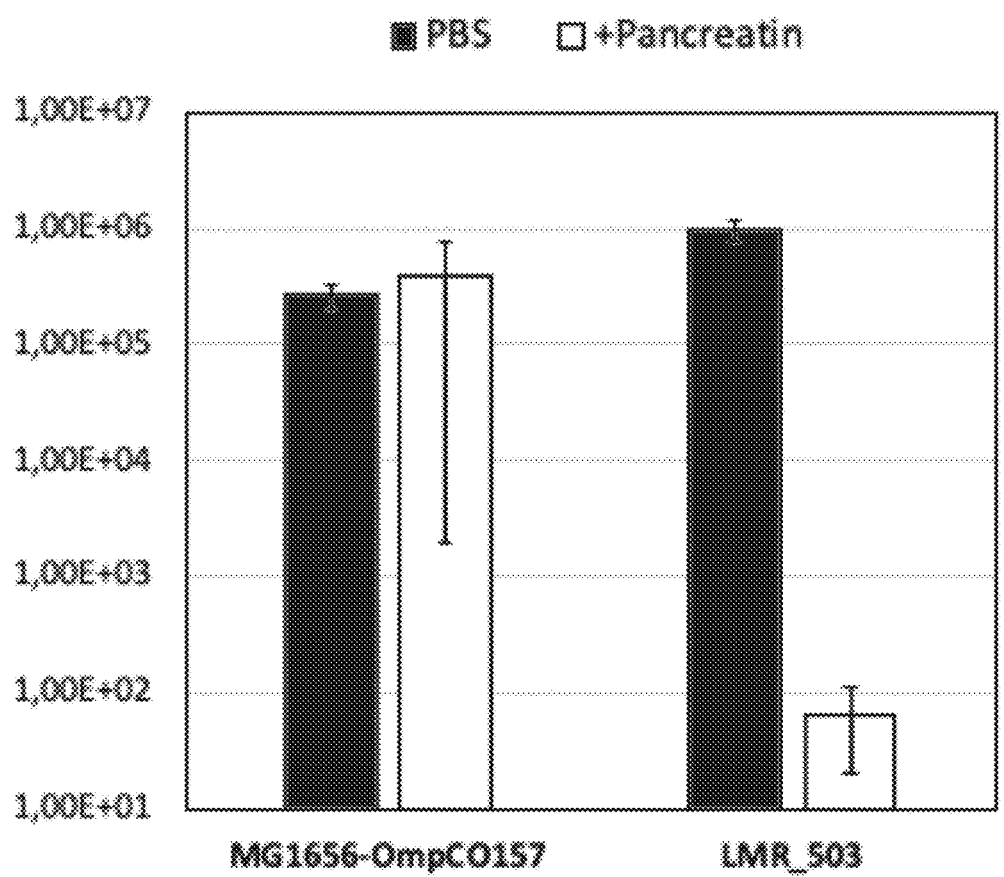
FIG. 10: Stability of lambda packaged phagemids 1A2-K5 in PBS. Black bars, PBS only; white bars, PBS plus pancreatin at pH 6.8. Left group of bars, activity in MG1656-OmpCO157; right group of bars, LMR_503 strain. Y axis shows particle titer per µL.

As can be seen in FIG. 10, although the lambda-K5 STF chimera was completely functional as measured by its ability to inject into the LMR_503 strain in PBS, it was not very stable in the presence of pancreatin, showing up to 4-log loss in the number of functional particles. This was similar to what was observed for the lambda-STF-V10 chimeric STF.

Next, the crystal structure was analyzed for the original K5 STF (PDB ID: 2X3H) and it was observed that it also contained a three helical bundle at its N-terminus. However, as opposed to the V10 structure, the helical bundle of K5 was capped by a turn, which in the lambda-K5 STF was directly at the fusion point. It was hypothesized that this non-natural insertion point may be the cause for the pancreatin reduced stability observed. To test this hypothesis, several lambda-K5 variants were constructed in which the fusion point was modified to contain different versions of the helical bundle.

Lambda K5 5.0 (SEQ ID NO: 13): contains part of the helical bundle from V10 (GSATDVMIQL (SEQ ID NO: 6)) fused to the K5 STF without its original helical bundle Lambda K5 5.1 (SEQ ID NO: 14): contains the helical bundle from V10 (GSATDVMIQLA (SED ID NO: 7)) fused to the K5 STF without its original bundle Packaged phagemids harboring the 1A2 gpJ and each of the K5 helix chimeras were produced and titrated on MG1656-OmpCO157 or LMR_503, as explained above.

Figure 11:
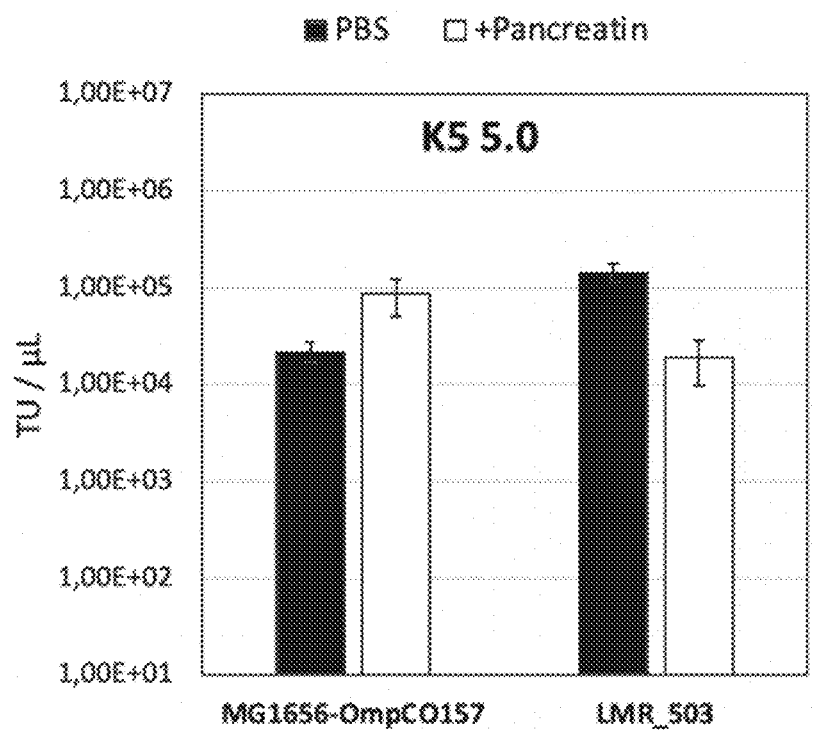
FIG. 11: Stability of lambda packaged phagemids 1A2-K5 5.0 Helix variant. Black bars, PBS only; white bars, PBS plus pancreatin at pH 6.8. Left group of bars, activity in MG1656-OmpCO157; right group of bars, LMR_503 strain. Y axis shows particle titer per µL.
Figure 12:
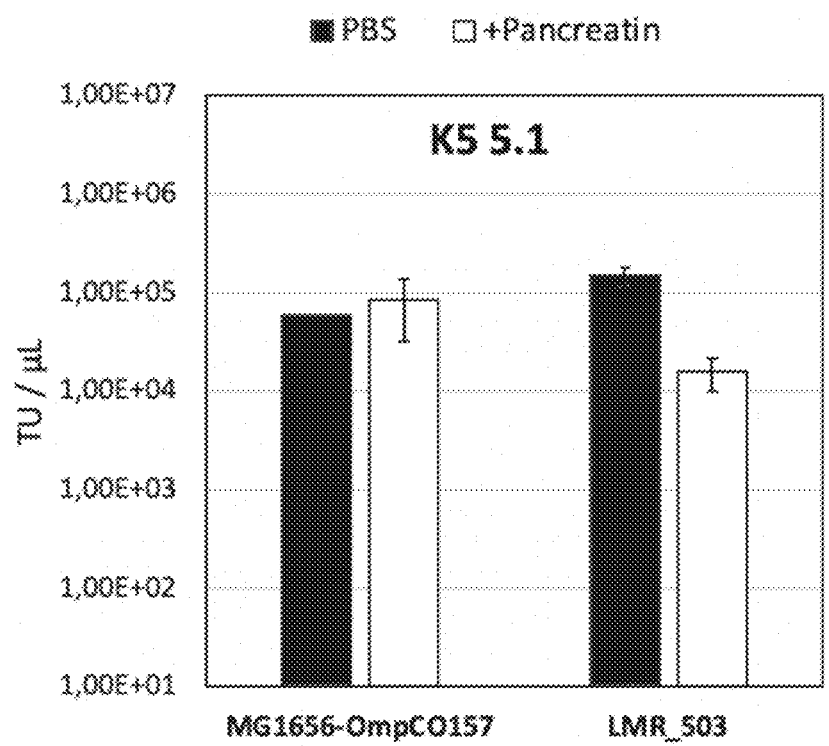
FIG. 12: Stability of lambda packaged phagemids 1A2-K5 5.1 Helix variant. Black bars, PBS only; white bars, PBS plus pancreatin at pH 6.8. Left group of bars, activity in MG1656-OmpCO157; right group of bars, LMR_503 strain. Y axis shows particle titer per µL.

FIGS. 11 and 12 show that the variants containing V10 helix versions K5 5.0 and K5 5.1 were mostly resistant to pancreatin treatment, as there was only 1 log loss compared to other STF fusions. It is also important to note that no functional differences in terms of titers were observed for any of the K5 variants constructed, which suggests a high degree of flexibility in terms of linkers to be used when creating non-homologous STF chimeras.

It has thus been shown that there was no correlation between function (injection in a given strain) and stability, and that the latter was dependent on the amino acid content of the fusion point. Additionally, the inventors showed that the sequence GSATDVMIQL(A) (SEQ ID NO: 6 and 7) originating from V10 Helix can be used as a pancreatin-resistant linker even in proteins that contain no homology to V10 STF (K5 STF) and protect the new chimera from degradation by pancreatin.

Example 3

Alternative pancreatin-resistant linkers conferring stability to a lambda STF-K5 chimera were designed from a STF protein having homology, at its C-terminal portion, with the C-terminal portion of the K5 STF starting at amino acid G62, namely candidate STF protein from *Escherichia* phage ZG49 (SEQ ID NO: 43 and SEQ ID NO: 44).

An analysis of this ZG49 STF protein using HHPRED software (Söding et al. (2005) *Nucleic Acids Res.* 33:W244-8) showed that it contains a helical bundle from amino acid 212 to amino acid 217. This helical bundle was included in the linkers designed by the inventors. More particularly, these linkers comprise the amino acid sequence located between amino acids G210 or D211 and amino acid E272 of the ZG49 phage STF protein. They are typically of sequence SEQ ID NO: 34 or SEQ ID NO: 36.

Two chimeric STFs were then built that contain the N-terminus of Lambda STF up to amino acid sequence GAGENS (SEQ ID NO: 5), followed by the linker designed above of sequence SEQ ID NO: 34 or SEQ ID NO: 36, and followed by the K5 moiety starting from position G62. The DNA sequences of the designed linkers were recoded for expression in *Escherichia coli* and were respectively of sequence SEQ ID NO: 35 and SEQ ID NO: 37. The two chimeric STFs were called K5 9.0 (for linker starting at position G210, SEQ ID NO: 38 and SEQ ID NO: 39) and K5 9.1 (for linker starting at position D211, SEQ ID NO: 40 and SEQ ID NO: 41) and only differ in the presence or absence, respectively, of a glycine at the start of the linker.

Figure 15:
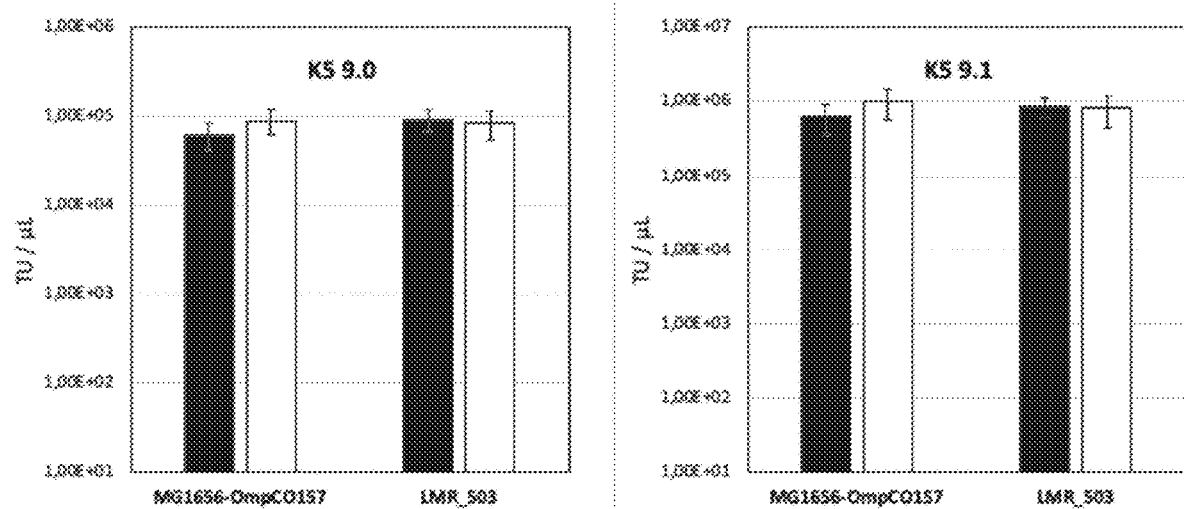
FIG. 15: Stability of lambda packaged phagemids 1A2-K5 in PBS. Black bars: PBS only; white bars: PBS plus pancreatin at pH 6.8. Left group of bars: activity in MG1656-OmpCO157; right group of bars: LMR_503 strain. Y axis shows particle titer per µL.

The production and pancreatin tests of both chimeric STFs were done as shown in Examples 1 and 2, and showed that the use of a linker designed from a STF protein having homology at this C-terminal portion with the K5 STF also provided pancreatin resistance to the chimeric STFs, and even improved the pancreatin resistance of the chimera as compared to K5 5.0 and K5 5.1 (FIG. 15).

Figure 16:
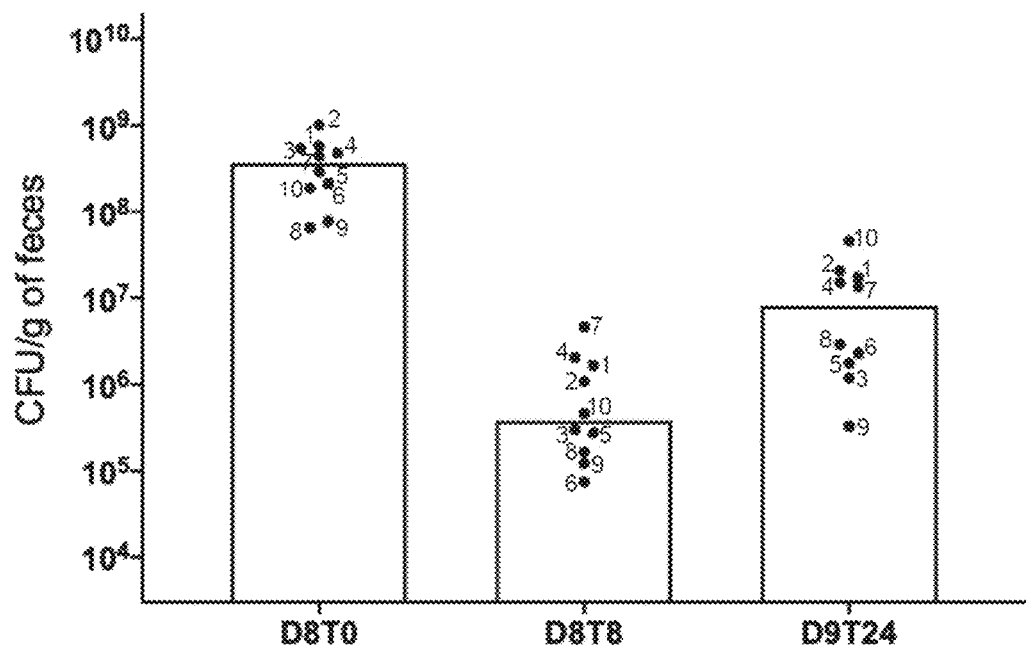
FIG. 16: Intestinal decolonization of the LMR_503 strain over time after 1 dose of Eligobiotic®. Colonization over time of the test group treated with Eligobiotic® harboring the A8 gpJ, the K5 9.1 STF and the plasmid p775. D8 represents the days after colonization of mice with the LMR_503 strain; T0, T8 represent the time 0 (pre-treatment levels) and 8 h after treatment with Eligobiotic®.

Finally, in vivo assays were performed to attempt decolonization of the LMR_503 strain, which should be targeted in the gut only if the chimeric STF is resistant to proteolytic enzymes, as has been shown in Example 2. To do this, 10 BALB/c mice were treated with streptomycin and colonized with strain LMR_503. An Eligobiotic® harboring the A8 gpJ and the chimeric K5 9.1 STF was produced carrying a plasmid (p775, SEQ ID NO: 45) encoding a nuclease and a guide targeting the ctx gene found in strain LMR_503. The decolonization assay was identical to that described for strain H10WT, following a single dose of Eligobiotic® (FIG. 16).

A 2.6 log median reduction in strain levels was observed after treatment with Eligobiotic®, which shows that the engineering of the K5 9.1 STF was successful, and that K5 9.1 STF was able to withstand proteolytic degradation in the mouse gut.

The inventors thus showed that other linkers could be designed to confer pancreatin resistance to chimeric RBP proteins. In particular, it is herein shown that the sequences SEQ ID NO: SEQ ID NO: 34 and SEQ ID NO:36 designed from the ZG49 phage STF protein can be used as a pancreatin-resistant linker to protect chimera comprising a lambda STF N-terminal portion and a K5 STF C-terminal portion from degradation by pancreatin.

Example 4

To evaluate the effect of DNA payload size on the number of payloads packaged in Eligobiotics®, 3 different payloads were used to produce Eligobiotics® as summarized in Table 1.

TABLE 1

Batches of Eligobiotics ® produced

| Eligobiotic code/batch number | Payload | Size (kb) |
| --- | --- | --- |
| eb512/EB003-DS-008 | p1085 | 12.125 |
| eb393/EB003-DS-009 | p779 | 12.428 |
| eb827/EB003-DS-011 | p1392 | 11.615 |

After fermentation, lysis (3 h incubation at 37° C. with 0.1% Triton X-100, 2000 U/L Benzonase) and clarification on a Zeta Plus Capsule (3M), the Eligobiotics® were purified by anion exchange chromatography on a Sartobind Q capsule (Sartorius). This initial purification was followed by a buffer exchange and concentration step by tangential flow filtration on a Pellicon 2 minicassette Biomax 300 kDa (Millipore). A final polishing step of size exclusion chromatography on Sepharose 6FF resin (GE Healthcare) was performed to yield the purified Eligobiotics®.

Analysis of the Eligobiotics®'s DNA content was performed by analytical ultracentrifugation in a Beckman Coulter Optima AUC using an AN50Ti rotor at 6 krpm. The sedimentation coefficients of different particles present in solution for each EB batch were extracted from sedimentation velocity data (acquired at 260 and 280 nm).

Figure 13:
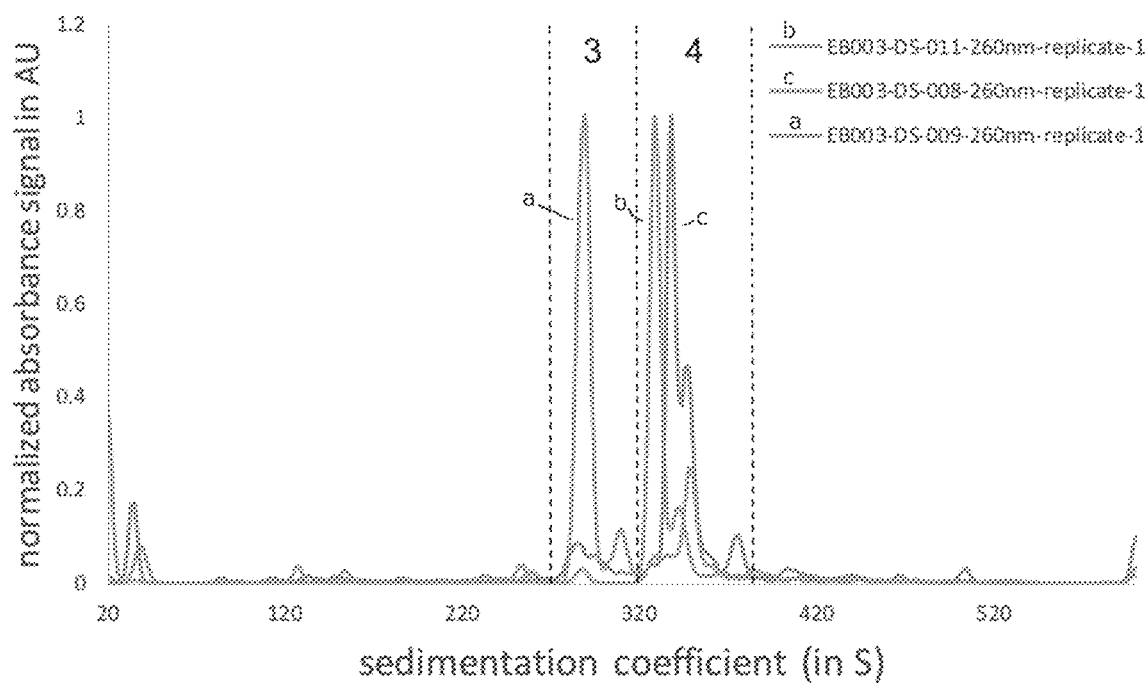
FIG. 13: Overlay of the sedimentation coefficient distribution data of the 3 Eligobiotics (EB) batches analyzed by svAUC in Example 3. The integration ranges for EB packaged with 3 or 4 copies of the payload are depicted by dotted lines.

Based on the molecular weight calculated from their sedimentation coefficient and their 260/280 nm ratios, the different populations of particles detected could be separated as Eligobiotics® containing either 3 copies (centered on 290 S) or 4 copies (centered on 330-340 S) of the payload (FIG. 13).

Figure 14:
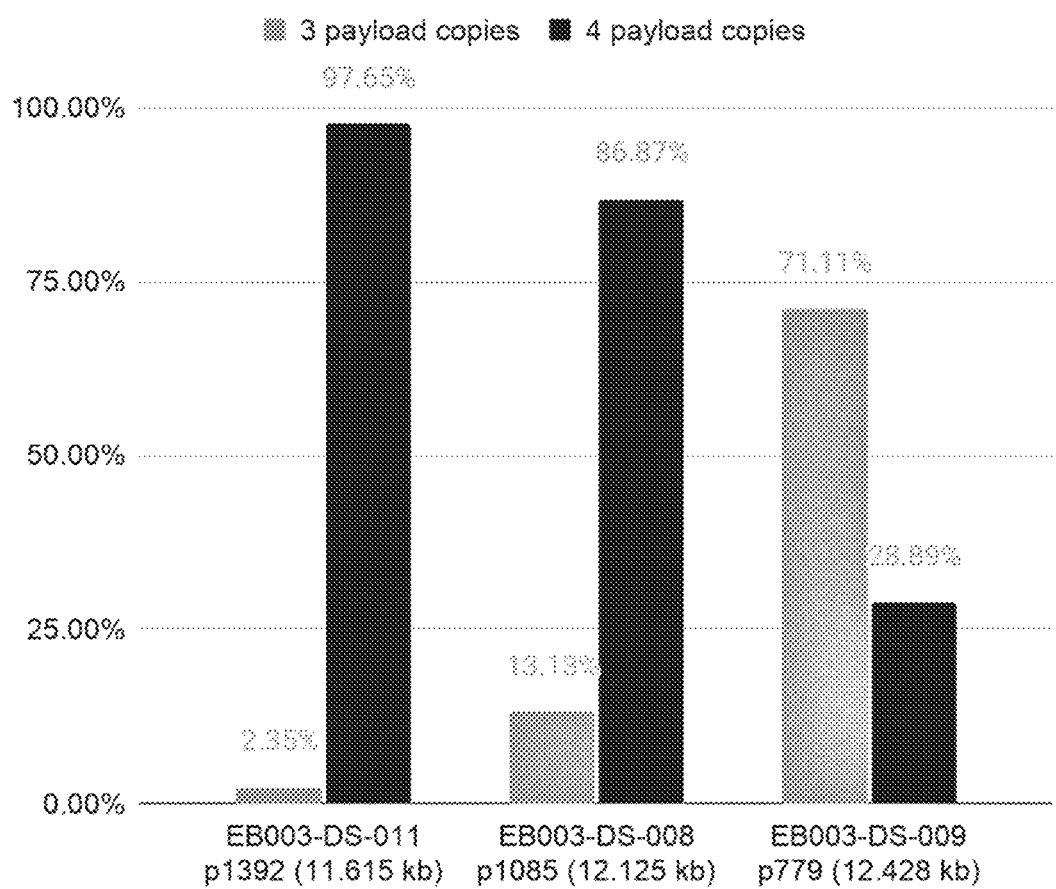
FIG. 14: Relative abundance of Eligobiotics® containing either 3 or 4 copies of the payload. Absorbance signals at 260 and 280 nm for each population defined in svAUC were integrated and used to calculate their relative abundance in each batch of Eligobiotics®.

Important differences were observed between Eligobiotics® depending on the size of the packaged payload. Although Eligobiotics® packaging the smaller p1392 (11.615 kb) yielded almost exclusively particles containing 4 copies of the payload, small increases (up to 800 bp) in the size of the payload correlate with a shift towards packaging 3 copies. As such, Eligobiotics® produced with p779 (12.428 kb) packaged preferentially 3 copies of the payload while approximately a third of the particles contained 4 copies (FIG. 14).

Thus, it appears that p1392 is close to an ideal size to package exclusively 4 copies of payload in Eligobiotics® particles, yielding an homogenous population. Increasing the size of the payload compared to p1392 generates more heterogeneous Eligobiotics® populations, with increasing proportions of particles containing 3 copies of payload. From this dataset, it appears that there is a lower limit for concatemer packaging close to 36 kb, as described in the literature [28]. p1085, with a size of 12.125 kb, could package 3 copies per head (36.375 kb) or 4 copies per head (48.5 kb), although the 4 copies species is preferred as seen in FIG. 14. Increasing the size to 12.428 kb would allow packaging of 3 copies per head (37.284 kb) and 4 copies per head (49.712 kb); in this case, 4 copies are preferred, From these two data points, the inventors inferred that the lower limit for packaging is indeed around 36 kb but with a lower efficiency. Increasing the size just by 909 bp completely shifts the packaged species to 4 copies: the limit for optimal efficiency of packaging, probably driven by a pressure signal in the capsid, lies within these two sizes. Finally, the 11.615 kb payload packages virtually only 4 copies per head (46.46 kb), as the 3-copy species is slightly below the packaging limit, even at low efficiency (34.845 kb).

From these data, it can also be predicted which sizes would give packaging of single and multimeric species, as shown below in Tables 2 and 3. Smaller sizes yielding single packaged species are generally preferred for several reasons, including ease of manipulation and lower probability of introducing unwanted restriction sites. Finally, sizes that allow for very efficient packaged species that are not too small (26-39 kb) or too large (50-51 kb) are also preferred in some cases as it has been shown that the amount of DNA present in the capsid may alter the packaging and stability of the particles due to intracapsid pressure [29]-[30]. Finally, sizes that are large enough to allow for production of packaged phagemids at high titer are also more particularly preferred.

TABLE 2

Predicted number of concatemers packaged in a capsid depending on the monomer size.

| | Plasmid size (kb) | Number of copies in the concatemer | | | | | | | | | |
|---|---|---|---|---|---|---|---|---|---|---|---|
| | | 2 | 3 | 4 | 5 | 6 | 7 | 8 | 9 | 10 | 11 |
| | 3 | 6 | 9 | 12 | 15 | 18 | 21 | 24 | 27 | 30 | 33 |
| | 4 | 8 | 12 | 16 | 20 | 24 | 28 | 32 | 36 | 40 | 44 |
| | 5 | 10 | 15 | 20 | 25 | 30 | 35 | 40 | 45 | 50 | 55 |
| | 6 | 12 | 18 | 24 | 30 | 36 | 42 | 48 | 54 | 60 | 66 |
| | 7 | 14 | 21 | 28 | 35 | 42 | 49 | 56 | 63 | 70 | 77 |
| | 8 | 16 | 24 | 32 | 40 | 48 | 56 | 64 | 72 | 80 | 88 |
| | 9 | 18 | 27 | 36 | 45 | 54 | 63 | 72 | 81 | 90 | 99 |
| | 10 | 20 | 30 | 40 | 50 | 60 | 70 | 80 | 90 | 100 | 110 |
| Single conformation possible, 4 copies | 11 | 22 | 33 | 44 | 55 | 66 | 77 | 88 | 99 | 110 | 121 |
| | 12 | 24 | 36 | 48 | 60 | 72 | 84 | 96 | 108 | 120 | 132 |
| Single conformation possible | 13 | 26 | 39 | 52 | 65 | 78 | 91 | 104 | 117 | 130 | 143 |
| Single conformation possible | 14 | 28 | 42 | 56 | 70 | 84 | 98 | 112 | 126 | 140 | 154 |
| Single conformation possible | 15 | 30 | 45 | 60 | 75 | 90 | 105 | 120 | 135 | 150 | 165 |
| Single conformation possible | 16 | 32 | 48 | 64 | 80 | 96 | 112 | 128 | 144 | 160 | 176 |
| Single conformation possible, high limit | 17 | 34 | 51 | 68 | 85 | 102 | 119 | 136 | 153 | 170 | 187 |
| Single conformation possible | 18 | 36 | 54 | 72 | 90 | 108 | 126 | 144 | 162 | 180 | 198 |
| Single conformation possible | 19 | 38 | 57 | 76 | 95 | 114 | 133 | 152 | 171 | 190 | 209 |
| Single conformation possible | 20 | 40 | 60 | 80 | 100 | 120 | 140 | 160 | 180 | 200 | 220 |
| Single conformation possible | 21 | 42 | 63 | 84 | 105 | 126 | 147 | 168 | 189 | 210 | 231 |
| Single conformation possible | 22 | 44 | 66 | 88 | 110 | 132 | 154 | 176 | 198 | 220 | 242 |
| Single conformation possible | 23 | 46 | 69 | 92 | 115 | 138 | 161 | 184 | 207 | 230 | 253 |
| Single conformation possible | 24 | 48 | 72 | 96 | 120 | 144 | 168 | 192 | 216 | 240 | 264 |

Cells with heavy dark borders and in bold represent better species, cells with thin borders and non-bolded represent species either too small or too large for optimal packaging. The lower and higher limits for efficient packaging have been set to 36 kb and 51 kb, respectively.

TABLE 3

Predicted number of concatemers packaged in a capsid depending on the monomer size between 9 and 13 kb.

| | Plasmid size (kb) | Number of copies in the concatemer | | | | |
|---|---|---|---|---|---|---|
| | | 2 | 3 | 4 | 5 | 6 |
| | 9 | 18 | 27 | 36 | 45 | 54 |
| | 9.25 | 18.5 | 27.75 | 37 | 46.25 | 55.5 |
| | 9.5 | 19 | 28.5 | 38 | 47.5 | 57 |
| | 9.75 | 19.5 | 29.25 | 39 | 48.75 | 58.5 |
| | 10 | 20 | 30 | 40 | 50 | 60 |
| Single conformation possible, 4 copies | 10.25 | 20.5 | 30.75 | 41 | 51.25 | 61.5 |
| Single conformation possible, 4 copies | 10.5 | 21 | 31.5 | 42 | 52.5 | 63 |
| Single conformation possible, 4 copies | 10.75 | 21.5 | 32.25 | 43 | 53.75 | 64.5 |
| Single conformation possible, 4 copies | 11 | 22 | 33 | 44 | 55 | 66 |
| Single conformation possible, 4 copies | 11.25 | 22.5 | 33.75 | 45 | 56.25 | 67.5 |
| Single conformation possible, 4 copies | 11.5 | 23 | 34.5 | 46 | 57.5 | 69 |
| Single conformation possible, 4 copies | 11.75 | 23.5 | 35.25 | 47 | 58.75 | 70.5 |
| | 12 | 24 | 36 | 48 | 60 | 72 |
| | 12.25 | 24.5 | 36.75 | 49 | 61.25 | 73.5 |
| | 12.5 | 25 | 37.5 | 50 | 62.5 | 75 |
| Single conformation possible | 12.75 | 25.5 | 38.25 | 51 | 63.75 | 76.5 |
| Single conformation possible | 13 | 26 | 39 | 52 | 65 | 78 |

Cells with heavy dark borders and in bold represent better species, cells with thin borders and non-bolded represent species either too small or too large for optimal packaging. The lower and higher limits for efficient packaging have been set to 36 kb and 51 kb, respectively.

REFERENCES

[1] E. Jonczyk, M. Klak, R. Miedzybrodzki, and A. Górski, "The influence of external factors on bacteriophages-review," Folia Microbiol. (Praha), vol. 56, no. 3, pp. 191-200, May 2011, doi: 10.1007/s12223-011-0039-8.

[2] K. Dąbrowska, "Phage therapy: What factors shape phage pharmacokinetics and bioavailability?Systematic and critical review," Med. Res. Rev., vol. 39, no. 5, pp. 2000-2025, September 2019, doi: 10.1002/med.21572.

[3] H. W. Smith, M. B. Huggins, and K. M. Shaw, "Factors influencing the survival and multiplication of bacteriophages in calves and in their environment," J. Gen. Microbiol., vol. 133, no. 5, pp. 1127-1135, May 1987, doi: 10.1099/00221287-133-5-1127.

[4] K. Verthé, S. Possemiers, N. Boon, M. Vaneechoutte, and W. Verstraete, "Stability and activity of an *Enterobacter aerogenes*-specific bacteriophage under simulated gastro-intestinal conditions," Appl. Microbiol. Biotechnol., vol. 65, no. 4, pp. 465-472, September 2004, doi: 10.1007/s00253-004-1585-7.

[5] N. Jamalludeen, R. P. Johnson, P. E. Shewen, and C. L. Gyles, "Evaluation of bacteriophages for prevention and treatment of diarrhea due to experimental enterotoxigenic *Escherichia coli* O149 infection of pigs," Vet. Microbiol., vol. 136, no. 1, pp. 135-141, April 2009, doi: 10.1016/j.vetmic.2008.10.021.

[6] Y. Tanji, T. Shimada, H. Fukudomi, K. Miyanaga, Y. Nakai, and H. Unno, "Therapeutic use of phage cocktail for controlling *Escherichia coli* O157:H7 in gastrointestinal tract of mice," J. Biosci. Bioeng., vol. 100, no. 3, pp. 280-287, September 2005, doi: 10.1263/jbb.100.280.

[7] J. H. Northrop, "THE EFFECT OF PROTEOLYTIC ENZYMES ON *E. coli* PHAGES AND ON NATIVE PROTEINS," J. Gen. Physiol., vol. 48, pp. 73-78, September 1964, doi: 10.1085/jgp.48.1.73.

[8] P. K. Chanda and S. N. Chatterjee, "Properties of the cholera phage PL 163/10," Acta Virol., vol. 19, no. 3, pp. 197-203, May 1975.

[9] Y. Zivanovic et al., J. Virol., vol. 88, no. 2, pp. 1162-1174, January 2014.

[10] J. Wang, M. Hofnung, and A. Charbit, "The C-terminal portion of the tail fiber protein of bacteriophage lambda is responsible for binding to LamB, its receptor at the surface of *Escherichia coli* K-12," J. Bacteriol., vol. 182, no. 2, pp. 508-512, January 2000, doi: 10.1 128/jb.182.2.508-512.2000.

[11] James E Thompson, Meraj Pourhossein, Amy Waterhouse, Thomas Hudson, Marie Goldrick, Jeremy P Derrick, Ian S Roberts, "The K5 lyase KflA combines a viral tail spike structure with a bacterial polysaccharide lyase mechanism", J Biol Chem, vol. 285, no. 31, pp. 23963-9, July 2010.

The invention claimed is:

1. A chimeric receptor binding protein (RBP) resistant to proteolytic digestion,
wherein said chimeric RBP comprises an N-terminal region of a side tail fiber (STF) protein from a lambdoid bacteriophage, fused through a designed linker region consisting of 1 to 70 amino acids or 1 to 30 amino acids, to a C-terminal region of a RBP protein from a different bacteriophage, wherein said N-terminal region and C-terminal region are fused within an insertion site of the N-terminal STF region, said insertion site, having at least 80% identity with a site selected from the group consisting of amino acids SAGDAS (SEQ ID NO: 1), ADAKKS (SEQ ID NO: 2), MDETNR (SEQ ID NO: 3), SASAAA (SEQ ID NO: 4), and GAGENS (SEQ ID NO: 5); and wherein said designed linker region comprises a helix or helical bundle and wherein said linker region is resistant to proteolytic cleavage.

2. The chimeric RBP according to claim 1, wherein the designed linker region consists of 1 to 30 amino acids.

3. The chimeric RBP according to claim 1, wherein said chimeric RBP is resistant to proteolytic digestion by pancreatin, and said linker region is designed to be resistant to proteolytic digestion by pancreatin.

4. The chimeric RBP according to claim 1, wherein said insertion site has at least 80% identity with sequence GAGENS (SEQ ID NO: 5).

5. The chimeric RBP according to claim 1, wherein said designed linker region is at the C-terminal end of the insertion site.

6. The chimeric RBP according to claim 1, wherein said designed linker region is part of the N-terminal region or of the C-terminal region of the chimeric RBP.

7. The chimeric RBP according to claim 6, wherein said N-terminal region or said C-terminal region comprises the sequence of the linker region, said sequence being identical to the corresponding sequence in the N-terminal region or C-terminal region of the RBP from which it is derived, and said sequence restoring resistance to proteolytic digestion to said chimeric RBP compared to a chimeric RBP only differing by the absence of said linker region.

8. The chimeric RBP according to claim 1, wherein said designed linker region comprises, or consists of, an heterologous amino acid sequence which is not derived from one of the RBP from which the N-terminal region and the C-terminal region of the chimeric RBP are derived.

9. The chimeric RBP according to claim 1, wherein said designed linker region comprises, or consists of, an amino acid sequence GSATDVMIQL (SEQ ID NO: 6) or GSATDVMIQLA (SEQ ID NO: 7).

10. The chimeric RBP according to claim 1, wherein said designed linker region comprises, or consists of, the amino acid sequence of SEQ ID NO: 34 or SEQ ID NO: 36.

11. The chimeric RBP according to claim 1, wherein the N-terminal region of said STF protein from said lambdoid bacteriophage corresponds to amino acids 1 to 528 of the lambda STF protein of SEQ ID NO: 8.

12. The chimeric RBP according to claim 1, wherein the C-terminal region of said STF protein from said different bacteriophage corresponds to amino acids 208 to 875 of the STF protein of SEQ ID NO: 16 or to amino acids 218 to 875 of the STF protein of SEQ ID NO: 16.

13. The chimeric RBP according to claim 12, wherein said chimeric RBP comprises, or consists of, the sequence of SEQ ID NO: 9, SEQ ID NO: 10 or SEQ ID NO: 11.

14. The chimeric RBP according to claim 1, wherein the C-terminal region of said STF protein from said different bacteriophage corresponds to amino acids 28 to 632 of the STF protein of SEQ ID NO: 12 or amino acids 62 to 632 of the STF protein of SEQ ID NO: 12.

15. The chimeric RBP according to claim 14, wherein said chimeric RBP comprises, or consists of, the sequence of SEQ ID NO: 13, SEQ ID NO: 14, SEQ ID NO: 38 or SEQ ID NO: 40.

16. A chimeric receptor binding protein (RBP) resistant to proteolytic digestion,
wherein said chimeric RBP comprises an N-terminal region of a side tail fiber (STF) protein from a lambdoid bacteriophage, fused through a designed linker region consisting of 1 to 70 amino acids or 1 to 30 amino acids, to a C-terminal region of a RBP protein from a different bacteriophage, wherein said N-terminal region and C-terminal region are fused within a site of the N-terminal STF region, called insertion site, having at least 80% identity with a site selected from the group consisting of amino acids SAGDAS (SEQ ID NO: 1), ADAKKS (SEQ ID NO: 2), MDETNR (SEQ ID NO: 3), SASAAA (SEQ ID NO: 4), and GAGENS (SEQ ID NO: 5); and
(i) wherein said N-terminal region or said C-terminal region comprises the sequence of the linker region, said sequence being identical to the corresponding sequence in the N-terminal region or C-terminal region of the RBP from which it is derived, and said sequence restoring resistance to proteolytic digestion to said chimeric RBP compared to a chimeric RBP only differing by the absence of said linker region, and wherein said designed linker region comprises, or consists of, the amino acid sequence GSATDVMIQL (SEQ ID NO: 6) or GSATDVMIQLA (SEQ ID NO: 7); or
(ii) wherein said designed linker region comprises or consists of an heterologous amino acid sequence which is not from one of the RBP from which the N-terminal region and the C-terminal region of the chimeric RBP are derived, and wherein said designed linker region comprises, or consists of, the amino acid sequence of SEQ ID NO: 34 or SEQ ID NO: 36 wherein said designed linker region comprises a helix or helical bundle and wherein said linker region is designed to be resistant to proteolytic digestion.

17. A chimeric receptor binding protein (RBP) resistant to proteolytic digestion, wherein said RBP comprises a portion of a receptor binding protein from a bacteriophage fused through a designed linker region consisting of 1 to 70 amino acids, to a portion of a receptor binding protein from a different bacteriophage, wherein said linker region is designed to be resistant to proteolytic digestion, wherein said chimeric RBP comprises, or consists of, the sequence of SEQ ID NO: 9, SEQ ID NO: 10, SEQ ID NO: 11, SEQ ID NO: 13, SEQ ID NO: 14, SEQ ID NO: 38 or SEQ ID NO: 40.

* * * * *

SEQUENCE LISTING

```
<160> NUMBER OF SEQ ID NOS: 51

<210> SEQ ID NO 1
<211> LENGTH: 6
<212> TYPE: PRT
<213> ORGANISM: Artificial Sequence
<220> FEATURE:
<223> OTHER INFORMATION: Insertion site sequence SAGDAS

<400> SEQUENCE: 1

Ser Ala Gly Asp Ala Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Insertion site sequence ADAKKS

<400> SEQUENCE: 2

Ala Asp Ala Lys Lys Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Insertion site sequence MDETNR

<400> SEQUENCE: 3

Met Asp Glu Thr Asn Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Insertion site sequence SASAAA

<400> SEQUENCE: 4

Ser Ala Ser Ala Ala Ala
1               5

<210> SEQ ID NO 5
<211> LENGTH: 6
<212> TYPE: PRT
```

```
<213> ORGANISM: Artificial Sequence
<220> FEATURE:
<223> OTHER INFORMATION: Insertion site sequence GAGENS

<400> SEQUENCE: 5

Gly Ala Gly Glu Asn Ser
1               5

<210> SEQ ID NO 6
<211> LENGTH: 10
<212> TYPE: PRT
<213> ORGANISM: Artificial Sequence
<220> FEATURE:
<223> OTHER INFORMATION: GSATDVMIQL sequence

<400> SEQUENCE: 6

Gly Ser Ala Thr Asp Val Met Ile Gln Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: GSATDVMIQLA sequence

<400> SEQUENCE: 7

Gly Ser Ala Thr Asp Val Met Ile Gln Leu Ala
1               5                   10

<210> SEQ ID NO 8
<211> LENGTH: 774
<212> TYPE: PRT
<213> ORGANISM: Bacteriophage lambda

<400> SEQUENCE: 8

Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
                20                  25                  30

Val Val Val Asn Thr Val Gly Ser Glu Asn Pro Asp Glu Ala Gly Arg
            35                  40                  45

Tyr Ser Met Asp Val Glu Tyr Gly Gln Tyr Ser Val Ile Leu Gln Val
    50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ser Ala Ala Gln Val Ala Ala Leu
    130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Ala Glu Ser
            180                 185                 190
```

```
Ser Lys Asn Ala Ala Ala Thr Ser Ala Gly Ala Ala Lys Thr Ser Glu
    195                 200                 205
Thr Asn Ala Ala Ala Ser Gln Gln Ser Ala Ala Thr Ser Ala Ser Thr
210                 215                 220
Ala Ala Thr Lys Ala Ser Glu Ala Ala Thr Ser Ala Arg Asp Ala Val
225                 230                 235                 240
Ala Ser Lys Glu Ala Ala Lys Ser Ser Glu Thr Asn Ala Ser Ser Ser
                245                 250                 255
Ala Gly Arg Ala Ala Ser Ser Ala Thr Ala Ala Glu Asn Ser Ala Arg
            260                 265                 270
Ala Ala Lys Thr Ser Glu Thr Asn Ala Arg Ser Ser Glu Thr Ala Ala
        275                 280                 285
Glu Arg Ser Ala Ser Ala Ala Ala Asp Ala Lys Thr Ala Ala Ala Gly
    290                 295                 300
Ser Ala Ser Thr Ala Ser Thr Lys Ala Thr Glu Ala Ala Gly Ser Ala
305                 310                 315                 320
Val Ser Ala Ser Gln Ser Lys Ser Ala Ala Glu Ala Ala Ala Ile Arg
                325                 330                 335
Ala Lys Asn Ser Ala Lys Arg Ala Glu Asp Ile Ala Ser Ala Val Ala
            340                 345                 350
Leu Glu Asp Ala Asp Thr Thr Arg Lys Gly Ile Val Gln Leu Ser Ser
        355                 360                 365
Ala Thr Asn Ser Thr Ser Glu Thr Leu Ala Ala Thr Pro Lys Ala Val
    370                 375                 380
Lys Val Val Met Asp Glu Thr Asn Arg Lys Ala Pro Leu Asp Ser Pro
385                 390                 395                 400
Ala Leu Thr Gly Thr Pro Thr Ala Pro Thr Ala Leu Arg Gly Thr Asn
                405                 410                 415
Asn Thr Gln Ile Ala Asn Thr Ala Phe Val Leu Ala Ala Ile Ala Asp
            420                 425                 430
Val Ile Asp Ala Ser Pro Asp Ala Leu Asn Thr Leu Asn Glu Leu Ala
        435                 440                 445
Ala Ala Leu Gly Asn Asp Pro Asp Phe Ala Thr Thr Met Thr Asn Ala
    450                 455                 460
Leu Ala Gly Lys Gln Pro Lys Asn Ala Thr Leu Thr Ala Leu Ala Gly
465                 470                 475                 480
Leu Ser Thr Ala Lys Asn Lys Leu Pro Tyr Phe Ala Glu Asn Asp Ala
                485                 490                 495
Ala Ser Leu Thr Glu Leu Thr Gln Val Gly Arg Asp Ile Leu Ala Lys
            500                 505                 510
Asn Ser Val Ala Asp Val Leu Glu Tyr Leu Gly Ala Gly Glu Asn Ser
        515                 520                 525
Ala Phe Pro Ala Gly Ala Pro Ile Pro Trp Pro Ser Asp Ile Val Pro
    530                 535                 540
Ser Gly Tyr Val Leu Met Gln Gly Gln Ala Phe Asp Lys Ser Ala Tyr
545                 550                 555                 560
Pro Lys Leu Ala Val Ala Tyr Pro Ser Gly Val Leu Pro Asp Met Arg
                565                 570                 575
Gly Trp Thr Ile Lys Gly Lys Pro Ala Ser Gly Arg Ala Val Leu Ser
            580                 585                 590
Gln Glu Gln Asp Gly Ile Lys Ser His Thr His Ser Ala Ser Ala Ser
        595                 600                 605
Gly Thr Asp Leu Gly Thr Lys Thr Thr Ser Ser Phe Asp Tyr Gly Thr
```

```
               610                 615                 620
Lys Thr Thr Gly Ser Phe Asp Tyr Gly Thr Lys Ser Thr Asn Asn Thr
625                 630                 635                 640

Gly Ala His Ala His Ser Leu Ser Gly Ser Thr Gly Ala Ala Gly Ala
                645                 650                 655

His Ala His Thr Ser Gly Leu Arg Met Asn Ser Ser Gly Trp Ser Gln
                660                 665                 670

Tyr Gly Thr Ala Thr Ile Thr Gly Ser Leu Ser Thr Val Lys Gly Thr
            675                 680                 685

Ser Thr Gln Gly Ile Ala Tyr Leu Ser Lys Thr Asp Ser Gln Gly Ser
        690                 695                 700

His Ser His Ser Leu Ser Gly Thr Ala Val Ser Ala Gly Ala His Ala
705                 710                 715                 720

His Thr Val Gly Ile Gly Ala His Gln His Pro Val Val Ile Gly Ala
                725                 730                 735

His Ala His Ser Phe Ser Ile Gly Ser His Gly His Thr Ile Thr Val
                740                 745                 750

Asn Ala Ala Gly Asn Ala Glu Asn Thr Val Lys Asn Ile Ala Phe Asn
            755                 760                 765

Tyr Ile Val Arg Leu Ala
        770

<210> SEQ ID NO 9
<211> LENGTH: 1186
<212> TYPE: PRT
<213> ORGANISM: Artificial Sequence
<220> FEATURE:
<223> OTHER INFORMATION: STF-V10-[FA]

<400> SEQUENCE: 9

Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
                20                  25                  30

Val Val Val Asn Thr Val Gly Ser Glu Asn Pro Asp Glu Ala Gly Arg
            35                  40                  45

Tyr Ser Met Asp Val Glu Tyr Gly Gln Tyr Ser Val Ile Leu Gln Val
        50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ala Gln Val Ala Ala Leu
    130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Gly Ala Glu Ala Ala
                165                 170                 175

Ser Ala Lys Ala Thr Glu Ala Glu Lys Ser Ala Ala Ala Glu Ser
            180                 185                 190

Ser Lys Asn Ala Ala Ala Thr Ser Ala Gly Ala Ala Lys Thr Ser Glu
```

```
            195                 200                 205
Thr Asn Ala Ala Ala Ser Gln Gln Ser Ala Ala Thr Ser Ala Ser Thr
210                 215                 220

Ala Ala Thr Lys Ala Ser Glu Ala Ala Thr Ser Ala Arg Asp Ala Val
225                 230                 235                 240

Ala Ser Lys Glu Ala Lys Ser Ser Glu Thr Asn Ala Ser Ser Ser
                245                 250                 255

Ala Gly Arg Ala Ala Ser Ser Ala Thr Ala Ala Glu Asn Ser Ala Arg
                260                 265                 270

Ala Ala Lys Thr Ser Glu Thr Asn Ala Arg Ser Ser Glu Thr Ala Ala
                275                 280                 285

Glu Arg Ser Ala Ser Ala Ala Ala Asp Ala Lys Thr Ala Ala Ala Gly
                290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ile Arg
                325                 330                 335

Ala Lys Asn Ser Ala Lys Arg Ala Glu Asp Ile Ala Ser Ala Val Ala
                340                 345                 350

Leu Glu Asp Ala Asp Thr Thr Arg Lys Gly Ile Val Gln Leu Ser Ser
                355                 360                 365

Ala Thr Asn Ser Thr Ser Glu Thr Leu Ala Ala Thr Pro Lys Ala Val
370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
                420                 425                 430

Val Ile Asp Ala Ser Pro Asp Ala Leu Asn Thr Leu Asn Glu Leu Ala
                435                 440                 445

Ala Ala Leu Gly Asn Asp Pro Asp Phe Ala Thr Thr Met Thr Asn Ala
450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
                485                 490                 495

Ala Ser Leu Thr Glu Leu Thr Gln Val Gly Arg Asp Ile Leu Ala Lys
                500                 505                 510

Asn Ser Val Ala Asp Val Leu Glu Tyr Leu Gly Ala Gly Glu Asn Ser
                515                 520                 525

Ala Ala Asn Asp Gly Phe Ala Phe Ile Gly Gln Cys Pro Asp Ile Leu
                530                 535                 540

Thr Leu Arg Thr Ile Glu Pro Glu Lys Asn Gly Gln Arg Ile Thr Leu
545                 550                 555                 560

Arg Gln His Thr Ile Gly Thr Gly Leu Gly Gly Val Phe Arg Ala
                565                 570                 575

Val Leu Asp Gly Thr Gly Tyr Thr Asp Asp Gly Val Ile Lys
                580                 585                 590

Thr Ala Gly Gly Ser Val Trp Leu Arg Val Asn Ala Asp Lys Val Asn
                595                 600                 605

Pro Phe Met Phe Gly Ala Thr Gly Val Ala Asp Asp Thr Ala Ala Leu
610                 615                 620
```

```
Gln Lys Met Leu Glu Cys Gly Arg Ala Ala Glu Leu Gly Thr Asn Val
625                 630                 635                 640

Trp Lys Ala Ser Asn Leu Glu Leu Asn Asn Lys Ser Cys Ser Leu Ser
            645                 650                 655

Gly Ser Gly Leu His Val Ser Arg Ile Glu Gln Ile Ser Gly Ala Thr
            660                 665                 670

Gly Ala Leu Leu Thr Ile Thr Gln Asp Cys Ser Leu Ile Tyr Leu Ser
            675                 680                 685

Asp Cys Gly Leu Tyr Gly Asp Gly Ile Thr Ala Gly Thr Ser Gly Val
            690                 695                 700

Thr Met Glu Thr Gly Asn Pro Gly Gly Ala Pro Ser Tyr Pro Phe Asn
705                 710                 715                 720

Thr Ala Pro Asp Val Arg Arg Asp Leu Tyr Ile Ser Asn Val His Ile
            725                 730                 735

Thr Gly Phe Asp Glu Leu Gly Phe Asp Tyr Pro Glu Thr Asn Phe Ser
            740                 745                 750

Val Ser Thr His Gly Leu Phe Ile Arg Asn Ile Lys Lys Thr Gly Ala
            755                 760                 765

Lys Ile Gly Thr Thr Asp Phe Thr Trp Thr Asn Leu Gln Ile Asp Thr
770                 775                 780

Cys Gly Gln Glu Cys Leu Val Leu Asp Gly Ala Gly Asn Cys Arg Ile
785                 790                 795                 800

Ile Gly Ala Lys Leu Ile Trp Ala Gly Ser Glu Asn Glu Thr Pro Tyr
            805                 810                 815

Ser Gly Leu Arg Ile Ser Asn Ser Gln Asn Val Asn Met Thr Gly Val
            820                 825                 830

Glu Leu Gln Asp Cys Ala Tyr Asp Gly Leu Tyr Ile Lys Asn Ser Thr
            835                 840                 845

Val Ala Ile Ser Gly Leu Asn Thr Asn Arg Asn Ser Ala Ser Ser Asn
850                 855                 860

Leu Ser Tyr His Asn Met Val Phe Glu Asn Ser Ile Val Thr Val Asp
865                 870                 875                 880

Gly Tyr Val Cys Arg Asn Tyr Ala Ala Thr Ser Leu Tyr Asp Leu Asn
            885                 890                 895

Ser Gln Ala Gly Asn Val Arg Cys Ile Gly Ser Asp Ser Thr Val Leu
            900                 905                 910

Ile Asn Gly Ile Tyr Glu Ser Glu Val Asn Ser Glu Arg Leu Met Gly
            915                 920                 925

Asp Asn Asn Leu Ile Gln Pro Tyr Ser Gly Asp Leu Ile Ile Asn Gly
            930                 935                 940

Leu Lys Asn Tyr Tyr Thr Tyr Thr Gly Ser Val Lys Asn Asn Ile Pro
945                 950                 955                 960

Thr Phe Asp Gly Val Thr Thr Ala Thr Tyr Val Ser Ala Pro Ser
            965                 970                 975

Ile Leu Gly Gln Gly Asn Met Leu Lys Leu Thr Gln Ser Asn Lys Asp
            980                 985                 990

Lys Leu Leu Phe Ser Asp Lys Val Ser Arg His Gly Cys Thr Ile Gly
            995                 1000                1005

Leu Val Leu Ile Pro Ser Phe Thr Gly Ala Thr Thr Met Thr Ala
        1010            1015                1020

Phe Thr Leu Gly Ser Gly Tyr Ser Pro Ser Gly Asn Ser Ala Val
        1025            1030                1035
```

```
Met Gln Phe Ile Val Asn Ser Ser Gly Val Gln Thr Ile Ala Ile
    1040                1045                1050

Leu Leu Ser Gly Asp Gly Ile Thr Gln Thr Leu Thr Ser Asp Leu
    1055                1060                1065

Thr Thr Glu Gln Ala Leu Ala Ser Gly Gly Val Tyr His Phe Ala
    1070                1075                1080

Met Gly Phe Ala Pro Gly Arg Leu Trp Trp Ser Ile Ile Asp Ile
    1085                1090                1095

Asn Thr Gly Arg Arg Ile Arg Arg Ala Tyr Arg Gln Pro Asp Leu
    1100                1105                1110

His Ala Ala Phe Asn Ser Ile Phe Asn Ser Gly Thr Ser Ser Ile
    1115                1120                1125

Thr Ala Phe Ser Gly Pro Leu Ala Gly Asp Ile Ala Cys Glu Gly
    1130                1135                1140

Ala Gly Ser His Val Tyr Val Gly Gly Phe Ser Ser Glu Ser Asp
    1145                1150                1155

Tyr Ala Ala Ser Arg Met Tyr Gly Leu Phe Thr Pro Val Asp Leu
    1160                1165                1170

Asp Lys Gln Tyr Ser Phe Arg Thr Leu Asn Gly Asn Ile
    1175                1180                1185

<210> SEQ ID NO 10
<211> LENGTH: 1186
<212> TYPE: PRT
<213> ORGANISM: Artificial Sequence
<220> FEATURE:
<223> OTHER INFORMATION: STF-V10-[AAH]

<400> SEQUENCE: 10

Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
                20                  25                  30

Val Val Val Asn Thr Val Gly Ser Glu Asn Pro Asp Glu Ala Gly Arg
            35                  40                  45

Tyr Ser Met Asp Val Glu Tyr Gly Gln Tyr Ser Val Ile Leu Gln Val
        50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
                100                 105                 110

Val Ala Arg Asn Ala Ser Val Val Ala Gln Ser Thr Ala Asp Ala Lys
            115                 120                 125

Lys Ser Ala Gly Asp Ala Ser Ala Ser Ala Ala Gln Val Ala Ala Leu
        130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Ala Glu Ser
                180                 185                 190

Ser Lys Asn Ala Ala Ala Thr Ser Ala Gly Ala Ala Lys Thr Ser Glu
            195                 200                 205
```

```
Thr Asn Ala Ala Ala Ser Gln Gln Ser Ala Ala Thr Ser Ala Ser Thr
    210                 215                 220

Ala Ala Thr Lys Ala Ser Glu Ala Ala Thr Ser Ala Arg Asp Ala Val
225                 230                 235                 240

Ala Ser Lys Glu Ala Ala Lys Ser Ser Glu Thr Asn Ala Ser Ser Ser
                245                 250                 255

Ala Gly Arg Ala Ala Ser Ser Ala Thr Ala Ala Glu Asn Ser Ala Arg
            260                 265                 270

Ala Ala Lys Thr Ser Glu Thr Asn Ala Arg Ser Ser Glu Thr Ala Ala
        275                 280                 285

Glu Arg Ser Ala Ser Ala Ala Asp Ala Lys Thr Ala Ala Ala Gly
    290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ile Arg
                325                 330                 335

Ala Lys Asn Ser Ala Lys Arg Ala Glu Asp Ile Ala Ser Ala Val Ala
            340                 345                 350

Leu Glu Asp Ala Asp Thr Thr Arg Lys Gly Ile Val Gln Leu Ser Ser
        355                 360                 365

Ala Thr Asn Ser Thr Ser Glu Thr Leu Ala Ala Thr Pro Lys Ala Val
    370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
            420                 425                 430

Val Ile Asp Ala Ser Pro Asp Ala Leu Asn Thr Leu Asn Glu Leu Ala
        435                 440                 445

Ala Ala Leu Gly Asn Asp Pro Asp Phe Ala Thr Thr Met Thr Asn Ala
    450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
                485                 490                 495

Ala Ser Leu Thr Glu Leu Thr Gln Val Gly Arg Asp Ile Leu Ala Lys
            500                 505                 510

Asn Ser Val Ala Asp Val Leu Glu Tyr Leu Gly Ala Gly Glu Asn Ser
        515                 520                 525

Ala Ala Asn Asp Gly Ala Ala His Ile Gly Gln Cys Pro Asp Ile Leu
    530                 535                 540

Thr Leu Arg Thr Ile Glu Pro Glu Lys Asn Gly Gln Arg Ile Thr Leu
545                 550                 555                 560

Arg Gln His Thr Ile Gly Thr Gly Leu Gly Gly Val Phe Arg Ala
                565                 570                 575

Val Leu Asp Gly Thr Gly Tyr Thr Asp Asp Gly Val Val Ile Lys
            580                 585                 590

Thr Ala Gly Gly Ser Val Trp Leu Arg Val Asn Ala Asp Lys Val Asn
        595                 600                 605

Pro Phe Met Phe Gly Ala Thr Gly Val Ala Asp Thr Ala Ala Leu
    610                 615                 620

Gln Lys Met Leu Glu Cys Gly Arg Ala Ala Glu Leu Gly Thr Asn Val
```

```
            625                 630                 635                 640
    Trp Lys Ala Ser Asn Leu Glu Leu Asn Lys Ser Cys Ser Leu Ser
                        645                 650                 655

Gly Ser Gly Leu His Val Ser Arg Ile Glu Gln Ile Ser Gly Ala Thr
                660                 665                 670

Gly Ala Leu Leu Thr Ile Thr Gln Asp Cys Ser Leu Ile Tyr Leu Ser
                675                 680                 685

Asp Cys Gly Leu Tyr Gly Asp Gly Ile Thr Ala Gly Thr Ser Gly Val
                690                 695                 700

Thr Met Glu Thr Gly Asn Pro Gly Gly Ala Pro Ser Tyr Pro Phe Asn
    705                 710                 715                 720

Thr Ala Pro Asp Val Arg Arg Asp Leu Tyr Ile Ser Asn Val His Ile
                        725                 730                 735

Thr Gly Phe Asp Glu Leu Gly Phe Asp Tyr Pro Glu Thr Asn Phe Ser
                        740                 745                 750

Val Ser Thr His Gly Leu Phe Ile Arg Asn Ile Lys Lys Thr Gly Ala
                        755                 760                 765

Lys Ile Gly Thr Thr Asp Phe Thr Trp Thr Asn Leu Gln Ile Asp Thr
                770                 775                 780

Cys Gly Gln Glu Cys Leu Val Leu Asp Gly Ala Gly Asn Cys Arg Ile
    785                 790                 795                 800

Ile Gly Ala Lys Leu Ile Trp Ala Gly Ser Glu Asn Glu Thr Pro Tyr
                        805                 810                 815

Ser Gly Leu Arg Ile Ser Asn Ser Gln Asn Val Asn Met Thr Gly Val
                        820                 825                 830

Glu Leu Gln Asp Cys Ala Tyr Asp Gly Leu Tyr Ile Lys Asn Ser Thr
                835                 840                 845

Val Ala Ile Ser Gly Leu Asn Thr Asn Arg Asn Ser Ala Ser Ser Asn
                850                 855                 860

Leu Ser Tyr His Asn Met Val Phe Glu Asn Ser Ile Val Thr Val Asp
    865                 870                 875                 880

Gly Tyr Val Cys Arg Asn Tyr Ala Ala Thr Ser Leu Tyr Asp Leu Asn
                        885                 890                 895

Ser Gln Ala Gly Asn Val Arg Cys Ile Gly Ser Asp Ser Thr Val Leu
                900                 905                 910

Ile Asn Gly Ile Tyr Glu Ser Glu Val Asn Ser Glu Arg Leu Met Gly
                915                 920                 925

Asp Asn Asn Leu Ile Gln Pro Tyr Ser Gly Asp Leu Ile Ile Asn Gly
    930                 935                 940

Leu Lys Asn Tyr Tyr Thr Tyr Thr Gly Ser Val Lys Asn Asn Ile Pro
    945                 950                 955                 960

Thr Phe Asp Gly Val Val Thr Thr Ala Thr Tyr Val Ser Ala Pro Ser
                        965                 970                 975

Ile Leu Gly Gln Gly Asn Met Leu Lys Leu Thr Gln Ser Asn Lys Asp
                980                 985                 990

Lys Leu Leu Phe Ser Asp Lys Val  Ser Arg His Gly Cys  Thr Ile Gly
                995                 1000                1005

Leu Val  Leu Ile Pro Ser Phe  Thr Gly Ala Thr  Thr Met Thr Ala
        1010                1015                1020

Phe Thr  Leu Gly Ser Gly Tyr  Ser Pro Ser Gly Asn  Ser Ala Val
            1025                1030                1035

Met Gln  Phe Ile Val Asn Ser  Ser Gly Val Gln Thr  Ile Ala Ile
            1040                1045                1050
```

```
Leu Leu Ser Gly Asp Gly Ile Thr Gln Thr Leu Thr Ser Asp Leu
    1055                1060                1065

Thr Thr Glu Gln Ala Leu Ala Ser Gly Gly Val Tyr His Phe Ala
    1070                1075                1080

Met Gly Phe Ala Pro Gly Arg Leu Trp Trp Ser Ile Ile Asp Ile
    1085                1090                1095

Asn Thr Gly Arg Arg Ile Arg Arg Ala Tyr Arg Gln Pro Asp Leu
    1100                1105                1110

His Ala Ala Phe Asn Ser Ile Phe Asn Ser Gly Thr Ser Ser Ile
    1115                1120                1125

Thr Ala Phe Ser Gly Pro Leu Ala Gly Asp Ile Ala Cys Glu Gly
    1130                1135                1140

Ala Gly Ser His Val Tyr Val Gly Gly Phe Ser Ser Glu Ser Asp
    1145                1150                1155

Tyr Ala Ala Ser Arg Met Tyr Gly Leu Phe Thr Pro Val Asp Leu
    1160                1165                1170

Asp Lys Gln Tyr Ser Phe Arg Thr Leu Asn Gly Asn Ile
    1175                1180                1185

<210> SEQ ID NO 11
<211> LENGTH: 1196
<212> TYPE: PRT
<213> ORGANISM: Artificial Sequence
<220> FEATURE:
<223> OTHER INFORMATION: STF-V10-[Helix]

<400> SEQUENCE: 11

Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
                20                  25                  30

Val Val Val Asn Thr Val Gly Ser Glu Asn Pro Asp Glu Ala Gly Arg
            35                  40                  45

Tyr Ser Met Asp Val Glu Tyr Gly Gln Tyr Ser Val Ile Leu Gln Val
        50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
                100                 105                 110

Val Ala Arg Asn Ala Ser Val Val Ala Gln Ser Thr Ala Asp Ala Lys
            115                 120                 125

Lys Ser Ala Gly Asp Ala Ser Ala Ser Ala Ala Gln Val Ala Ala Leu
        130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Glu Ser
                180                 185                 190

Ser Lys Asn Ala Ala Ala Thr Ser Ala Gly Ala Ala Lys Thr Ser Glu
        195                 200                 205

Thr Asn Ala Ala Ala Ser Gln Gln Ser Ala Ala Thr Ser Ala Ser Thr
    210                 215                 220
```

```
Ala Ala Thr Lys Ala Ser Glu Ala Thr Ser Ala Arg Asp Ala Val
225                 230                 235                 240

Ala Ser Lys Glu Ala Lys Ser Ser Glu Thr Asn Ala Ser Ser Ser
            245                 250                 255

Ala Gly Arg Ala Ala Ser Ser Ala Thr Ala Ala Glu Asn Ser Ala Arg
        260                 265                 270

Ala Ala Lys Thr Ser Glu Thr Asn Ala Arg Ser Ser Glu Thr Ala Ala
        275                 280                 285

Glu Arg Ser Ala Ser Ala Ala Ala Asp Ala Lys Thr Ala Ala Ala Gly
        290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ala Ile Arg
                325                 330                 335

Ala Lys Asn Ser Ala Lys Arg Ala Glu Asp Ile Ala Ser Ala Val Ala
            340                 345                 350

Leu Glu Asp Ala Asp Thr Thr Arg Lys Gly Ile Val Gln Leu Ser Ser
            355                 360                 365

Ala Thr Asn Ser Thr Ser Glu Thr Leu Ala Ala Thr Pro Lys Ala Val
    370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
            420                 425                 430

Val Ile Asp Ala Ser Pro Asp Ala Leu Asn Thr Leu Asn Glu Leu Ala
            435                 440                 445

Ala Ala Leu Gly Asn Asp Pro Asp Phe Ala Thr Thr Met Thr Asn Ala
        450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
            485                 490                 495

Ala Ser Leu Thr Glu Leu Thr Gln Val Gly Arg Asp Ile Leu Ala Lys
            500                 505                 510

Asn Ser Val Ala Asp Val Leu Glu Tyr Leu Gly Ala Gly Glu Asn Ser
            515                 520                 525

Gly Ser Ala Thr Asp Val Met Ile Gln Leu Ala Ala Asn Asp Gly Phe
        530                 535                 540

Lys Phe Ile Gly Gln Cys Pro Asp Ile Leu Thr Leu Arg Thr Ile Glu
545                 550                 555                 560

Pro Glu Lys Asn Gly Gln Arg Ile Thr Leu Arg Gln His Thr Ile Gly
            565                 570                 575

Thr Gly Leu Gly Gly Val Phe Arg Ala Val Leu Asp Gly Thr Gly
                580                 585                 590

Tyr Thr Asp Asp Asp Gly Val Val Ile Lys Thr Ala Gly Gly Ser Val
            595                 600                 605

Trp Leu Arg Val Asn Ala Asp Lys Val Asn Pro Phe Met Phe Gly Ala
        610                 615                 620

Thr Gly Val Ala Asp Asp Thr Ala Ala Leu Gln Lys Met Leu Glu Cys
625                 630                 635                 640
```

Gly Arg Ala Ala Glu Leu Gly Thr Asn Val Trp Lys Ala Ser Asn Leu
            645                 650                 655

Glu Leu Asn Asn Lys Ser Cys Ser Leu Ser Gly Ser Gly Leu His Val
            660                 665                 670

Ser Arg Ile Glu Gln Ile Ser Gly Ala Thr Gly Ala Leu Leu Thr Ile
            675                 680                 685

Thr Gln Asp Cys Ser Leu Ile Tyr Leu Ser Asp Cys Gly Leu Tyr Gly
            690                 695                 700

Asp Gly Ile Thr Ala Gly Thr Ser Gly Val Thr Met Glu Thr Gly Asn
705                 710                 715                 720

Pro Gly Gly Ala Pro Ser Tyr Pro Phe Asn Thr Ala Pro Asp Val Arg
            725                 730                 735

Arg Asp Leu Tyr Ile Ser Asn Val His Ile Thr Gly Phe Asp Glu Leu
            740                 745                 750

Gly Phe Asp Tyr Pro Glu Thr Asn Phe Ser Val Ser Thr His Gly Leu
            755                 760                 765

Phe Ile Arg Asn Ile Lys Lys Thr Gly Ala Lys Ile Gly Thr Thr Asp
            770                 775                 780

Phe Thr Trp Thr Asn Leu Gln Ile Asp Thr Cys Gly Gln Glu Cys Leu
785                 790                 795                 800

Val Leu Asp Gly Ala Gly Asn Cys Arg Ile Ile Gly Ala Lys Leu Ile
            805                 810                 815

Trp Ala Gly Ser Glu Asn Glu Thr Pro Tyr Ser Gly Leu Arg Ile Ser
            820                 825                 830

Asn Ser Gln Asn Val Asn Met Thr Gly Val Glu Leu Gln Asp Cys Ala
            835                 840                 845

Tyr Asp Gly Leu Tyr Ile Lys Asn Ser Thr Val Ala Ile Ser Gly Leu
            850                 855                 860

Asn Thr Asn Arg Asn Ser Ala Ser Ser Asn Leu Ser Tyr His Asn Met
865                 870                 875                 880

Val Phe Glu Asn Ser Ile Val Thr Val Asp Gly Tyr Val Cys Arg Asn
            885                 890                 895

Tyr Ala Ala Thr Ser Leu Tyr Asp Leu Asn Ser Gln Ala Gly Asn Val
            900                 905                 910

Arg Cys Ile Gly Ser Asp Ser Thr Val Leu Ile Asn Gly Ile Tyr Glu
            915                 920                 925

Ser Glu Val Asn Ser Glu Arg Leu Met Gly Asp Asn Leu Ile Gln
            930                 935                 940

Pro Tyr Ser Gly Asp Leu Ile Ile Asn Gly Leu Lys Asn Tyr Tyr Thr
945                 950                 955                 960

Tyr Thr Gly Ser Val Lys Asn Asn Ile Pro Thr Phe Asp Gly Val Val
            965                 970                 975

Thr Thr Ala Thr Tyr Val Ser Ala Pro Ser Ile Leu Gly Gln Gly Asn
            980                 985                 990

Met Leu Lys Leu Thr Gln Ser Asn Lys Asp Lys Leu Leu Phe Ser Asp
            995                 1000                1005

Lys Val Ser Arg His Gly Cys Thr Ile Gly Leu Val Leu Ile Pro
            1010                1015                1020

Ser Phe Thr Gly Ala Thr Thr Met Thr Ala Phe Thr Leu Gly Ser
            1025                1030                1035

Gly Tyr Ser Pro Ser Gly Asn Ser Ala Val Met Gln Phe Ile Val
            1040                1045                1050

Asn Ser Ser Gly Val Gln Thr Ile Ala Ile Leu Leu Ser Gly Asp

-continued

```
                1055                1060                1065

Gly Ile Thr Gln Thr Leu Thr Ser Asp Leu Thr Thr Glu Gln Ala
            1070                1075                1080

Leu Ala Ser Gly Gly Val Tyr His Phe Ala Met Gly Phe Ala Pro
        1085                1090                1095

Gly Arg Leu Trp Trp Ser Ile Ile Asp Ile Asn Thr Gly Arg Arg
    1100                1105                1110

Ile Arg Arg Ala Tyr Arg Gln Pro Asp Leu His Ala Ala Phe Asn
1115                1120                1125

Ser Ile Phe Asn Ser Gly Thr Ser Ser Ile Thr Ala Phe Ser Gly
    1130                1135                1140

Pro Leu Ala Gly Asp Ile Ala Cys Glu Gly Ala Gly Ser His Val
        1145                1150                1155

Tyr Val Gly Gly Phe Ser Ser Glu Ser Asp Tyr Ala Ala Ser Arg
            1160                1165                1170

Met Tyr Gly Leu Phe Thr Pro Val Asp Leu Asp Lys Gln Tyr Ser
                1175                1180                1185

Phe Arg Thr Leu Asn Gly Asn Ile
                    1190                1195

<210> SEQ ID NO 12
<211> LENGTH: 632
<212> TYPE: PRT
<213> ORGANISM: Bacteriophage K5

<400> SEQUENCE: 12

Met Ala Lys Leu Thr Lys Pro Lys Thr Glu Gly Ile Leu His Lys Gly
1               5                   10                  15

Gln Ser Leu Tyr Glu Tyr Leu Asp Ala Arg Val Leu Thr Ser Lys Pro
            20                  25                  30

Phe Gly Ala Ala Gly Asp Ala Thr Thr Asp Thr Glu Val Ile Ala
        35                  40                  45

Ala Ser Leu Asn Ser Gln Lys Ala Val Thr Ile Ser Asp Gly Val Phe
    50                  55                  60

Ser Ser Ser Gly Ile Asn Ser Asn Tyr Cys Asn Leu Asp Gly Arg Gly
65                  70                  75                  80

Ser Gly Val Leu Ser His Arg Ser Ser Thr Gly Asn Tyr Leu Val Phe
                85                  90                  95

Asn Asn Pro Arg Thr Gly Arg Leu Ser Asn Ile Thr Val Glu Ser Asn
            100                 105                 110

Lys Ala Thr Asp Thr Thr Gln Gly Gln Gln Val Ser Leu Ala Gly Gly
        115                 120                 125

Ser Asp Val Thr Val Ser Asp Val Asn Phe Ser Asn Val Lys Gly Thr
    130                 135                 140

Gly Phe Ser Leu Ile Ala Tyr Pro Asn Asp Ala Pro Pro Asp Gly Leu
145                 150                 155                 160

Met Ile Lys Gly Ile Arg Gly Ser Tyr Ser Gly Tyr Ala Thr Asn Lys
                165                 170                 175

Ala Ala Gly Cys Val Leu Ala Asp Ser Ser Val Asn Ser Leu Ile Asp
            180                 185                 190

Asn Val Ile Ala Lys Asn Tyr Pro Gln Phe Gly Ala Val Glu Leu Lys
        195                 200                 205

Gly Thr Ala Ser Tyr Asn Ile Val Ser Asn Val Ile Gly Ala Asp Cys
    210                 215                 220
```

-continued

```
Gln His Val Thr Tyr Asn Gly Thr Glu Gly Pro Ile Ala Pro Ser Asn
225                 230                 235                 240

Asn Leu Ile Lys Gly Val Met Ala Asn Pro Lys Tyr Ala Ala Val
            245                 250                 255

Val Ala Gly Lys Gly Ser Thr Asn Leu Ile Ser Asp Val Leu Val Asp
            260                 265                 270

Tyr Ser Thr Ser Asp Ala Arg Gln Ala His Gly Val Thr Val Glu Gly
        275                 280                 285

Ser Asp Asn Val Ile Asn Asn Val Leu Met Ser Gly Cys Asp Gly Thr
    290                 295                 300

Asn Ser Leu Gly Gln Arg Gln Thr Ala Thr Ile Ala Arg Phe Ile Gly
305                 310                 315                 320

Thr Ala Asn Asn Asn Tyr Ala Ser Val Phe Pro Ser Tyr Ser Ala Thr
                325                 330                 335

Gly Val Ile Thr Phe Glu Ser Gly Ser Thr Arg Asn Phe Val Glu Val
            340                 345                 350

Lys His Pro Gly Arg Arg Asn Asp Leu Leu Ser Ser Ala Ser Thr Ile
        355                 360                 365

Asp Gly Ala Ala Thr Ile Asp Gly Thr Ser Asn Ser Asn Val Val His
    370                 375                 380

Ala Pro Ala Leu Gly Gln Tyr Ile Gly Ser Met Ser Gly Arg Phe Glu
385                 390                 395                 400

Trp Arg Ile Lys Ser Met Ser Leu Pro Ser Gly Val Leu Thr Ser Ala
                405                 410                 415

Asp Lys Tyr Arg Met Leu Gly Asp Gly Ala Val Ser Leu Ala Val Gly
            420                 425                 430

Gly Gly Thr Ser Ser Gln Val Arg Leu Phe Thr Ser Asp Gly Thr Ser
        435                 440                 445

Arg Thr Val Ser Leu Thr Asn Gly Asn Val Arg Leu Ser Thr Ser Ser
    450                 455                 460

Thr Gly Tyr Leu Gln Leu Gly Ala Asp Ala Met Thr Pro Asp Ser Thr
465                 470                 475                 480

Gly Thr Tyr Ala Leu Gly Ser Ala Ser Arg Ala Trp Ser Gly Gly Phe
                485                 490                 495

Thr Gln Ala Ala Phe Thr Val Thr Ser Asp Ala Arg Cys Lys Thr Glu
        500                 505                 510

Pro Leu Thr Ile Ser Asp Ala Leu Leu Asp Ala Trp Ser Glu Val Asp
    515                 520                 525

Phe Val Gln Phe Gln Tyr Leu Asp Arg Val Glu Glu Lys Gly Ala Asp
530                 535                 540

Ser Ala Arg Trp His Phe Gly Ile Ile Ala Gln Arg Ala Lys Glu Ala
545                 550                 555                 560

Phe Glu Arg His Gly Ile Asp Ala His Arg Tyr Gly Phe Leu Cys Phe
                565                 570                 575

Asp Ser Trp Asp Asp Val Tyr Glu Glu Asp Ala Asn Gly Ser Arg Lys
            580                 585                 590

Leu Ile Thr Pro Ala Gly Ser Arg Tyr Gly Ile Arg Tyr Glu Glu Val
        595                 600                 605

Leu Ile Leu Glu Ala Ala Leu Met Arg Arg Thr Ile Lys Arg Met Gln
    610                 615                 620

Glu Ala Leu Ala Ala Leu Pro Lys
625                 630
```

<210> SEQ ID NO 13
<211> LENGTH: 1143
<212> TYPE: PRT
<213> ORGANISM: Artificial Sequence
<220> FEATURE:
<223> OTHER INFORMATION: K5 5.0

<400> SEQUENCE: 13

```
Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
            20                  25                  30

Val Val Val Asn Thr Val Gly Ser Glu Asn Pro Asp Glu Ala Gly Arg
        35                  40                  45

Tyr Ser Met Asp Val Glu Tyr Gly Gln Tyr Ser Val Ile Leu Gln Val
    50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ala Ala Gln Val Ala Ala Leu
    130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Ala Glu Ser
            180                 185                 190

Ser Lys Asn Ala Ala Ala Thr Ser Ala Gly Ala Ala Lys Thr Ser Glu
        195                 200                 205

Thr Asn Ala Ala Ala Ser Gln Gln Ser Ala Ala Thr Ser Ala Ser Thr
    210                 215                 220

Ala Ala Thr Lys Ala Ser Glu Ala Ala Thr Ser Ala Arg Asp Ala Val
225                 230                 235                 240

Ala Ser Lys Glu Ala Ala Lys Ser Ser Glu Thr Asn Ala Ser Ser Ser
                245                 250                 255

Ala Gly Arg Ala Ala Ser Ser Ala Thr Ala Ala Glu Asn Ser Ala Arg
            260                 265                 270

Ala Ala Lys Thr Ser Glu Thr Asn Ala Arg Ser Ser Glu Thr Ala Ala
        275                 280                 285

Glu Arg Ser Ala Ser Ala Ala Ala Asp Ala Lys Thr Ala Ala Ala Gly
    290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ala Ile Arg
                325                 330                 335

Ala Lys Asn Ser Ala Lys Arg Ala Glu Asp Ile Ala Ser Ala Val Ala
            340                 345                 350

Leu Glu Asp Ala Asp Thr Thr Arg Lys Gly Ile Val Gln Leu Ser Ser
        355                 360                 365

Ala Thr Asn Ser Thr Ser Glu Thr Leu Ala Ala Thr Pro Lys Ala Val
```

```
            370                 375                 380
Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
                420                 425                 430

Val Ile Asp Ala Ser Pro Asp Ala Leu Asn Thr Leu Asn Glu Leu Ala
            435                 440                 445

Ala Ala Leu Gly Asn Asp Pro Asp Phe Ala Thr Thr Met Thr Asn Ala
            450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
                485                 490                 495

Ala Ser Leu Thr Glu Leu Thr Gln Val Gly Arg Asp Ile Leu Ala Lys
                500                 505                 510

Asn Ser Val Ala Asp Val Leu Glu Tyr Leu Gly Ala Gly Glu Asn Ser
            515                 520                 525

Gly Ser Ala Thr Asp Val Met Ile Gln Leu Leu Thr Ser Lys Pro Phe
            530                 535                 540

Gly Ala Ala Gly Asp Ala Thr Thr Asp Thr Glu Val Ile Ala Ala
545                 550                 555                 560

Ser Leu Asn Ser Gln Lys Ala Val Thr Ile Ser Asp Gly Val Phe Ser
                565                 570                 575

Ser Ser Gly Ile Asn Ser Asn Tyr Cys Asn Leu Asp Gly Arg Gly Ser
                580                 585                 590

Gly Val Leu Ser His Arg Ser Ser Thr Gly Asn Tyr Leu Val Phe Asn
            595                 600                 605

Asn Pro Arg Thr Gly Arg Leu Ser Asn Ile Thr Val Glu Ser Asn Lys
            610                 615                 620

Ala Thr Asp Thr Thr Gln Gly Gln Gln Val Ser Leu Ala Gly Gly Ser
625                 630                 635                 640

Asp Val Thr Val Ser Asp Val Asn Phe Ser Asn Val Lys Gly Thr Gly
                645                 650                 655

Phe Ser Leu Ile Ala Tyr Pro Asn Asp Ala Pro Pro Asp Gly Leu Met
                660                 665                 670

Ile Lys Gly Ile Arg Gly Ser Tyr Ser Gly Tyr Ala Thr Asn Lys Ala
            675                 680                 685

Ala Gly Cys Val Leu Ala Asp Ser Ser Val Asn Ser Leu Ile Asp Asn
            690                 695                 700

Val Ile Ala Lys Asn Tyr Pro Gln Phe Gly Val Glu Leu Lys Gly
705                 710                 715                 720

Thr Ala Ser Tyr Asn Ile Val Ser Asn Val Ile Gly Ala Asp Cys Gln
                725                 730                 735

His Val Thr Tyr Asn Gly Thr Glu Gly Pro Ile Ala Pro Ser Asn Asn
                740                 745                 750

Leu Ile Lys Gly Val Met Ala Asn Asn Pro Lys Tyr Ala Ala Val Val
            755                 760                 765

Ala Gly Lys Gly Ser Thr Asn Leu Ile Ser Asp Val Leu Val Asp Tyr
            770                 775                 780

Ser Thr Ser Asp Ala Arg Gln Ala His Gly Val Thr Val Glu Gly Ser
785                 790                 795                 800
```

Asp Asn Val Ile Asn Val Leu Met Ser Gly Cys Asp Gly Thr Asn
                805                 810                 815

Ser Leu Gly Gln Arg Gln Thr Ala Thr Ile Ala Arg Phe Ile Gly Thr
            820                 825                 830

Ala Asn Asn Asn Tyr Ala Ser Val Phe Pro Ser Tyr Ser Ala Thr Gly
            835                 840                 845

Val Ile Thr Phe Glu Ser Gly Ser Thr Arg Asn Phe Val Glu Val Lys
850                 855                 860

His Pro Gly Arg Arg Asn Asp Leu Leu Ser Ser Ala Ser Thr Ile Asp
865                 870                 875                 880

Gly Ala Ala Thr Ile Asp Gly Thr Ser Asn Ser Asn Val Val His Ala
                885                 890                 895

Pro Ala Leu Gly Gln Tyr Ile Gly Ser Met Ser Gly Arg Phe Glu Trp
            900                 905                 910

Arg Ile Lys Ser Met Ser Leu Pro Ser Gly Val Leu Thr Ser Ala Asp
            915                 920                 925

Lys Tyr Arg Met Leu Gly Asp Gly Ala Val Ser Leu Ala Val Gly Gly
            930                 935                 940

Gly Thr Ser Ser Gln Val Arg Leu Phe Thr Ser Asp Gly Thr Ser Arg
945                 950                 955                 960

Thr Val Ser Leu Thr Asn Gly Asn Val Arg Leu Ser Thr Ser Ser Thr
                965                 970                 975

Gly Tyr Leu Gln Leu Gly Ala Asp Ala Met Thr Pro Asp Ser Thr Gly
            980                 985                 990

Thr Tyr Ala Leu Gly Ser Ala Ser Arg Ala Trp Ser Gly Gly Phe Thr
            995                 1000                1005

Gln Ala Ala Phe Thr Val Thr Ser Asp Ala Arg Cys Lys Thr Glu
    1010                1015                1020

Pro Leu Thr Ile Ser Asp Ala Leu Leu Asp Ala Trp Ser Glu Val
    1025                1030                1035

Asp Phe Val Gln Phe Gln Tyr Leu Asp Arg Val Glu Glu Lys Gly
    1040                1045                1050

Ala Asp Ser Ala Arg Trp His Phe Gly Ile Ile Ala Gln Arg Ala
    1055                1060                1065

Lys Glu Ala Phe Glu Arg His Gly Ile Asp Ala His Arg Tyr Gly
    1070                1075                1080

Phe Leu Cys Phe Asp Ser Trp Asp Asp Val Tyr Glu Glu Asp Ala
    1085                1090                1095

Asn Gly Ser Arg Lys Leu Ile Thr Pro Ala Gly Ser Arg Tyr Gly
    1100                1105                1110

Ile Arg Tyr Glu Glu Val Leu Ile Leu Glu Ala Ala Leu Met Arg
    1115                1120                1125

Arg Thr Ile Lys Arg Met Gln Glu Ala Leu Ala Ala Leu Pro Lys
    1130                1135                1140

<210> SEQ ID NO 14
<211> LENGTH: 1144
<212> TYPE: PRT
<213> ORGANISM: Artificial Sequence
<220> FEATURE:
<223> OTHER INFORMATION: K5 5.1

<400> SEQUENCE: 14

Met Ala Val Lys Ile Ser Gly Val Leu Lys Asp Gly Thr Gly Lys Pro
1               5                   10                  15

```
Val Gln Asn Cys Thr Ile Gln Leu Lys Ala Arg Arg Asn Ser Thr Thr
            20                  25                  30

Val Val Val Asn Thr Val Gly Ser Glu Asn Pro Asp Glu Ala Gly Arg
        35                  40                  45

Tyr Ser Met Asp Val Glu Tyr Gly Gln Tyr Ser Val Ile Leu Gln Val
 50                  55                  60

Asp Gly Phe Pro Pro Ser His Ala Gly Thr Ile Thr Val Tyr Glu Asp
 65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ser Ala Ala Gln Val Ala Ala Leu
130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Glu Ser
                180                 185                 190

Ser Lys Asn Ala Ala Ala Thr Ser Ala Gly Ala Ala Lys Thr Ser Glu
        195                 200                 205

Thr Asn Ala Ala Ala Ser Gln Gln Ser Ala Ala Thr Ser Ala Ser Thr
        210                 215                 220

Ala Ala Thr Lys Ala Ser Glu Ala Ala Thr Ser Ala Arg Asp Ala Val
225                 230                 235                 240

Ala Ser Lys Glu Ala Ala Lys Ser Ser Glu Thr Asn Ala Ser Ser Ser
                245                 250                 255

Ala Gly Arg Ala Ala Ser Ser Ala Thr Ala Ala Glu Asn Ser Ala Arg
                260                 265                 270

Ala Ala Lys Thr Ser Glu Thr Asn Ala Arg Ser Ser Glu Thr Ala Ala
                275                 280                 285

Glu Arg Ser Ala Ser Ala Ala Asp Ala Lys Thr Ala Ala Ala Gly
            290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ala Ile Arg
                325                 330                 335

Ala Lys Asn Ser Ala Lys Arg Ala Glu Asp Ile Ala Ser Ala Val Ala
                340                 345                 350

Leu Glu Asp Ala Asp Thr Thr Arg Lys Gly Ile Val Gln Leu Ser Ser
                355                 360                 365

Ala Thr Asn Ser Thr Ser Glu Thr Leu Ala Ala Thr Pro Lys Ala Val
        370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
            420                 425                 430
```

-continued

```
Val Ile Asp Ala Ser Pro Asp Ala Leu Asn Thr Leu Asn Glu Leu Ala
            435                 440                 445
Ala Ala Leu Gly Asn Asp Pro Asp Phe Ala Thr Thr Met Thr Asn Ala
450                 455                 460
Leu Ala Gly Lys Gln Pro Lys Asn Ala Thr Leu Thr Ala Leu Ala Gly
465                 470                 475                 480
Leu Ser Thr Ala Lys Asn Lys Leu Pro Tyr Phe Ala Glu Asn Asp Ala
            485                 490                 495
Ala Ser Leu Thr Glu Leu Thr Gln Val Gly Arg Asp Ile Leu Ala Lys
            500                 505                 510
Asn Ser Val Ala Asp Val Leu Glu Tyr Leu Gly Ala Gly Glu Asn Ser
            515                 520                 525
Gly Ser Ala Thr Asp Val Met Ile Gln Leu Ala Leu Thr Ser Lys Pro
530                 535                 540
Phe Gly Ala Ala Gly Asp Ala Thr Thr Asp Thr Glu Val Ile Ala
545                 550                 555                 560
Ala Ser Leu Asn Ser Gln Lys Ala Val Thr Ile Ser Asp Gly Val Phe
            565                 570                 575
Ser Ser Ser Gly Ile Asn Ser Asn Tyr Cys Asn Leu Asp Gly Arg Gly
            580                 585                 590
Ser Gly Val Leu Ser His Arg Ser Thr Gly Asn Tyr Leu Val Phe
            595                 600                 605
Asn Asn Pro Arg Thr Gly Arg Leu Ser Asn Ile Thr Val Glu Ser Asn
            610                 615                 620
Lys Ala Thr Asp Thr Thr Gln Gly Gln Gln Val Ser Leu Ala Gly Gly
625                 630                 635                 640
Ser Asp Val Thr Val Ser Asp Val Asn Phe Ser Asn Val Lys Gly Thr
            645                 650                 655
Gly Phe Ser Leu Ile Ala Tyr Pro Asn Asp Ala Pro Pro Asp Gly Leu
            660                 665                 670
Met Ile Lys Gly Ile Arg Gly Ser Tyr Ser Gly Tyr Ala Thr Asn Lys
            675                 680                 685
Ala Ala Gly Cys Val Leu Ala Asp Ser Ser Val Asn Ser Leu Ile Asp
690                 695                 700
Asn Val Ile Ala Lys Asn Tyr Pro Gln Phe Gly Ala Val Glu Leu Lys
705                 710                 715                 720
Gly Thr Ala Ser Tyr Asn Ile Val Ser Asn Val Ile Gly Ala Asp Cys
            725                 730                 735
Gln His Val Thr Tyr Asn Gly Thr Glu Gly Pro Ile Ala Pro Ser Asn
            740                 745                 750
Asn Leu Ile Lys Gly Val Met Ala Asn Pro Lys Tyr Ala Ala Val
            755                 760                 765
Val Ala Gly Lys Gly Ser Thr Asn Leu Ile Ser Asp Val Leu Val Asp
770                 775                 780
Tyr Ser Thr Ser Asp Ala Arg Gln Ala His Gly Val Thr Val Glu Gly
785                 790                 795                 800
Ser Asp Asn Val Ile Asn Asn Val Leu Met Ser Gly Cys Asp Gly Thr
            805                 810                 815
Asn Ser Leu Gly Gln Arg Gln Thr Ala Thr Ile Ala Arg Phe Ile Gly
            820                 825                 830
Thr Ala Asn Asn Asn Tyr Ala Ser Val Phe Pro Ser Tyr Ser Ala Thr
835                 840                 845
Gly Val Ile Thr Phe Glu Ser Gly Ser Thr Arg Asn Phe Val Glu Val
```

```
                850                 855                 860

Lys His Pro Gly Arg Arg Asn Asp Leu Leu Ser Ser Ala Ser Thr Ile
865                 870                 875                 880

Asp Gly Ala Ala Thr Ile Asp Gly Thr Ser Asn Ser Asn Val Val His
                885                 890                 895

Ala Pro Ala Leu Gly Gln Tyr Ile Gly Ser Met Ser Gly Arg Phe Glu
                900                 905                 910

Trp Arg Ile Lys Ser Met Ser Leu Pro Ser Gly Val Leu Thr Ser Ala
                915                 920                 925

Asp Lys Tyr Arg Met Leu Gly Asp Gly Ala Val Ser Leu Ala Val Gly
            930                 935                 940

Gly Gly Thr Ser Ser Gln Val Arg Leu Phe Thr Ser Asp Gly Thr Ser
945                 950                 955                 960

Arg Thr Val Ser Leu Thr Asn Gly Asn Val Arg Leu Ser Thr Ser Ser
                965                 970                 975

Thr Gly Tyr Leu Gln Leu Gly Ala Asp Ala Met Thr Pro Asp Ser Thr
            980                 985                 990

Gly Thr Tyr Ala Leu Gly Ser Ala Ser Arg Ala Trp Ser Gly Gly Phe
            995                 1000                1005

Thr Gln Ala Ala Phe Thr Val Thr Ser Asp Ala Arg Cys Lys Thr
    1010                1015                1020

Glu Pro Leu Thr Ile Ser Asp Ala Leu Leu Asp Ala Trp Ser Glu
    1025                1030                1035

Val Asp Phe Val Gln Phe Gln Tyr Leu Asp Arg Val Glu Glu Lys
    1040                1045                1050

Gly Ala Asp Ser Ala Arg Trp His Phe Gly Ile Ile Ala Gln Arg
    1055                1060                1065

Ala Lys Glu Ala Phe Glu Arg His Gly Ile Asp Ala His Arg Tyr
    1070                1075                1080

Gly Phe Leu Cys Phe Asp Ser Trp Asp Asp Val Tyr Glu Glu Asp
    1085                1090                1095

Ala Asn Gly Ser Arg Lys Leu Ile Thr Pro Ala Gly Ser Arg Tyr
    1100                1105                1110

Gly Ile Arg Tyr Glu Glu Val Leu Ile Leu Glu Ala Ala Leu Met
    1115                1120                1125

Arg Arg Thr Ile Lys Arg Met Gln Glu Ala Leu Ala Ala Leu Pro
    1130                1135                1140

Lys

<210> SEQ ID NO 15
<211> LENGTH: 1186
<212> TYPE: PRT
<213> ORGANISM: Artificial Sequence
<220> FEATURE:
<223> OTHER INFORMATION: STF-V10

<400> SEQUENCE: 15

Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
                20                  25                  30

Val Val Val Asn Thr Val Gly Ser Glu Asn Pro Asp Glu Ala Gly Arg
            35                  40                  45

Tyr Ser Met Asp Val Glu Tyr Gly Gln Tyr Ser Val Ile Leu Gln Val
        50                  55                  60
```

-continued

```
Asp Gly Phe Pro Pro Ser His Ala Gly Thr Ile Thr Val Tyr Glu Asp
 65                  70                  75                  80

Ser Gln Pro Gly Thr Leu Asn Asp Phe Leu Cys Ala Met Thr Glu Asp
                 85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ser Ala Ala Gln Val Ala Ala Leu
130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Glu Ser
            180                 185                 190

Ser Lys Asn Ala Ala Ala Thr Ser Ala Gly Ala Ala Lys Thr Ser Glu
        195                 200                 205

Thr Asn Ala Ala Ala Ser Gln Gln Ser Ala Ala Thr Ser Ala Ser Thr
210                 215                 220

Ala Ala Thr Lys Ala Ser Glu Ala Ala Thr Ser Ala Arg Asp Ala Val
225                 230                 235                 240

Ala Ser Lys Glu Ala Ala Lys Ser Ser Glu Thr Asn Ala Ser Ser Ser
                245                 250                 255

Ala Gly Arg Ala Ala Ser Ser Ala Thr Ala Ala Glu Asn Ser Ala Arg
            260                 265                 270

Ala Ala Lys Thr Ser Glu Thr Asn Ala Arg Ser Ser Glu Thr Ala Ala
        275                 280                 285

Glu Arg Ser Ala Ser Ala Ala Asp Ala Lys Thr Ala Ala Ala Gly
290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ala Ile Arg
                325                 330                 335

Ala Lys Asn Ser Ala Lys Arg Ala Glu Asp Ile Ala Ser Ala Val Ala
            340                 345                 350

Leu Glu Asp Ala Asp Thr Thr Arg Lys Gly Ile Val Gln Leu Ser Ser
        355                 360                 365

Ala Thr Asn Ser Thr Ser Glu Thr Leu Ala Ala Thr Pro Lys Ala Val
370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
            420                 425                 430

Val Ile Asp Ala Ser Pro Asp Ala Leu Asn Thr Leu Asn Glu Leu Ala
        435                 440                 445

Ala Ala Leu Gly Asn Asp Pro Asp Phe Ala Thr Thr Met Thr Asn Ala
450                 455                 460

Leu Ala Gly Lys Gln Pro Lys Asn Ala Thr Leu Thr Ala Leu Ala Gly
465                 470                 475                 480
```

```
Leu Ser Thr Ala Lys Asn Lys Leu Pro Tyr Phe Ala Glu Asn Asp Ala
                485                 490                 495

Ala Ser Leu Thr Glu Leu Thr Gln Val Gly Arg Asp Ile Leu Ala Lys
            500                 505                 510

Asn Ser Val Ala Asp Val Leu Glu Tyr Leu Gly Ala Gly Glu Asn Ser
        515                 520                 525

Ala Ala Asn Asp Gly Phe Lys Phe Ile Gly Gln Cys Pro Asp Ile Leu
    530                 535                 540

Thr Leu Arg Thr Ile Glu Pro Glu Lys Asn Gly Gln Arg Ile Thr Leu
545                 550                 555                 560

Arg Gln His Thr Ile Gly Thr Gly Leu Gly Gly Val Phe Arg Ala
                565                 570                 575

Val Leu Asp Gly Thr Gly Tyr Thr Asp Asp Gly Val Val Ile Lys
            580                 585                 590

Thr Ala Gly Gly Ser Val Trp Leu Arg Val Asn Ala Asp Lys Val Asn
        595                 600                 605

Pro Phe Met Phe Gly Ala Thr Gly Val Ala Asp Thr Ala Ala Leu
    610                 615                 620

Gln Lys Met Leu Glu Cys Gly Arg Ala Ala Glu Leu Gly Thr Asn Val
625                 630                 635                 640

Trp Lys Ala Ser Asn Leu Glu Leu Asn Asn Lys Ser Cys Ser Leu Ser
                645                 650                 655

Gly Ser Gly Leu His Val Ser Arg Ile Glu Gln Ile Ser Gly Ala Thr
            660                 665                 670

Gly Ala Leu Leu Thr Ile Thr Gln Asp Cys Ser Leu Ile Tyr Leu Ser
        675                 680                 685

Asp Cys Gly Leu Tyr Gly Asp Gly Ile Thr Ala Gly Thr Ser Gly Val
    690                 695                 700

Thr Met Glu Thr Gly Asn Pro Gly Gly Ala Pro Ser Tyr Pro Phe Asn
705                 710                 715                 720

Thr Ala Pro Asp Val Arg Arg Asp Leu Tyr Ile Ser Asn Val His Ile
                725                 730                 735

Thr Gly Phe Asp Glu Leu Gly Phe Asp Tyr Pro Glu Thr Asn Phe Ser
            740                 745                 750

Val Ser Thr His Gly Leu Phe Ile Arg Asn Ile Lys Lys Thr Gly Ala
        755                 760                 765

Lys Ile Gly Thr Thr Asp Phe Thr Trp Thr Asn Leu Gln Ile Asp Thr
    770                 775                 780

Cys Gly Gln Glu Cys Leu Val Leu Asp Gly Ala Gly Asn Cys Arg Ile
785                 790                 795                 800

Ile Gly Ala Lys Leu Ile Trp Ala Gly Ser Glu Asn Glu Thr Pro Tyr
                805                 810                 815

Ser Gly Leu Arg Ile Ser Asn Ser Gln Asn Val Asn Met Thr Gly Val
            820                 825                 830

Glu Leu Gln Asp Cys Ala Tyr Asp Gly Leu Tyr Ile Lys Asn Ser Thr
        835                 840                 845

Val Ala Ile Ser Gly Leu Asn Thr Asn Arg Asn Ser Ala Ser Ser Asn
    850                 855                 860

Leu Ser Tyr His Asn Met Val Phe Glu Asn Ser Ile Val Thr Val Asp
865                 870                 875                 880

Gly Tyr Val Cys Arg Asn Tyr Ala Ala Thr Ser Leu Tyr Asp Leu Asn
                885                 890                 895

Ser Gln Ala Gly Asn Val Arg Cys Ile Gly Ser Asp Ser Thr Val Leu
```

```
                        900                 905                 910
Ile Asn Gly Ile Tyr Glu Ser Glu Val Asn Ser Glu Arg Leu Met Gly
            915                 920                 925

Asp Asn Asn Leu Ile Gln Pro Tyr Ser Gly Asp Leu Ile Ile Asn Gly
        930                 935                 940

Leu Lys Asn Tyr Tyr Thr Tyr Thr Gly Ser Val Lys Asn Asn Ile Pro
945                 950                 955                 960

Thr Phe Asp Gly Val Val Thr Thr Ala Thr Tyr Val Ser Ala Pro Ser
                965                 970                 975

Ile Leu Gly Gln Gly Asn Met Leu Lys Leu Thr Gln Ser Asn Lys Asp
            980                 985                 990

Lys Leu Leu Phe Ser Asp Lys Val Ser Arg His Gly Cys Thr Ile Gly
        995                 1000                1005

Leu Val Leu Ile Pro Ser Phe Thr Gly Ala Thr Thr Met Thr Ala
    1010                1015                1020

Phe Thr Leu Gly Ser Gly Tyr Ser Pro Ser Gly Asn Ser Ala Val
    1025                1030                1035

Met Gln Phe Ile Val Asn Ser Ser Gly Val Gln Thr Ile Ala Ile
    1040                1045                1050

Leu Leu Ser Gly Asp Gly Ile Thr Gln Thr Leu Thr Ser Asp Leu
    1055                1060                1065

Thr Thr Glu Gln Ala Leu Ala Ser Gly Gly Val Tyr His Phe Ala
    1070                1075                1080

Met Gly Phe Ala Pro Gly Arg Leu Trp Trp Ser Ile Ile Asp Ile
    1085                1090                1095

Asn Thr Gly Arg Arg Ile Arg Arg Ala Tyr Arg Gln Pro Asp Leu
    1100                1105                1110

His Ala Ala Phe Asn Ser Ile Phe Asn Ser Gly Thr Ser Ser Ile
    1115                1120                1125

Thr Ala Phe Ser Gly Pro Leu Ala Gly Asp Ile Ala Cys Glu Gly
    1130                1135                1140

Ala Gly Ser His Val Tyr Val Gly Gly Phe Ser Ser Glu Ser Asp
    1145                1150                1155

Tyr Ala Ala Ser Arg Met Tyr Gly Leu Phe Thr Pro Val Asp Leu
    1160                1165                1170

Asp Lys Gln Tyr Ser Phe Arg Thr Leu Asn Gly Asn Ile
    1175                1180                1185

<210> SEQ ID NO 16
<211> LENGTH: 875
<212> TYPE: PRT
<213> ORGANISM: Bacteriophage V10

<400> SEQUENCE: 16

Met Thr Val Ser Thr Glu Val Asn His Asn Glu Tyr Thr Gly Asn Gly
1               5                   10                  15

Val Thr Thr Ser Phe Pro Tyr Thr Phe Arg Val Phe Lys Glu Ser Asp
            20                  25                  30

Leu Val Val Gln Val Val Asp Leu Asn Asp Asn Ile Thr Val Leu Thr
        35                  40                  45

Leu Asp Thr Asp Tyr Thr Val Thr Gly Ala Gly Gly Tyr Glu Gly Gly
    50                  55                  60

Asn Val Ile Leu Ala Thr Ala Leu Ala Asn Gly Tyr Gln Ile Ser Ile
65                  70                  75                  80
```

```
Ser Arg Glu Leu Ser Val Thr Gln Glu Thr Asp Leu Arg Asn Gln Gly
                85                  90                  95

Lys Phe Phe Ala Glu Val His Glu Asp Ala Phe Asp Lys Leu Thr Met
            100                 105                 110

Leu Ile Gln Gln Val Arg Ser Trp Phe Ser Leu Ala Leu Arg Lys Pro
        115                 120                 125

Ser Phe Val Ala Asn Tyr Tyr Asp Ala Met Asp Asn Tyr Ile Arg Asn
130                 135                 140

Leu Arg Asp Pro Val Arg Pro Gln Asp Ala Ala Thr Lys Lys Tyr Val
145                 150                 155                 160

Asp Gly Val Ala Glu Thr Asn Leu Ser Arg Thr Leu Arg Thr Pro Glu
                165                 170                 175

Pro Ile Pro Ala Leu Pro Gly Ile Glu Gln Arg Lys Asn Lys Ile Val
            180                 185                 190

Ala Met Asp Asp Thr Gly Asn Pro Ile Met Val Leu Pro Glu Ser Gly
        195                 200                 205

Ser Ala Thr Asp Val Met Ile Gln Leu Ala Ala Asn Asp Gly Phe Lys
210                 215                 220

Phe Ile Gly Gln Cys Pro Asp Ile Leu Thr Leu Arg Thr Ile Glu Pro
225                 230                 235                 240

Glu Lys Asn Gly Gln Arg Ile Thr Leu Arg Gln His Thr Ile Gly Thr
                245                 250                 255

Gly Leu Gly Gly Gly Val Phe Arg Ala Val Leu Asp Gly Thr Gly Tyr
            260                 265                 270

Thr Asp Asp Asp Gly Val Val Ile Lys Thr Ala Gly Gly Ser Val Trp
        275                 280                 285

Leu Arg Val Asn Ala Asp Lys Val Asn Pro Phe Met Phe Gly Ala Thr
290                 295                 300

Gly Val Ala Asp Asp Thr Ala Ala Leu Gln Lys Met Leu Glu Cys Gly
305                 310                 315                 320

Arg Ala Ala Glu Leu Gly Thr Asn Val Trp Lys Ala Ser Asn Leu Glu
                325                 330                 335

Leu Asn Asn Lys Ser Cys Ser Leu Ser Gly Ser Gly Leu His Val Ser
            340                 345                 350

Arg Ile Glu Gln Ile Ser Gly Ala Thr Gly Ala Leu Leu Thr Ile Thr
        355                 360                 365

Gln Asp Cys Ser Leu Ile Tyr Leu Ser Asp Cys Gly Leu Tyr Gly Asp
370                 375                 380

Gly Ile Thr Ala Gly Thr Ser Gly Val Thr Met Glu Thr Gly Asn Pro
385                 390                 395                 400

Gly Gly Ala Pro Ser Tyr Pro Phe Asn Thr Ala Pro Asp Val Arg Arg
                405                 410                 415

Asp Leu Tyr Ile Ser Asn Val His Ile Thr Gly Phe Asp Glu Leu Gly
            420                 425                 430

Phe Asp Tyr Pro Glu Thr Asn Phe Ser Val Ser Thr His Gly Leu Phe
        435                 440                 445

Ile Arg Asn Ile Lys Lys Thr Gly Ala Lys Ile Gly Thr Thr Asp Phe
450                 455                 460

Thr Trp Thr Asn Leu Gln Ile Asp Thr Cys Gly Gln Glu Cys Leu Val
465                 470                 475                 480

Leu Asp Gly Ala Gly Asn Cys Arg Ile Ile Gly Ala Lys Leu Ile Trp
                485                 490                 495

Ala Gly Ser Glu Asn Glu Thr Pro Tyr Ser Gly Leu Arg Ile Ser Asn
```

```
            500                 505                 510
Ser Gln Asn Val Asn Met Thr Gly Val Glu Leu Gln Asp Cys Ala Tyr
            515                 520                 525

Asp Gly Leu Tyr Ile Lys Asn Ser Thr Val Ala Ile Ser Gly Leu Asn
            530                 535                 540

Thr Asn Arg Asn Ser Ala Ser Ser Asn Leu Ser Tyr His Asn Met Val
545                 550                 555                 560

Phe Glu Asn Ser Ile Val Thr Val Asp Gly Tyr Val Cys Arg Asn Tyr
                565                 570                 575

Ala Ala Thr Ser Leu Tyr Asp Leu Asn Ser Gln Ala Gly Asn Val Arg
            580                 585                 590

Cys Ile Gly Ser Asp Ser Thr Val Leu Ile Asn Gly Ile Tyr Glu Ser
            595                 600                 605

Glu Val Asn Ser Glu Arg Leu Met Gly Asp Asn Leu Ile Gln Pro
            610                 615                 620

Tyr Ser Gly Asp Leu Ile Ile Asn Gly Leu Lys Asn Tyr Tyr Thr Tyr
625                 630                 635                 640

Thr Gly Ser Val Lys Asn Asn Ile Pro Thr Phe Asp Gly Val Val Thr
                645                 650                 655

Thr Ala Thr Tyr Val Ser Ala Pro Ser Ile Leu Gly Gln Gly Asn Met
            660                 665                 670

Leu Lys Leu Thr Gln Ser Asn Lys Asp Lys Leu Leu Phe Ser Asp Lys
            675                 680                 685

Val Ser Arg His Gly Cys Thr Ile Gly Leu Val Leu Ile Pro Ser Phe
            690                 695                 700

Thr Gly Ala Thr Thr Met Thr Ala Phe Thr Leu Gly Ser Gly Tyr Ser
705                 710                 715                 720

Pro Ser Gly Asn Ser Ala Val Met Gln Phe Ile Val Asn Ser Ser Gly
                725                 730                 735

Val Gln Thr Ile Ala Ile Leu Leu Ser Gly Asp Gly Ile Thr Gln Thr
            740                 745                 750

Leu Thr Ser Asp Leu Thr Thr Glu Gln Ala Leu Ala Ser Gly Gly Val
            755                 760                 765

Tyr His Phe Ala Met Gly Phe Ala Pro Gly Arg Leu Trp Trp Ser Ile
            770                 775                 780

Ile Asp Ile Asn Thr Gly Arg Arg Ile Arg Ala Tyr Arg Gln Pro
785                 790                 795                 800

Asp Leu His Ala Ala Phe Asn Ser Ile Phe Asn Ser Gly Thr Ser Ser
                805                 810                 815

Ile Thr Ala Phe Ser Gly Pro Leu Ala Gly Asp Ile Ala Cys Glu Gly
            820                 825                 830

Ala Gly Ser His Val Tyr Val Gly Gly Phe Ser Ser Glu Ser Asp Tyr
            835                 840                 845

Ala Ala Ser Arg Met Tyr Gly Leu Phe Thr Pro Val Asp Leu Asp Lys
            850                 855                 860

Gln Tyr Ser Phe Arg Thr Leu Asn Gly Asn Ile
865                 870                 875

<210> SEQ ID NO 17
<211> LENGTH: 3558
<212> TYPE: DNA
<213> ORGANISM: Artificial Sequence
<220> FEATURE:
<223> OTHER INFORMATION: STF-V10-[FA]
```

<400> SEQUENCE: 17

```
atggcagtaa agatttcagg agtcctgaaa gacggcacag gaaaaccggt acagaactgc      60
accattcagc tgaaagccag acgtaacagc accacggtgg tggtgaacac ggtgggctca     120
gagaatccgg atgaagccgg gcgttacagc atggatgtgg agtacggtca gtacagtgtc     180
atcctgcagg ttgacggttt tccaccatcg cacgccggga ccatcaccgt gtatgaagat     240
tcacaaccgg ggacgctgaa tgattttctc tgtgccatga cggaggatga tgcccggccg     300
gaggtgctgc gtcgtcttga actgatggtg gaagaggtgg cgcgtaacgc gtccgtggtg     360
gcacagagta cggcagacgc gaagaaatca gccggcgatg ccagtgcatc agctgctcag     420
gtcgcggccc ttgtgactga tgcaactgac tcagcacgcg ccgccagcac gtccgccgga     480
caggctgcat cgtcagctca ggaagcgtcc tccggcgcag aagcggcatc agcaaaggcc     540
actgaagcgg aaaaaagtgc cgcagccgca gagtcctcaa aaaacgcggc ggccaccagt     600
gccggtgcgg cgaaaacgtc agaaacgaat gctgcagcgt cacaacaatc agccgccacg     660
tctgcctcca ccgcggccac gaaagcgtca gaggccgcca cttcagcacg agatgcggtg     720
gcctcaaaag aggcagcaaa atcatcagaa acgaacgcat catcaagtgc cggtcgtgca     780
gcttcctcgg caacggcggc agaaaattct gccaggcgg caaaaacgtc cgagacgaat     840
gccaggtcat ctgaaacagc agcggaacgg agcgcctctg ccgcggcaga cgcaaaaaca     900
gcggcggcg gagtgcgtc aacggcatcc acgaaggcga cagaggctgc gggaagtgcg     960
gtatcagcat cgcagagcaa aagtgcggca aagcggcgg caatacgtgc aaaaaattcg    1020
gcaaaacgtg cagaagatat agcttcagct gtcgcgcttg aggatgcgga cacaacgaga    1080
aaggggatag tgcagctcag cagtgcaacc aacagcacgt ctgaaacgct tgctgcaacg    1140
ccaaaggcgt taaggtggt aatggatgag actaatcgta aggcacctct ggacagtccg    1200
gcactgaccg gaacgccaac agcaccaacc gcgctcaggg aacaaacaa tacccagatt    1260
gcgaacaccg cttttgtact ggccgcgatt gcagatgtta tcgacgcgtc acctgacgca    1320
ctgaatacgc tgaatgaact ggccgcagcg ctcgggaatg atccagattt tgctaccacc    1380
atgactaacg cgcttgcggg taaacaaccg aagaatgcga cactgacggc gctggcaggg    1440
cttttccacgg cgaaaaataa attaccgtat tttgcggaaa atgatgccgc cagcctgact    1500
gaactgactc aggttggcag ggatattctg gcaaaaaatt ccgttgcaga tgttcttgaa    1560
taccttgggg ccggtgagaa ttcggcggca aatgatggct tcgcattcat cggtcagtgc    1620
ccagacatct tgaccctgcg tactatcgag ccggaaaaaa acggtcagcg tatcaccctta   1680
cgtcaacata cgattggcac tggcttaggc ggtggcgttt ccgtgcagt tctggacggc    1740
actggctata ccgatgacga cggtgtggtg atcaaaaccg ctgggggcag cgtttggctg    1800
cgtgtcaacg ctgacaaagt taacccgttc atgttcggtg caaccggagt agcggacgac    1860
accgccgccc tgcaaaaaat gctggaatgc ggtcgtgcgg cggaactggg gactaacgta    1920
tggaaagcaa gcaatctgga actgaacaac aaatcttgct ctctgtccgg cagtggcctg    1980
cacgtttctc gtattgaaca gatttccggt gcaaccggag cattgttaac catcacccaa    2040
gactgttcgc tgatttacct gtccgattgt ggcctgacg gcgatggcat caccgcaggc    2100
acgagcggtg ttactatgga aacgggtaat ccgggtggcg ctccgtctta ccctttcaat    2160
accgctccgg acgttcgtcg tgacctgtac atctctaacg tgcacatcac gggcttcgac    2220
gagctgggtt ttgattatcc ggaaaccaat ttctctgttt cgacgcatgg cctcttcatc    2280
cgtaacatca aaaaaacggg tgcaaagatt ggtactacgg acttcacttg gactaacctg    2340
```

```
caaattgata cttgcggtca ggaatgtctg gtgctggacg gtgcgggtaa ctgccgtatt    2400
attggtgcaa aactgatttg ggcaggtagc gaaaacgaaa cgccatactc tggcctgcgt    2460
attagcaact ctcaaaatgt aaatatgact ggcgtagagt tacaagactg cgcgtatgat    2520
ggtttataca tcaagaactc tacgcttgca atttcaggct taaacaccaa tcgcaatagc    2580
gcatcctcta atctgtccta ccataacatg gtattcgaaa attctattgt aactgttgat    2640
ggttatgtgt gtcgtaacta cgcggcgact tcgctgtacg acctgaacag ccaagcaggc    2700
aacgtccgtt gcatcggtag cgacagcacc gttttaatca acggcatcta cgaaagcgaa    2760
gtcaatagcg agcgcctgat gggtgataac aacctgatcc agccgtatag tggtgatctg    2820
atcattaacg gcctgaaaaa ttactacacc tatactggta gcgtaaaaaa caacattccg    2880
accttcgacg gcgttgttac tacggcaacc tatgtgagcg caccgtctat tctgggtcag    2940
ggcaatatgc tcaaactgac ccagtctaat aaagacaaac tgttatttag cgataaagtt    3000
agccgtcatg gctgtaccat cggcttagtt ctgattccgt cctttacggg cgcgaccact    3060
atgacggcgt tcacgctggg tagcggttac tctccatccg gtaactccgc cgtgatgcag    3120
ttcattgtta acagttccgg tgtacaaacc attgcgattt tattatccgg cgacggtatt    3180
acccaaaccc tgaccagcga tctgaccacg gaacaagcac tggcgagcgg tggcgtgtat    3240
cattttgcaa tgggttttgc gccgggtcgt ttatggtgga gcattatcga tattaacacg    3300
ggcaggcgta ttcgtcgcgc ctaccgtcag ccggatctgc acgcggcgtt caactctatc    3360
ttcaactccg gcacgtcgtc tattaccgca tttagcgggc cactggcggg cgacattgct    3420
tgcgaaggtg caggtagcca tgtatacgtt ggcggttttt cgtcggaatc tgattacgcg    3480
gctagccgta tgtatggcct gttcactccg gtcgatctgg acaagcagta tagcttccgt    3540
accctgaacg gtaacatt                                                  3558
```

<210> SEQ ID NO 18
<211> LENGTH: 3558
<212> TYPE: DNA
<213> ORGANISM: Artificial Sequence
<220> FEATURE:
<223> OTHER INFORMATION: STF-V10-[AAH]

<400> SEQUENCE: 18

```
atggcagtaa agatttcagg agtcctgaaa gacggcacag gaaaaccggt acagaactgc     60
accattcagc tgaaagccag acgtaacagc accacggtgg tggtgaacac ggtgggctca    120
gagaatccgg atgaagccgg cgcgttacagc atggatgtgt agtacggtca gtacagtgtc    180
atcctgcagg ttgacggttt tccaccatcg cacgccggga ccatcaccgt gtatgaagat    240
tcacaaccgg ggacgctgaa tgattttctc tgtgccatga cggaggatga tgcccggccg    300
gaggtgctgc gtcgtcttga actgatggtg gaagaggtgg cgcgtaacgc gtccgtggtg    360
gcacagagta cggcagacgc gaagaaatca gccggcgatg ccagtgcatc agctgctcag    420
gtcgcggccc ttgtgactga tgcaactgac tcagcacgcg ccgccagcac gtccgccgga    480
caggctgcat cgtcagctca ggaagcgtcc tccggcgcag aagcggcatc agcaaaggcc    540
actgaagcgg aaaaaagtgc cgcagccgca gagtcctcaa aaaacgcggc ggccaccagt    600
gccggtgcgg cgaaaacgtc agaaacgaat gctgcagcgt cacaacaatc agccgccacg    660
tctgcctcca ccgcggccac gaaagcgtca gaggccgcca cttcagcacg agatgcggtg    720
gcctcaaaag aggcagcaaa atcatcagaa acgaacgcat catcaagtgc cggtcgtgca    780
```

```
gcttcctcgg caacggcggc agaaaattct gccagggcgg caaaaacgtc cgagacgaat     840
gccaggtcat ctgaaacagc agcggaacgg agcgcctctg ccgcggcaga cgcaaaaaca     900
gcggcggcgg ggagtgcgtc aacggcatcc acgaaggcga cagaggctgc gggaagtgcg     960
gtatcagcat cgcagagcaa aagtgcggca gaagcggcgg caatacgtgc aaaaaattcg    1020
gcaaaacgtg cagaagatat agcttcagct gtcgcgcttg aggatgcgga cacaacgaga    1080
aaggggatag tgcagctcag cagtgcaacc aacagcacgt ctgaaacgct tgctgcaacg    1140
ccaaaggcgg ttaaggtggt aatggatgag actaatcgta aggcacctct ggacagtccg    1200
gcactgaccg gaacgccaac agcaccaacc gcgctcaggg gaacaaacaa tacccagatt    1260
gcgaacaccg cttttgtact ggccgcgatt gcagatgtta tcgacgcgtc acctgacgca    1320
ctgaatacgc tgaatgaact ggccgcagcg ctcgggaatg atccagattt tgctaccacc    1380
atgactaacg cgcttgcggg taaacaaccg aagaatgcga cactgacggc gctggcaggg    1440 cttttccacgg cgaaaaataa attaccgtat tttgcggaaa atgatgccgc cagcctgact    1500
gaactgactc aggttggcag ggatattctg gcaaaaaatt ccgttgcaga tgttcttgaa    1560
taccttgggg ccggtgagaa ttcggcggca aatgatggcg cggcacacat cggtcagtgc    1620
ccagacatct tgaccctgcg tactatcgag ccggaaaaaa acggtcagcg tatcaccta    1680 cgtcaacata cgattggcac tggcttaggc ggtggcgttt ccgtgcagt tctggacggc    1740 actggctata ccgatgacga cggtgtggtg atcaaaaccg ctgggggcag cgtttggctg    1800
cgtgtcaacg ctgacaaagt taacccgttc atgttcggtg caaccggagt agcggacgac    1860
accgccgccc tgcaaaaaat gctggaatgc ggtcgtgcgg cggaactggg gactaacgta    1920
tggaaagcaa gcaatctgga actgaacaac aaatcttgct ctctgtccgg cagtggcctg    1980
cacgtttctc gtattgaaca gatttccggt gcaaccggag cattgttaac catcaccca    2040 gactgttcgc tgatttacct gtccgattgt ggcctgtacg gcgatggcat caccgcaggc    2100
acgagcggtt ttactatgga aacgggtaat ccggtggcg ctccgtctta ccctttcaat    2160
accgctccgg acgttcgtcg tgacctgtac atctctaacg tgcacatcac gggcttcgac    2220
gagctgggtt ttgattatcc ggaaaccaat ttctctgttt cgacgcatgg cctcttcatc    2280
cgtaacatca aaaaaacggg tgcaaagatt ggtactacgg acttcacttg gactaacctg    2340
caaattgata cttgcggtca ggaatgtctg gtgctggacg gtgcgggtaa ctgccgtatt    2400
attggtgcaa aactgatttg ggcaggtagc gaaaacgaaa cgccatactc tggcctgcgt    2460
attagcaact ctcaaaatgt aaatatgact ggcgtagagt tacaagactg cgcgtatgat    2520
ggtttataca tcaagaactc tacggttgca atttcaggct taaacaccaa tcgcaatagc    2580
gcatcctcta atctgtccta ccataacatg gtattcgaaa attctattgt aactgttgat    2640
ggttatgtgt gtcgtaacta cgcggcgact tcgctgtacg acctgaacag ccaagcaggc    2700
aacgtccgtt gcatcggtag cgacagcacc gttttaatca acggcatcta cgaaagcgaa    2760
gtcaatagcg agcgcctgat gggtgataac aacctgatcc agccgtatag tggtgatctg    2820
atcattaacg gcctgaaaaa ttactacacc tatactggta gcgtaaaaaa caacattccg    2880
accttcgacg gcgttgttac tacggcaacc tatgtgagcg caccgtctat tctgggtcag    2940
ggcaatatgc tcaaactgac ccagtctaat aaagacaaac tgttatttag cgataaagtt    3000
agccgtcatg gctgtaccat cggcttagtt ctgattccgt cctttacggg cgcgaccact    3060 atgacgcgcgt tcacgctggg tagcggttac tctccatccg gtaactccgc cgtgatgcag    3120
ttcattgtta acagttccgg tgtacaaacc attgcgattt tattatccgg cgacggtatt    3180
```

```
acccaaaccc tgaccagcga tctgaccacg gaacaagcac tggcgagcgg tggcgtgtat    3240 catttttgcaa tgggttttgc gccgggtcgt ttatggtgga gcattatcga tattaacacg    3300
ggcaggcgta ttcgtcgcgc ctaccgtcag ccggatctgc acgcggcgtt caactctatc    3360
ttcaactccg gcacgtcgtc tattaccgca tttagcgggc cactggcggg cgacattgct    3420
tgcgaaggtg caggtagcca tgtatacgtt ggcggttttt cgtcggaatc tgattacgcg    3480
gctagccgta tgtatggcct gttcactccg gtcgatctgg acaagcagta tagcttccgt    3540
accctgaacg gtaacatt                                                  3558
```

<210> SEQ ID NO 19
<211> LENGTH: 3588
<212> TYPE: DNA
<213> ORGANISM: Artificial Sequence
<220> FEATURE:
<223> OTHER INFORMATION: STF-V10-[Helix]

<400> SEQUENCE: 19

```
atggcagtaa agatttcagg agtcctgaaa gacggcacag gaaaaccggt acagaactgc      60
accattcagc tgaaagccag acgtaacagc accacggtgg tggtgaacac ggtgggctca     120
gagaatccgg atgaagccgg gcgttacagc atggatgtgg agtacggtca gtacagtgtc     180
atcctgcagg ttgacggttt tccaccatcg cacgccggga ccatcaccgt gtatgaagat     240
tcacaaccgg ggacgctgaa tgattttctc tgtgccatga cggaggatga tgcccggccg     300
gaggtgctgc gtcgtcttga actgatggtg gaagaggtgg cgcgtaacgc gtccgtggtg     360
gcacagagta cggcagacgc gaagaaatca gccggcgatg ccagtgcatc agctgctcag     420
gtcgcggccc ttgtgactga tgcaactgac tcagcacgcg ccgccagcac gtccgccgga     480
caggctgcat cgtcagctca ggaagcgtcc tccggcgcag aagcggcatc agcaaaggcc     540
actgaagcgg aaaaaagtgc cgcagccgca gagtcctcaa aaaacgcggc ggccaccagt     600
gccggtgcgg cgaaaacgtc agaaacgaat gctgcagcgt cacaacaatc agccgccacg     660
tctgcctcca ccgcggccac gaaagcgtca gaggccgcca cttcagcacg agatgcggtg     720
gcctcaaaag aggcagcaaa atcatcagaa acgaacgcat catcaagtgc cggtcgtgca     780
gcttcctcgg caacggcggc agaaaaattct gccagggcgg caaaaacgtc cgagacgaat     840
gccaggtcat ctgaaacagc agcggaacgg agcgcctctg ccgcggcaga cgcaaaaaca     900
gcggcggcgg ggagtgcgtc aacggcatcc acgaaggcga cagaggctgc gggaagtgcg     960
gtatcagcat cgcagagcaa aagtgcggca gaagcggcgg caatacgtgc aaaaaattcg    1020
gcaaaacgtg cagaagatat agcttcagct gtcgcgcttg aggatgcgga cacaacgaga    1080 aagggggatag tgcagctcag cagtgcaacc aacagcacgt ctgaaacgct tgctgcaacg    1140
ccaaaggcgg ttaaggtggt aatggatgag actaatcgta aggcacctct ggacagtccg    1200
gcactgaccg aacgccaac agcaccaacc gcgctcaggg gaacaaacaa tacccagatt    1260
gcgaacaccg cttttgtact ggccgcgatt gcagatgtta tcgacgcgtc acctgacgca    1320
ctgaatacgc tgaatgaact ggccgcagcg ctcgggaatg atccagattt tgctaccacc    1380
atgactaacg cgcttgcggg taaacaaccg aagaatgcga cactgacggc gctggcaggg    1440
ctttccacgg cgaaaaataa attaccgtat tttgcggaaa atgatgccgc cagcctgact    1500
gaactgactc aggttggcag ggatattctg gcaaaaaatt ccgttgcaga tgttcttgaa    1560
taccttgggg ccggtgagaa ttcggggagc gctacagacg ttatgattca gctggcggca    1620
```

```
aatgatggct tcaaattcat cggtcagtgc ccagacatct tgaccctgcg tactatcgag    1680
ccggaaaaaa acggtcagcg tatcaccta cgtcaacata cgattggcac tggcttaggc    1740
ggtggcgttt tccgtgcagt tctggacggc actggctata ccgatgacga cggtgtggtg    1800
atcaaaaccg ctgggggcag cgtttggctg cgtgtcaacg ctgacaaagt taacccgttc    1860
atgttcggtg caaccggagt agcggacgac accgccgccc tgcaaaaaat gctggaatgc    1920
ggtcgtgcgg cggaactggg gactaacgta tggaaagcaa gcaatctgga actgaacaac    1980
aaatcttgct ctctgtccgg cagtggcctg cacgtttctc gtattgaaca gatttccggt    2040
gcaaccggag cattgttaac catcacccaa gactgttcgc tgatttacct gtccgattgt    2100
ggcctgtacg gcgatggcat caccgcaggc acgagcggtg ttactatgga aacgggtaat    2160
ccgggtggcg ctccgtctta cccttttcaat accgctccgg acgttcgtcg tgacctgtac    2220
atctctaacg tgcacatcac gggcttcgac gagctgggtt ttgattatcc ggaaaccaat    2280
ttctctgttt cgacgcatgg cctcttcatc cgtaacatca aaaaaacggg tgcaaagatt    2340
ggtactacgg acttcacttg gactaacctg caaattgata cttgcggtca ggaatgtctg    2400
gtgctggacg tgcgggtaa ctgccgtatt attggtgcaa aactgatttg gcaggtagc    2460
gaaaacgaaa cgccatactc tggcctgcgt attagcaact ctcaaaatgt aaatatgact    2520
ggcgtagagt tacaagactg cgcgtatgat ggtttataca tcaagaactc tacggttgca    2580
atttcaggct taaacaccaa tcgcaatagc gcatcctcta atctgtccta ccataacatg    2640
gtattcgaaa attctattgt aactgttgat ggttatgtgt gtcgtaacta cgcggcgact    2700
tcgctgtacg acctgaacag ccaagcaggc aacgtccgtt gcatcggtag cgacagcacc    2760
gtttaatca acggcatcta cgaaagcgaa gtcaatagcg agcgcctgat gggtgataac    2820
aacctgatcc agccgtatag tggtgatctg atcattaacg gcctgaaaaa ttactacacc    2880
tatactggta gcgtaaaaaa caacattccg accttcgacg gcgttgttac tacggcaacc    2940
tatgtgagcg caccgtctat tctgggtcag ggcaatatgc tcaaactgac ccagtctaat    3000
aaagacaaac tgttatttag cgataaagtt agccgtcatg gctgtaccat cggcttagtt    3060
ctgattccgt cctttacggg cgcgaccact atgacggcgt tcacgctggg tagcggttac    3120
tctccatccg gtaactccgc cgtgatgcag ttcattgtta acagttccgg tgtacaaacc    3180
attgcgattt tattatccgg cgacggtatt acccaaaccc tgaccagcga tctgaccacg    3240
gaacaagcac tggcgagcgg tggcgtgtat cattttgcaa tgggttttgc gccgggtcgt    3300
ttatggtgga gcattatcga tattaacacg ggcaggcgta ttcgtcgcgc ctaccgtcag    3360
ccggatctgc acgcggcgtt caactctatc ttcaactccg gcacgtcgtc tattaccgca    3420
tttagcgggc cactggcggg cgacattgct tgcgaaggtg caggtagcca tgtatacgtt    3480
ggcggttttt cgtcggaatc tgattacgcg gctagccgta tgtatggcct gttcactccg    3540
gtcgatctgg acaagcagta tagcttccgt accctgaacg gtaacatt                3588
```

<210> SEQ ID NO 20
<211> LENGTH: 3429
<212> TYPE: DNA
<213> ORGANISM: Artificial Sequence
<220> FEATURE:
<223> OTHER INFORMATION: K5 5.0

<400> SEQUENCE: 20

```
atggcagtaa agatttcagg agtcctgaaa gacggcacag gaaaaccggt acagaactgc      60
accattcagc tgaaagccag acgtaacagc accacggtgg tggtgaacac ggtgggctca     120
```

```
gagaatccgg atgaagccgg gcgttacagc atggatgtgg agtacggtca gtacagtgtc    180
atcctgcagg ttgacggttt tccaccatcg cacgccggga ccatcaccgt gtatgaagat    240
tcacaaccgg ggacgctgaa tgattttctc tgtgccatga cggaggatga tgcccggccg    300
gaggtgctgc gtcgtcttga actgatggtg gaagaggtgg cgcgtaacgc gtccgtggtg    360
gcacagagta cggcagacgc gaagaaatca gccggcgatg ccagtgcatc agctgctcag    420
gtcgcggccc ttgtgactga tgcaactgac tcagcacgcg ccgccagcac gtccgccgga    480
caggctgcat cgtcagctca ggaagcgtcc tccggcgcag aagcggcatc agcaaaggcc    540
actgaagcgg aaaaaagtgc cgcagccgca gagtcctcaa aaaacgcggc ggccaccagt    600
gccggtgcgg cgaaaacgtc agaaacgaat gctgcagcgt cacaacaatc agccgccacg    660
tctgcctcca ccgcggccac gaaagcgtca gaggccgcca cttcagcacg agatgcggtg    720
gcctcaaaag aggcagcaaa atcatcagaa acgaacgcat catcaagtgc cggtcgtgca    780
gcttcctcgg caacggcggc agaaaattct gccaggggcgg caaaaacgtc cgagacgaat    840
gccaggtcat ctgaaacagc agcggaacgg agcgcctctg ccgcggcaga cgcaaaaaca    900
gcggcggcgg ggagtgcgtc aacggcatcc acgaaggcga cagaggctgc gggaagtgcg    960
gtatcagcat cgcagagcaa aagtgcggca gaagcggcgg caatacgtgc aaaaaattcg   1020
gcaaaacgtg cagaagatat agcttcagct gtcgcgcttg aggatgcgga cacaacgaga   1080
aaggggatag tgcagctcag cagtgcaacc aacagcacgt ctgaaacgct tgctgcaacg   1140
ccaaaggcgt taaggtggt aatggatgag actaatcgta aggcacctct ggacagtccg   1200
gcactgaccg gaacgccaac agcaccaacc gcgctcaggg gaacaaacaa tacccagatt   1260
gcgaacaccg cttttgtact ggccgcgatt gcagatgtta tcgacgcgtc acctgacgca   1320
ctgaatacgc tgaatgaact ggccgcagcg ctcgggaatg atccagattt tgctaccacc   1380
atgactaacg cgcttgcggg taaacaaccg aagaatgcga cactgacggc gctggcaggg   1440
cttcccacgg cgaaaaataa attaccgtat tttgcggaaa atgatgccgc cagcctgact   1500
gaactgactc aggttggcag ggatattctg gcaaaaaatt ccgttgcaga tgttcttgaa   1560
taccttgggg ccggtgagaa ttcggggagc gctacagacg ttatgattca gctgcttact   1620
tctaagccat tcggtgcagc gggtgatgca acgaccgacg cacgggaggt tatcgctgcg   1680
agcctgaaca gccagaaagc tgttaccatc tctgacggct ttttcagttc ttctggcatc   1740
aactccaact actgtaacct ggatggtcgc ggatccggtg tgctcagcca ccgtagctct   1800
actggtaatt acctggtgtt taacaatccg cgtactggtc gtctgagcaa tatcactgtt   1860
gaatctaaca aagcgaccga taccactcag ggccaacagg tgtccctggc aggtggcagt   1920
gacgtgaccg tgtcagatgt caacttctcc aacgtgaaag cactggtttt tagcctgatt   1980
gcctacccaa acgatgctcc gccggatggc ctgatgatca aaggcattcg cggatcttac   2040
agcggttacg cgaccaacaa agcagctggt tgcgtcctgg cggatagctc cgttaacagc   2100
ctgatcgaca atgtgatcgc taagaattac ccgcaattcg gtgctgttga attaaagggc   2160
actgcaagct acaacattgt atcgaacgtt atcggtgcgg attgtcagca cgtgacttac   2220
aacggcactg agggaccgat cgctcctagt aacaatctga tcaagggcgt tatggcgaac   2280
aacccgaaat acgcggcagt tgtggcgggt aaaggctcga cgaatctgat ctctgatgta   2340
ctggtagact attctaccag cgatgctcgt caggcgcatg tgttaccgt cgaaggatct   2400 gataacgtga ttaacaacgt actgatgtcc ggttgcgacg gaactaattc cctgggtcag   2460
```

| | | | |
|---|---|---|---|
| cgtcaaaccg | caactatcgc gcgtttcatc ggtactgcaa ataacaacta tgctagcgtg | 2520 |
| ttcccatcct | attctgccac tggtgtgatc acgtttgagt ctggcagtac ccgtaacttc | 2580 |
| gtcgaggtta | agcatccggg ccgtcgcaac gatcttctgt catcggcaag cacgattgac | 2640 |
| ggcgctgcga | ccatcgacgg gacttctaac tctaacgtag tacacgcgcc tgctctgggc | 2700 |
| caatacattg | gctccatgag tggtcgcttt gaatggcgta ttaagtcaat gagcctgccg | 2760 |
| tccggcgtac | tcactagcgc ggataaatac cgtatgctgg gtgacggtgc tgttagcctt | 2820 |
| gctgttggcg | gaggaactag cagtcaggtg cgcttgttca cctcagacgg tacttctcgc | 2880 |
| actgtttctc | tgaccaatgg taacgtgcgc ctgagcacgt cctctactgg ctatttacag | 2940 |
| ctgggtgcag | acgcaatgac tccggactcc actggtactt acgcgttagg ctccgcatct | 3000 |
| cgtgcttgga | gtggcggatt cactcaggca gcattcaccg ttacttctga cgcacgttgc | 3060 |
| aaaactgagc | ctttaaccat ctctgacgct ttactggatg cttggagtga agtggacttt | 3120 |
| gtccagttcc | agtatctgga tcgtgttgaa gagaaaggtg ctgactccgc gcgttggcat | 3180 |
| ttcggaatca | tcgcccagcg tgctaaagag gcattcgaac gtcacggcat cgatgcgcat | 3240 |
| cgttacggtt | tcttatgctt tgactcttgg gacgatgtgt acgaagagga tgcaaatgga | 3300 |
| tctcgcaaac | tgatcactcc ggcgggtagt cgctatggta ttcgctatga ggaagttctg | 3360 |
| atcctcgaag | cagcgctgat gcgtcgcacg atcaagcgca tgcaggaagc actggctgcg | 3420 |
| ttaccgaag | | 3429 |

<210> SEQ ID NO 21
<211> LENGTH: 3432
<212> TYPE: DNA
<213> ORGANISM: Artificial Sequence
<220> FEATURE:
<223> OTHER INFORMATION: K5 5.1

<400> SEQUENCE: 21

| | | | |
|---|---|---|---|
| atggcagtaa | agatttcagg agtcctgaaa gacggcacag gaaaaccggt acagaactgc | 60 |
| accattcagc | tgaaagccag acgtaacagc accacggtgg tggtgaacac ggtgggctca | 120 |
| gagaatccgg | atgaagccgg gcgttacagc atggatgtgg agtacggtca gtacagtgtc | 180 |
| atcctgcagg | ttgacggttt tccaccatcg cacgccggga ccatcaccgt gtatgaagat | 240 |
| tcacaaccgg | ggacgctgaa tgattttctc tgtgccatga cggaggatga tgcccggccg | 300 |
| gaggtgctgc | gtcgtcttga actgatggtg gaagaggtgg cgcgtaacgc gtccgtggtg | 360 |
| gcacagagta | cggcagacgc gaagaaatca gccggcgatg ccagtgcatc agctgctcag | 420 |
| gtcgcggccc | ttgtgactga tgcaactgac tcagcacgcg ccgccagcac gtccgccgga | 480 |
| caggctgcat | cgtcagctca ggaagcgtcc tccggcgcag aagcggcatc agcaaaggcc | 540 |
| actgaagcgg | aaaaaagtgc cgcagccgca gagtcctcaa aaaacgcggc ggccaccagt | 600 |
| gccggtgcgg | cgaaaacgtc agaaacgaat gctgcagcgt cacaacaatc agccgccacg | 660 |
| tctgcctcca | ccgcggccac gaaagcgtca gaggccgcca cttcagcacg agatgcggtg | 720 |
| gcctcaaaag | aggcagcaaa atcatcagaa acgaacgcat catcaagtgc cggtcgtgca | 780 |
| gcttcctcgg | caacggcggc agaaaattct gccaggcgg caaaaacgtc cgagacgaat | 840 |
| gccaggtcat | ctgaaacagc agcggaacgg agcgcctctg ccgcggcaga cgcaaaaaca | 900 |
| gcggcgcgg | ggagtgcgtc aacggcatcc acgaaggcga caggctgc gggaagtgcg | 960 |
| gtatcagcat | cgcagagcaa aagtgcggca gaagcggcgc caatacgtgc aaaaaattcg | 1020 |
| gcaaaacgtg | cagaagatat agcttcagct gtcgcgcttg aggatgcgga cacaacgaga | 1080 |

```
aagggatag tgcagctcag cagtgcaacc aacagcacgt ctgaaacgct tgctgcaacg   1140
ccaaaggcgg ttaaggtggt aatggatgag actaatcgta aggcacctct ggacagtccg   1200
gcactgaccg gaacgccaac agcaccaacc gcgctcaggg gaacaaacaa tacccagatt   1260
gcgaacaccg cttttgtact ggccgcgatt gcagatgtta tcgacgcgtc acctgacgca   1320
ctgaatacgc tgaatgaact ggccgcagcg ctcgggaatg atccagattt tgctaccacc   1380
atgactaacg cgcttgcggg taaacaaccg aagaatgcga cactgacggc gctggcaggg   1440 cttttccacgg cgaaaaataa attaccgtat tttgcggaaa atgatgccgc cagcctgact   1500
gaactgactc aggttggcag ggatattctg gcaaaaaatt ccgttgcaga tgttcttgaa   1560
taccttgggg ccggtgagaa ttcggggagc gctacagacg ttatgattca gctggcgctt   1620
acttctaagc cattcggtgc agcgggtgat gcaacgaccg acgacacgga ggttatcgct   1680
gcgagcctga acagccagaa agctgttacc atctctgacg gcgttttcag ttcttctggc   1740
atcaactcca actactgtaa cctggatggt cgcggatccg gtgtgctcag ccaccgtagc   1800
tctactggta attacctggt gtttaacaat ccgcgtactg gtcgtctgag caatatcact   1860
gttgaatcta acaaagcgac cgataccact cagggccaac aggtgtccct ggcaggtggc   1920
agtgacgtga ccgtgtcaga tgtcaacttc tccaacgtga aaggcactgg ttttagcctg   1980
attgcctacc caaacgatgc tccgccggat ggcctgatga tcaaaggcat cgcggatct    2040 tacagcggtt acgcgaccaa caaagcagct ggttgcgtcc tggcggatag ctccgttaac   2100
agcctgatcg acaatgtgat cgctaagaat tacccgcaat tcggtgctgt tgaattaaag   2160
ggcactgcaa gctacaacat tgtatcgaac gttatcggtg cggattgtca gcacgtgact   2220
tacaacggca ctgagggacc gatcgctcct agtaacaatc tgatcaaggg cgttatggcg   2280 aacaaccga atacgcggc agttgtggcg ggtaaaggct cgacgaatct gatctctgat   2340
gtactggtag actattctac cagcgatgct cgtcaggcgc atggtgttac cgtcgaagga   2400
tctgataacg tgattaacaa cgtactgatg tccggttgcg acggaactaa ttccctgggt   2460
cagcgtcaaa ccgcaactat cgcgcgtttc atcggtactg caataacaa ctatgctagc   2520 gtgttcccat cctattctgc cactggtgtg atcacgtttg agtctggcag tacccgtaac   2580
ttcgtcgagg ttaagcatcc gggccgtcgc aacgatcttc tgtcatcggc aagcacgatt   2640
gacggcgctg cgaccatcga cgggacttct aactctaacg tagtacacgc gcctgctctg   2700
ggccaataca ttggctccat gagtggtcgc tttgaatggc gtattaagtc aatgagcctg   2760
ccgtccggcg tactcactag cgcggataaa taccgtatgc tgggtgacgg tgctgttagc   2820
cttgctgttg gcggaggaac tagcagtcag gtgcgcttgt tcacctcaga cggtacttct   2880
cgcactgttt ctctgaccaa tggtaacgtg cgcctgagca cgtcctctac tggctattta   2940
cagctgggtg cagacgcaat gactccggac tccactggta cttacgcgtt aggctccgca   3000
tctcgtgctt ggagtggcgg attcactcag gcagcattca ccgttacttc tgacgcacgt   3060
tgcaaaactg agcctttaac catctctgac gctttactgg atgcttggag tgaagtggac   3120
tttgtccagt tccagtatct ggatcgtgtt gaagagaaag gtgctgactc cgcgcgttgg   3180
catttcggaa tcatcgccca gcgtgctaaa gaggcattcg aacgtcacgg catcgatgcg   3240
catcgttacg gtttcttatg ctttgactct tgggacgatg tgtacgaaga ggatgcaaat   3300
ggatctcgca aactgatcac tccggcgggt agtcgctatg gtattcgcta tgaggaagtt   3360
ctgatcctcg aagcagcgct gatgcgtcgc acgatcaagc gcatgcagga agcactggct   3420
```

-continued

```
gcgttaccga ag                                                          3432
```

<210> SEQ ID NO 22
<211> LENGTH: 1132
<212> TYPE: PRT
<213> ORGANISM: Bacteriophage lambda

<400> SEQUENCE: 22

```
Met Gly Lys Gly Ser Ser Lys Gly His Thr Pro Arg Glu Ala Lys Asp
1               5                   10                  15

Asn Leu Lys Ser Thr Gln Leu Leu Ser Val Ile Asp Ala Ile Ser Glu
            20                  25                  30

Gly Pro Ile Glu Gly Pro Val Asp Gly Leu Lys Ser Val Leu Leu Asn
        35                  40                  45

Ser Thr Pro Val Leu Asp Thr Glu Gly Asn Thr Asn Ile Ser Gly Val
    50                  55                  60

Thr Val Val Phe Arg Ala Gly Glu Gln Glu Gln Thr Pro Pro Glu Gly
65                  70                  75                  80

Phe Glu Ser Ser Gly Ser Glu Thr Val Leu Gly Thr Glu Val Lys Tyr
                85                  90                  95

Asp Thr Pro Ile Thr Arg Thr Ile Thr Ser Ala Asn Ile Asp Arg Leu
            100                 105                 110

Arg Phe Thr Phe Gly Val Gln Ala Leu Val Glu Thr Thr Ser Lys Gly
        115                 120                 125

Asp Arg Asn Pro Ser Glu Val Arg Leu Leu Val Gln Ile Gln Arg Asn
    130                 135                 140

Gly Gly Trp Val Thr Glu Lys Asp Ile Thr Ile Lys Gly Lys Thr Thr
145                 150                 155                 160

Ser Gln Tyr Leu Ala Ser Val Val Met Gly Asn Leu Pro Pro Arg Pro
                165                 170                 175

Phe Asn Ile Arg Met Arg Arg Met Thr Pro Asp Ser Thr Thr Asp Gln
            180                 185                 190

Leu Gln Asn Lys Thr Leu Trp Ser Ser Tyr Thr Glu Ile Ile Asp Val
        195                 200                 205

Lys Gln Cys Tyr Pro Asn Thr Ala Leu Val Gly Val Gln Val Asp Ser
    210                 215                 220

Glu Gln Phe Gly Ser Gln Gln Val Ser Arg Asn Tyr His Leu Arg Gly
225                 230                 235                 240

Arg Ile Leu Gln Val Pro Ser Asn Tyr Asn Pro Gln Thr Arg Gln Tyr
                245                 250                 255

Ser Gly Ile Trp Asp Gly Thr Phe Lys Pro Ala Tyr Ser Asn Asn Met
            260                 265                 270

Ala Trp Cys Leu Trp Asp Met Leu Thr His Pro Arg Tyr Gly Met Gly
        275                 280                 285

Lys Arg Leu Gly Ala Ala Asp Val Asp Lys Trp Ala Leu Tyr Val Ile
    290                 295                 300

Gly Gln Tyr Cys Asp Gln Ser Val Pro Asp Gly Phe Gly Gly Thr Glu
305                 310                 315                 320

Pro Arg Ile Thr Cys Asn Ala Tyr Leu Thr Thr Gln Arg Lys Ala Trp
                325                 330                 335

Asp Val Leu Ser Asp Phe Cys Ser Ala Met Arg Cys Met Pro Val Trp
            340                 345                 350

Asn Gly Gln Thr Leu Thr Phe Val Gln Asp Arg Pro Ser Asp Lys Thr
        355                 360                 365
```

-continued

Trp Thr Tyr Asn Arg Ser Asn Val Val Met Pro Asp Asp Gly Ala Pro
    370             375             380

Phe Arg Tyr Ser Phe Ser Ala Leu Lys Asp Arg His Asn Ala Val Glu
385             390             395             400

Val Asn Trp Ile Asp Pro Asn Asn Gly Trp Glu Thr Ala Thr Glu Leu
            405             410             415

Val Glu Asp Thr Gln Ala Ile Ala Arg Tyr Gly Arg Asn Val Thr Lys
        420             425             430

Met Asp Ala Phe Gly Cys Thr Ser Arg Gly Gln Ala His Arg Ala Gly
        435             440             445

Leu Trp Leu Ile Lys Thr Glu Leu Leu Glu Thr Gln Thr Val Asp Phe
450             455             460

Ser Val Gly Ala Glu Gly Leu Arg His Val Pro Gly Asp Val Ile Glu
465             470             475             480

Ile Cys Asp Asp Asp Tyr Ala Gly Ile Ser Thr Gly Gly Arg Val Leu
            485             490             495

Ala Val Asn Ser Gln Thr Arg Thr Leu Thr Leu Asp Arg Glu Ile Thr
            500             505             510

Leu Pro Ser Ser Gly Thr Ala Leu Ile Ser Leu Val Asp Gly Ser Gly
        515             520             525

Asn Pro Val Ser Val Glu Val Gln Ser Val Thr Asp Gly Val Lys Val
    530             535             540

Lys Val Ser Arg Val Pro Asp Gly Val Ala Glu Tyr Ser Val Trp Glu
545             550             555             560

Leu Lys Leu Pro Thr Leu Arg Gln Arg Leu Phe Arg Cys Val Ser Ile
            565             570             575

Arg Glu Asn Asp Asp Gly Thr Tyr Ala Ile Thr Ala Val Gln His Val
        580             585             590

Pro Glu Lys Glu Ala Ile Val Asp Asn Gly Ala His Phe Asp Gly Glu
    595             600             605

Gln Ser Gly Thr Val Asn Gly Val Thr Pro Ala Val Gln His Leu
    610             615             620

Thr Ala Glu Val Thr Ala Asp Ser Gly Glu Tyr Gln Val Leu Ala Arg
625             630             635             640

Trp Asp Thr Pro Lys Val Val Lys Gly Val Ser Phe Leu Leu Arg Leu
            645             650             655

Thr Val Thr Ala Asp Asp Gly Ser Glu Arg Leu Val Ser Thr Ala Arg
            660             665             670

Thr Thr Glu Thr Thr Tyr Arg Phe Thr Gln Leu Ala Leu Gly Asn Tyr
        675             680             685

Arg Leu Thr Val Arg Ala Val Asn Ala Trp Gly Gln Gln Gly Asp Pro
690             695             700

Ala Ser Val Ser Phe Arg Ile Ala Ala Pro Ala Ala Pro Ser Arg Ile
705             710             715             720

Glu Leu Thr Pro Gly Tyr Phe Gln Ile Thr Ala Thr Pro His Leu Ala
            725             730             735

Val Tyr Asp Pro Thr Val Gln Phe Glu Phe Trp Phe Ser Glu Lys Gln
        740             745             750

Ile Ala Asp Ile Arg Gln Val Glu Thr Ser Thr Arg Tyr Leu Gly Thr
        755             760             765

Ala Leu Tyr Trp Ile Ala Ala Ser Ile Asn Ile Lys Pro Gly His Asp
770             775             780

Tyr Tyr Phe Tyr Ile Arg Ser Val Asn Thr Val Gly Lys Ser Ala Phe

-continued

```
            785                 790                 795                 800
Val Glu Ala Val Gly Arg Ala Ser Asp Asp Ala Glu Gly Tyr Leu Asp
                805                 810                 815
Phe Phe Lys Gly Lys Ile Thr Glu Ser His Leu Gly Lys Glu Leu Leu
                820                 825                 830
Glu Lys Val Glu Leu Thr Asp Asn Ala Ser Arg Leu Glu Glu Phe
                835                 840                 845
Ser Lys Glu Trp Lys Asp Ala Ser Asp Lys Trp Asn Ala Met Trp Ala
        850                 855                 860
Val Lys Ile Glu Gln Thr Lys Asp Gly Lys His Tyr Val Ala Gly Ile
        865                 870                 875                 880
Gly Leu Ser Met Glu Asp Thr Glu Glu Gly Lys Leu Ser Gln Phe Leu
                885                 890                 895
Val Ala Ala Asn Arg Ile Ala Phe Ile Asp Pro Ala Asn Gly Asn Glu
                900                 905                 910
Thr Pro Met Phe Val Ala Gln Gly Asn Gln Ile Phe Met Asn Asp Val
                915                 920                 925
Phe Leu Lys Arg Leu Thr Ala Pro Thr Ile Thr Ser Gly Gly Asn Pro
            930                 935                 940
Pro Ala Phe Ser Leu Thr Pro Asp Gly Lys Leu Thr Ala Lys Asn Ala
945                 950                 955                 960
Asp Ile Ser Gly Ser Val Asn Ala Asn Ser Gly Thr Leu Ser Asn Val
                965                 970                 975
Thr Ile Ala Glu Asn Cys Thr Ile Asn Gly Thr Leu Arg Ala Glu Lys
            980                 985                 990
Ile Val Gly Asp Ile Val Lys Ala  Ala Ser Ala Ala Phe  Pro Arg Gln
            995                 1000                1005
Arg Glu  Ser Ser Val Asp Trp  Pro Ser Gly Thr Arg  Thr Val Thr
        1010                1015                1020
Val Thr  Asp Asp His Pro Phe  Asp Arg Gln Ile Val  Val Leu Pro
        1025                1030                1035
Leu Thr  Phe Arg Gly Ser Lys  Arg Thr Val Ser Gly  Arg Thr Thr
        1040                1045                1050
Tyr Ser  Met Cys Tyr Leu Lys  Val Leu Met Asn Gly  Ala Val Ile
        1055                1060                1065
Tyr Asp  Gly Ala Ala Asn Glu  Ala Val Gln Val Phe  Ser Arg Ile
        1070                1075                1080
Val Asp  Met Pro Ala Gly Arg  Gly Asn Val Ile Leu  Thr Phe Thr
        1085                1090                1095
Leu Thr  Ser Thr Arg His Ser  Ala Asp Ile Pro Pro  Tyr Thr Phe
        1100                1105                1110
Ala Ser  Asp Val Gln Val Met  Val Ile Lys Lys Gln  Ala Leu Gly
        1115                1120                1125
Ile Ser  Val Val
        1130

<210> SEQ ID NO 23
<211> LENGTH: 1132
<212> TYPE: PRT
<213> ORGANISM: Artificial Sequence
<220> FEATURE:
<223> OTHER INFORMATION: H591

<400> SEQUENCE: 23

Met Gly Lys Gly Ser Ser Lys Gly His Thr Pro Arg Glu Ala Lys Asp
```

```
  1               5                  10                 15
Asn Leu Lys Ser Thr Gln Leu Leu Ser Val Ile Asp Ala Ile Ser Glu
             20                 25                 30
Gly Pro Ile Glu Gly Pro Val Asp Gly Leu Lys Ser Val Leu Leu Asn
             35                 40                 45
Ser Thr Pro Val Leu Asp Thr Glu Gly Asn Thr Asn Ile Ser Gly Val
         50                 55                 60
Thr Val Val Phe Arg Ala Gly Glu Gln Glu Gln Thr Pro Pro Glu Gly
65                  70                 75                 80
Phe Glu Ser Ser Gly Ser Glu Thr Val Leu Gly Thr Glu Val Lys Tyr
                 85                 90                 95
Asp Thr Pro Ile Thr Arg Thr Ile Thr Ser Ala Asn Ile Asp Arg Leu
             100                105                110
Arg Phe Thr Phe Gly Val Gln Ala Leu Val Glu Thr Thr Ser Lys Gly
             115                120                125
Asp Arg Asn Pro Ser Glu Val Arg Leu Leu Val Gln Ile Gln Arg Asn
         130                135                140
Gly Gly Trp Val Thr Glu Lys Asp Ile Thr Ile Lys Gly Lys Thr Thr
145                150                155                160
Ser Gln Tyr Leu Ala Ser Val Val Met Gly Asn Leu Pro Pro Arg Pro
                 165                170                175
Phe Asn Ile Arg Met Arg Arg Met Thr Pro Asp Ser Thr Thr Asp Gln
             180                185                190
Leu Gln Asn Lys Thr Leu Trp Ser Ser Tyr Thr Glu Ile Ile Asp Val
             195                200                205
Lys Gln Cys Tyr Pro Asn Thr Ala Leu Val Gly Val Gln Val Asp Ser
210                215                220
Glu Gln Phe Gly Ser Gln Val Ser Arg Asn Tyr His Leu Arg Gly
225                230                235                240
Arg Ile Leu Gln Val Pro Ser Asn Tyr Asn Pro Gln Thr Arg Gln Tyr
             245                250                255
Ser Gly Ile Trp Asp Gly Thr Phe Lys Pro Ala Tyr Ser Asn Asn Met
             260                265                270
Ala Trp Cys Leu Trp Asp Met Leu Thr His Pro Arg Tyr Gly Met Gly
             275                280                285
Lys Arg Leu Gly Ala Ala Asp Val Asp Lys Trp Ala Leu Tyr Val Ile
290                295                300
Gly Gln Tyr Cys Asp Gln Ser Val Pro Asp Gly Phe Gly Gly Thr Glu
305                310                315                320
Pro Arg Ile Thr Cys Asn Ala Tyr Leu Thr Thr Gln Arg Lys Ala Trp
             325                330                335
Asp Val Leu Ser Asp Phe Cys Ser Ala Met Arg Cys Met Pro Val Trp
             340                345                350
Asn Gly Gln Thr Leu Thr Phe Val Gln Asp Arg Pro Ser Asp Lys Thr
             355                360                365
Trp Thr Tyr Asn Arg Ser Asn Val Val Met Pro Asp Asp Gly Ala Pro
         370                375                380
Phe Arg Tyr Ser Phe Ser Ala Leu Lys Asp Arg His Asn Ala Val Glu
385                390                395                400
Val Asn Trp Ile Asp Pro Asn Asn Gly Trp Glu Thr Ala Thr Glu Leu
             405                410                415
Val Glu Asp Thr Gln Ala Ile Ala Arg Tyr Gly Arg Asn Val Thr Lys
             420                425                430
```

```
Met Asp Ala Phe Gly Cys Thr Ser Arg Gly Gln Ala His Arg Ala Gly
        435                 440                 445

Leu Trp Leu Ile Lys Thr Glu Leu Leu Glu Thr Gln Thr Val Asp Phe
        450                 455                 460

Ser Val Gly Ala Glu Gly Leu Arg His Val Pro Gly Asp Val Ile Glu
465                 470                 475                 480

Ile Cys Asp Asp Tyr Ala Gly Ile Ser Thr Gly Gly Arg Val Leu
                485                 490                 495

Ala Val Asn Ser Gln Thr Arg Thr Leu Thr Leu Asp Arg Glu Ile Thr
            500                 505                 510

Leu Pro Ser Ser Gly Thr Ala Leu Ile Ser Leu Val Asp Gly Ser Gly
            515                 520                 525

Asn Pro Val Ser Val Glu Val Gln Ser Val Thr Asp Gly Val Lys Val
        530                 535                 540

Lys Val Ser Arg Val Pro Asp Gly Val Ala Glu Tyr Ser Val Trp Glu
545                 550                 555                 560

Leu Lys Leu Pro Thr Leu Arg Gln Arg Leu Phe Arg Cys Val Ser Ile
                565                 570                 575

Arg Glu Asn Asp Asp Gly Thr Tyr Ala Ile Thr Ala Val Gln His Val
            580                 585                 590

Pro Glu Lys Glu Ala Ile Val Asp Asn Gly Ala His Phe Asp Gly Glu
        595                 600                 605

Gln Ser Gly Thr Val Asn Gly Val Thr Pro Ala Val Gln His Leu
        610                 615                 620

Thr Ala Glu Val Thr Ala Asp Ser Gly Glu Tyr Gln Val Leu Ala Arg
625                 630                 635                 640

Trp Asp Thr Pro Lys Val Val Lys Gly Val Ser Phe Leu Leu Arg Leu
                645                 650                 655

Thr Val Thr Ala Asp Asp Gly Ser Glu Arg Leu Val Ser Thr Ala Arg
            660                 665                 670

Thr Thr Glu Thr Thr Tyr Arg Phe Thr Gln Leu Ala Leu Gly Asn Tyr
        675                 680                 685

Arg Leu Thr Val Arg Ala Val Asn Ala Trp Gly Gln Gln Gly Asp Pro
        690                 695                 700

Ala Ser Val Ser Phe Arg Ile Ala Ala Pro Ala Ala Pro Ser Arg Ile
705                 710                 715                 720

Glu Leu Thr Pro Gly Tyr Phe Gln Ile Thr Ala Thr Pro His Leu Ala
                725                 730                 735

Val Tyr Asp Pro Thr Val Gln Phe Glu Phe Trp Phe Ser Glu Lys Gln
            740                 745                 750

Ile Ala Asp Ile Arg Gln Val Glu Thr Ser Thr Arg Tyr Leu Gly Thr
        755                 760                 765

Ala Leu Tyr Trp Ile Ala Ala Ser Ile Asn Ile Lys Pro Gly His Asp
        770                 775                 780

Tyr Tyr Phe Tyr Ile Arg Ser Val Asn Thr Val Gly Lys Ser Ala Phe
785                 790                 795                 800

Val Glu Ala Val Gly Arg Ala Ser Asp Asp Ala Glu Gly Tyr Leu Asp
                805                 810                 815

Phe Phe Lys Gly Lys Ile Thr Glu Ser His Leu Gly Lys Glu Leu Leu
            820                 825                 830

Glu Lys Val Glu Leu Thr Glu Asp Asn Ala Ser Arg Leu Glu Glu Phe
        835                 840                 845
```

```
Ser Lys Glu Trp Lys Asp Ala Ser Asp Lys Trp Asn Ala Met Trp Ala
    850                 855                 860

Val Lys Ile Glu Gln Thr Lys Asp Gly Lys His Tyr Val Ala Gly Ile
865                 870                 875                 880

Gly Leu Ser Met Glu Asp Thr Glu Gly Lys Leu Ser Gln Phe Leu
                885                 890                 895

Val Ala Ala Asn Arg Ile Ala Phe Ile Asp Pro Ala Asn Gly Asn Glu
            900                 905                 910

Thr Pro Met Phe Val Ala Gln Gly Asn Gln Ile Phe Met Asn Asp Val
        915                 920                 925

Phe Leu Lys Arg Leu Thr Ala Pro Thr Ile Thr Ser Gly Gly Asn Pro
    930                 935                 940

Pro Ala Phe Ser Leu Thr Pro Asp Gly Lys Leu Thr Ala Lys Asn Ala
945                 950                 955                 960

Asp Ile Ser Gly Asn Val Asn Ala Asn Ser Gly Thr Leu Asn Asn Val
                965                 970                 975

Thr Ile Asn Glu Asn Cys Gln Ile Lys Gly Lys Leu Ser Ala Asn Gln
            980                 985                 990

Ile Glu Gly Asp Ile Val Lys Thr  Val Ser Lys Ser Phe  Pro Arg Thr
        995                 1000                1005

Asn Ser  Tyr Ala Ser Gly Thr  Ile Thr Val Arg Ile  Ser Asp Asp
    1010                1015                1020

Gln Lys  Phe Asp Arg Gln Val  Met Ile Pro Pro Val  Leu Phe Arg
    1025                1030                1035

Gly Gly  Lys His Glu Asn Phe  Asn Ser Asn Asn Gln  Gln Ser Tyr
    1040                1045                1050

Trp Tyr  Ser Thr Cys Arg Leu  Arg Val Thr Arg Asn  Gly Gln Glu
    1055                1060                1065

Ile Phe  Asn Gln Ser Thr Thr  Asp Ala Gln Gly Val  Phe Ser Ser
    1070                1075                1080

Val Ile  Asp Met Pro Ala Gly  Gln Gly Thr Leu Thr  Leu Thr Phe
    1085                1090                1095

Thr Val  Ser Ser Ser Gly Ala  Asn Asn Trp Thr Pro  Thr Thr Ser
    1100                1105                1110

Ile Ser  Asp Leu Leu Val Val  Met Lys Lys Ser  Thr Ala Gly
    1115                1120                1125

Ile Ser  Ile Ser
    1130

<210> SEQ ID NO 24
<211> LENGTH: 3396
<212> TYPE: DNA
<213> ORGANISM: Artificial Sequence
<220> FEATURE:
<223> OTHER INFORMATION: H591

<400> SEQUENCE: 24
atgggtaaag gaagcagtaa ggggcatacc ccgcgcgaag cgaaggacaa cctgaagtcc      60
acgcagttgc tgagtgtgat cgatgccatc agcgaagggc cgattgaagg tccggtggat     120
ggcttaaaaa gcgtgctgct gaacagtacg ccggtgctgg acactgaggg gaataccaac     180
atatccggtg tcacggtggt gttccgggct ggtgagcagg agcagactcc gccggaggga     240
tttgaatcct ccggctccga gacggtgctg ggtacggaag tgaaatatga cacgccgatc     300
acccgcacca ttacgtctgc aaacatcgac cgtctgcgct ttaccttcgg tgtacaggca     360
```

```
ctggtggaaa ccacctcaaa gggtgacagg aatccgtcgg aagtccgcct gctggttcag    420
atacaacgta acggtggctg ggtgacggaa aaagacatca ccattaaggg caaaaccacc    480
tcgcagtatc tggcctcggt ggtgatgggt aacctgccgc cgcgcccgtt taatatccgg    540
atgcgcagga tgacgccgga cagcaccaca gaccagctgc agaacaaaac gctctggtcg    600
tcatacactg aaatcatcga tgtgaaacag tgctacccga cacggcact ggtcggcgtg     660
caggtggact cggagcagtt cggcagccag caggtgagcc gtaattatca tctgcgcggg    720
cgtattctgc aggtgccgtc gaactataac ccgcagacgc ggcaatacag cggtatctgg    780
gacggaacgt ttaaaccggc atacagcaac aacatggcct ggtgtctgtg ggatatgctg    840
acccatccgc gctacggcat ggggaaacgt cttggtgcgg cggatgtgga taaatgggcg    900
ctgtatgtca tcggccagta ctgcgaccag tcagtgccgg acggctttgg cggcacggag    960
ccgcgcatca cctgtaatgc gtacctgacc acacagcgta aggcgtggga tgtgctcagc   1020
gatttctgct cggcgatgcg ctgtatgccg gtatggaacg ggcagacgct gacgttcgtg   1080
caggaccgac cgtcggataa gacgtggacc tataaccgca gtaatgtggt gatgccggat   1140
gatggcgcgc cgttccgcta cagcttcagc gccctgaagg accgccataa tgccgttgag   1200
gtgaactgga ttgaccccgaa caacggctgg gagacggcga cagagcttgt tgaagatacg   1260
caggccattg cccgttacgg tcgtaatgtt acgaagatgg atgcctttgg ctgtaccagc   1320
cgggggcagg cacaccgcgc cgggctgtgg ctgattaaaa cagaactgct ggaaacgcag   1380
accgtggatt tcagcgtcgg cgcagaaggg cttcgccatg taccgggcga tgttattgaa   1440
atctgcgatg atgactatgc cggtatcagc accgtggtc gtgtgctggc ggtgaacagc    1500
cagacccgga cgctgacgct cgaccgtgaa atcacgctgc catcctccgg taccgcgctg   1560
ataagcctgt tgacggaag tggcaatccg gtcagcgtgg aggttcagtc cgtcaccgac    1620
ggcgtgaagg taaaagtgag ccgtgttcct gacggtgttg ctgaatacag cgtatgggag   1680
ctgaagctgc cgacgctgcg ccagcgactg ttccgctgcg tgagtatccg tgagaacgac   1740
gacggcacgt atgccatcac cgccgtgcag catgtgccgg aaaagagc atcgtggat     1800
aacggggcgc actttgacgg cgaacagagt ggcacggtga atggtgtcac gccgccagcg   1860
gtgcagcacc tgaccgcaga agtcactgca gacagcgggg aatatcaggt gctggcgcga   1920
tgggacacac cgaaggtggt gaagggcgtg agtttcctgc tccgtctgac cgtaacagcg   1980
gacgacggca gtgagcggct ggtcagcacg gcccggacga cggaaaccac ataccgcttc   2040
acgcaactgg cgctggggaa ctacaggctg acagtccggg cggtaaatgc gtgggggcag   2100
cagggcgatc cggcgtcggt atcgttccgg attgccgcac cggcagcacc gtcgaggatt   2160
gagctgacgc cgggctattt tcagataacc gccacgccgc atcttgccgt ttatgacccg   2220
acggtacagt ttgagttctg gttctcggaa aagcagattg cggatatcag acaggttgaa   2280
accagcacgc gttatcttgg tacgcgctg tactggatag ccgccagtat caatatcaaa    2340
ccgggccatg attattactt ttatatccgc agtgtgaaca ccgttggcaa atcggcattc   2400
gtggaggccg tcggtcgggc gagcgatgat gcggaaggtt acctggattt tttcaaaggc   2460
aagataaccg aatcccatct cggcaaggag ctgctgaaa aagtcgagct gacgaggat     2520
aacgccagca gactggagga gttttcgaaa gagtggaagg atgccagtga aagtggaat    2580
gccatgtggg ctgtcaaaat tgagcagacc aaagacggca acattatgt cgcgggtatt   2640
ggcctcagca tggaggacac ggaggaaggc aaactgagcc agtttctggt tgccgccaat   2700
cgtatcgcat ttattgaccc ggcaaacggg aatgaaacgc cgatgtttgt ggcgcagggc   2760
```

-continued

```
aaccagatat tcatgaacga cgtgttcctg aagcgcctga cggcccccac cattaccagc    2820
ggcggcaatc ctccggcctt ttccctgaca ccggacggaa agctgaccgc taaaaatgcg    2880
gatatcagtg gcaatgtgaa tgcaaattca gggacgctca acaatgtcac gattaatgaa    2940
aactgtcaga ttaaagggaa actgtcagcc aatcagattg aaggcgatat tgtcaaaacg    3000
gtcagcaagt ctttcccccg cacgaacagt tatgccagtg caccatcac ggtaagaatc     3060 agtgatgatc agaaatttga ccggcaggtc atgataccgc cagtgttatt ccgcggtggt    3120
aagcatgaga atttcaacag taataaccaa cagtcatact ggtattcaac ctgccggtta    3180
agagtgaccc gcaatggtca ggagatttt  aatcagtcca cgacggatgc tcagggcgta    3240
ttttcctcag ttatagatat gcctgccgga caggggacac tgacactgac attcaccgta    3300
tcttcatcag gagcgaataa ctggacacca acaaccagta tcagcgatct gctggttgtg    3360
gtgatgaaga aatccacagc aggtatcagt atcagc                              3396
```

<210> SEQ ID NO 25
<211> LENGTH: 1159
<212> TYPE: PRT
<213> ORGANISM: Artificial Sequence
<220> FEATURE:
<223> OTHER INFORMATION: Z2145

<400> SEQUENCE: 25

```
Met Gly Lys Gly Ser Ser Lys Gly His Thr Pro Arg Glu Ala Lys Asp
1               5                   10                  15

Asn Leu Lys Ser Thr Gln Leu Leu Ser Val Ile Asp Ala Ile Ser Glu
            20                  25                  30

Gly Pro Ile Glu Gly Pro Val Asp Gly Leu Lys Ser Val Leu Leu Asn
        35                  40                  45

Ser Thr Pro Val Leu Asp Thr Glu Gly Asn Thr Asn Ile Ser Gly Val
    50                  55                  60

Thr Val Val Phe Arg Ala Gly Glu Gln Glu Gln Thr Pro Pro Glu Gly
65                  70                  75                  80

Phe Glu Ser Ser Gly Ser Glu Thr Val Leu Gly Thr Glu Val Lys Tyr
                85                  90                  95

Asp Thr Pro Ile Thr Arg Thr Ile Thr Ser Ala Asn Ile Asp Arg Leu
            100                 105                 110

Arg Phe Thr Phe Gly Val Gln Ala Leu Val Glu Thr Thr Ser Lys Gly
        115                 120                 125

Asp Arg Asn Pro Ser Glu Val Arg Leu Leu Val Gln Ile Gln Arg Asn
    130                 135                 140

Gly Gly Trp Val Thr Glu Lys Asp Ile Thr Ile Lys Gly Lys Thr Thr
145                 150                 155                 160

Ser Gln Tyr Leu Ala Ser Val Val Met Gly Asn Leu Pro Pro Arg Pro
                165                 170                 175

Phe Asn Ile Arg Met Arg Arg Met Thr Pro Asp Ser Thr Thr Asp Gln
            180                 185                 190

Leu Gln Asn Lys Thr Leu Trp Ser Ser Tyr Thr Glu Ile Ile Asp Val
        195                 200                 205

Lys Gln Cys Tyr Pro Asn Thr Ala Leu Val Gly Val Gln Val Asp Ser
    210                 215                 220

Glu Gln Phe Gly Ser Gln Gln Val Ser Arg Asn Tyr His Leu Arg Gly
225                 230                 235                 240

Arg Ile Leu Gln Val Pro Ser Asn Tyr Asn Pro Gln Thr Arg Gln Tyr
```

-continued

```
                245                 250                 255
Ser Gly Ile Trp Asp Gly Thr Phe Lys Pro Ala Tyr Ser Asn Asn Met
            260                 265                 270
Ala Trp Cys Leu Trp Asp Met Leu Thr His Pro Arg Tyr Gly Met Gly
            275                 280                 285
Lys Arg Leu Gly Ala Ala Asp Val Asp Lys Trp Ala Leu Tyr Val Ile
            290                 295                 300
Gly Gln Tyr Cys Asp Gln Ser Val Pro Asp Gly Phe Gly Gly Thr Glu
305                 310                 315                 320
Pro Arg Ile Thr Cys Asn Ala Tyr Leu Thr Thr Gln Arg Lys Ala Trp
                325                 330                 335
Asp Val Leu Ser Asp Phe Cys Ser Ala Met Arg Cys Met Pro Val Trp
                340                 345                 350
Asn Gly Gln Thr Leu Thr Phe Val Gln Asp Arg Pro Ser Asp Lys Thr
                355                 360                 365
Trp Thr Tyr Asn Arg Ser Asn Val Val Met Pro Asp Asp Gly Ala Pro
            370                 375                 380
Phe Arg Tyr Ser Phe Ser Ala Leu Lys Asp Arg His Asn Ala Val Glu
385                 390                 395                 400
Val Asn Trp Ile Asp Pro Asn Asn Gly Trp Glu Thr Ala Thr Glu Leu
                405                 410                 415
Val Glu Asp Thr Gln Ala Ile Ala Arg Tyr Gly Arg Asn Val Thr Lys
                420                 425                 430
Met Asp Ala Phe Gly Cys Thr Ser Arg Gly Gln Ala His Arg Ala Gly
            435                 440                 445
Leu Trp Leu Ile Lys Thr Glu Leu Leu Glu Thr Gln Thr Val Asp Phe
            450                 455                 460
Ser Val Gly Ala Glu Gly Leu Arg His Val Pro Gly Asp Val Ile Glu
465                 470                 475                 480
Ile Cys Asp Asp Asp Tyr Ala Gly Ile Ser Thr Gly Gly Arg Val Leu
                485                 490                 495
Ala Val Asn Ser Gln Thr Arg Thr Leu Thr Leu Asp Arg Glu Ile Thr
                500                 505                 510
Leu Pro Ser Ser Gly Thr Ala Leu Ile Ser Leu Val Asp Gly Ser Gly
            515                 520                 525
Asn Pro Val Ser Val Glu Val Gln Ser Val Thr Asp Gly Val Lys Val
            530                 535                 540
Lys Val Ser Arg Val Pro Asp Gly Val Ala Glu Tyr Ser Val Trp Glu
545                 550                 555                 560
Leu Lys Leu Pro Thr Leu Arg Gln Arg Leu Phe Arg Cys Val Ser Ile
                565                 570                 575
Arg Glu Asn Asp Asp Gly Thr Tyr Ala Ile Thr Ala Val Gln His Val
                580                 585                 590
Pro Glu Lys Glu Ala Ile Val Asp Asn Gly Ala His Phe Asp Gly Glu
            595                 600                 605
Gln Ser Gly Thr Val Asn Gly Val Thr Pro Pro Ala Val Gln His Leu
            610                 615                 620
Thr Ala Glu Val Thr Ala Asp Ser Gly Glu Tyr Gln Val Leu Ala Arg
625                 630                 635                 640
Trp Asp Thr Pro Lys Val Val Lys Gly Val Ser Phe Leu Leu Arg Leu
                645                 650                 655
Thr Val Thr Ala Asp Asp Gly Ser Glu Arg Leu Val Ser Thr Ala Arg
                660                 665                 670
```

-continued

Thr Thr Glu Thr Thr Tyr Arg Phe Thr Gln Leu Ala Leu Gly Asn Tyr
            675                 680                 685

Arg Leu Thr Val Arg Ala Val Asn Ala Trp Gly Gln Gln Gly Asp Pro
    690                 695                 700

Ala Ser Val Ser Phe Arg Ile Ala Ala Pro Ala Pro Ser Arg Ile
705                 710                 715                 720

Glu Leu Thr Pro Gly Tyr Phe Gln Ile Thr Ala Thr Pro His Leu Ala
                725                 730                 735

Val Tyr Asp Pro Thr Val Gln Phe Glu Phe Trp Ser Glu Lys Gln
                740                 745                 750

Ile Ala Asp Ile Arg Gln Val Glu Thr Ser Thr Arg Tyr Leu Gly Thr
            755                 760                 765

Ala Leu Tyr Trp Ile Ala Ala Ser Ile Asn Ile Lys Pro Gly His Asp
    770                 775                 780

Tyr Tyr Phe Tyr Ile Arg Ser Val Asn Thr Val Gly Lys Ser Ala Phe
785                 790                 795                 800

Val Glu Ala Val Gly Arg Ala Ser Asp Asp Ala Glu Gly Tyr Leu Asp
                805                 810                 815

Phe Phe Lys Gly Glu Ile Gly Lys Thr His Leu Ala Gln Glu Leu Trp
            820                 825                 830

Thr Gln Ile Asp Asn Gly Gln Leu Ala Pro Asp Leu Ala Glu Ile Arg
    835                 840                 845

Thr Ser Ile Thr Asp Val Ser Asn Glu Ile Thr Gln Thr Val Asn Lys
850                 855                 860

Lys Leu Glu Asp Gln Ser Ala Ala Ile Gln Gln Ile Gln Lys Val Gln
865                 870                 875                 880

Val Asp Thr Asn Asn Asn Leu Asn Ser Met Trp Ala Val Lys Leu Gln
                885                 890                 895

Gln Met Gln Asp Gly Arg Leu Tyr Ile Ala Gly Ile Gly Ala Gly Ile
            900                 905                 910

Glu Asn Thr Ser Asp Gly Met Gln Ser Gln Val Leu Leu Ala Ala Asp
    915                 920                 925

Arg Ile Ala Met Ile Asn Pro Ala Asn Gly Asn Thr Lys Pro Met Phe
930                 935                 940

Val Gly Gln Gly Asp Gln Ile Phe Met Asn Glu Val Phe Leu Lys Tyr
945                 950                 955                 960

Leu Thr Ala Pro Thr Ile Thr Ser Gly Gly Asn Pro Pro Ala Phe Ser
                965                 970                 975

Leu Thr Ser Asp Gly Lys Leu Thr Ala Lys Asn Ala Asp Ile Ser Gly
            980                 985                 990

Ser Val Asn Ala Asn Ser Gly Thr Leu Asn Asn Val Thr Ile Asn Glu
    995                 1000                1005

Asn Cys Arg Val Leu Gly Lys Leu Ser Ala Asn Gln Ile Glu Gly
1010                1015                1020

Asp Leu Val Lys Thr Val Gly Lys Ala Phe Pro Arg Asp Ser Arg
    1025                1030                1035

Ala Pro Glu Arg Trp Pro Ser Gly Thr Ile Thr Val Arg Val Tyr
    1040                1045                1050

Asp Asp Gln Pro Phe Asp Arg Gln Ile Val Ile Pro Ala Val Ala
    1055                1060                1065

Phe Ser Gly Ala Lys His Glu Arg Glu His Thr Asp Ile Tyr Ser
    1070                1075                1080

| Ser | Cys | Arg | Leu | Ile | Val | Arg | Lys | Asn | Gly | Ala | Glu | Ile | Tyr | Asn |
|-----|-----|-----|-----|-----|-----|-----|-----|-----|-----|-----|-----|-----|-----|-----|
| 1085 |    |     |     |     | 1090 |    |    |    |    | 1095 |    |    |    |    |

Arg Thr Ala Leu Asp Asn Thr Leu Ile Tyr Ser Gly Val Ile Asp
    1100                1105                1110

Met Pro Ala Gly His Gly His Met Thr Leu Glu Phe Ser Val Ser
    1115                1120                1125

Ala Trp Leu Val Asn Asn Trp Tyr Pro Thr Ala Ser Ile Ser Asp
    1130                1135                1140

Leu Leu Val Val Val Met Lys Lys Ala Thr Ala Gly Ile Ser Ile
    1145                1150                1155

Ser

<210> SEQ ID NO 26
<211> LENGTH: 3477
<212> TYPE: DNA
<213> ORGANISM: Artificial Sequence
<220> FEATURE:
<223> OTHER INFORMATION: Z2145

<400> SEQUENCE: 26

```
atgggtaaag gaagcagtaa ggggcatacc ccgcgcgaag cgaaggacaa cctgaagtcc      60
acgcagttgc tgagtgtgat cgatgccatc agcgaagggc cgattgaagg tccggtggat     120
ggcttaaaaa gcgtgctgct gaacagtacg ccggtgctgg acactgaggg gaataccaac     180
atatccggtg tcacggtggt gttccgggct ggtgagcagg agcagactcc gccggaggga     240
tttgaatcct ccggctccga gacggtgctg gtacggaag tgaaatatga cacgccgatc     300
acccgcacca ttacgtctgc aaacatcgac cgtctgcgct ttaccttcgg tgtacaggca     360
ctggtggaaa ccacctcaaa gggtgacagg aatccgtcgg aagtccgcct gctggttcag     420
atacaacgta acggtggctg ggtgacggaa aaagacatca ccattaaggg caaaaccacc     480
tcgcagtatc tggcctcggt ggtgatgggt aacctgccgc cgcgcccgtt taatatccgg     540
atgcgcagga tgacgccgga cagcaccaca gaccagctga gaacaaaaac gctctggtcg     600
tcatacactg aaatcatcga tgtgaaacag tgctacccga cacggcact ggtcggcgtg     660
caggtggact cggagcagtt cggcagccag caggtgagcc gtaattatca tctgcgcggg     720
cgtattctgc aggtgccgtc gaactataac ccgcagacgc ggcaatacag cggtatctgg     780
gacgaaacgt ttaaaccggc atacagcaac aacatggcct ggtgtctgtg ggatatgctg     840
acccatccgc gctacggcat ggggaaacgt cttggtgcgg cggatgtgga taaatgggcg     900
ctgtatgtca tcgccagta ctgcgaccag tcagtgccgg acggctttgg cggcacggag     960
ccgcgcatca cctgtaatgc gtacctgacc acacagcgta aggcgtggga tgtgctcagc    1020
gatttctgct cggcgatgcg ctgtatgccg gtatggaacg ggcagacgct gacgttcgtg    1080
caggaccgac cgtcggataa gacgtggacc tataaccgca gtaatgtggt gatgccggat    1140
gatggcgcgc cgttccgcta cagcttcagc gccctgaagg accgccataa tgccgttgag    1200
gtgaactgga ttgaccccga aacggctgg gagacggcga cagagcttgt tgaagatacg    1260
caggccattg cccgttacgg tcgtaatgtt cgaagatgg atgcctttgg ctgtaccagc    1320
cgggggcagg cacaccgcgc cgggctgtgg ctgattaaaa cagaactgct ggaaacgcag    1380
accgtggatt tcagcgtcgg cgcagaaggg cttcgccatg taccgggcga tgttattgaa    1440
atctgcgatg atgactatgc cggtatcagc accggtggtc gtgtgctggc ggtgaacagc    1500
cagacccgga cgctgacgct cgaccgtgaa atcacgctgc catcctccgg taccgcgctg    1560
```

-continued

| | |
|---|---|
| ataagcctgg ttgacggaag tggcaatccg gtcagcgtgg aggttcagtc cgtcaccgac | 1620 |
| ggcgtgaagg taaaagtgag ccgtgttcct gacggtgttg ctgaatacag cgtatgggag | 1680 |
| ctgaagctgc cgacgctgcg ccagcgactg ttccgctgcg tgagtatccg tgagaacgac | 1740 |
| gacggcacgt atgccatcac cgccgtgcag catgtgccgg aaaaagaggc catcgtggat | 1800 |
| aacggggcgc actttgacgg cgaacagagt ggcacggtga atggtgtcac gccgccagcg | 1860 |
| gtgcagcacc tgaccgcaga agtcactgca gacagcgggg aatatcaggt gctggcgcga | 1920 |
| tgggacacac cgaaggtggt gaagggcgtg agtttcctgc tccgtctgac cgtaacagcg | 1980 |
| gacgacggca gtgagcggct ggtcagcacg gcccggacga cggaaaccac ataccgcttc | 2040 |
| acgcaactgg cgctggggaa ctacaggctg acagtccggg cggtaaatgc gtgggggcag | 2100 |
| cagggcgatc cggcgtcggt atcgttccgg attgccgcac cggcagcacc gtcgaggatt | 2160 |
| gagctgacgc cgggctattt tcagataacc gccacgccgc atcttgccgt ttatgacccg | 2220 |
| acggtacagt ttgagttctg gttctcggaa aagcagattg cggatatcag acaggttgaa | 2280 |
| accagcacgc gttatcttgg tacggcgctg tactggatag ccgccagtat caatatcaaa | 2340 |
| ccgggccatg attattactt ttatatccgc agtgtgaaca ccgttggcaa atcggcattc | 2400 |
| gtggaggccg tcgtcgggc gagcgatgat gcggaaggtt acctggattt tttcaaaggc | 2460 |
| gagatagga aacccatct ggctcaggag ttgtggactc agattgataa cggtcagctt | 2520 |
| gcgcctgacc tggcggaaat cagaacgtcc atcacggatg tcagtaatga aatcacgcag | 2580 |
| accgtcaata gaaaactgga agaccagagt gcagcgatcc agcagataca gaaggttcag | 2640 |
| gttgatacaa ataataacct gaacagcatg tgggcagtga agctgcagca gatgcaggac | 2700 |
| ggacgccttt atattgcggg tatcggtgcc ggtattgaga cacctctga cggcatgcag | 2760 |
| agtcaggtgc tgctggcggc agacaggatt gcgatgatta tcctgcgaa tggcaacaca | 2820 |
| aagccgatgt ttgttggtca gggcgatcag atattcatga atgaagtgtt cctgaaatat | 2880 |
| ctgacggctc ccaccattac cagtggcggc aatcctccgg catttcccct gacatcagac | 2940 |
| ggaaagctga ccgctaaaaa tgcggatatc agtggcagtg tgaatgcgaa ctccgggacg | 3000 |
| ctcaacaacg tcacgattaa cgagaactgt cgggttctgg gaaaactgtc cgcgaaccag | 3060 |
| attgaaggcg atctcgttaa aacagtgggc aaagctttcc cccgggactc ccgtgcaccg | 3120 |
| gaacggtggc catcagggac cattaccgtc agggtttatg acgatcagcc gtttgaccgg | 3180 |
| cagattgtta ttccggcggt ggcattcagc ggcgctaaac atgagagaga gcatactgat | 3240 |
| atttactcct catgccgtct gatagtgcga aaaaacggtg ctgaaattta taaccgtacc | 3300 |
| gcgctggata atacgctgat ttacagtggc gttattgata tgcctgccgg tcacggtcac | 3360 |
| atgacgctgg agttttcggt gtcagcatgg ctggtgaata actggtatcc cacagcaagt | 3420 |
| atcagcgatt tgctggttgt ggtgatgaag aaagccaccg caggcatcag tatcagc | 3477 |

<210> SEQ ID NO 27
<211> LENGTH: 1131
<212> TYPE: PRT
<213> ORGANISM: Artificial Sequence
<220> FEATURE:
<223> OTHER INFORMATION: 1A2

<400> SEQUENCE: 27

Met Gly Lys Gly Ser Ser Lys Gly His Thr Pro Arg Glu Ala Lys Asp
1               5                   10                  15

Asn Leu Lys Ser Thr Gln Leu Leu Ser Val Ile Asp Ala Ile Ser Glu
            20                  25                  30

```
Gly Pro Ile Glu Gly Pro Val Asp Gly Leu Lys Ser Val Leu Leu Asn
             35                  40                  45

Ser Thr Pro Val Leu Asp Thr Glu Gly Asn Thr Asn Ile Ser Gly Val
 50                  55                  60

Thr Val Val Phe Arg Ala Gly Glu Gln Glu Gln Thr Pro Pro Glu Gly
 65                  70                  75                  80

Phe Glu Ser Ser Gly Ser Glu Thr Val Leu Gly Thr Glu Val Lys Tyr
                 85                  90                  95

Asp Thr Pro Ile Thr Arg Thr Ile Thr Ser Ala Asn Ile Asp Arg Leu
                100                 105                 110

Arg Phe Thr Phe Gly Val Gln Ala Leu Val Glu Thr Thr Ser Lys Gly
             115                 120                 125

Asp Arg Asn Pro Ser Glu Val Arg Leu Leu Val Gln Ile Gln Arg Asn
 130                 135                 140

Gly Gly Trp Val Thr Glu Lys Asp Ile Thr Ile Lys Gly Lys Thr Thr
145                 150                 155                 160

Ser Gln Tyr Leu Ala Ser Val Val Met Gly Asn Leu Pro Pro Arg Pro
                165                 170                 175

Phe Asn Ile Arg Met Arg Arg Met Thr Pro Asp Ser Thr Thr Asp Gln
                180                 185                 190

Leu Gln Asn Lys Thr Leu Trp Ser Ser Tyr Thr Glu Ile Ile Asp Val
            195                 200                 205

Lys Gln Cys Tyr Pro Asn Thr Ala Leu Val Gly Val Gln Val Asp Ser
210                 215                 220

Glu Gln Phe Gly Ser Gln Val Ser Arg Asn Tyr His Leu Arg Gly
225                 230                 235                 240

Arg Ile Leu Gln Val Pro Ser Asn Tyr Asn Pro Gln Thr Arg Gln Tyr
                245                 250                 255

Ser Gly Ile Trp Asp Gly Thr Phe Lys Pro Ala Tyr Ser Asn Asn Met
            260                 265                 270

Ala Trp Cys Leu Trp Asp Met Leu Thr His Pro Arg Tyr Gly Met Gly
        275                 280                 285

Lys Arg Leu Gly Ala Ala Asp Val Asp Lys Trp Ala Leu Tyr Val Ile
290                 295                 300

Gly Gln Tyr Cys Asp Gln Ser Val Pro Asp Gly Phe Gly Gly Thr Glu
305                 310                 315                 320

Pro Arg Ile Thr Cys Asn Ala Tyr Leu Thr Thr Gln Arg Lys Ala Trp
                325                 330                 335

Asp Val Leu Ser Asp Phe Cys Ser Ala Met Arg Cys Met Pro Val Trp
                340                 345                 350

Asn Gly Gln Thr Leu Thr Phe Val Gln Asp Arg Pro Ser Asp Lys Thr
            355                 360                 365

Trp Thr Tyr Asn Arg Ser Asn Val Val Met Pro Asp Asp Gly Ala Pro
370                 375                 380

Phe Arg Tyr Ser Phe Ser Ala Leu Lys Asp Arg His Asn Ala Val Glu
385                 390                 395                 400

Val Asn Trp Ile Asp Pro Asn Asn Gly Trp Glu Thr Ala Thr Glu Leu
                405                 410                 415

Val Glu Asp Thr Gln Ala Ile Ala Arg Tyr Gly Arg Asn Val Thr Lys
                420                 425                 430

Met Asp Ala Phe Gly Cys Thr Ser Arg Gly Gln Ala His Arg Ala Gly
435                 440                 445
```

```
Leu Trp Leu Ile Lys Thr Glu Leu Leu Glu Thr Gln Thr Val Asp Phe
    450                 455                 460

Ser Val Gly Ala Glu Gly Leu Arg His Val Pro Gly Asp Val Ile Glu
465                 470                 475                 480

Ile Cys Asp Asp Tyr Ala Gly Ile Ser Thr Gly Gly Arg Val Leu
                485                 490                 495

Ala Val Asn Ser Gln Thr Arg Thr Leu Thr Leu Asp Arg Glu Ile Thr
            500                 505                 510

Leu Pro Ser Ser Gly Thr Ala Leu Ile Ser Leu Val Asp Gly Ser Gly
        515                 520                 525

Asn Pro Val Ser Val Glu Val Gln Ser Val Thr Asp Gly Val Lys Val
530                 535                 540

Lys Val Ser Arg Val Pro Asp Gly Val Ala Glu Tyr Ser Val Trp Glu
545                 550                 555                 560

Leu Lys Leu Pro Thr Leu Arg Gln Arg Leu Phe Arg Cys Val Ser Ile
                565                 570                 575

Arg Glu Asn Asp Asp Gly Thr Tyr Ala Ile Thr Ala Val Gln His Val
            580                 585                 590

Pro Glu Lys Glu Ala Ile Val Asp Asn Gly Ala His Phe Asp Gly Glu
        595                 600                 605

Gln Ser Gly Thr Val Asn Gly Val Thr Pro Ala Val Gln His Leu
610                 615                 620

Thr Ala Glu Val Thr Ala Asp Ser Gly Glu Tyr Gln Val Leu Ala Arg
625                 630                 635                 640

Trp Asp Thr Pro Lys Val Val Lys Gly Val Ser Phe Leu Leu Arg Leu
                645                 650                 655

Thr Val Thr Ala Asp Asp Gly Ser Glu Arg Leu Val Ser Thr Ala Arg
            660                 665                 670

Thr Thr Glu Thr Thr Tyr Arg Phe Thr Gln Leu Ala Leu Gly Asn Tyr
        675                 680                 685

Arg Leu Thr Val Arg Ala Val Asn Ala Trp Gly Gln Gln Gly Asp Pro
    690                 695                 700

Ala Ser Val Ser Phe Arg Ile Ala Ala Pro Ala Ala Pro Ser Arg Ile
705                 710                 715                 720

Glu Leu Thr Pro Gly Tyr Phe Gln Ile Thr Ala Thr Pro His Leu Ala
                725                 730                 735

Val Tyr Asp Pro Thr Val Gln Phe Glu Phe Trp Phe Ser Glu Lys Gln
            740                 745                 750

Ile Ala Asp Ile Arg Gln Val Glu Thr Ser Thr Arg Tyr Leu Gly Thr
        755                 760                 765

Ala Leu Tyr Trp Ile Ala Ala Ser Ile Asn Ile Lys Pro Gly His Asp
    770                 775                 780

Tyr Tyr Phe Tyr Ile Arg Ser Val Asn Thr Val Gly Lys Ser Ala Phe
785                 790                 795                 800

Val Glu Ala Val Gly Arg Ala Ser Asp Asp Ala Glu Gly Tyr Leu Asp
                805                 810                 815

Phe Phe Lys Gly Lys Ile Thr Glu Ser His Leu Gly Lys Glu Leu Leu
            820                 825                 830

Glu Lys Val Glu Leu Thr Glu Asp Asn Ala Ser Arg Leu Glu Glu Phe
        835                 840                 845

Ser Lys Glu Trp Lys Asp Ala Ser Asp Lys Trp Asn Ala Met Trp Ala
    850                 855                 860

Val Lys Ile Glu Gln Thr Lys Asp Gly Lys His Tyr Val Ala Gly Ile
```

```
                865                 870                 875                 880
Gly Leu Ser Met Glu Asp Thr Glu Gly Lys Leu Ser Gln Phe Leu
                885                 890                 895
Val Ala Ala Asn Arg Ile Ala Phe Ile Asp Pro Ala Asn Gly Asn Glu
            900                 905                 910
Thr Pro Met Phe Val Ala Gln Gly Asn Gln Ile Phe Met Asn Asp Val
            915                 920                 925
Phe Leu Lys Arg Leu Thr Ala Pro Thr Ile Thr Ser Gly Gly Asn Pro
        930                 935                 940
Pro Ala Phe Ser Leu Thr Pro Asp Gly Lys Leu Thr Ala Lys Asn Ala
945                 950                 955                 960
Asp Ile Ser Gly Asn Val Asn Ala Asn Ser Gly Thr Leu Asn Asn Val
            965                 970                 975
Thr Ile Asn Glu Asn Cys Arg Val Leu Gly Lys Leu Ser Ala Asn Gln
        980                 985                 990
Ile Glu Gly Asp Leu Val Lys Thr Val Gly Lys Ala Phe Pro Arg Asp
    995                 1000                1005
Ser Arg Ala Pro Glu Arg Trp Pro Ser Gly Thr Ile Thr Val Arg
    1010                1015                1020
Val Tyr Asp Asp Gln Pro Phe Asp Arg Gln Ile Val Ile Pro Ala
    1025                1030                1035
Val Ala Phe Ser Gly Ala Lys His Glu Lys Glu His Thr Asp Ile
    1040                1045                1050
Tyr Ser Ser Cys Arg Leu Ile Val Arg Lys Asn Gly Ala Glu Ile
    1055                1060                1065
Tyr Asn Arg Thr Ala Leu Asp Asn Thr Leu Ile Tyr Ser Gly Val
    1070                1075                1080
Ile Asp Met Pro Ala Gly His Gly His Met Thr Leu Glu Phe Ser
    1085                1090                1095
Val Ser Ala Trp Leu Val Asn Asn Trp Tyr Pro Thr Ala Ser Ile
    1100                1105                1110
Ser Asp Leu Leu Val Val Val Met Lys Lys Ala Thr Ala Gly Ile
    1115                1120                1125
Thr Ile Ser
    1130

<210> SEQ ID NO 28
<211> LENGTH: 3393
<212> TYPE: DNA
<213> ORGANISM: Artificial Sequence
<220> FEATURE:
<223> OTHER INFORMATION: 1A2

<400> SEQUENCE: 28
atgggtaaag gaagcagtaa ggggcatacc ccgcgcgaag cgaaggacaa cctgaagtcc      60
acgcagttgc tgagtgtgat cgatgccatc agcgaagggc cgattgaagg tccggtggat     120
ggcttaaaaa gcgtgctgct gaacagtacg ccggtgctgg acactgaggg gaataccaac     180
atatccggtg tcacggtggt gttccgggct ggtgagcagg agcagactcc gccggaggga     240
tttgaatcct ccggctccga gacggtgctg ggtacggaag tgaaatatga cacgccgatc     300
acccgcacca ttacgtctgc aaacatcgac cgtctgcgct ttaccttcgg tgtacaggca     360
ctggtggaaa ccacctcaaa gggtgacagg aatccgtcgg aagtccgcct gctggttcag     420
atacaacgta acggtggctg ggtgacggaa aaagacatca ccattaaggg caaaaccacc     480
```

-continued

```
tcgcagtatc tggcctcggt ggtgatgggt aacctgccgc cgcgcccgtt taatatccgg    540
atgcgcagga tgacgccgga cagcaccaca gaccagctgc agaacaaaac gctctggtcg    600
tcatacactg aaatcatcga tgtgaaacag tgctacccga cacggcact ggtcggcgtg     660 caggtggact cggagcagtt cggcagccag caggtgagcc gtaattatca tctgcgcggg    720
cgtattctgc aggtgccgtc gaactataac ccgcagacgc ggcaatacag cggtatctgg    780
gacggaacgt ttaaaccggc atacagcaac aacatggcct ggtgtctgtg ggatatgctg    840
acccatccgc gctacggcat ggggaaacgt cttggtgcgg cggatgtgga taaatgggcg    900
ctgtatgtca tcggccagta ctgcgaccag tcagtgccgg acggctttgg cggcacggag    960
ccgcgcatca cctgtaatgc gtacctgacc acacagcgta aggcgtggga tgtgctcagc   1020
gatttctgct cggcgatgcg ctgtatgccg gtatggaacg ggcagacgct gacgttcgtg   1080
caggaccgac cgtcggataa gacgtggacc tataaccgca gtaatgtggt gatgccggat   1140
gatggcgcgc cgttccgcta cagcttcagc gccctgaagg accgccataa tgccgttgag   1200
gtgaactgga ttgaccccgaa caacggctgg gagacggcga cagagcttgt tgaagatacg   1260
caggccattg cccgttacgg tcgtaatgtt acgaagatgg atgcctttgg ctgtaccagc   1320
cgggggcagg cacaccgcgc cgggctgtgg ctgattaaaa cagaactgct ggaaacgcag   1380
accgtggatt tcagcgtcgg cgcagaaggg cttcgccatg taccgggcga tgttattgaa   1440
atctgcgatg atgactatgc cggtatcagc accggtggtc gtgtgctggc ggtgaacagc   1500
cagacccgga cgctgacgct cgaccgtgaa atcacgctgc catcctccgg taccgcgctg   1560
ataagcctgt tgacggaag tggcaatccg gtcagcgtgg aggttcagtc cgtcaccgac    1620
ggcgtgaagg taaaagtgag ccgtgttcct gacggtgttg ctgaatacag cgtatgggag   1680
ctgaagctgc cgacgctgcg ccagcgactg ttccgctgcg tgagtatccg tgagaacgac   1740
gacggcacgt atgccatcac cgccgtgcag catgtgccgg aaaaagaggc catcgtggat   1800
aacggggcgc actttgacgg cgaacagagt ggcacggtga atggtgtcac gccgccagcg   1860
gtgcagcacc tgaccgcaga agtcactgca gacagcgggg aatatcaggt gctggcgcga   1920
tgggacacac cgaaggtggt gaagggcgtg agtttcctgc tccgtctgac cgtaacagcg   1980
gacgacggca gtgagcggct ggtcagcacg gcccggacga cggaaaccac ataccgcttc   2040
acgcaactgg cgctggggaa ctacaggctg acagtccggg cggtaaatgc gtgggggcag   2100
cagggcgatc cggcgtcggt atcgttccgg attgccgcac cggcagcacc gtcgaggatt   2160
gagctgacgc cgggctattt tcagataacc gccacgccgc atcttgccgt ttatgacccg   2220
acggtacagt ttgagttctg gttctcggaa aagcagattg cggatatcag acaggttgaa   2280
accagcacgc gttatcttgg tacgcgctg tactggatag ccgccagtat caatatcaaa   2340
ccgggccatg attattactt ttatatccgc agtgtgaaca ccgttggcaa atcggcattc   2400
gtggaggccg tcggtcgggc gagcgatgat gcggaaggtt acctggattt tttcaaaggc   2460
aagataaccg aatcccatct cggcaaggag ctgctgaaaa agtcgagct gacggaggat   2520 aacgccagca gactggagga gttttcgaaa gagtggaagg atgccagtga aagtggaat   2580 gccatgtggg ctgtcaaaat tgagcagacc aaagacggca acattatgt cgcgggtatt   2640 ggcctcagca tggaggacac ggaggaaggc aaactgagcc agtttctggt tgccgccaat   2700
cgtatcgcat ttattgaccc ggcaaacggg aatgaaacgc cgatgtttgt ggcgcagggc   2760
aaccagatat tcatgaacga cgtgttcctg aagcgcctga cggcccccac cattaccagc   2820
ggcggcaatc ctccggcctt ttccctgaca ccggacggaa agctgaccgc taaaaatgcg   2880
```

```
gatatcagcg gtaacgtgaa tgcgaactcc gggacgctca acaacgtcac gattaacgag    2940
aactgtcggg ttctgggaaa attgtccgcg aaccagattg aaggcgatct cgttaaaaca    3000
gtgggcaaag ctttcccccg ggactcccgt gcaccggagc ggtggccatc aggaaccatt    3060
accgtcaggt tttatgacga tcagccgttt gaccggcaga ttgttattcc ggcggtggca    3120
ttcagcggcg ctaaacatga gaaagagcat actgatattt actcctcatg ccgtctgata    3180
gtgcggaaaa acggtgctga aatttataac cgtaccgcgc tggataatac gctgatttac    3240
agtggcgtta ttgatatgcc tgccggtcac ggtcacatga cactggagtt ttcggtgtca    3300
gcatggctgg taaataactg gtatcccaca gcaagtatca gcgatttgct ggttgtggtg    3360
atgaagaaag ccactgcagg catcacgatt agc                                 3393
```

<210> SEQ ID NO 29
<211> LENGTH: 1132
<212> TYPE: PRT
<213> ORGANISM: Artificial Sequence
<220> FEATURE:
<223> OTHER INFORMATION: A8

<400> SEQUENCE: 29

```
Met Gly Lys Gly Ser Ser Lys Gly His Thr Pro Arg Glu Ala Lys Asp
1               5                   10                  15

Asn Leu Lys Ser Thr Gln Leu Leu Ser Val Ile Asp Ala Ile Ser Glu
            20                  25                  30

Gly Pro Ile Glu Gly Pro Val Asp Gly Leu Lys Ser Val Leu Leu Asn
        35                  40                  45

Ser Thr Pro Val Leu Asp Thr Glu Gly Asn Thr Asn Ile Ser Gly Val
    50                  55                  60

Thr Val Val Phe Arg Ala Gly Glu Gln Glu Gln Thr Pro Pro Glu Gly
65                  70                  75                  80

Phe Glu Ser Ser Gly Ser Glu Thr Val Leu Gly Thr Glu Val Lys Tyr
                85                  90                  95

Asp Thr Pro Ile Thr Arg Thr Ile Thr Ser Ala Asn Ile Asp Arg Leu
            100                 105                 110

Arg Phe Thr Phe Gly Val Gln Ala Leu Val Glu Thr Ser Lys Gly
        115                 120                 125

Asp Arg Asn Pro Ser Glu Val Arg Leu Leu Val Gln Ile Gln Arg Asn
    130                 135                 140

Gly Gly Trp Val Thr Glu Lys Asp Ile Thr Ile Lys Gly Lys Thr Thr
145                 150                 155                 160

Ser Gln Tyr Leu Ala Ser Val Val Met Gly Asn Leu Pro Pro Arg Pro
                165                 170                 175

Phe Asn Ile Arg Met Arg Arg Met Thr Pro Asp Ser Thr Thr Asp Gln
            180                 185                 190

Leu Gln Asn Lys Thr Leu Trp Ser Ser Tyr Thr Glu Ile Ile Asp Val
        195                 200                 205

Lys Gln Cys Tyr Pro Asn Thr Ala Leu Val Gly Val Gln Val Asp Ser
    210                 215                 220

Glu Gln Phe Gly Ser Gln Gln Val Ser Arg Asn Tyr His Leu Arg Gly
225                 230                 235                 240

Arg Ile Leu Gln Val Pro Ser Asn Tyr Asn Pro Gln Thr Arg Gln Tyr
                245                 250                 255

Ser Gly Ile Trp Asp Gly Thr Phe Lys Pro Ala Tyr Ser Asn Asn Met
            260                 265                 270
```

Ala Trp Cys Leu Trp Asp Met Leu Thr His Pro Arg Tyr Gly Met Gly
            275                 280                 285

Lys Arg Leu Gly Ala Ala Asp Val Asp Lys Trp Ala Leu Tyr Val Ile
            290                 295                 300

Gly Gln Tyr Cys Asp Gln Ser Val Pro Asp Gly Phe Gly Gly Thr Glu
305                 310                 315                 320

Pro Arg Ile Thr Cys Asn Ala Tyr Leu Thr Thr Gln Arg Lys Ala Trp
                325                 330                 335

Asp Val Leu Ser Asp Phe Cys Ser Ala Met Arg Cys Met Pro Val Trp
            340                 345                 350

Asn Gly Gln Thr Leu Thr Phe Val Gln Asp Arg Pro Ser Asp Lys Thr
            355                 360                 365

Trp Thr Tyr Asn Arg Ser Asn Val Val Met Pro Asp Asp Gly Ala Pro
    370                 375                 380

Phe Arg Tyr Ser Phe Ser Ala Leu Lys Asp Arg His Asn Ala Val Glu
385                 390                 395                 400

Val Asn Trp Ile Asp Pro Asn Asn Gly Trp Glu Thr Ala Thr Glu Leu
                405                 410                 415

Val Glu Asp Thr Gln Ala Ile Ala Arg Tyr Gly Arg Asn Val Thr Lys
            420                 425                 430

Met Asp Ala Phe Gly Cys Thr Ser Arg Gly Gln Ala His Arg Ala Gly
            435                 440                 445

Leu Trp Leu Ile Lys Thr Glu Leu Leu Glu Thr Gln Thr Val Asp Phe
    450                 455                 460

Ser Val Gly Ala Glu Gly Leu Arg His Val Pro Gly Asp Val Ile Glu
465                 470                 475                 480

Ile Cys Asp Asp Asp Tyr Ala Gly Ile Ser Thr Gly Gly Arg Val Leu
                485                 490                 495

Ala Val Asn Ser Gln Thr Arg Thr Leu Thr Leu Asp Arg Glu Ile Thr
            500                 505                 510

Leu Pro Ser Ser Gly Thr Ala Leu Ile Ser Leu Val Asp Gly Ser Gly
            515                 520                 525

Asn Pro Val Ser Val Glu Val Gln Ser Val Thr Asp Gly Val Lys Val
    530                 535                 540

Lys Val Ser Arg Val Pro Asp Gly Val Ala Glu Tyr Ser Val Trp Glu
545                 550                 555                 560

Leu Lys Leu Pro Thr Leu Arg Gln Arg Leu Phe Arg Cys Val Ser Ile
                565                 570                 575

Arg Glu Asn Asp Asp Gly Thr Tyr Ala Ile Thr Ala Val Gln His Val
            580                 585                 590

Pro Glu Lys Glu Ala Ile Val Asp Asn Gly Ala His Phe Asp Gly Glu
            595                 600                 605

Gln Ser Gly Thr Val Asn Gly Val Thr Pro Ala Val Gln His Leu
    610                 615                 620

Thr Ala Glu Val Thr Ala Asp Ser Gly Glu Tyr Gln Val Leu Ala Arg
625                 630                 635                 640

Trp Asp Thr Pro Lys Val Val Lys Gly Val Ser Phe Leu Leu Arg Leu
                645                 650                 655

Thr Val Thr Ala Asp Asp Gly Ser Glu Arg Leu Val Ser Thr Ala Arg
            660                 665                 670

Thr Thr Glu Thr Thr Tyr Arg Phe Thr Gln Leu Ala Leu Gly Asn Tyr
            675                 680                 685

```
Arg Leu Thr Val Arg Ala Val Asn Ala Trp Gly Gln Gln Gly Asp Pro
    690                 695                 700

Ala Ser Val Ser Phe Arg Ile Ala Ala Pro Ala Ala Pro Ser Arg Ile
705                 710                 715                 720

Glu Leu Thr Pro Gly Tyr Phe Gln Ile Thr Ala Thr Pro His Leu Ala
                725                 730                 735

Val Tyr Asp Pro Thr Val Gln Phe Glu Phe Trp Phe Ser Glu Lys Gln
            740                 745                 750

Ile Ala Asp Ile Arg Gln Val Glu Thr Ser Thr Arg Tyr Leu Gly Thr
        755                 760                 765

Ala Leu Tyr Trp Ile Ala Ala Ser Ile Asn Ile Lys Pro Gly His Asp
770                 775                 780

Tyr Tyr Phe Tyr Ile Arg Ser Val Asn Thr Val Gly Lys Ser Ala Phe
785                 790                 795                 800

Val Glu Ala Val Gly Arg Ala Ser Asp Asp Ala Glu Gly Tyr Leu Asp
                805                 810                 815

Phe Phe Lys Gly Lys Ile Thr Glu Ser His Leu Gly Lys Glu Leu Leu
            820                 825                 830

Glu Lys Val Glu Leu Thr Glu Asp Asn Ala Ser Arg Leu Glu Glu Phe
        835                 840                 845

Ser Lys Glu Trp Lys Asp Ala Ser Asp Lys Trp Asn Ala Met Trp Ala
850                 855                 860

Val Lys Ile Glu Gln Thr Lys Asp Gly Lys His Tyr Val Ala Gly Ile
865                 870                 875                 880

Gly Leu Ser Met Glu Asp Thr Glu Glu Gly Lys Leu Ser Gln Phe Leu
                885                 890                 895

Val Ala Ala Asn Arg Ile Ala Phe Ile Asp Pro Ala Asn Gly Asn Glu
            900                 905                 910

Thr Pro Met Phe Val Ala Gln Gly Asn Gln Ile Phe Met Asn Asp Val
        915                 920                 925

Phe Leu Lys Arg Leu Thr Ala Pro Thr Ile Thr Ser Gly Gly Asn Pro
930                 935                 940

Pro Ala Phe Ser Leu Thr Pro Asp Gly Lys Leu Thr Ala Lys Asn Ala
945                 950                 955                 960

Asp Ile Ser Gly Ser Val Asn Ala Asn Ser Gly Thr Leu Asn Asn Val
                965                 970                 975

Thr Ile Asn Glu Asn Cys Gln Ile Lys Gly Lys Leu Ser Ala Asn Gln
            980                 985                 990

Ile Glu Gly Asp Ile Val Lys Thr Val Ser Lys Ser Phe Pro Arg Thr
        995                 1000                1005

Asn Ser Tyr Ala Ser Gly Thr Ile Thr Val Arg Ile Ser Asp Asp
    1010                1015                1020

Gln Lys Phe Asp Arg Gln Val Met Ile Pro Pro Val Leu Phe Arg
    1025                1030                1035

Gly Gly Lys His Glu Asn Phe Asn Ser Asn Asn Gln Gln Ser Tyr
    1040                1045                1050

Trp Tyr Ser Thr Cys Arg Leu Arg Val Thr Arg Asn Gly Gln Glu
    1055                1060                1065

Ile Phe Asn Gln Ser Thr Thr Asp Ala Gln Gly Val Phe Ser Ser
    1070                1075                1080

Val Ile Asp Met Pro Ala Gly Gln Gly Thr Leu Thr Leu Thr Phe
    1085                1090                1095

Thr Val Ser Ser Ser Gly Ala Asn Asn Trp Thr Pro Thr Thr Ser
```

1100                1105                1110

Ile Ser  Asp Leu Leu Val Val  Val Met Lys Lys Ser  Thr Ala Gly
         1115                1120                1125

Ile Ser  Ile Ser
         1130

<210> SEQ ID NO 30
<211> LENGTH: 2032
<212> TYPE: DNA
<213> ORGANISM: Artificial Sequence
<220> FEATURE:
<223> OTHER INFORMATION: A8

<400> SEQUENCE: 30

| | | | | | |
|---|---|---|---|---|---|
| atgggtaaag | gaagcagtaa | ggggcatacc | ccgcgcgaag | cgaaggacaa | cctgaagtcc | 60 |
| acgcagttgc | tgagtgtgat | cgatgccatc | agcgaagggc | cgattgaagg | tccggtggat | 120 |
| ggcttaaaaa | gcgtgctgct | gaacagtacg | ccggtgctgg | acactgaggg | gaataccaac | 180 |
| atatccggtg | tcacggtggt | gttccgggct | ggtgagcagg | agcagactcc | gccggaggga | 240 |
| tttgaatcct | ccggctccga | gacggtgctg | ggtacggaag | tgaaatatga | cacgccgatc | 300 |
| acccgcacca | ttacgtctgc | aaacatcgac | cgtctgcgct | ttaccttcgg | tgtacaggca | 360 |
| ctggtggaaa | ccacctcaaa | gggtgacagg | aatccgtcgg | aagtccgcct | gctggttcag | 420 |
| atacaacgta | acggtggctg | ggtgacggaa | aaagacatca | ccattaaggg | caaaaccacc | 480 |
| tcgcagtatc | tggcctcggt | ggtgatgggt | aacctgccgc | cgcgcccgtt | taatatccgg | 540 |
| atgcgcagga | tgacgccgga | cagcaccaca | gaccagctgc | agaacaaaac | gctctggtcg | 600 |
| tcatacactg | aaatcatcga | tgtgaaacag | tgctacccga | cacggcact | ggtcggcgtg | 660 |
| caggtggact | cggagcagtt | cggcagccag | caggtgagcc | gtaattatca | tctgcgcggg | 720 |
| cgtattctgc | aggtgccgtc | gaactataac | ccgcagacgc | ggcaatacag | cggtatctgg | 780 |
| gacggaacgt | ttaaaccggc | atacagcaac | aacatggcct | ggtgtctgtg | ggatatgctg | 840 |
| acccatccgc | gctacggcat | ggggaaacgt | cttggtgcgg | cggatgtgga | taaatgggcg | 900 |
| ctgtatgtca | tcggccagta | ctgcgaccag | tcagtgccgg | acggctttgg | cggcacggag | 960 |
| ccgcgcatca | cctgtaatgc | gtacctgacc | acacagcgta | aggcgtggga | tgtgctcagc | 1020 |
| gatttctgct | cggcgatgcg | ctgtatgccg | gtatggaacg | ggcagacgct | gacgttcgtg | 1080 |
| caggaccgac | cgtcggataa | gacgtggacc | tataaccgca | gtaatgtggt | gatgccggat | 1140 |
| gatggcgcgc | cgttccgcta | cagcttcagc | gccctgaagg | accgccataa | tgccgttgag | 1200 |
| gtgaactgga | ttgacccgaa | caacggctgg | gagacggcga | cagagcttgt | tgaagatacg | 1260 |
| caggccattg | cccgttacgg | tcgtaatgtt | acgaagatgg | atgcctttgg | ctgtaccagc | 1320 |
| cggggggcagg | cacaccgcgc | cgggctgtgg | ctgattaaaa | cagaactgct | ggaaacgcag | 1380 |
| accgtggatt | tcagcgtcgg | cgcagaaggg | cttcgccatg | taccgggcga | tgttattgaa | 1440 |
| atctgcgatg | atgactatgc | cggtatcagc | accgtggtc | gtgtgctggc | ggtgaacagc | 1500 |
| cagacccgga | cgctgacgct | cgaccgtgaa | atcacgctgc | catcctccgg | taccgcgctg | 1560 |
| ataagcctgg | ttgacggaag | tggcaatccg | gtcagcgtgg | aggttcagtc | cgtcaccgac | 1620 |
| ggcgtgaagg | taaaagtgag | ccgtgttcct | gacggtgttg | ctgaatacag | cgtatgggag | 1680 |
| ctgaagctgc | cgacgctgcg | ccagcgactg | ttccgctgcg | tgagtatccg | tgagaacgac | 1740 |
| gacggcacgt | atgccatcac | cgccgtgcag | catgtgccgg | aaaagagggc | catcgtggat | 1800 |
| aacggggcgc | actttgacgg | cgaacagagt | ggcacggtga | atggtgtcac | gccgccagcg | 1860 |

-continued

```
gtgcagcacc tgaccgcaga agtcactgca gacagcgggg aatatcaggt gctggcgcga    1920
tgggacacac cgaaggtggt gaagggcgtg agtttcctgc tccgtctgac cgtaacagcg    1980
gacgacggca gtgagcggct ggtcagcacg gcccggacga cggaaaccac at            2032
```

<210> SEQ ID NO 31
<211> LENGTH: 859
<212> TYPE: PRT
<213> ORGANISM: Artificial Sequence
<220> FEATURE:
<223> OTHER INFORMATION: gpH-IAI

<400> SEQUENCE: 31

```
Met Ala Glu Pro Val Gly Asp Leu Val Val Asp Leu Ser Leu Asp Ala
1               5                   10                  15

Ala Arg Phe Asp Glu Gln Met Ala Arg Val Arg His Phe Ser Gly
            20                  25                  30

Thr Glu Ser Asp Ala Lys Lys Thr Ala Ala Val Val Glu Gln Ser Leu
        35                  40                  45

Ser Arg Gln Ala Leu Ala Ala Gln Lys Ala Gly Ile Ser Val Gly Gln
    50                  55                  60

Tyr Lys Ala Ala Met Arg Met Leu Pro Ala Gln Phe Thr Asp Val Ala
65                  70                  75                  80

Thr Gln Leu Ala Gly Gly Gln Ser Pro Trp Leu Ile Leu Gln Gln
                85                  90                  95

Gly Gly Gln Val Lys Asp Ser Phe Gly Gly Met Ile Pro Met Phe Arg
            100                 105                 110

Gly Leu Ala Gly Ala Ile Thr Leu Pro Met Val Gly Ala Thr Ser Leu
        115                 120                 125

Ala Val Ala Thr Gly Ala Leu Ala Tyr Ala Trp Tyr Gln Gly Asn Ser
    130                 135                 140

Thr Leu Ser Asp Phe Asn Lys Thr Leu Val Leu Ser Gly Asn Gln Ala
145                 150                 155                 160

Gly Leu Thr Ala Asp Arg Met Leu Val Leu Ser Arg Ala Gly Gln Ala
                165                 170                 175

Ala Gly Leu Thr Phe Asn Gln Thr Ser Glu Ser Leu Thr Ala Leu Val
            180                 185                 190

Asn Ala Gly Val Arg Gly Gly Glu Gln Phe Glu Ala Ile Ser Gln Ser
        195                 200                 205

Val Ala Arg Phe Ser Ser Ala Ser Gly Val Glu Val Asp Lys Val Ala
    210                 215                 220

Glu Ala Phe Gly Lys Leu Thr Thr Asp Pro Thr Ser Gly Leu Thr Ala
225                 230                 235                 240

Met Ala Arg Gln Phe His Asn Val Thr Ala Glu Gln Ile Ala Tyr Val
                245                 250                 255

Ala Gln Leu Gln Arg Ser Gly Asp Glu Ala Gly Ala Leu Gln Ala Ala
            260                 265                 270

Asn Glu Ala Ala Thr Lys Gly Phe Asp Asp Gln Thr Arg Arg Leu Lys
        275                 280                 285

Glu Asn Met Gly Thr Leu Glu Thr Trp Ala Asp Arg Thr Ala Arg Ala
    290                 295                 300

Phe Lys Ser Met Trp Asp Ser Val Leu Asp Ile Gly Arg Pro Asp Thr
305                 310                 315                 320

Ala Gln Gly Met Leu Glu Lys Ala Glu Lys Ala Phe Asp Glu Ala Asp
                325                 330                 335
```

```
Lys Lys Trp Gln Trp Tyr Gln Ser Arg Ser His Arg Arg Gly Lys Thr
            340                 345                 350

Ser Ala Phe Leu Ala Asn Leu Arg Gly Ala Trp Glu Asp Arg Ala Asn
            355                 360                 365

Ala Gln Leu Gly Leu Ser Ala Ala Thr Leu Gln Ala Asp Leu Glu Lys
    370                 375                 380

Ala Arg Glu Met Ala Ala Lys Asp Trp Ala Glu Ser Glu Ala Ser Arg
385                 390                 395                 400

Leu Lys Tyr Thr Glu Glu Ala Gln Lys Ala Tyr Glu Arg Leu Gln Thr
                405                 410                 415

Pro Leu Glu Lys Tyr Thr Ala Arg Gln Glu Leu Asn Lys Ala Leu
            420                 425                 430

Lys Asp Gly Lys Ile Leu Gln Ala Asp Tyr Asn Thr Leu Met Ala Ala
            435                 440                 445

Ala Lys Lys Asp Tyr Glu Ala Thr Leu Lys Lys Pro Lys Gln Ser Ser
    450                 455                 460

Val Lys Val Ser Ala Gly Asp Arg Gln Glu Asp Ser Ala His Ala Ala
465                 470                 475                 480

Leu Leu Thr Leu Gln Ala Glu Leu Arg Thr Leu Glu Lys His Ala Gly
                485                 490                 495

Ala Asn Glu Lys Ile Ser Gln Gln Arg Arg Asp Leu Trp Lys Ala Glu
            500                 505                 510

Ser Gln Phe Ala Val Leu Glu Glu Ala Ala Gln Arg Arg Gln Leu Ser
    515                 520                 525

Ala Gln Glu Lys Ser Leu Leu Ala His Lys Asp Glu Thr Leu Glu Tyr
    530                 535                 540

Lys Arg Gln Leu Ala Ala Leu Gly Asp Lys Val Thr Tyr Gln Glu Arg
545                 550                 555                 560

Leu Asn Ala Leu Ala Gln Gln Ala Asp Lys Phe Ala Gln Gln Arg
                565                 570                 575

Ala Lys Arg Ala Ala Ile Asp Ala Lys Ser Arg Gly Leu Thr Asp Arg
            580                 585                 590

Gln Ala Glu Arg Glu Ala Thr Glu Gln Arg Leu Lys Glu Gln Tyr Gly
            595                 600                 605

Asp Asn Pro Leu Ala Leu Asn Asn Val Met Ser Glu Gln Lys Lys Thr
            610                 615                 620

Trp Ala Ala Glu Asp Gln Leu Arg Gly Asn Trp Met Ala Gly Leu Lys
625                 630                 635                 640

Ser Gly Trp Ser Glu Trp Glu Glu Ser Ala Thr Asp Ser Met Ser Gln
                645                 650                 655

Val Lys Ser Ala Ala Thr Gln Thr Phe Asp Gly Ile Ala Gln Asn Met
            660                 665                 670

Ala Ala Met Leu Thr Gly Ser Glu Gln Asn Trp Arg Ser Phe Thr Arg
            675                 680                 685

Ser Val Leu Ser Met Met Thr Glu Ile Leu Leu Lys Gln Ala Met Val
            690                 695                 700

Gly Ile Val Gly Ser Ile Gly Ser Ala Ile Gly Gly Ala Val Gly Gly
705                 710                 715                 720

Gly Ala Ser Ala Ser Gly Gly Thr Ala Ile Gln Ala Ala Ala Lys
                725                 730                 735

Phe His Phe Ala Thr Gly Gly Phe Thr Gly Thr Gly Gly Lys Tyr Glu
            740                 745                 750
```

-continued

```
Pro Ala Gly Ile Val His Arg Gly Glu Phe Val Phe Thr Lys Glu Ala
            755                 760                 765

Thr Ser Arg Ile Gly Val Gly Asn Leu Tyr Arg Leu Met Arg Gly Tyr
        770                 775                 780

Ala Thr Gly Gly Tyr Val Gly Thr Pro Gly Ser Met Ala Asp Ser Arg
785                 790                 795                 800

Ser Gln Ala Ser Gly Thr Phe Glu Gln Asn Asn His Val Val Ile Asn
                805                 810                 815

Asn Asp Gly Thr Asn Gly Gln Ile Gly Pro Ala Ala Leu Lys Ala Val
            820                 825                 830

Tyr Asp Met Ala Arg Lys Gly Ala Arg Asp Glu Ile Gln Thr Gln Met
        835                 840                 845

Arg Asp Gly Gly Leu Phe Ser Gly Gly Gly Arg
    850                 855

<210> SEQ ID NO 32
<211> LENGTH: 1154
<212> TYPE: PRT
<213> ORGANISM: Artificial Sequence
<220> FEATURE:
<223> OTHER INFORMATION: Lambda-K5

<400> SEQUENCE: 32

Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
            20                  25                  30

Val Val Val Asn Thr Val Gly Ser Glu Asn Pro Asp Glu Ala Gly Arg
        35                  40                  45

Tyr Ser Met Asp Val Glu Tyr Gly Gln Tyr Ser Val Ile Leu Gln Val
50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ser Ala Ala Gln Val Ala Ala Leu
130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Glu Ser
            180                 185                 190

Ser Lys Asn Ala Ala Ala Thr Ser Ala Gly Ala Ala Lys Thr Ser Glu
        195                 200                 205

Thr Asn Ala Ala Ala Ser Gln Gln Ser Ala Ala Thr Ser Ala Ser Thr
    210                 215                 220

Ala Ala Thr Lys Ala Ser Glu Ala Ala Thr Ser Ala Arg Asp Ala Val
225                 230                 235                 240

Ala Ser Lys Glu Ala Ala Lys Ser Ser Glu Thr Asn Ala Ser Ser Ser
                245                 250                 255
```

```
Ala Gly Arg Ala Ala Ser Ser Ala Thr Ala Ala Glu Asn Ser Ala Arg
            260                 265                 270

Ala Ala Lys Thr Ser Glu Thr Asn Ala Arg Ser Ser Glu Thr Ala Ala
        275                 280                 285

Glu Arg Ser Ala Ser Ala Ala Asp Ala Lys Thr Ala Ala Ala Gly
    290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ala Ile Arg
                325                 330                 335

Ala Lys Asn Ser Ala Lys Arg Ala Glu Asp Ile Ala Ser Ala Val Ala
            340                 345                 350

Leu Glu Asp Ala Asp Thr Thr Arg Lys Gly Ile Val Gln Leu Ser Ser
            355                 360                 365

Ala Thr Asn Ser Thr Ser Glu Thr Leu Ala Ala Thr Pro Lys Ala Val
            370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
                405                 410                 415

Asn Thr Gln Ile Ala Asn Thr Ala Phe Val Leu Ala Ala Ile Ala Asp
            420                 425                 430

Val Ile Asp Ala Ser Pro Asp Ala Leu Asn Thr Leu Asn Glu Leu Ala
            435                 440                 445

Ala Ala Leu Gly Asn Asp Pro Asp Phe Ala Thr Thr Met Thr Asn Ala
            450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
                485                 490                 495

Ala Ser Leu Thr Glu Leu Thr Gln Val Gly Arg Asp Ile Leu Ala Lys
            500                 505                 510

Asn Ser Val Ala Asp Val Leu Glu Tyr Leu Gly Ala Gly Glu Asn Ser
            515                 520                 525

Pro Lys Thr Glu Gly Ile Leu His Lys Gly Gln Ser Leu Tyr Glu Tyr
            530                 535                 540

Leu Asp Ala Arg Val Leu Thr Ser Lys Pro Phe Gly Ala Ala Gly Asp
545                 550                 555                 560

Ala Thr Thr Asp Asp Thr Glu Val Ile Ala Ala Ser Leu Asn Ser Gln
                565                 570                 575

Lys Ala Val Thr Ile Ser Asp Gly Val Phe Ser Ser Gly Ile Asn
            580                 585                 590

Ser Asn Tyr Cys Asn Leu Asp Gly Arg Gly Ser Gly Val Leu Ser His
            595                 600                 605

Arg Ser Thr Gly Asn Tyr Leu Val Phe Asn Asn Pro Arg Thr Gly
    610                 615                 620

Arg Leu Ser Asn Ile Thr Val Glu Ser Asn Lys Ala Thr Asp Thr Thr
625                 630                 635                 640

Gln Gly Gln Gln Val Ser Leu Ala Gly Gly Ser Asp Val Thr Val Ser
                645                 650                 655

Asp Val Asn Phe Ser Asn Val Lys Gly Thr Gly Phe Ser Leu Ile Ala
                660                 665                 670

Tyr Pro Asn Asp Ala Pro Pro Asp Gly Leu Met Ile Lys Gly Ile Arg
```

```
                675                 680                 685
Gly Ser Tyr Ser Gly Tyr Ala Thr Asn Lys Ala Ala Gly Cys Val Leu
    690                 695                 700
Ala Asp Ser Ser Val Asn Ser Leu Ile Asp Asn Val Ile Ala Lys Asn
705                 710                 715                 720
Tyr Pro Gln Phe Gly Ala Val Glu Leu Lys Gly Thr Ala Ser Tyr Asn
                725                 730                 735
Ile Val Ser Asn Val Ile Gly Ala Asp Cys Gln His Val Thr Tyr Asn
            740                 745                 750
Gly Thr Glu Gly Pro Ile Ala Pro Ser Asn Asn Leu Ile Lys Gly Val
        755                 760                 765
Met Ala Asn Asn Pro Lys Tyr Ala Val Val Ala Gly Lys Gly Ser
    770                 775                 780
Thr Asn Leu Ile Ser Asp Val Leu Val Asp Tyr Ser Thr Ser Asp Ala
785                 790                 795                 800
Arg Gln Ala His Gly Val Thr Val Glu Gly Ser Asp Asn Val Ile Asn
                805                 810                 815
Asn Val Leu Met Ser Gly Cys Asp Gly Thr Asn Ser Leu Gly Gln Arg
            820                 825                 830
Gln Thr Ala Thr Ile Ala Arg Phe Ile Gly Thr Ala Asn Asn Asn Tyr
        835                 840                 845
Ala Ser Val Phe Pro Ser Tyr Ser Ala Thr Gly Val Ile Thr Phe Glu
    850                 855                 860
Ser Gly Ser Thr Arg Asn Phe Val Glu Val Lys His Pro Gly Arg Arg
865                 870                 875                 880
Asn Asp Leu Leu Ser Ser Ala Ser Thr Ile Asp Gly Ala Ala Thr Ile
                885                 890                 895
Asp Gly Thr Ser Asn Ser Asn Val Val His Ala Pro Ala Leu Gly Gln
            900                 905                 910
Tyr Ile Gly Ser Met Ser Gly Arg Phe Glu Trp Arg Ile Lys Ser Met
        915                 920                 925
Ser Leu Pro Ser Gly Val Leu Thr Ser Ala Asp Lys Tyr Arg Met Leu
    930                 935                 940
Gly Asp Gly Ala Val Ser Leu Ala Val Gly Gly Thr Ser Ser Gln
945                 950                 955                 960
Val Arg Leu Phe Thr Ser Asp Gly Thr Ser Arg Thr Val Ser Leu Thr
                965                 970                 975
Asn Gly Asn Val Arg Leu Ser Thr Ser Ser Thr Gly Tyr Leu Gln Leu
            980                 985                 990
Gly Ala Asp Ala Met Thr Pro Asp Ser Thr Gly Thr Tyr Ala Leu Gly
        995                 1000                1005
Ser Ala Ser Arg Ala Trp Ser Gly Gly Phe Thr Gln Ala Ala Phe
    1010                1015                1020
Thr Val Thr Ser Asp Ala Arg Cys Lys Thr Glu Pro Leu Thr Ile
    1025                1030                1035
Ser Asp Ala Leu Leu Asp Ala Trp Ser Glu Val Asp Phe Val Gln
    1040                1045                1050
Phe Gln Tyr Leu Asp Arg Val Glu Glu Lys Gly Ala Asp Ser Ala
    1055                1060                1065
Arg Trp His Phe Gly Ile Ile Ala Gln Arg Ala Lys Glu Ala Phe
    1070                1075                1080
Glu Arg His Gly Ile Asp Ala His Arg Tyr Gly Phe Leu Cys Phe
    1085                1090                1095
```

```
Asp Ser Trp Asp Asp Val Tyr Glu Glu Asp Ala Asn Gly Ser Arg
    1100            1105                1110

Lys Leu Ile Thr Pro Ala Gly Ser Arg Tyr Gly Ile Arg Tyr Glu
    1115            1120                1125

Glu Val Leu Ile Leu Glu Ala Ala Leu Met Arg Arg Thr Ile Lys
    1130            1135                1140

Arg Met Gln Glu Ala Leu Ala Ala Leu Pro Lys
    1145            1150

<210> SEQ ID NO 33
<211> LENGTH: 11615
<212> TYPE: DNA
<213> ORGANISM: Artificial Sequence
<220> FEATURE:
<223> OTHER INFORMATION: payload p1392 plasmid

<400> SEQUENCE: 33
gtttgcaata agggacaagt tacgagtgta gacacgcaga attatccagc ctttagtctt      60
taggaaggca aagctattgt acgcggtagc cgtcgtagca atttaccaac tgtagaatta     120
ttggacacac gtaacaaggg cttacagttg aagtttaata aggtcacacg caaaaccgct     180
aaggaataat cgcaccgtta gcgaaagaat atttcagagc ggttagtaaa ggttgagtaa     240
agtgagattc caaagtgagc ctttataaaa agtaaagagc tataataaaa ccgtcgatcg     300
gaaaacaatc gcctgaaatc tcaagcacgt tgcccttcct aacgtcgcta aggtttcgta     360
aacccgtttg attaggaaga agaataagta acccgattag gtttgagatc gcgggttatc     420
ggtttggatt aaaagtggat accagcggag tcaacgccga cgcaaacgta cagtgatcca     480
atcctgttcc acggtcaagc acaatcagct agcaagatct tggaatagag tcgttgcacc     540
gctttgattt acatgctctc cattgcacaa cattccggaa ggactggctt ctctgccatg     600
atcggataat gaaaacatc agtatgccct gtcattttc tttgggtgtc ctcaaataat        660
tgccctcacg ttatcgtatg tgacgcgctc atctatgctc gaagtattcc ttgttctccc     720
atcttttaat agaaagtctt taatgaacgt gtcgttacgc agtgtatgaa ctcttgtttt     780 ataggcaga ctttggcgtg gcctaagtgt gttcgataag aaggcaagga caactagctg      840
acgcgctgta atacggatat tatggcacgg ttgatacaaa cgctgatatc ctgatttgct     900
aatgtgccca acactttagt tgagtgccac gttccgacta caagttgctt caagagggga     960
atttggattt ggcaatagcc ccccgtttct acctcaagag gcgacgagta ttaaccgcgc    1020
cagctttcgg cacaagggcc aaagaagatt ccaatttctt attcccgaat aacctccgaa    1080
tccctgcggg aaaatcaccg accgaatagc ctagaagcaa ggggaacag ataggtataa      1140 ttagcttaag agagtaccag ccgtgacaac accgtagtaa ccacaaactt acgctggggc    1200
ttctttggcg gattttaca gatactaaca aggtgatttg aagtaccttag gttgaggatt     1260 taaacgcgct atccggtagt ctacaaattg gaaataccg ttcaaagagg ctagaatta      1320 cttaaaagcc ttcacaccgc ctgcgctata cgcgcccact ctcccgttta tccgtccaag    1380
cggaagcagg gcgaacttcc gctaagatat tcttacgtgt aacgtagcta agtatcccaa    1440
atagctggcg tacgcgttga acaccgccta gaggatcggg agtcgccgga cgagcgtgtt    1500
attggggact tacgccagcg tagactacaa cgcgcccaga ttaaccctgc acgtattgcc    1560
ttgaataacg tactaatctc tccggctctc gacaatctat cgagcgactc gattatcaac    1620
gggtgtcttg cagttctaat ctcttgcccc cgcccgtaat agcctccaag tgattcaaga    1680
```

```
tagtaaaggg caagagctta ttcggcgttg aaggatagcg gactttcggt caaccacaat    1740
tccccactcg acaaaaccag ccgtgcgaag aactctgaaa gtacaagcaa cccaagaggg    1800
ctgagcctaa actcagctaa ttcctaagtg agctaaagac tcgaagtgac agctattaat    1860
aaatagagcg ggaacgtcga acggtcgtga aagtaatagt acaacgggta ttaacttact    1920
gaggatattg cttgaagctg taccgtttta ttgggtgaac gaataagatc cagcaattca    1980
gccaaagaag ctaccaattt ttagtttaag agtgtcacgt ctgacctcgc gggtggatag    2040
ccgaacgtag agcttacgag ccagcggaaa cagtagccgc aggataagta aggggagtaa    2100
gtgatcgaac gaatcagaag tgacaatata cttaggctgg atctcgtccc gtgaatccca    2160
accctcacca actacgagat aagaggtaag ccagaaatcg gcatggtggc gaccaacgac    2220
tgttccccc ctgtaactaa tcgttccgtc aaaacctgac ttacttcaag gccaattcca    2280
agcgcaaaca ataccgtcct agttcttcgg ttaagtttcc gaagtaggag tgagcctacc    2340
tccgtttgcg tcttgttacc actgacccag ctatttactt tgtattgcct gcaatcgaat    2400
ttctgaactc tcagatagtg gggataacgg gaaagttcct atatttgcga actaacttag    2460
ccgtccacct cgaagctacc tactcacacc caccccgcgc ggggtaaata aggcactaat    2520
cccagcttag agcttgcgta gcacttagcc acaagttaat taacagttgt ctggtagttt    2580
ggcggtatta gcgagatcct agaagcaagg cagagttagt tctaacctaa gccacaaat    2640
aagacaggtt gccaaagccc gccggaaatt aaatcttgct cagttcggta acggagtttc    2700
cctcccgcgt acttaattcc caataagaaa cgcgcccaag tcctatcagg caaaattcag    2760
cccttcccg tgttagaacg agggtaaaaa tacaagccga ttgaacaagg gttgggggct    2820
tcaaatcgtc gtttacccca ctttacaacg gagggtaagt agttcaccct atagtacgaa    2880
gcagaactat ttcgaggggc gtgcaataat cgaatcttct gcggttgact taacacgcta    2940
gggacgtgcc ctcgattcag tcgcaggtac tcctactcag actgcctcac acccagctag    3000
tcactgagcg ataaaattga cccgcccctct aaggtagcga gtacgtccca aagggctccg    3060
gacagggcta tataggagag tttgatctcg ccccgacaac tgcaaccctc aactccctta    3120
gataatattg ttagccgaag ttgcacgacc cgccgtccac ggactgctct tagggtgtgg    3180
ctccttaatc tgacaacgtg caacccctat cgagggcgat tgtttctgcg aaaggtgttg    3240
tcctaatagt cgcgacattt ggcccttgta ggtgtgaaac cacttagctt cgcgccgtag    3300
tcctaaaggc ccacctattg actttgtttc gggtagcact aggaatctta acaatttgaa    3360
tttggacgtg gaacgcgtac accttgatct tcgaataatt ctagggatt ggaagtcctc    3420
tacgttgaca cacctacaat gctccaagta aatatacgaa taacgcgggc ctcgcggagc    3480
cgttccgaat cgtcacgtgt tcgtttactg ttaattggtg gcaaataagc aatatcgtag    3540
tccgtcaggc ccagccctgt tatccacggc gttatttgtc aaattgcgta gaactggatt    3600
gactgcctga caatacctaa ttatcggtac gaagtcccg aatctgtccg gctatttcac    3660
taatactttc caaacgcccc gtatccaaga agaacgaatt tatccacgct cccgtctttg    3720
ggacgaatac cgctacaagt ggacagagga tcggtacggg cctctaataa atccaacact    3780
ctacgccctc ttcaagagct agaagaacag ggtgcagttg gaaagggaat tatttcgtaa    3840
ggcgagccaa taccgtaatt aattcggaag agttaacacg attggaagta ggaatagttt    3900
ctaaccacgg ttactaatcc taataacgga acgctgtctg atagattagt gtcagcgctc    3960
actaccaaag aaaaataaaa agacgctgaa aagcgtctt ttatttttcg gtccagtgta    4020
actcaggcaa aagcacgtaa tattcgtact caccaaacga aactcatccg gcgcatcgcg    4080
```

```
cttcttcctc cgtaagcgtc accccccatta cttaaagagt gcatgtgcat attttgttat   4140
caataaaaaa ggccgcgatt tgcggcctta ttgttcgtct tgccggatta gatagctacc   4200
ggtgctttaa tacccggatg cggatcatag ccttcgattt cgaagtcctc aaaacgataa   4260
tcgaagatgc tttccggttt gcgtttgata atcagtttcg ggagcgggcg tggctcacgg   4320
cttaattgta aatgcgtctg atccatgtga tttgagtaca ggtgagtatc cccaccagtc   4380
caaacaaagt caccaacttc cagatcacac tgctgtgcca tcatatgaac taataaggcg   4440
taggaggcaa tgttaaacgg taagcccaga aacacgtcgc aagaacgctg gtacagttgg   4500
cacgataact taccatccgc aacatagaat tgaaagaagg catgacacgg tgctaaagcc   4560
attttgtcta attccccccac gttccatgcg gacacgataa tccggcgaga gtccggatca   4620
tttttcagtt ggttaagaac ggtagtgatc tgatcaatat gccgaccatc cggcgtaggc   4680
catgcacgcc attgcttacc atacactggc cctaagtcac cgttttcatc tgcccactca   4740
tcccagatgg taacgttatt ctcgtgcagg tacgcaatgt tcgtatcgcc ttgcagaaac   4800
cataataact cgtgaataat agaacggagg tggcaacgct tggtagtgac cagcgggaaa   4860
ccgtcttgca ggttgaaacg catctgatga ccaaagatag acagcgtacc agtgccagta   4920
cgatcattct tctgagtgcc ttcgtccagc acttttttgca tcagttccag atactgtttc   4980
attttagctt ccttagcttg cgaaatctcg ataactcaaa aaatagtagt gatcttattt   5040
cattatggtg aaagttgtct tacgtgcaac attttcgcaa aaagttggcg ctttatcaac   5100
actgtccgaa tgacaaatgg ttacaattat tgaacaccct tcggggtgtt ttttttgtttc   5160 tggtttcccg aggccgaact tttgttgcaa tggctgtcta ccctgtctac ctgagtaaag   5220
aaaaatacat ttaattcagt atattaactt gggtagacag ccttttttta ctgtctacct   5280
tctgtctacc ctctctacct gatttttacct gaatcagaca gggaggtaga cacggggtag   5340
acagtggata aaagcactct accccactga aagcagtgcc attactggca tggttgccag   5400
taaggttgat aaggtagaca aggggaggga caactcaaaa ctttttaaac gagggggtaa   5460
aacgcagatc aaaacgatct caagaagatc atcttattaa tcagataaaa tatttctaga   5520
tttcagtgca atttatctct tcaaatgtag caccggcgcg ccgtgaccaa ttattgaagg   5580
ccgctaacgc ggcctttttt tgtttctggt ttcccgaata gagcgacttc tccccaaaaa   5640
gcctcgcttt cagcacctgt cgtttccttt cttttcagag ggtattttaa ataaaaacat   5700
taagttatga cgaagaagaa cggaaacgcc ttaaaccgga aaattttcat aaatagcgaa   5760
aacccgcgag gtcgccgccc cgtaacctgt cggatcaccg aaagaacct gtaaagtgat   5820 aatgattatc atctacatat cacaacgtgc gtaaagggta agtatgaagg tcgtgtactc   5880
catcgctacc aaattccaga aaacagacg tttcgagcgt ctttttttcgt tttggtcacg   5940 acgtacggtg gaagattcgt taccaattga cagctagctc agtcctaggt atatacatac   6000
atgcttgttt gtttgtaaac tactgttttc attaaagagg agaaaggaag ccatgtccat   6060
ctatcaggag tttgttaaca agtattccct gtctaaaacc ctgcgttttg aactgatccc   6120
gcagggcaaa actttggaaa acattaaagc gcgtggcctg attctggatg acgaaaaacg   6180
tgcaaaggat tacaagaaag ctaaacgat catcgacaaa tatcaccagt tctttatcga   6240
agaaattctg tcctcggtgt gcatcagtga ggatctgtta cagaattatt ctgatgtata   6300
ctttaaactt aaaaagtccg atgacgataa tctgcaaaaa gatttcaagt cagccaaaga   6360
taccatcaag aaacagatct cagaatatat taaagatagc gaaaagttca aaaacctgtt   6420
```

```
taaccaaaac ctcattgatg ctaagaaagg ccaagaatct gacctgatct tatggctgaa    6480
acagagcaaa gataacggca ttgaactgtt caaagctaat agcgacatca ccgatattga    6540
tgaagcgctc gaaatcatca agtctttcaa aggctggacg acgtatttca aaggttttca    6600
tgaaaaccgt aagaatgtat attcgagcaa cgatattccg acctctatta tttatcgtat    6660
cgtggacgac aacctgccga gtttctggaa aacaaagcg aaatatgaat ctctgaaaga    6720
caaagcaccg gaagctatta actatgaaca gatcaagaaa gatctggcgg aagaactgac    6780
cttcgacatc gactataaaa cctccgaagt taaccagcgt gttttctcac tggacgaggt    6840
tttcgaaatc gctaatttca caattaccct gaatcaatct ggcatcacca aattcaacac    6900
cattattggt ggcaaatttg ttaacggcga aaacaccaag cgtaagggca tcaacgaata    6960
cattaacctc tatagccaac aaatcaacga caaaaccctg aaaaagtata aaatgtccgt    7020
tctgtttaaa cagattttat cggacaccga atctaaatcc ttcgtaattg ataaactgga    7080
agatgatagc gacgttgtca ccacgatgca gagcttttat gagcagattg cggcgttcaa    7140
aaccgtcgaa gagaaatcta ttaaagaaac tctgtccctg ctctttgacg acctcaaagc    7200
gcagaaacta gatctgtcta agatttactt taaaaacgac aaatctctga ccgatctcag    7260
tcaacaagtt ttcgatgact atagcgtgat cggcacggca gttttggaat acatcaccca    7320
acaaatcgcg ccgaaaaatc tggacaaccc gtccaagaag gaacaggaac tgattgcaaa    7380
gaaaacagaa aaagctaaat acctgagctt agaaactatc aaactggcac ttgaggaatt    7440
taataaacat cgtgatattg ataaacagtg tcgttttgag gaaattctgg cgaactttgc    7500
ggcaatcccg atgatcttcg acgaaattgc tcaaaacaaa gacaatctgg cgcagatctc    7560
tatcaagtac cagaatcagg gtaagaaaga tctgcttcaa gcatctgcgg aggacgatgt    7620
caaagcaatt aaagacttat tagatcagac gaataactta ttacacaagc tcaaaatctt    7680
ccacatcagc cagagcgagg acaaggcgaa cattctggat aaagatgaac acttctatct    7740
ggtgttcgaa gaatgttact tcgaactggc aaacatcgta cctctctaca ataaaatccg    7800
caactacatc acgcagaagc cttacagtga cgagaaattc aaactgaact tcgaaaacag    7860
cacgctggcg aacggctggg ataagaacaa agagccggac aacaccgcaa tcctgttcat    7920
caaagacgac aaatactatc tgggcgtaat gaacaagaag aacaacaaga tcttcgacga    7980
taaagcgatc aaagaaaaca agggtgaagg ctataagaaa atcgtgtaca agctcctgcc    8040
gggtgcgaac aaaatgttac cgaaagtgtt cttttccgcg aaaagcatca aattctacaa    8100
cccgtctgag gatattctgc gcatccgcaa tcatagcacg cacactaaaa acggtagccc    8160
gcagaaaggg tatgaaaaat cgaatttaa tatagaggac tgccgtaaat tcatcgactt    8220
ctataaacag agcatttcca acatccgga atggaaagac ttcggcttcc gtttctctga    8280
cactcagcgc tataatagca tcgacgagtt ctaccgcgaa gtggagaatc agggctataa    8340
actgaccttc gagaacatta gtgagtcgta catcgactcc gttgtgaatc agggtaaact    8400
gtacctgttt cagatctata taaagactt tagcgcgtac agcaaaggcc gcccgaatct    8460
gcacacccct tactggaaag cattatttga cgaacgtaac ctgcaagatg tggtgtataa    8520
actgaacggt gaggcggaac ttttctaccg taaacagagt atcccgaaga aaatcacgca    8580
tccggcaaaa gaagctattg ccaacaaaaa caaagacaac ccgaagaaag aaagtgtatt    8640
cgaatatgac ctgatcaaag ataaacgttt caccgaagat aagttctttt tccactgtcc    8700
gattaccatc aacttcaaat ctagcggtgc gaacaagttc aacgatgaaa ttaacttatt    8760
actgaaagag aaagctaatg acgtacacat cttatctatt gatcgcggtg aacgtcattt    8820
```

```
agcatactat acactggtag acggtaaagg taatattatt aaacaggata ctttcaatat    8880
tatcggtaat gaccgtatga aaaccaacta tcacgataag ctggcggcga tcgaaaaga     8940
tcgtgattct gcgcgtaaag attggaagaa aattaacaat atcaaagaaa tgaaagaagg    9000
ctatctgagc caagtggtgc acgagatcgc aaaactggtg attgaatata acgctatcgt    9060
ggttttcgaa gatctgaact ttggttttaa acgtggtcgc ttcaaagtag aaaaacaggt    9120
gtaccaaaaa ctggaaaaaa tgctgattga aaaactgaac tatctggttt ttaaagacaa    9180
cgaatttgac aaaacgggtg gcgtactccg tgcctatcag cttaccgctc cgttcgaaac    9240
gtttaagaaa atgggtaaac aaacggggat tatctattat gtgccagccg gtttcacctc    9300
caagatttgt ccagttacgg gcttcgttaa ccagctttac ccgaaatacg agagcgttag    9360
caaatctcaa gaatttttca gcaaattcga caagatctgc tataatctgg ataaaggcta    9420
tttcgagttc agctttgatt acaaaaactt cggcgataaa gcggctaaag gtaagtggac    9480
tattgctagc tttggtagcc gtctgattaa cttccgcaac tccgacaaaa accataattg    9540
ggacacgcgt gaagtgtatc cgaccaaaga actggaaaaa ttactgaaag actattccat    9600
cgaatatggt catggggagt gcattaaagc ggcgatttgc ggtgaatccg ataagaaatt    9660
tttcgccaaa ctgaccagcg tgcttaacac cattctccaa atgcgtaatt ctaaaacggg    9720
tacggagctt gactacctga tttctccggt agccgacgtt aacggcaact tcttcgattc    9780
tcgtcaagca ccgaaaaata tgccacaaga cgcggatgcc aacggtgcat accatatcgg    9840
ccttaaaggc ttaatgttat taggccgtat caagaataat caggagggca agaaattaaa    9900
tctggttatc aaaaacgaag aatacttcga gttcgttcag aatcgtaaca attaatgtat    9960
gcttaagcag atcggtaata aagacgaaca ataagacgct gaaaagcgtc tttttcgtt    10020
ttggtcctgt tccggcgcga tagtgtgaac atgctataga cttctggtgc tacccgactg   10080
acaattaatc atccggctcg tataatgcta gcaatttcta ctgttgtaga tcattccgga    10140
acgttccagc gctgcaattt ctactgttgt agatctgatt tttcacatgt tacctttcaa    10200
tttctactgt tgtagatccg aaaacgtaaa gcttcagctg taatttctac tgttgtagat    10260
atcatatctg gcgttaatgg agtttcgtga cgaacaataa gtcctcccta acgggggca    10320
atttttattg ataacaaaag taacttcgag cttgtctacc tcctagctcg taaattgcac    10380
gctgatagtc tcccaattgc gaaggaccaa aacgaaaaaa caccctttcg ggtgtctttt    10440
ctggaatttg gtacgcagta ctaggtatcg tgtaagtagc gaaggcccgt acgcgagata    10500
aactgctagg caaccgcgac tctacgactg gtgctcgatt taatttcgct gacgtaaaga    10560
aattatcggc agtgcgtcaa ctgccgtatc tttatcttaa ttaggtagtt ggacaagccc    10620
ttgaaagaaa tagcaagagc ctgcctctct attgaagtca cggcgaaagt cgggtagaaa    10680
tcaaagaaag cagaaattaa atcggagtaa tactaagttg ggataactcc gtaactgact    10740
acgcctttct ctagacttta cttgaccaga tacactgtct ttgacacgtt gaaggattag    10800
agcaatcaaa tccaagactg gctaagcacg aagcaactct tgagtgttaa aaagttactt    10860
cctgtattcg ggacgagggt actagaagat tgcagggact ccgacgttaa gtaaattaca    10920
aagtaataag tatcgttcag gatcacgtta ccgcaataag aagcgagaat aatataattt    10980
ccgaagtgct taccccagta gtgactattc ctataaccct tctgagtgtc cggaggcgga    11040
aatttgccac gaaagagaaa gtatttcccc gacaataata aaggggcgct cctcagcttt    11100
tccacttggt tgggtaagct aggcaactct gaaaggagtt tcggcgaagt gaagccgaca    11160
```

-continued

```
ccttttgaatt gttttagggg cgttattcga gggcaatcgg agctaacttc aagactactt    11220
ctttgttgaa tactaaatag tgcaaaggtc gtgtttcctc aaggatactc cgctaacaat    11280
ataggattcc aatcagattc agcactggcg gtacgggtgt tgcggtgagg cgttcgggtt    11340
tacggctcga agctagcacg gtaggaagcc tgacaatcac caagcaaaag gccgtcgaa    11400 ggcccacaag atacgaaagc tctcgaagcc ttatccttga ccgatccacc tatttaggca    11460
gttacgcaca aaagctaccc aataatccgt gacaggcaca atatcacgga acaaaaccga    11520
aaactctcgt acacggttag gttttcgcta ggaagaataa acctctatct tgattataag    11580
aaggctcccc aagcaccccc aaaaccgaaa tagcg                                11615
```

<210> SEQ ID NO 34
<211> LENGTH: 63
<212> TYPE: PRT
<213> ORGANISM: Artificial Sequence
<220> FEATURE:
<223> OTHER INFORMATION: helical bundle 1 and linker from STF protein
      from Escherichia phage ZG49

<400> SEQUENCE: 34

Gly Asp Ala Ala Leu Arg Ser Gln Ile Ser Asn Pro Glu Gly Ala Ile
1               5                   10                  15

Leu Tyr Pro Glu Leu Gln Met Ala Arg Trp Arg Asp Glu Gly Asp Val
                20                  25                  30

Arg Gly Trp Gly Ala Lys Gly Asp Gly Val Thr Asp Ser Thr Glu Asn
            35                  40                  45

Ile Ala Ala Ser Leu Asn Ser Gln Lys Ala Val Val Ala Ser Glu
        50                  55                  60

<210> SEQ ID NO 35
<211> LENGTH: 189
<212> TYPE: DNA
<213> ORGANISM: Artificial Sequence
<220> FEATURE:
<223> OTHER INFORMATION: recoded helical bundle 1 and linker from STF
      protein from Escherichia phage ZG49

<400> SEQUENCE: 35

```
ggtgacgcag cactgcgctc tcaaatcagc aacccagaag cgcgattct gtacccggaa     60 ctgcagatgg cgcgctggcg tgatgaaggc gacgttcgtg gttggggtgc caaaggtgat    120
ggtgtaaccg actccactga aaacatcgca gcatccttga ctctcagaa agcagttgtt    180 gccagcgaa                                                             189
```

<210> SEQ ID NO 36
<211> LENGTH: 62
<212> TYPE: PRT
<213> ORGANISM: Artificial Sequence
<220> FEATURE:
<223> OTHER INFORMATION: helical bundle 2 and linker from STF protein
      from Escherichia phage ZG49

<400> SEQUENCE: 36

Asp Ala Ala Leu Arg Ser Gln Ile Ser Asn Pro Glu Gly Ala Ile Leu
1               5                   10                  15

Tyr Pro Glu Leu Gln Met Ala Arg Trp Arg Asp Glu Gly Asp Val Arg
                20                  25                  30

Gly Trp Gly Ala Lys Gly Asp Gly Val Thr Asp Ser Thr Glu Asn Ile
            35                  40                  45

Ala Ala Ser Leu Asn Ser Gln Lys Ala Val Val Ala Ser Glu

<210> SEQ ID NO 37
<211> LENGTH: 186
<212> TYPE: DNA
<213> ORGANISM: Artificial Sequence
<220> FEATURE:
<223> OTHER INFORMATION: recoded helical bundle 2 and linker from STF
      protein from Escherichia phage ZG49

<400> SEQUENCE: 37

```
gacgcagcac tgcgctctca aatcagcaac ccagaaggcg cgattctgta cccggaactg      60
cagatggcgc gctggcgtga tgaaggcgac gttcgtggtt ggggtgccaa aggtgatggt     120
gtaaccgact ccactgaaaa catcgcagca tccttgaact ctcagaaagc agttgttgcc     180
agcgaa                                                                186
```

<210> SEQ ID NO 38
<211> LENGTH: 1162
<212> TYPE: PRT
<213> ORGANISM: Artificial Sequence
<220> FEATURE:
<223> OTHER INFORMATION: K5 9.0

<400> SEQUENCE: 38

```
Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
            20                  25                  30

Val Val Val Asn Thr Val Gly Ser Glu Asn Pro Asp Glu Ala Gly Arg
        35                  40                  45

Tyr Ser Met Asp Val Glu Tyr Gly Gln Tyr Ser Val Ile Leu Gln Val
    50                  55                  60

Asp Gly Phe Pro Pro Ser His Ala Gly Thr Ile Thr Val Tyr Glu Asp
65                  70                  75                  80

Ser Gln Pro Gly Thr Leu Asn Asp Phe Leu Cys Ala Met Thr Glu Asp
                85                  90                  95

Asp Ala Arg Pro Glu Val Leu Arg Arg Leu Glu Leu Met Val Glu Glu
            100                 105                 110

Val Ala Arg Asn Ala Ser Val Val Ala Gln Ser Thr Ala Asp Ala Lys
        115                 120                 125

Lys Ser Ala Gly Asp Ala Ser Ala Ser Ala Ala Gln Val Ala Ala Leu
    130                 135                 140

Val Thr Asp Ala Thr Asp Ser Ala Arg Ala Ala Ser Thr Ser Ala Gly
145                 150                 155                 160

Gln Ala Ala Ser Ser Ala Gln Glu Ala Ser Ser Gly Ala Glu Ala Ala
                165                 170                 175

Ser Ala Lys Ala Thr Glu Ala Glu Lys Ser Ala Ala Ala Glu Ser
            180                 185                 190

Ser Lys Asn Ala Ala Ala Thr Ser Ala Gly Ala Ala Lys Thr Ser Glu
    195                 200                 205

Thr Asn Ala Ala Ala Ser Gln Gln Ser Ala Ala Thr Ser Ala Ser Thr
    210                 215                 220

Ala Ala Thr Lys Ala Ser Glu Ala Ala Thr Ser Ala Arg Asp Ala Val
225                 230                 235                 240

Ala Ser Lys Glu Ala Ala Lys Ser Ser Glu Thr Asn Ala Ser Ser Ser
                245                 250                 255
```

```
Ala Gly Arg Ala Ala Ser Ser Ala Thr Ala Ala Glu Asn Ser Ala Arg
            260                 265                 270

Ala Ala Lys Thr Ser Glu Thr Asn Ala Arg Ser Ser Glu Thr Ala Ala
            275                 280                 285

Glu Arg Ser Ala Ser Ala Ala Asp Ala Lys Thr Ala Ala Ala Gly
        290                 295                 300

Ser Ala Ser Thr Ala Ser Thr Lys Ala Thr Glu Ala Ala Gly Ser Ala
305                 310                 315                 320

Val Ser Ala Ser Gln Ser Lys Ser Ala Ala Glu Ala Ala Ala Ile Arg
                325                 330                 335

Ala Lys Asn Ser Ala Lys Arg Ala Glu Asp Ile Ala Ser Ala Val Ala
            340                 345                 350

Leu Glu Asp Ala Asp Thr Thr Arg Lys Gly Ile Val Gln Leu Ser Ser
            355                 360                 365

Ala Thr Asn Ser Thr Ser Glu Thr Leu Ala Ala Thr Pro Lys Ala Val
            370                 375                 380

Lys Val Val Met Asp Glu Thr Asn Arg Lys Ala Pro Leu Asp Ser Pro
385                 390                 395                 400

Ala Leu Thr Gly Thr Pro Thr Ala Pro Thr Ala Leu Arg Gly Thr Asn
            405                 410                 415

Asn Thr Gln Ile Ala Asn Thr Ala Phe Val Leu Ala Ala Ile Ala Asp
            420                 425                 430

Val Ile Asp Ala Ser Pro Asp Ala Leu Asn Thr Leu Asn Glu Leu Ala
            435                 440                 445

Ala Ala Leu Gly Asn Asp Pro Asp Phe Ala Thr Thr Met Thr Asn Ala
            450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
            485                 490                 495

Ala Ser Leu Thr Glu Leu Thr Gln Val Gly Arg Asp Ile Leu Ala Lys
            500                 505                 510

Asn Ser Val Ala Asp Val Leu Glu Tyr Leu Gly Ala Gly Glu Asn Ser
            515                 520                 525

Gly Asp Ala Ala Leu Arg Ser Gln Ile Ser Asn Pro Glu Gly Ala Ile
530                 535                 540

Leu Tyr Pro Glu Leu Gln Met Ala Arg Trp Arg Asp Glu Gly Asp Val
545                 550                 555                 560

Arg Gly Trp Gly Ala Lys Gly Asp Gly Val Thr Asp Ser Thr Glu Asn
            565                 570                 575

Ile Ala Ala Ser Leu Asn Ser Gln Lys Ala Val Val Ala Ser Glu Gly
            580                 585                 590

Val Phe Ser Ser Ser Gly Ile Asn Ser Asn Tyr Cys Asn Leu Asp Gly
            595                 600                 605

Arg Gly Ser Gly Val Leu Ser His Arg Ser Ser Thr Gly Asn Tyr Leu
            610                 615                 620

Val Phe Asn Asn Pro Arg Thr Gly Arg Leu Ser Asn Ile Thr Val Glu
625                 630                 635                 640

Ser Asn Lys Ala Thr Asp Thr Thr Gln Gly Gln Gln Val Ser Leu Ala
                645                 650                 655

Gly Gly Ser Asp Val Thr Val Ser Asp Val Asn Phe Ser Asn Val Lys
            660                 665                 670

Gly Thr Gly Phe Ser Leu Ile Ala Tyr Pro Asn Asp Ala Pro Pro Asp
```

-continued

```
            675                 680                 685
Gly Leu Met Ile Lys Gly Ile Arg Gly Ser Tyr Ser Gly Tyr Ala Thr
        690                 695                 700
Asn Lys Ala Ala Gly Cys Val Leu Ala Asp Ser Ser Val Asn Ser Leu
705                 710                 715                 720
Ile Asp Asn Val Ile Ala Lys Asn Tyr Pro Gln Phe Gly Ala Val Glu
                725                 730                 735
Leu Lys Gly Thr Ala Ser Tyr Asn Ile Val Ser Asn Val Ile Gly Ala
            740                 745                 750
Asp Cys Gln His Val Thr Tyr Asn Gly Thr Glu Gly Pro Ile Ala Pro
            755                 760                 765
Ser Asn Asn Leu Ile Lys Gly Val Met Ala Asn Asn Pro Lys Tyr Ala
770                 775                 780
Ala Val Val Ala Gly Lys Gly Ser Thr Asn Leu Ile Ser Asp Val Leu
785                 790                 795                 800
Val Asp Tyr Ser Thr Ser Asp Ala Arg Gln Ala His Gly Val Thr Val
                805                 810                 815
Glu Gly Ser Asp Asn Val Ile Asn Asn Val Leu Met Ser Gly Cys Asp
                820                 825                 830
Gly Thr Asn Ser Leu Gly Gln Arg Gln Thr Ala Thr Ile Ala Arg Phe
            835                 840                 845
Ile Gly Thr Ala Asn Asn Asn Tyr Ala Ser Val Phe Pro Ser Tyr Ser
850                 855                 860
Ala Thr Gly Val Ile Thr Phe Glu Ser Gly Ser Thr Arg Asn Phe Val
865                 870                 875                 880
Glu Val Lys His Pro Gly Arg Arg Asn Asp Leu Leu Ser Ser Ala Ser
                885                 890                 895
Thr Ile Asp Gly Ala Ala Thr Ile Asp Gly Thr Ser Asn Ser Asn Val
            900                 905                 910
Val His Ala Pro Ala Leu Gly Gln Tyr Ile Gly Ser Met Ser Gly Arg
            915                 920                 925
Phe Glu Trp Arg Ile Lys Ser Met Ser Leu Pro Ser Gly Val Leu Thr
        930                 935                 940
Ser Ala Asp Lys Tyr Arg Met Leu Gly Asp Gly Ala Val Ser Leu Ala
945                 950                 955                 960
Val Gly Gly Gly Thr Ser Ser Gln Val Arg Leu Phe Thr Ser Asp Gly
                965                 970                 975
Thr Ser Arg Thr Val Ser Leu Thr Asn Gly Asn Val Arg Leu Ser Thr
            980                 985                 990
Ser Ser Thr Gly Tyr Leu Gln Leu Gly Ala Asp Ala Met Thr Pro Asp
        995                 1000                1005
Ser Thr Gly Thr Tyr Ala Leu Gly Ser Ala Ser Arg Ala Trp Ser
        1010                1015                1020
Gly Gly Phe Thr Gln Ala Ala Phe Thr Val Thr Ser Asp Ala Arg
        1025                1030                1035
Cys Lys Thr Glu Pro Leu Thr Ile Ser Asp Ala Leu Leu Asp Ala
        1040                1045                1050
Trp Ser Glu Val Asp Phe Val Gln Phe Gln Tyr Leu Asp Arg Val
        1055                1060                1065
Glu Glu Lys Gly Ala Asp Ser Ala Arg Trp His Phe Gly Ile Ile
        1070                1075                1080
Ala Gln Arg Ala Lys Glu Ala Phe Glu Arg His Gly Ile Asp Ala
        1085                1090                1095
```

His Arg Tyr Gly Phe Leu Cys Phe Asp Ser Trp Asp Asp Val Tyr
1100                1105                1110

Glu Glu Asp Ala Asn Gly Ser Arg Lys Leu Ile Thr Pro Ala Gly
1115                1120                1125

Ser Arg Tyr Gly Ile Arg Tyr Glu Glu Val Leu Ile Leu Glu Ala
1130                1135                1140

Ala Leu Met Arg Arg Thr Ile Lys Arg Met Gln Glu Ala Leu Ala
1145                1150                1155

Ala Leu Pro Lys
1160

<210> SEQ ID NO 39
<211> LENGTH: 3486
<212> TYPE: DNA
<213> ORGANISM: Artificial Sequence
<220> FEATURE:
<223> OTHER INFORMATION: K5 9.0

<400> SEQUENCE: 39

```
atggcagtaa agatttcagg agtcctgaaa gacggcacag gaaaaccggt acagaactgc      60
accattcagc tgaaagccag acgtaacagc accacggtgg tggtgaacac ggtgggctca     120
gagaatccgg atgaagccgg gcgttacagc atggatgtgg agtacggtca gtacagtgtc     180
atcctgcagg ttgacggttt tccaccatcg cacgccggga ccatcaccgt gtatgaagat     240
tcacaaccgg ggacgctgaa tgattttctc tgtgccatga cggaggatga tgcccggccg     300
gaggtgctgc gtcgtcttga actgatggtg gaagaggtgg cgcgtaacgc gtccgtggtg     360
gcacagagta cggcagacgc gaagaaatca gccggcgatg ccagtgcatc agctgctcag     420
gtcgcggccc ttgtgactga tgcaactgac tcagcacgcg ccgccagcac gtccgccgga     480
caggctgcat cgtcagctca ggaagcgtcc tccggcgcag aagcggcatc agcaaaggcc     540
actgaagcgg aaaaaagtgc cgcagccgca gagtcctcaa aaaacgcggc ggccaccagt     600
gccggtgcgg cgaaaacgtc agaaacgaat gctgcagcgt cacaacaatc agccgccacg     660
tctgcctcca ccgcggccac gaaagcgtca gaggccgcca cttcagcacg agatgcggtg     720
gcctcaaaag aggcagcaaa atcatcagaa acgaacgcat catcaagtgc cggtcgtgca     780
gcttcctcgg caacggcggc agaaaattct gccaggcggg caaaaacgtc cgagacgaat     840
gccaggtcat ctgaaacagc agcggaacgg agcgcctctg ccgcggcaga cgcaaaaaca     900
gcggcggcgg ggagtgcgtc aacggcatcc acgaaggcga cagaggctgc gggaagtgcg     960
gtatcagcat cgcagagcaa aagtgcggca gaagcggcgg caatacgtgc aaaaaattcg    1020
gcaaaacgtg cagaagatat agcttcagct gtcgcgcttg aggatgcgga cacaacgaga    1080
aaggggatag tgcagctcag cagtgcaacc aacagcacgt ctgaaacgct tgctgcaacg    1140
ccaaaggcgg ttaaggtggt aatggatgag actaatcgta aggcacctct ggacagtccg    1200
gcactgaccg gaacgccaac agcaccaacc gcgctcaggg gaacaaacaa tacccagatt    1260
gcgaacaccg cttttgtact ggccgcgatt gcagatgtta tcgacgcgtc acctgacgca    1320
ctgaatacgc tgaatgaact ggccgcagcg ctcgggaatg atccagattt tgctaccacc    1380
atgactaacg cgcttgcggg taaacaaccg aagaatgcga cactgacggc gctggcaggg    1440
cttttccacg gcgaaaaataa attaccgtat tttgcggaaa atgatgccgc cagcctgact    1500
gaactgactc aggttggcag ggatattctg gcaaaaaatt ccgttgcaga tgttcttgaa    1560
taccttgggg ccggtgagaa ttcgggtgac gcagcactgc gctctcaaat cagcaaccca    1620
```

-continued

```
gaaggcgcga ttctgtaccc ggaactgcag atggcgcgct ggcgtgatga aggcgacgtt    1680
cgtggttggg gtgccaaagg tgatggtgta accgactcca ctgaaaacat cgcagcatcc    1740
ttgaactctc agaaagcagt tgttgccagc gaaggcgttt tcagttcttc tggcatcaac    1800
tccaactact gtaacctgga tggtcgcgga tccggtgtgc tcagccaccg tagctctact    1860
ggtaattacc tggtgtttaa caatccgcgt actggtcgtc tgagcaatat cactgttgaa    1920
tctaacaaag cgaccgatac cactcagggc aacaggtgt ccctggcagg tggcagtgac    1980
gtgaccgtgt cagatgtcaa cttctccaac gtgaaaggca ctggttttag cctgattgcc    2040
tacccaaacg atgctccgcc ggatggcctg atgatcaaag cattcgcgg atcttacagc    2100
ggttacgcga ccaacaaagc agctggttgc gtcctggcgg atagctccgt taacagcctg    2160
atcgacaatg tgatcgctaa gaattacccg caattcggtg ctgttgaatt aaagggcact    2220
gcaagctaca acattgtatc gaacgttatc ggtgcggatt gtcagcacgt gacttacaac    2280
ggcactgagg gaccgatcgc tcctagtaac aatctgatca agggcgttat ggcgaacaac    2340
ccgaaatacg cggcagttgt ggcgggtaaa ggctcgacga atctgatctc tgatgtactg    2400
gtagactatt ctaccagcga tgctcgtcag gcgcatggtg ttaccgtcga aggatctgat    2460
aacgtgatta caacgtact gatgtccggt tgcgacggaa ctaattccct gggtcagcgt    2520
caaaccgcaa ctatcgcgcg tttcatcggt actgcaaata caactatgc tagcgtgttc    2580
ccatcctatt ctgccactgg tgtgatcacg tttgagtctg gcagtacccg taacttcgtc    2640
gaggttaagc atccgggccg tgcaacgat cttctgtcat cggcaagcac gattgacggc    2700
gctgcgacca tcgacgggac ttctaactct aacgtagtac acgcgcctgc tctgggccaa    2760
tacattggct ccatgagtgg tcgctttgaa tggcgtatta agtcaatgag cctgccgtcc    2820
ggcgtactca ctagcgcgga taaataccgt atgctgggtg acggtgctgt tagccttgct    2880
gttggcggag gaactagcag tcaggtgcgc ttgttcacct cagacggtac ttctcgcact    2940
gtttctctga ccaatggtaa cgtgcgcctg agcacgtcct ctactggcta tttacagctg    3000
ggtgcagacg caatgactcc ggactccact ggtacttacg cgttaggctc cgcatctcgt    3060
gcttggagtg gcggattcac tcaggcagca ttcaccgtta cttctgacgc acgttgcaaa    3120
actgagcctt taaccatctc tgacgcttta ctggatgctt ggagtgaagt ggactttgtc    3180
cagttccagt atctggatcg tgttgaagag aaaggtgctg actccgcgcg ttggcatttc    3240
ggaatcatcg cccagcgtgc taaagaggca ttcgaacgtc acggcatcga tgcgcatcgt    3300
tacggttct tatgctttga ctcttgggac gatgtgtacg aagaggatgc aaatggatct    3360
cgcaaactga tcactccggc gggtagtcgc tatggtattc gctatgagga agttctgatc    3420
ctcgaagcag cgctgatgcg tcgcacgatc aagcgcatgc aggaagcact ggctgcgtta    3480
ccgaag                                                               3486
```

<210> SEQ ID NO 40
<211> LENGTH: 1161
<212> TYPE: PRT
<213> ORGANISM: Artificial Sequence
<220> FEATURE:
<223> OTHER INFORMATION: K5 9.1

<400> SEQUENCE: 40

```
Met Ala Val Lys Ile Ser Gly Val Leu Lys Asp Gly Thr Gly Lys Pro
1               5                   10                  15

Val Gln Asn Cys Thr Ile Gln Leu Lys Ala Arg Arg Asn Ser Thr Thr
```

-continued

```
            20                  25                  30
Val Val Val Asn Thr Val Gly Ser Glu Asn Pro Asp Glu Ala Gly Arg
                35                  40                  45
Tyr Ser Met Asp Val Glu Tyr Gly Gln Tyr Ser Val Ile Leu Gln Val
        50                  55                  60
Asp Gly Phe Pro Pro Ser His Ala Gly Thr Ile Thr Val Tyr Glu Asp
65                  70                  75                  80
Ser Gln Pro Gly Thr Leu Asn Asp Phe Leu Cys Ala Met Thr Glu Asp
                85                  90                  95
Asp Ala Arg Pro Glu Val Leu Arg Arg Leu Glu Leu Met Val Glu Glu
            100                 105                 110
Val Ala Arg Asn Ala Ser Val Val Ala Gln Ser Thr Ala Asp Ala Lys
            115                 120                 125
Lys Ser Ala Gly Asp Ala Ser Ala Ser Ala Ala Gln Val Ala Ala Leu
        130                 135                 140
Val Thr Asp Ala Thr Asp Ser Ala Arg Ala Ala Ser Thr Ser Ala Gly
145                 150                 155                 160
Gln Ala Ala Ser Ser Ala Gln Glu Ala Ser Ser Gly Ala Glu Ala Ala
                165                 170                 175
Ser Ala Lys Ala Thr Glu Ala Glu Lys Ser Ala Ala Ala Ala Glu Ser
            180                 185                 190
Ser Lys Asn Ala Ala Ala Thr Ser Ala Gly Ala Ala Lys Thr Ser Glu
        195                 200                 205
Thr Asn Ala Ala Ala Ser Gln Gln Ser Ala Ala Thr Ser Ala Ser Thr
    210                 215                 220
Ala Ala Thr Lys Ala Ser Glu Ala Ala Thr Ser Ala Arg Asp Ala Val
225                 230                 235                 240
Ala Ser Lys Glu Ala Ala Lys Ser Ser Glu Thr Asn Ala Ser Ser Ser
                245                 250                 255
Ala Gly Arg Ala Ala Ser Ser Ala Thr Ala Ala Glu Asn Ser Ala Arg
            260                 265                 270
Ala Ala Lys Thr Ser Glu Thr Asn Ala Arg Ser Ser Glu Thr Ala Ala
        275                 280                 285
Glu Arg Ser Ala Ser Ala Ala Ala Asp Ala Lys Thr Ala Ala Ala Gly
    290                 295                 300
Ser Ala Ser Thr Ala Ser Thr Lys Ala Thr Glu Ala Ala Gly Ser Ala
305                 310                 315                 320
Val Ser Ala Ser Gln Ser Lys Ser Ala Ala Glu Ala Ala Ala Ile Arg
                325                 330                 335
Ala Lys Asn Ser Ala Lys Arg Ala Glu Asp Ile Ala Ser Ala Val Ala
            340                 345                 350
Leu Glu Asp Ala Asp Thr Thr Arg Lys Gly Ile Val Gln Leu Ser Ser
        355                 360                 365
Ala Thr Asn Ser Thr Ser Glu Thr Leu Ala Ala Thr Pro Lys Ala Val
    370                 375                 380
Lys Val Val Met Asp Glu Thr Asn Arg Lys Ala Pro Leu Asp Ser Pro
385                 390                 395                 400
Ala Leu Thr Gly Thr Pro Thr Ala Pro Thr Ala Leu Arg Gly Thr Asn
                405                 410                 415
Asn Thr Gln Ile Ala Asn Thr Ala Phe Val Leu Ala Ala Ile Ala Asp
            420                 425                 430
Val Ile Asp Ala Ser Pro Asp Ala Leu Asn Thr Leu Asn Glu Leu Ala
        435                 440                 445
```

-continued

Ala Ala Leu Gly Asn Asp Pro Asp Phe Ala Thr Thr Met Thr Asn Ala
        450                 455                 460

Leu Ala Gly Lys Gln Pro Lys Asn Ala Thr Leu Thr Ala Leu Ala Gly
465                 470                 475                 480

Leu Ser Thr Ala Lys Asn Lys Leu Pro Tyr Phe Ala Glu Asn Asp Ala
                485                 490                 495

Ala Ser Leu Thr Glu Leu Thr Gln Val Gly Arg Asp Ile Leu Ala Lys
            500                 505                 510

Asn Ser Val Ala Asp Val Leu Glu Tyr Leu Gly Ala Gly Glu Asn Ser
        515                 520                 525

Asp Ala Ala Leu Arg Ser Gln Ile Ser Asn Pro Glu Gly Ala Ile Leu
    530                 535                 540

Tyr Pro Glu Leu Gln Met Ala Arg Trp Arg Asp Glu Gly Asp Val Arg
545                 550                 555                 560

Gly Trp Gly Ala Lys Gly Asp Gly Val Thr Asp Ser Thr Glu Asn Ile
                565                 570                 575

Ala Ala Ser Leu Asn Ser Gln Lys Ala Val Val Ala Ser Glu Gly Val
            580                 585                 590

Phe Ser Ser Ser Gly Ile Asn Ser Asn Tyr Cys Asn Leu Asp Gly Arg
        595                 600                 605

Gly Ser Gly Val Leu Ser His Arg Ser Ser Thr Gly Asn Tyr Leu Val
    610                 615                 620

Phe Asn Asn Pro Arg Thr Gly Arg Leu Ser Asn Ile Thr Val Glu Ser
625                 630                 635                 640

Asn Lys Ala Thr Asp Thr Thr Gln Gly Gln Gln Val Ser Leu Ala Gly
                645                 650                 655

Gly Ser Asp Val Thr Val Ser Asp Val Asn Phe Ser Asn Val Lys Gly
            660                 665                 670

Thr Gly Phe Ser Leu Ile Ala Tyr Pro Asn Asp Ala Pro Pro Asp Gly
        675                 680                 685

Leu Met Ile Lys Gly Ile Arg Gly Ser Tyr Ser Gly Tyr Ala Thr Asn
    690                 695                 700

Lys Ala Ala Gly Cys Val Leu Ala Asp Ser Ser Val Asn Ser Leu Ile
705                 710                 715                 720

Asp Asn Val Ile Ala Lys Asn Tyr Pro Gln Phe Gly Ala Val Glu Leu
                725                 730                 735

Lys Gly Thr Ala Ser Tyr Asn Ile Val Ser Asn Val Ile Gly Ala Asp
            740                 745                 750

Cys Gln His Val Thr Tyr Asn Gly Thr Glu Gly Pro Ile Ala Pro Ser
        755                 760                 765

Asn Asn Leu Ile Lys Gly Val Met Ala Asn Pro Lys Tyr Ala Ala
    770                 775                 780

Val Val Ala Gly Lys Gly Ser Thr Asn Leu Ile Ser Asp Val Leu Val
785                 790                 795                 800

Asp Tyr Ser Thr Ser Asp Ala Arg Gln Ala His Gly Val Thr Val Glu
                805                 810                 815

Gly Ser Asp Asn Val Ile Asn Asn Val Leu Met Ser Gly Cys Asp Gly
            820                 825                 830

Thr Asn Ser Leu Gly Gln Arg Gln Thr Ala Thr Ile Ala Arg Phe Ile
        835                 840                 845

Gly Thr Ala Asn Asn Tyr Ala Ser Val Phe Pro Ser Tyr Ser Ala
    850                 855                 860

```
Thr Gly Val Ile Thr Phe Glu Ser Gly Ser Thr Arg Asn Phe Val Glu
865                 870                 875                 880

Val Lys His Pro Gly Arg Arg Asn Asp Leu Leu Ser Ser Ala Ser Thr
                885                 890                 895

Ile Asp Gly Ala Ala Thr Ile Asp Gly Thr Ser Asn Ser Asn Val Val
            900                 905                 910

His Ala Pro Ala Leu Gly Gln Tyr Ile Gly Ser Met Ser Gly Arg Phe
        915                 920                 925

Glu Trp Arg Ile Lys Ser Met Ser Leu Pro Ser Gly Val Leu Thr Ser
930                 935                 940

Ala Asp Lys Tyr Arg Met Leu Gly Asp Gly Ala Val Ser Leu Ala Val
945                 950                 955                 960

Gly Gly Gly Thr Ser Ser Gln Val Arg Leu Phe Thr Ser Asp Gly Thr
                965                 970                 975

Ser Arg Thr Val Ser Leu Thr Asn Gly Asn Val Arg Leu Ser Thr Ser
            980                 985                 990

Ser Thr Gly Tyr Leu Gln Leu Gly Ala Asp Ala Met Thr Pro Asp Ser
        995                 1000                1005

Thr Gly Thr Tyr Ala Leu Gly Ser Ala Ser Arg Ala Trp Ser Gly
    1010                1015                1020

Gly Phe Thr Gln Ala Ala Phe Thr Val Thr Ser Asp Ala Arg Cys
    1025                1030                1035

Lys Thr Glu Pro Leu Thr Ile Ser Asp Ala Leu Leu Asp Ala Trp
    1040                1045                1050

Ser Glu Val Asp Phe Val Gln Phe Gln Tyr Leu Asp Arg Val Glu
    1055                1060                1065

Glu Lys Gly Ala Asp Ser Ala Arg Trp His Phe Gly Ile Ile Ala
    1070                1075                1080

Gln Arg Ala Lys Glu Ala Phe Glu Arg His Gly Ile Asp Ala His
    1085                1090                1095

Arg Tyr Gly Phe Leu Cys Phe Asp Ser Trp Asp Val Tyr Glu
    1100                1105                1110

Glu Asp Ala Asn Gly Ser Arg Lys Leu Ile Thr Pro Ala Gly Ser
    1115                1120                1125

Arg Tyr Gly Ile Arg Tyr Glu Glu Val Leu Ile Leu Glu Ala Ala
    1130                1135                1140

Leu Met Arg Arg Thr Ile Lys Arg Met Gln Glu Ala Leu Ala Ala
    1145                1150                1155

Leu Pro Lys
    1160

<210> SEQ ID NO 41
<211> LENGTH: 3483
<212> TYPE: DNA
<213> ORGANISM: Artificial Sequence
<220> FEATURE:
<223> OTHER INFORMATION: K5 9.1

<400> SEQUENCE: 41
atggcagtaa agatttcagg agtcctgaaa gacggcacag gaaaaccggt acagaactgc    60
accattcagc tgaaagccag acgtaacagc accacggtgg tggtgaacac ggtgggctca   120
gagaatccgg atgaagccgg gcgttacagc atggatgtgg agtacggtca gtacagtgtc   180
atcctgcagg ttgacggttt tccaccatcg cacgccggga ccatcaccgt gtatgaagat   240
tcacaaccgg ggacgctgaa tgattttctc tgtgccatga cggaggatga tgcccggccg   300
```

```
gaggtgctgc gtcgtcttga actgatggtg gaagaggtgg cgcgtaacgc gtccgtggtg     360
gcacagagta cggcagacgc gaagaaatca gccggcgatg ccagtgcatc agctgctcag     420
gtcgcggccc ttgtgactga tgcaactgac tcagcacgcg ccgccagcac gtccgccgga     480
caggctgcat cgtcagctca ggaagcgtcc tccggcgcag aagcggcatc agcaaaggcc     540
actgaagcgg aaaaaagtgc cgcagccgca gagtcctcaa aaaacgcggc ggccaccagt     600
gccggtgcgg cgaaaacgtc agaaacgaat gctgcagcgt cacaacaatc agccgccacg     660
tctgcctcca ccgcggccac gaaagcgtca gaggccgcca cttcagcacg agatgcggtg     720
gcctcaaaag aggcagcaaa atcatcagaa acgaacgcat catcaagtgc cggtcgtgca     780
gcttcctcgg caacggcggc agaaaattct gccagggcgg caaaaacgtc cgagacgaat     840
gccaggtcat ctgaaacagc agcggaacgg agcgcctctg ccgcggcaga cgcaaaaaca     900
gcggcggcgg ggagtgcgtc aacggcatcc acgaaggcga cagaggctgc gggaagtgcg     960
gtatcagcat cgcagagcaa aagtgcggca gaagcggcgg caatacgtgc aaaaaattcg    1020
gcaaaacgtg cagaagatat agcttcagct gtcgcgcttg aggatgcgga cacaacgaga    1080
aaggggatag tgcagctcag cagtgcaacc aacagcacgt ctgaaacgct tgctgcaacg    1140
ccaaaggcgg ttaaggtggt aatggatgag actaatcgta aggcacctct ggacagtccg    1200
gcactgaccg gaacgccaac agcaccaacc gcgctcaggg gaacaaacaa tacccagatt    1260
gcgaacaccg cttttgtact ggccgcgatt gcagatgtta tcgacgcgtc acctgacgca    1320
ctgaatacgc tgaatgaact ggccgcagcg ctcgggaatg atccagattt tgctaccacc    1380
atgactaacg cgcttgcggg taaacaaccg aagaatgcga cactgacggc gctggcaggg    1440
cttttccacgg cgaaaaataa attaccgtat tttgcggaaa atgatgccgc cagcctgact    1500
gaactgactc aggttggcag ggatattctg gcaaaaaatt ccgttgcaga tgttcttgaa    1560
taccttgggg ccggtgagaa ttcggacgca gcactgcgct ctcaaatcag caacccagaa    1620
ggcgcgattc tgtacccgga actgcagatg gcgcgctggc gtgatgaagg cgacgttcgt    1680
ggttggggtg ccaaaggtga tggtgtaacc gactccactg aaaacatcgc agcatccttg    1740
aactctcaga aagcagttgt tgccagcgaa ggcgttttca gttcttctgg catcaactcc    1800
aactactgta acctggatgg tcgcggatcc ggtgtgctca gccaccgtag ctctactggt    1860
aattacctgg tgtttaacaa tccgcgtact ggtcgtctga gcaatatcac tgttgaatct    1920
aacaaagcga ccgataccac tcagggccaa caggtgtccc tggcaggtgg cagtgacgtg    1980
accgtgtcag atgtcaactt ctccaacgtg aaaggcactg gttttagcct gattgcctac    2040
ccaaacgatg ctccgccgga tggcctgatg atcaaaggca ttcgcggatc ttacagcggt    2100
tacgcgacca acaaagcagc tggttgcgtc ctggcggata gctccgttaa cagcctgatc    2160
gacaatgtga tcgctaagaa ttacccgcaa ttcggtgctg ttgaattaaa gggcactgca    2220
agctacaaca ttgtatcgaa cgttatcggt gcggattgtc agcacgtgac ttacaacggc    2280
actgagggac cgatcgctcc tagtaacaat ctgatcaagg gcgttatggc gaacaacccg    2340
aaatacgcgg cagttgtggc gggtaaaggc tcgacgaatc tgatctctga tgtactggta    2400
gactattcta ccagcgatgc tcgtcaggcg catggtgtta ccgtcgaagg atctgataac    2460
gtgattaaca acgtactgat gtccggttgc gacggaacta attccctggg tcagcgtcaa    2520
accgcaacta tcgcgcgttt catcggtact gcaaataaca actatgctag cgtgttccca    2580
tcctattctg ccactggtgt gatcacgttt gagtctggca gtaccgtaa cttcgtcgag    2640
```

| | |
|---|---:|
| gttaagcatc cgggccgtcg caacgatctt ctgtcatcgg caagcacgat tgacggcgct | 2700 |
| gcgaccatcg acgggacttc taactctaac gtagtacacg cgcctgctct gggccaatac | 2760 |
| attggctcca tgagtggtcg cttttgaatgg cgtattaagt caatgagcct gccgtccggc | 2820 |
| gtactcacta gcgcggataa ataccgtatg ctgggtgacg gtgctgttag ccttgctgtt | 2880 |
| ggcggaggaa ctagcagtca ggtgcgcttg ttcacctcag acggtacttc tcgcactgtt | 2940 |
| tctctgacca atggtaacgt gcgcctgagc acgtcctcta ctggctattt acagctgggt | 3000 |
| gcagacgcaa tgactccgga ctccactggt acttacgcgt taggctccgc atctcgtgct | 3060 |
| tggagtggcg gattcactca ggcagcattc accgttactt ctgacgcacg ttgcaaaact | 3120 |
| gagcctttaa ccatctctga cgctttactg gatgcttgga gtgaagtgga ctttgtccag | 3180 |
| ttccagtatc tggatcgtgt tgaagagaaa ggtgctgact ccgcgcgttg gcatttcgga | 3240 |
| atcatcgccc agcgtgctaa agaggcattc gaacgtcacg gcatcgatgc gcatcgttac | 3300 |
| ggtttcttat gctttgactc ttgggacgat gtgtacgaag aggatgcaaa tggatctcgc | 3360 |
| aaactgatca ctccggcggg tagtcgctat ggtattcgct atgaggaagt tctgatcctc | 3420 |
| gaagcagcgc tgatgcgtcg cacgatcaag cgcatgcagg aagcactggc tgcgttaccg | 3480 |
| aag | 3483 |

<210> SEQ ID NO 42
<211> LENGTH: 11609
<212> TYPE: DNA
<213> ORGANISM: Artificial Sequence
<220> FEATURE:
<223> OTHER INFORMATION: payload p1900 plasmid

<400> SEQUENCE: 42

| | |
|---|---:|
| tcccgcgtac ttaattccca ataagaaacg cgcccaagtc ctatcaggca aaattcagcc | 60 |
| ccttcccgtg ttagaacgag ggtaaaaata caagccgatt gaacaagggt tgggggcttc | 120 |
| aaatcgtcgt ttaccccact ttacaacgga gggtaagtag ttcaccctat agtacgaagc | 180 |
| agaactattt cgaggggcgt gcaataatcg aatcttctgc ggttgactta acacgctagg | 240 |
| gacgtgccct cgattcagtc gcaggtactc ctactcagac tgcctcacac ccagctagtc | 300 |
| actgagcgat aaaattgacc cgccctctaa ggtagcgagt acgtcccaaa gggctccgga | 360 |
| cagggctata taggagagtt tgatctcgcc ccgacaactg caaccctcaa ctcccttaga | 420 |
| taatattgtt agccgaagtt gcacgacccg ccgtccacgg actgctctta gggtgtggct | 480 |
| ccttaatctg acaacgtgca acccctatcg agggcgattg tttctgcgaa aggtgttgtc | 540 |
| ctaatagtcg cgacatttgg cccttgtagg tgtgaaacca cttagcttcg cgccgtagtc | 600 |
| ctaaaggccc acctattgac tttgtttcgg gtagcactag gaatcttaac aatttgaatt | 660 |
| tggacgtgga acgcgtacac cttgatcttc gaataattct agggatttgg aagtcctcta | 720 |
| cgttgacaca cctacaatgc tccaagtaaa tatacgaata acgcgggcct cgcggagccg | 780 |
| ttccgaatcg tcacgtgttc gtttactgtt aattggtggc aaataagcaa tatcgtagtc | 840 |
| cgtcaggccc agccctgtta tccacggcgt tatttgtcaa attgcgtaga actggattga | 900 |
| ctgcctgaca atacctaatt atcggtacga agtccccgaa tctgtccggc tatttcacta | 960 |
| atactttcca aacgcccgt atccaagaag aacgaattta tccacgctcc cgtctttggg | 1020 |
| acgaataccg ctacagtgg acagaggatc ggtacgggcc tctaataaat ccaacactct | 1080 |
| acgccctctt caagagctag aagaacaggg tgcagttgga aagggaatta tttcgtaagg | 1140 |
| cgagccaata ccgtaattaa ttcggaagag ttaacacgat tggaagtagg aatagtttct | 1200 |

```
aaccacggtt actaatccta ataacggaac gctgtctgat agattagtgt cagcgctcac   1260
taccaaagaa aaataaaaag acgctgaaaa gcgtctttt  attttttcggt ccagtgtaac   1320 tcaggcaaaa gcacgtaata ttcgtactca ccaaacgaaa ctcatccggc gcatcgcgct   1380
tcttcctccg taagcgtcac ccccattact taaagagtgc atgtgcatat tttgttatca   1440
ataaaaaagg ccgcgatttg cggccttatt gttcgtcttg ccggattaga tagctaccgg   1500
tgctttaata cccggatgcg gatcatagcc ttcgatttcg aagtcctcaa aacgataatc   1560
gaagatgctt tccggtttgc gtttgataat cagtttcggg agcgggcgtg gctcacggct   1620
taattgtaaa tgcgtctgat ccatgtgatt tgagtacagg tgagtatccc caccagtcca   1680
aacaaagtca ccaacttcca gatcacactg ctgtgccatc atatgaacta ataaggcgta   1740
ggaggcaatg ttaaacggta agcccagaaa acgtcgcaa  gaacgctggt acagttggca   1800
cgataactta ccatccgcaa catagaattg aaagaaggca tgacacggtg ctaaagccat   1860
tttgtctaat tcccccacgt tccatgcgga cacgataatc cggcgagagt ccggatcatt   1920
tttcagttgg ttaagaacgg tagtgatctg atcaatatgc cgaccatccg gcgtaggcca   1980
tgcacgccat tgcttaccat acactggccc taagtcaccg ttttcatctg cccactcatc   2040
ccagatggta acgttattct cgtgcaggta cgcaatgttc gtatcgcctt gcagaaacca   2100
taataactcg tgaataatag aacggaggtg gcaacgcttg gtagtgacca gcgggaaacc   2160
gtcttgcagg ttgaaacgca tctgatgacc aaagatagac agcgtaccag tgccagtacg   2220
atcattcttc tgagtgcctt cgtccagcac ttttttgcatc agttccagat actgtttcat   2280
tttagcttcc ttagcttgcg aaatctcgat aactcaaaaa atagtagtga tcttatttca   2340
ttatggtgaa agttgtctta cgtgcaacat tttcgcaaaa agttggcgct ttatcaacac   2400
tgtccgaatg acaaatggtt acaattattg aacacccttc ggggtgtttt tttgtttctg   2460
gtttcccgag gccgaacttt tgttgcaatg gctgtctacc ctgtctacct gagtaaagaa   2520
aaatacattt aattcagtat attaacttgg gtagacagcc ttttttttact gtctaccttc   2580 tgtctaccct ctctacctga ttttacctga atcagacagg gaggtagaca cggggtagac   2640
agtggataaa agcactctac cccactgaaa gcagtgccat tactggcatg gttgccagta   2700
aggttgataa ggtagacaag gggagggaca actcaaaact ttttaaacga gggggtaaaa   2760
cgcagatcaa aacgatctca agaagatcat cttattaatc agataaaata tttctagatt   2820
tcagtgcaat ttatctcttc aaatgtagca ccggcgcgcc gtgaccaatt attgaaggcc   2880
gctaacgcgg ccttttttttg tttctggttt cccgaataga gcgacttctc cccaaaaagc   2940
ctcgctttca gcacctgtcg tttcctttct tttcagaggg tattttaaat aaaaacatta   3000 agttatgacaa agaagaacg gaaacgcctt aaaccggaaa atttctcataa atagcgaaaa   3060 cccgcgaggt cgccgccccg taacctgtcg gatcaccgga aagaacctgt aaagtgataa   3120
tgattatcat ctacatatca caacgtgcgt aaagggtaag tatgaaggtc gtgtactcca   3180
tcgctaccaa attccagaaa acagacgctt tcgagcgtct ttttttcgttt tggtcacgac   3240 gtacggtgga agattcgtta ccaattgaca gctagctcag tcctaggtat atacatacat   3300
gcttgtttgt ttgtaaacta ctgttttcat taaagaggag aaaggaagcc atgaccaaaa   3360
cgtttgatag cgagtttttt aacctgtaca gcctgcaaaa aaccgtgcgc tttgaattaa   3420
aaccagtggg cgaaaccgcg agctttgtgg aagattttaa aaacgaaggc ctgaaacgtg   3480
tggttagcga agatgaacgc cgtgcggtgg attatcagaa agtgaaagaa attattgatg   3540
```

```
attatcatcg cgattttatt gaagaaagtc tgaactattt tccggaacag gtgagcaaag    3600
atgcgctgga acaggcgttt catctgtatc agaaattaaa ggccgcgaaa gttgaagaaa    3660
gagaaaaagc gctgaaagaa tgggaagcac tgcaaaaaaa actgcgtgaa aaagtggtga    3720
aatgctttag cgatagcaat aaagcgcgtt tctcccgcat tgataaaaag gaactgatta    3780
aagaagatct gattaactgg ctggtcgcgc agaatcgcga agatgatatc ccgaccgtgg    3840
aaacctttaa caactttacc acgtatttta cgggcttcca tgaaaaccgt aaaaacattt    3900
atagcaaaga tgatcatgcg accgcgatta gctttcgcct gattcatgaa aacctgccga    3960
aatttttga taacgtgatt agctttaaca aactgaaaga aggttttccg gaactgaaat    4020
ttgataaagt gaaagaagat ttagaggtgg attatgatct gaaacatgcg tttgagattg    4080
aatattttgt taactttgtg acccaggcgg gcatagatca gtataactat ctgttaggcg    4140
gtaaaaccct ggaagatggc accaaaaagc agggcatgaa tgaacagatt aacctgttta    4200
aacagcaaca aacgcgcgat aaagcgcgtc agattccgaa actgatcccg ctgtttaaac    4260
agattttaag cgaaaggacc gaaagtcaga gctttattcc gaaacagttt gaaagcgatc    4320
aggaattgtt tgatagcttg cagaaattac ataacaactg ccaggataaa tttaccgtgt    4380
tgcaacaagc gattctgggc ctggcggagg cggatctgaa aaaagtgttt attaaaaacct   4440
ctgatctgaa cgcgctgtct aacaccattt ttggcaatta tagcgtgttt agcgatgcgc    4500
tgaatctgta taaagaaagt ctgaaaacca aaaagcgca ggaagcgttt gaaaaactgc    4560
cagcgcatag cattcatgat ctgattcagt atctggaaca gtttaactcc agcttggatg    4620
cggaaaaaca gcaaagcacc gataccgtgc tgaactattt tatcaaaacg gatgaactgt    4680
attctcgctt tattaaaagc accagcgaag cctttaccca ggtgcaaccg ttgtttgaac    4740
tggaagcgct gtccagcaaa cgtcgcccgc cggaaagcga agatgagggc gcgaaaggcc    4800
aggaaggctt cgaacaaatc aaacgtatta agcgtatct ggatacctg atggaagcgg    4860
tgcactttgc gaaaccgctg tatctggtga aggtcgtaa aatgatcgaa ggcctcgata    4920
aagatcagag cttttacgaa gcgtttgaaa tggcgtatca ggaattagaa agcttaatca    4980
ttccgatcta taacaaagcg cgtagctatt tgtcgcgcaa accgtttaaa gcggataaat    5040
ttaaaattaa ctttgataac aacaccctgt taagcggttg ggacgcgaac aaagaaaccg    5100
ccaacgcgtc cattctgttt aaaaaagatg gcctgtatta tctgggtatt atgccgaagg    5160
gtaaaaccct tctctttgat tattttgtgt cgagcgaaga tagcgaaaaa ctgaaacagc    5220
gtcgccagaa aaccgccgaa gaagcgctgg cgcaggatgg cgaaagctat tttgaaaaaa    5280
ttcgttataa actgttaccg ggcgcgagca aaatgttacc gaaagtgttt tttagcaaca    5340
aaaacattgg ctttatatac ccgagcgacg atattctgcg catccgcaac accgccagcc    5400
ataccaaaaa cggcaccccg cagaaaggcc atagcaaagt ggaatttaac ctgaacgatt    5460
gccataagat gattgatttt tttaaatcca gcattcagaa acatccggaa tggggatctt    5520
ttggctttac ctttagcgat accagcgatt ttgaagatat gagcgcgttt atcgcgaag    5580
tggaaaatca gggttacgtg attagctttg ataaaatcaa agaaacctat atccagagtc    5640
aggtggaaca gggtaatctg tatctgtttc agatttataa caagattttt agcccgtata    5700
gcaaaggcaa accaaacctg cacaccctgt attggaaagc gttatttgaa gaagccaacc    5760
tgaataacgt ggtggcgaaa ctgaacggtg aagcggaaat cttttttcgt cgtcatagca    5820
ttaaagcgag cgataaagtg gtgcatccgg caaaccaggc gattgataac aaaaatccgc    5880
ataccgaaaa aacgcagagc acctttgaat atgatctggt gaaagataaa cgctataccc    5940
```

```
aagataaatt ttttttttcac gtgccgatca gcctcaactt taaagcgcag ggcgtgagca    6000
aatttaacga taaagtgaac ggcttcctga aaggcaaccc ggatgtcaac attattggta    6060
ttgatcgggg cgagcgccat ctgctttatt ttaccgtggt gaatcagaaa ggtgaaattc    6120
tcgttcagga aagcttaaac accctgatga gcgataaagg ccatgtgaac gattatcagc    6180
aaaaactgga taaaaagaa caggagcgtg atgcggcacg taaatcttgg accacggtgg     6240
aaaacattaa agaattgaaa gaaggctatt taagccatgt ggtgcataaa ctggcgcacc    6300
tgatcattaa atataacgcg attgtgtgcc tggaggacct gaattttggc tttaaacgcg    6360
gtcgctttaa agtggaaaaa caggtttatc agaaatttga aaaagcgctg attgataaac    6420
tgaactatct ggtgtttaaa gaaaagaat taggtgaagt ggggcattat ctgaccgcgt     6480
atcaactgac cgcgccgttc gaaagcttta aaaaactggg taaacagtct ggcattctgt    6540
tttacgtccc ggcggattat acctccaaaa tcgatccgac cacgggcttc gttaactttc    6600
tggatctgcg ctatcagagc gtggaaaaag cgaaacagct tctgtccgat tttaacgcga    6660
ttcgttttaa cagcgtgcag aactattttg aatttgaaat tgattataaa aaactgaccc    6720
cgaaacgtaa agtcggcacc caaagtaaat gggttatttg cacctatggc gatgtgcgct    6780
atcagaatcg tcgcaatcag aaaggtcatt gggaaaccga agaagtgaac gtgaccgaaa    6840
agctgaaagc gttatttgcg agcgatagca aaacgaccac ggttatcgat tatgccaacg    6900
acgacaacct gattgatgtg attttagaac aggataaagc gagcttttt aaagaattat     6960 tgtggttact gaaactgacc atgaccctgc gccatagcaa aattaaaagc gaagatgatt    7020
ttattctgtc cccggtgaaa aatgaacagg gtgaattta tgatagccgt aaagcgggcg     7080
aagtttggcc taaagatgcg gatgccaacg gcgcgtatca tatcgcgctg aaaggccttt    7140
ggaatttaca gcaaattaac cagtgggaaa aaggtaaaac cctgaattta gcgatcaaaa    7200
accaggattg gtttagcttt atccaggaaa aaccgtatca ggaatgatga agcttatgc     7260 agatcggtaa taaagacgaa caataagacg ctgaaaagcg tcttttttcg ttttggtcct    7320
gttccggcgc gatagtgtga acatgctata gacttctggt gctacccgac tgacaattaa    7380
tcatccggct cgtataatgc tagcaatttc tactgttgta gatcattccg gaacgttcca    7440
gcgctgcaat ttctactgtt gtagatctga tttttcacat gttacctttc aatttctact    7500
gttgtagatc cgaaaacgta aagcttcagc tgtaatttct actgttgtag atatcatatc    7560
tggcgttaat ggagtttcgt gacgaacaat aagtcctccc taacgggggg caattttat     7620 tgataacaaa agtaacttcg agcttgtcta cctcctagct cgtaaattgc acgctgatag    7680
tctcccaatt gcgaaggacc aaaacgaaaa acacccttt cgggtgtctt ttctggaatt     7740
tggtacgcag tactaggtat cgtgtaagta gcgaaggccc gtacgcgaga taaactgcta    7800
ggcaaccgcg actctacgac tggtgctcga tttaatttcg ctgacgtaaa gaaattatcg    7860
gcagtgcgtc aactgccgta tctttatctt aattaggtag ttggacaagc ccttgaaaga    7920
aatagcaaga gcctgcctct ctattgaagt cacggcgaaa gtcgggtaga atcaaagaa     7980 agcagaaatt aaatcggagt aatactaagt tgggataact ccgtaactga ctacgccttt    8040
ctctagactt tacttgacca gatacactgt cttttgacacg ttgaaggatt agagcaatca   8100
aatccaagac tggctaagca cgaagcaact cttgagtgtt aaaaagttac ttcctgtatt    8160
cgggacgagg gtactagaag attgcaggga ctccgacgtt aagtaaatta caaagtaata    8220
agtatcgttc aggatcacgt taccgcaata agaagcgaga ataatataat ttccgaagtg    8280
```

```
cttaccccag tagtgactat tcctataacc cttctgagtg tccggaggcg gaaatttgcc    8340
acgaaagaga aagtatttcc ccgacaataa taaaggggcg ctcctcagct tttccacttg    8400
gttgggtaag ctaggcaact ctgaaaggag tttcggcgaa gtgaagccga cacctttgaa    8460
ttgttttagg ggcgttattc gagggcaatc ggagctaact tcaagactac ttctttgttg    8520
aatactaaat agtgcaaagg tcgtgtttcc tcaaggatac tccgctaaca atataggatt    8580
ccaatcagat tcagcactgg cggtacgggt gttgcggtga ggcgttcggg tttacggctc    8640
gaagctagca cggtaggaag cctgacaatc accaagcaaa agggccgtcg aaggcccaca    8700
agatacgaaa gctctcgaag cccttatcctt gaccgatcca cctatttagg cagttacgca    8760
caaaagctac ccaataatcc gtgacaggca caatatcacg gaacaaaacc gaaaactctc    8820
gtacacggtt aggttttcgc taggaagaat aaacctctat cttgattata agaaggctcc    8880
ccaagcaccc ccaaaaccga aatagcggtt tgcaataagg gacaagttac gagtgtagac    8940
acgcagaatt atccagcctt tagtctttag gaaggcaaag ctattgtacg cggtagccgt    9000
cgtagcaatt taccaactgt agaattattg gacacacgta acaagggctt acagttgaag    9060
tttaataagg tcacacgcaa aaccgctaag gaataatcgc accgttagcg aaagaatatt    9120
tcagagcggt tagtaaaggt tgagtaaagt gagattccaa agtgagcctt tataaaaagt    9180
aaagagctat aataaaaccg tcgatcggaa aacaatcgcc tgaaatctca agcacgttgc    9240
cctttctaac gtcgctaagg tttcgtaaac ccgtttgatt aggaagaaga ataagtaacc    9300
cgattaggtt tgagatcgcg ggttatcggt ttggattaaa agtggatacc agcggagtca    9360
acgccgacgc aaacgtacag tgatccaatc ctgttccacg gtcaagcaca atcagctagc    9420
aagatcttgg aatagagtcg ttgcaccgct ttgatttaca tgctctccat tgcacaacat    9480
tccggaagga ctggcttctc tgccatgatc ggataatgaa aaacatcagt atgccctgtc    9540
attttctttt gggtgtcctc aaataattgc cctcacgtta tcgtatgtga cgcgctcatc    9600
tatgctcgaa gtattccttg ttctcccatc ttttaataga aagtctttaa tgaacgtgtc    9660
gttacgcagt gtatgaactc ttgttttata gggcagactt tggcgtggcc taagtgtgtt    9720
cgataagaag gcaaggacaa ctagctgacg cgctgtaata cggatattat ggcacggttg    9780
atacaaacgc tgatatcctg atttgctaat gtgcccaaca ctttagttga gtgccacgtt    9840
ccgactacaa gttgcttcaa gaggggaatt tggatttggc aatagccccc cgttctacc    9900 tcaagaggcg acgagtatta accgcgccag cttcggcac aagggccaaa gaagattcca     9960
atttcttatt cccgaataac ctccgaatcc ctgcgggaaa atcaccgacc gaatagccta   10020
gaagcaaggg ggaacagata ggtataatta gcttaagaga gtaccagccg tgacaacacc   10080
gtagtaacca caaacttacg ctggggcttc ttttggcggat ttttacagat actaacaagg   10140
tgatttgaag taccttagtt gaggatttaa acgcgctatc cggtagtcta caaattggga   10200
aataccgttc aaagagggct agaattactt aaaagccttc acaccgcctg cgctatacgc   10260
gcccactctc ccgtttatcc gtccaagcgg aagcagggcg aacttccgct aagatattct   10320
tacgtgtaac gtagctaagt atcccaaata gctggcgtac gcgttgaaca ccgcctagag   10380
gatcgggagt cgccggacga gcgtgttatt ggggacttac gccagcgtag actcaaacgc   10440
gcccagatta accctgcacg tattgccttg aataacgtac taatctctcc ggctctcgac   10500
aatctatcga gcgactcgat tatcaacggg tgtcttgcag ttctaatctc ttgccccgc    10560 ccgtaatagc ctccaagtga ttcaagatag taaagggcaa gagcttattc ggcgttgaag   10620
gatagcggac tttcggtcaa ccacaattcc ccactcgaca aaaccagccg tgcgaagaac   10680
```

```
tctgaaagta caagcaaccc aagagggctg agcctaaact cagctaattc ctaagtgagc    10740
taaagactcg aagtgacagc tattaataaa tagagcggga acgtcgaacg gtcgtgaaag    10800
taatagtaca acgggtatta acttactgag gatattgctt gaagctgtac cgttttattg    10860
ggtgaacgaa taagatccag caattcagcc aaagaagcta ccaattttta gtttaagagt    10920
gtcacgtctg acctcgcggg tggatagccg aacgtagagc ttacgagcca gcggaaacag    10980
tagccgcagg ataagtaagg ggagtaagtg atcgaacgaa tcagaagtga caatatactt    11040
aggctggatc tcgtcccgtg aatcccaacc ctcaccaact acgagataag aggtaagcca    11100
gaaatcggca tggtggcgac caacgactgt tccccccctg taactaatcg ttccgtcaaa    11160
acctgactta cttcaaggcc aattccaagc gcaaacaata ccgtcctagt tcttcggtta    11220
agtttccgaa gtaggagtga gcctacctcc gtttgcgtct tgttaccact gacccagcta    11280
tttactttgt attgcctgca atcgaatttc tgaactctca gatagtgggg ataacgggaa    11340
agttcctata tttgcgaact aacttagccg tccacctcga agctacctac tcacacccac    11400
cccgcgcggg gtaaataagg cactaatccc agcttagagc ttgcgtagca cttagccaca    11460
agttaattaa cagttgtctg gtagtttggc ggtattagcg agatcctaga agcaaggcag    11520
agttagttct aacctaaagc cacaaataag acaggttgcc aaagcccgcc ggaaattaaa    11580
tcttgctcag ttcggtaacg gagtttccc                                      11609
```

<210> SEQ ID NO 43
<211> LENGTH: 686
<212> TYPE: PRT
<213> ORGANISM: Bacteriophage ZG49

<400> SEQUENCE: 43

```
Met Ser Thr Ile Thr Gln Phe Pro Ser Gly Asn Thr Gln Tyr Arg Ile
1               5                   10                  15

Glu Phe Asp Tyr Leu Ala Arg Thr Phe Val Val Thr Leu Val Asn
            20                  25                  30

Ser Ser Asn Pro Thr Leu Asn Arg Val Leu Glu Val Gly Arg Asp Tyr
        35                  40                  45

Arg Phe Leu Asn Pro Thr Met Ile Glu Met Leu Val Asp Gln Ser Gly
    50                  55                  60

Phe Asp Ile Val Arg Ile His Arg Gln Thr Gly Thr Asp Leu Val Val
65                  70                  75                  80

Asp Phe Arg Asn Gly Ser Val Leu Thr Ala Ser Asp Leu Thr Asn Ser
                85                  90                  95

Glu Leu Gln Ala Ile His Ile Ala Glu Glu Gly Arg Asp Gln Thr Val
            100                 105                 110

Asp Leu Ala Lys Glu Tyr Ala Asp Ala Ala Gly Ser Ser Ala Gly Asn
        115                 120                 125

Ala Lys Asp Ser Glu Asp Glu Ala Arg Arg Ile Ala Ala Ser Ile Arg
    130                 135                 140

Glu Ala Gly Leu Ile Gly Tyr Ile Thr Arg Arg Ser Phe Glu Lys Gly
145                 150                 155                 160

Tyr Asn Val Thr Thr Trp Ser Glu Val Leu Trp Glu Glu Asp Gly
                165                 170                 175

Asp Tyr Tyr Arg Trp Asp Gly Thr Leu Pro Lys Asn Val Pro Ala Gly
            180                 185                 190

Ser Thr Pro Glu Thr Ser Gly Gly Ile Gly Leu Gly Ala Trp Val Ser
        195                 200                 205
```

-continued

```
Val Gly Asp Ala Ala Leu Arg Ser Gln Ile Ser Asn Pro Glu Gly Ala
    210                 215                 220
Ile Leu Tyr Pro Glu Leu Gln Met Ala Arg Trp Asp Glu Gly Asp
225                 230                 235                 240
Val Arg Gly Trp Gly Ala Lys Gly Asp Gly Val Thr Asp Ser Thr Glu
                245                 250                 255
Asn Ile Ala Ala Ser Leu Asn Ser Gln Lys Ala Val Val Ala Ser Glu
            260                 265                 270
Gly Val Phe Ser Ser Ser Gly Ile Asn Ser Asn Tyr Cys Asn Leu Asp
        275                 280                 285
Gly Arg Gly Ser Gly Val Leu Ser His Arg Ser Ser Thr Gly Asn Tyr
    290                 295                 300
Leu Val Phe Asn Asn Leu Arg Ser Gly Arg Leu Ser Asn Ile Thr Val
305                 310                 315                 320
Glu Ser Asn Lys Ala Thr Asp Thr Thr Gln Gly Gln Gln Val Ser Leu
                325                 330                 335
Ala Gly Gly Ser Asp Val Thr Ile Ser Asp Val Asn Phe Ser Asn Val
            340                 345                 350
Lys Gly Ala Gly Phe Ser Leu Ile Thr Tyr Pro Asn Asp Ala Pro Ser
        355                 360                 365
Asp Gly Leu Met Ile Lys Gly Ile Arg Gly Ser Tyr Ser Gly Tyr Ala
    370                 375                 380
Thr Asn Lys Ala Ala Gly Cys Ile Leu Ala Asp Ser Ser Val Asn Ser
385                 390                 395                 400
Leu Ile Asn Asn Val Ile Ala Lys Asn Tyr Pro Gln Phe Gly Ala Val
                405                 410                 415
Glu Leu Lys Gly Thr Ala Ser Tyr Asn Ile Val Ser Asn Val Ile Gly
            420                 425                 430
Ala Asp Cys Gln His Val Thr Tyr Asn Gly Thr Glu Gly Ser Ile Ala
        435                 440                 445
Pro Ser Asn Asn Leu Ile Asn Gly Val Val Ala Asn Asn Pro Lys Tyr
    450                 455                 460
Ala Ala Val Val Ala Gly Lys Gly Ser Thr Asn Leu Ile Ser Asp Val
465                 470                 475                 480
Leu Val Asp Phe Ser Thr Ser Asp Ala Arg Gln Ala His Gly Val Thr
                485                 490                 495
Val Glu Gly Ser Asp Asn Val Ile Asn Asn Val Leu Met Ser Gly Cys
            500                 505                 510
Asp Gly Thr Asn Ser Leu Gly Gln Ala Gln Thr Ala Thr Ile Ala Arg
        515                 520                 525
Phe Ile Asp Thr Ala Asn Asn Tyr Ala Ser Val Phe Pro Ser Tyr
    530                 535                 540
Ser Ala Thr Gly Val Ile Thr Phe Glu Ser Gly Ser Thr Arg Asn Phe
545                 550                 555                 560
Val Glu Val Lys His Pro Gly Arg Arg Asn Asp Leu Leu Ser Ala Thr
                565                 570                 575
Gly Thr Ile Glu Gly Lys Val Thr Ile Asp Gly Thr Ser Asn Ser Asn
            580                 585                 590
Val Val His Ala Pro Ala Leu Gly Gln Tyr Ile Gly Ser Met Ser Gly
        595                 600                 605
Arg Phe Glu Trp Arg Ile Lys Ser Met Ser Leu Pro Ser Gly Val Leu
    610                 615                 620
```

Thr Ser Ala Asp Lys Tyr Arg Met Leu Gly Asp Gly Ala Val Ser Leu
625                 630                 635                 640

Ala Val Gly Gly Gly Thr Ser Ser Gln Val Arg Leu Phe Thr Ser Asp
            645                 650                 655

Gly Thr Tyr Arg Thr Val Ser Leu Thr Asn Gly Asn Val Arg Leu Pro
        660                 665                 670

Thr Ser Ser Thr Gly Tyr Leu Gln Leu Gly Ser Ser Leu
    675                 680                 685

<210> SEQ ID NO 44
<211> LENGTH: 2061
<212> TYPE: DNA
<213> ORGANISM: Bacteriophage ZG49

<400> SEQUENCE: 44

```
atgtccacga ttacacaatt cccttcagga aacactcagt acaggattga gttcgactac      60
ctagccagaa cgtttgttgt tgttacgctg gtgaatagct ctaaccctac cctgaaccgt     120
gtactggaag ttggtcgaga ttaccgattc cttaacccaa cgatgattga gatgttggtt     180
gaccaatcag gtttcgacat cgttcgtatt caccgtcaga ctggaactga cttagtggta     240
gacttcagga atggctcagt gttgacagct agtgacctga ccaattcaga gcttcaggct     300
atccatattg cagaagaagg tcgagaccaa acggttgact tagcgaagga atatgccgat     360
gctgctggta gctctgctgg caacgctaag gatagcgagg acgaagcacg ccgaatcgct     420
gcgagtatca gggaagctgg tctaattggc tatattaccc gtcgctcctt cgagaaaggc     480
tacaacgtta caacatggag cgaggtcctg ctatgggaag aggatggtga ttattaccgc     540
tgggatggta cgcttccaaa gaacgttcct gctggttcaa ctcctgaaac ttccggtggg     600
attggattag gtgcgtgggt tagtgttggt gatgctgctt taagaagtca gatttcaaac     660
ccggaagggg caatactcta cccggaattg cagatggcaa gatggcgtga tgagggtgat     720
gttcgaggct ggggtgctaa aggggatggt gtaacagata gtacggagaa tatagctgct     780
tcactaaatt ctcaaaaagc tgtcgtagca tcagaaggtg tattctctag ttctggtatt     840
aatagtaatt actgtaactt agacggtaga ggcagtggtg tactaagtca ccgttcaagt     900
acaggtaact acttagtatt taacaatcta cgctcaggtc gcttaagtaa tattacggta     960
gaaagtaata aggcgaccga taccactcaa gggcagcagg tatctcttgc tggtggcagt    1020
gatgttacta agtgatgt taatttctca acgttaagg gcgctggttt cagtttaatc    1080
acatacccta tgatgcacc ctctgatggg cttatgatta aaggcattcg aggtagctac    1140
tccggctatg ctactaataa ggcggctgga tgcatacttg ctgattcctc agttaactcc    1200
ctcataaata cgtcattgc taagaactac cctcagttcg gggctgtaga actgaaaggt    1260
acagccagtt ataacatagt cagcaatgtt ataggggcag actgccagca tgtaacttac    1320
aacggtacag aagggtcaat agctccctct aacaacctta tcaatggggt agtggctaat    1380
aatcctaaat atgcagcggt tgttgcaggc aaaggtagta ccaacttaat ctccgatgtg    1440
cttgtagatt tctcaaccctc tgatgctagg caggctcatg gtgttacagt agaaggttct    1500
gataacgtca taataatgt gcttatgtca gggtgtgatg gtactaactc tttagggcaa    1560
gctcagactg ctacaattgc gcgctttata gatacggcta ataacaacta tgcgtctgta    1620
tttcctagct acagtgctac aggtgttatt actttcgaat caggttctac ccgtaacttc    1680
gtagaggtaa agcatccggg aaggagaaac gaccttctca gtgctactgg tactattgaa    1740
ggtaaagtta ctattgacgg cactagtaat agcaacgtag tgcacgctcc tgcattagga    1800
```

```
cagtacatag gcagtatgtc cggtaggttc aatggcgga ttaagtccat gtcacttccg    1860
tcaggcgttc ttacctcggc tgataagtac agaatgcttg gggatggtgc tgtgtcatta    1920
gctgtaggtg ggggtacttc ttctcaagtt cgcctattta cttctgatgg tacttatcgg    1980
acagtatcac tcaccaacgg taacgtgcgt cttcctacca gtagcacagg ttatttgcag    2040
ttaggttcta gctccctcta a                                              2061
```

<210> SEQ ID NO 45
<211> LENGTH: 12299
<212> TYPE: DNA
<213> ORGANISM: Artificial Sequence
<220> FEATURE:
<223> OTHER INFORMATION: p775

<400> SEQUENCE: 45

```
actgtcggaa tgacaaatgg ttccaattat tgaacaccct tcggggtgtt tttttgtttc     60
tggtttcccg aggccggcct gcgctagcgg agtgtatact ggcttactat gttggcactg    120
atgagggtgt aagtgaagtg cttcatgtgg caggagaaaa aaggctgcat cggtgcgtca    180
gcagaatatg tgatacagga tatattccgc ttcctcgctc actgactcgc tacgctcggt    240
cgttcgactg tggcgagcgg aaatggctta cgaacggggc ggagatttcc tggaagatgc    300
caggaagata cttaacaggg aagtgagagg gtcgcggcaa agccgttttt ccataggctc    360 cgccccctg acaagcatca cgaaatctga cgctcaaatc agtggtggcg aaacctgaca    420
ggactataaa gataccaggc gtttccccct ggcggctccc tcgtgcgctc tcctgttcct    480
gcctttcggt ttgccggtgt cattcctctg ttacggccga gtttgtctca ttccacgcct    540
gacactcagt tccgggtagg cagttcgctc caagctggac tgtatgcacg aaccccccgt    600
tcagtccgac cgctgcgcct tatccggtaa ctatcgtctt gagtccaacc cggaaagaca    660
tgcaaaagca ccactggcag cagccactgg taattgattt agaggagtta gtcttgaagt    720
catgcgccgg ataaggctaa actgaaagga caagttttgg cgactgcgct cctccaagcc    780
agttacctcg gttcaaagag ttggtagctc agagaacctt cgaaaaaccg ccctgcaagg    840
cggttttttc gttttcagag caagagatta gcgcagacc aaaacgatct caagaagatc    900
atcttattaa tcagataaaa tatttctaga tttcagtgca atttatctct tcaaatgtag    960
caccggcgcg ccgtgaccaa ttattgaagg ccgctaacgc ggcctttttt tgtttctggt   1020
atcccgaatg gagcgacttc tccccaaaaa gcctcgcttt cagcacctgt cgtttccttt   1080
cttttcagag ggtattttaa ataaaaacat taagttatga cgaagaagaa cggaaacgcc   1140
ttaaaccgga aaattttcat aaatagcgaa aacccgcgag gtcgccgccc cgtaacctgt   1200
cggatcaccg gaaaggaccc gtaaagtgat aatgattatc atctacatat cacaacgtgc   1260
gtaaagggta agtatgaagg tcgtgtactc catcgctacc aaattccaga aaacagacgc   1320
tttcgagcgt ctttttcgt tttggtcacg acgtacggtg gaagattcgt taccaattga   1380
cagctagctc agtcctaggt atatacatac atgcttgttt gtttgtaaac tactgttttc   1440
attaaagagg agaaaggaag ccatgtccat ctatcaggag tttgttaaca agtattccct   1500
gtctaaaacc ctgcgttttg aactgatccc gcagggcaaa actttggaaa acattaaagc   1560
gcgtggcctg attctggatg acgaaaaacg tgcaaaggat tacaagaaag ctaaacagat   1620
catcgacaaa tatcaccagt tctttatcga agaaattctg tcgtcggtgt gcatcagtga   1680
ggatctgtta cagaattatt ctgatgtata ctttaaactt aaaaagtccg atgacgataa   1740
```

```
tctgcaaaaa gatttcaagt cagccaaaga taccatcaag aaacagatct cagaatatat      1800
taaagatagc gaaaagttca aaaacctgtt taaccaaaac ctcattgatg ctaagaaagg      1860
ccaagaatct gacctgatct tatggctgaa acagagcaaa gataacggca ttgaactgtt      1920
caaagctaat agcgacatca ccgatattga tgaagcgctc gaaatcatca agtcttcaa      1980 aggctggacg acgtatttca aaggttttca tgaaaaccgt aagaatgtat attcgagcaa      2040
cgatattccg acctctatta tttatcgtat cgtggacgac aacctgccga agtttctgga      2100
aaacaaagcg aaatatgaat ctctgaaaga caaagcaccg gaagctatta actatgaaca      2160
gatcaagaaa gatctggcgg aagaactgac cttcgacatc gactataaaa cctccgaagt      2220
taaccagcgt gttttctcac tggacgaggt tttcgaaatc gctaatttca acaattacct      2280
gaatcaatct ggcatcacca aattcaacac cattattggt ggcaaatttg ttaacggcga      2340
aaacaccaag cgtaagggca tcaacgaata cattaacctg tatagccaac aaatcaacga      2400 caaaccctg aaaagtata aaatgtccgt tctgtttaaa cagattttat cggacaccga      2460
atctaaatcc ttcgtaattg ataaactgga agatgatagc gacgttgtca ccacgatgca      2520
gagcttttat gagcagattg cggcgttcaa aaccgtggaa gagaaatcta ttaaagaaac      2580
tctgtccctg ctctttgacg acctcaaagc gcagaaacta gatctgtcta agatttactt      2640
taaaaacgac aaatctctga ccgatctcag tcaacaagtt ttcgatgact atagcgtgat      2700
cggcacggca gttttggaat acatcaccca acaaatcgcg ccgaaaaatc tggacaaccc      2760
gtccaagaag gaacaggaac tgattgcaaa gaaaacagaa aaagctaaat acctgagctt      2820
agaaactatc aaactggcac ttgaggaatt taataaacat cgtgatattg ataaacagtg      2880
tcgttttgag gaaattctgg cgaactttgc ggcaatcccg atgatcttcg acgaaattgc      2940 tcaaacaaa gacaatctgg cgcagatctc tatcaagtac cagaatcagg gtaagaaaga      3000
tctgcttcaa gcatctgcgg aggacgatgt gaaagcaatt aaagacttat tagatcagac      3060
gaataactta ttacacaagc tcaaaatctt ccacatcagc cagagcgagg acaaggcgaa      3120
cattctggat aaagatgaac acttctatct ggtgttcgaa aatgttact tcgaactggc      3180 aaacatcgtc cctctctaca ataaaatccg caactacatc acgcagaagc cttactctga      3240
cgagaaattc aaaactgaact tcgaaaacag cacgctggcg aacggctggg ataagaacaa      3300
agagccggac aacaccgcaa tcctgttcat caaagacgac aaatactatc tgggcgtaat      3360
gaacaagaag aacaacaaga tcttcgacga taaagcgatc aaagaaaaca agggtgaagg      3420
ctataagaaa atcgtgtaca agctcctgcc gggtgcgaat aaaatgttac cgaaagtgtt      3480
cttttccgcg aaaagcatca aattctacaa cccgtctgag gatattctgc gcatccgcaa      3540
tcatagcacg cacactaaaa acggtagccc gcagaaaggg tatgaaaaat tcgaatttaa      3600
tatagaggac tgccgtaagt tcatcgactt ctataaacag agcatttcca acatccgga      3660 atggaaagac ttcggcttcc gtttctctga cactcagcgc tataatagca tcgacgagtt      3720
ctaccgcgaa gtggagaatc agggctataa actgaccttc gagaacatta gtgagtcgta      3780
catcgactcc gttgtgaatc agggtaaact gtacctgttt cagatctata ataaagactt      3840
tagcgcgtac agcaaaggcc gtccgaatct gcacacctt tactggaaag cattatttga      3900
cgaacgtaac ctgcaagatg tggtgtataa actgaacggt gaggcggaac ttttctaccg      3960
taaacagagt atcccgaaga aaatcacgca tccggcaaaa gaagctattg ccaacaaaaa      4020
caaagacaac ccgaagaaag aatcagtatt cgaatatgac ctgatcaaag ataaacgttt      4080
caccgaagat aagttctttt tccactgtcc gattaccatc aacttcaaat ctagcggtgc      4140
```

```
gaacaagttc aacgatgaaa ttaacttatt actgaaagag aaagctaatg acgtacacat   4200
cttatctatt gatcgcggtg aacgtcattt agcatactat acactggtag atggtaaagg   4260
taatattatt aaacaggata cttteaatat tatcggtaat gaccgtatga aaaccaacta   4320
tcacgataag ctggcggcga tcgaaaaaga tcgtgattct gcgcgtaaag attggaagaa   4380
aattaacaat atcaaagaaa tgaaagaagg ctatctgagc caagtggtgc acgagatcgc   4440
aaaactggtg attgaatata acgctatcgt ggttttcgaa gatctgaact ttggttttaa   4500
acgtggtcgc ttcaaagtag aaaaacaggt gtaccaaaaa ctggaaaaaa tgctgattga   4560
aaaactgaac tatctggttt ttaaagacaa cgaatttgac aaaacgggtg gcgtactccg   4620
tgcctatcag ctgaccgctc cgttcgaaac gttcaagaaa atgggtaaac aaacggggat   4680
tatctattat gtgccagctg gtttcacctc caagatttgt ccagttacgg gcttcgttaa   4740
ccagctgtac ccgaaatacg agagcgttag caaatctcaa gaattttca gcaaattcga   4800 caagatctgc tataatctgg ataaaggcta tttcgagttc agcttcgatt acaaaaactt   4860
cggcgataaa gcggctaaag gtaagtggac tattgctagc tttggtagcc gtctgattaa   4920 cttcgcaac tccgacaaaa accataattg gacacgcgt gaagtgtatc cgaccaaaga   4980
actggaaaaa ttactgaaag actattccat cgaatatggt catggggagt gcattaaagc   5040
ggcgatttgc ggtgaatccg ataagaaatt tttcgccaaa ctgaccagcg tgcttaacac   5100
cattctgcaa atgcgtaatt ctaaaacggg tacggagctg gactacctga tttctccggt   5160
agccgacgtt aacggcaact tcttcgattc tcgtcaagca ccgaaaaata tgccacaaga   5220
cgcggatgcc aacggtgcat accatatcgg cttaaaaggc ttaatgttat taggccgtat   5280
caagaataat caggagggca agaaattaaa tctggttatc aaaaacgaag aatacttcga   5340
gttcgttcag aatcgtaaca attaatgtat gcttaagcag ctcggtacca agacgaaca   5400 ataagacgct gaaaagcgtc ttttttcgtt ttggtcctgt tgcggcgcga tagtgtgaac   5460
atgctataga cttctggtgc tacccgactg acaattaatc atccggctcg tataatgcta   5520
gcaatttcta ctgttgtaga tgccagatca ccgcgatatc gttggtcgag acgaacaata   5580
aggcctccct aacgggggc cttttttatt gataacaaaa gtaacttcga gcttgtctac   5640
ctcctagcac cattattgca attaataaac aactaacgga caattctacc taacagtttt   5700
catatatgac gagcagttaa gtgatgagta aaggtgagga attatttact ggtgttgttc   5760
cgatcttagt tgaactggac ggcgatgtta acggtcataa attcagtgtt cgtggtgaag   5820
gtgaaggtga tgcaaccaac ggtaagctga ccctgaaatt catctgcact actggaaaat   5880
taccagtacc gtggcctact ctggtgacta ccctgaccta tggtgttcag tgtttttctc   5940
gttaccctga ccacatgaag caacatgatt tcttcaaatc tgcaatgccg gaaggttatg   6000
tacaggagcg caccatttct ttcaaagacg atggcacgta taaacccgt gcagaggtta   6060 aatttgaagg tgacactctg gtgaatcgta ttgaactgaa aggcattgat ttcaaagagg   6120
acggcaatat tttaggccac aaactggaat ataacttcaa ctcccataac gtttacatca   6180
ccgcagacaa acagaagaac ggtatcaaag ctaacttcaa aattcgccat aacgttgaag   6240
atggtagcgt acagctggcg gatcattacc aacagaacac tccgattgga gatgctcctg   6300
ttttactgcc ggataaccac tacctgtcca cccagtctaa actgtcgaag gatccgaacg   6360
aaaagcgcga ccacatggtg ttattagagt tcgttaccgc tagtgtgatc acgcacggta   6420
tggatgaact ctacaaataa gacgaacaat aaggggagcg ggaaaccgct ccccttttt   6480
```

```
attgataaca aaagtaaatt gcacgctgat agtctcccaa ttgcgaagga ccaaaacgaa      6540
aaaacaccct ttcgggtgtc tttctggaa tttggtaccg agtactaggt atcgtgtaag      6600
tagcgaaggc ccgtacgcga gataaactgc taggcaaccg cgactctacg actggtgctc      6660
gatttaattt cgctgacgta aagaaattat cggcagtgcg tcaactgccg tatctttatc      6720
ttaattaggt agttggacaa gcccttgaaa gaaatagcaa gagcctgcct ctctattgaa      6780
gtcacggcga aagtcgggta gaaatcaaag aaagcagaaa ttaaatcgga gtaacactaa      6840
ggtgggataa ctccgtaact gactacgcct ttctctagac tttacttgac cagatacact      6900
gtctttgaca cgttgaagga ttagagcaat caaatccaag actggctaag cacgaagcaa      6960
ctcttgagtg ttaaaaagtt atctcctgta ttcgggaagc gggtactaga agattgcagg      7020
gactccgacg ttaagtaaat tacaaagtaa taagtatcgt tcaggatcac gttaccgcaa      7080
taagaagcga gaataatata atttccgaag tgcttacccc agtagtgact attcctataa      7140
cccttctgag tgtccggagg cggaaatttg ccacgaaaga gaaagtattt ccccgacaat      7200
aataaagggg cgctcctcag cttttccact tggttgggta agctaggcaa ctctgaaagg      7260
agtttcggcg aattgaagcc gacagctttg aattgtttta ggggcgttat tcgagggcaa      7320
tcggagctaa cttcaagact acttctttgt tgaatactaa atagtgcaaa ggtcgtgttt      7380
cctcaaggat actccgctaa caatatagga ttccaatcag attcagcact ggcggtacgg      7440
gtgttgcggt gaggcgttcg ggtttacggc tcgaagctag cacggtagga agcctgacaa      7500
tcaccaagca aaagggccgt cgaaggccca caagatacga aagctctcga agccttatcc      7560
ttgaccgatc cacctattta ggcagttacg cacaaaagct acccaataat ccgtgacagg      7620
cacaatatca cggaacaaaa ccgaaaactc tcgtacacgg ttaggttttc gctaggaaga      7680
ataaacctct atcttgatta taagaaggct ccccaagcac ccccaaaacc gaaatagcgg      7740
tttgcaataa gggacaagtt acgagtgtag acacgcagaa ttatccagcc tttagtcttt      7800
aggaaggcaa agctattgta cgcggtagcc gtcgtagcaa tttaccaact gtagaattat      7860
tggacacacg taggaagggc ttacagttga agtttaataa ggtcacacgc aaaaccgcta      7920
aggaataatc gcaccgttag cgaaagaata tttcagagcg gttagtaaag gttgagtaaa      7980
gtgagattcc aaagtgagcc tttataaaaa gtaaagagct ataataaaac cgtcgagcag      8040
aaaacaatcg cctgaaatct caagcacgtt gcccttcta acgtcgctaa ggtttcgtaa      8100
acccgtttga ttaggaagaa gaataagtaa cccgattagg tttgagatcg cgggttatcg      8160
gtttggatta aaagtggata ccagcggagt caacgccgac gcaaacgtac agtgatccaa      8220
tcctgttgca cggtcaagca caatcagctc gcaagatctt ggaatagtgt gcccaacagt      8280
ttagttgagg gccacgttcc gactacaagt tgcttcaaga ggggaatttg gatttggcaa      8340
tagcccccg tttctacctc aagaggcgac gagtattaac cgcgccagct gtcggcacaa      8400
gggccaaaga agattccaat ttcttattcc cgaataacct ccgaatccct gcgggaaaat      8460
caccgaccga atagcctaga agcaagggg aacagatagg tataattagc ttaagagagt      8520
accagccgtg acaacagcgt agtaaccaca aacttacgct ggggcttctt tggcggattt      8580
ttacagatac taacaaggtg atttgaagta ccttagttga ggatttaaac gcgctatccg      8640
gtaatctcca aattgggaaa taccgttcaa agagggctag aattacttaa aagccttcac      8700
accgcctgcg ctatacgcgc ccactctccc gtttatccgt ccaagcggaa gcagggcgat      8760
cctccgctaa gatattctta cgtgtaacgt agctaagtat cccaaatagc tggcgtacgc      8820
gttgaacacc gcctagagga tcgtgactcg ccggacgagc gtgttattgg ggacttacgc      8880
```

```
cagcgtagac tacaacgcgc ccagattaac cctgcacgta ttgccttgaa taacgtacta   8940
atctctccgg ctctcgacaa tctatcgagc gactcgatta tcaacgggtg tcttgcagtt   9000
ctaatctctt gcccccgccc gtaatagcct ccaagagatt gaagatagta aagggcaaga   9060
gctgattcgg cgttgaagga tagcggactt tcggtcaacc acaattcccc actcgacaaa   9120
accagccgtg cgaataactc tgaaagtaca agcaacccaa gagggctgag cctaaactca   9180
gctaattcct aagtgagcta aagactcgaa gtgacagctc ttaataaata gagcgggaac   9240
gtcgaacggt cgtgaaagta atagtacaac gggtattaac ttactgagga tattgcttga   9300
agctgtaccg tttattgggt tgaacgaata agatccagca attcagccaa agaagctacc   9360 aattttagt ttaagagtgt cacgtctgac ctcgcgggta gattgccgaa cgtagagctt   9420
acgagccagc ggaaacagta gccgcaggat aagtaagggg agtaagtgat cgaacgaatc   9480
agaagtgaca atatacttag gctggatctc gtcccgtgaa tcccaacccct caccaactac   9540 gagataagag gtaagccaaa aatcgacttg gtggcgacca acgactgttc cccccctgta   9600
actaatcgtt ccgtcaaaac ctgacttact tcaaggccaa ttccaagcgc aaacaatacc   9660
gtcctagttc ttcggttaag tttccgaagt aggagtgagc ctacctccgt ttgcgtcttg   9720
ttaccactga cccagctatt tactttgtat tgcctgcaat cgaatttctg aactctcaga   9780
tagtggggat aacgggaaag ttcctatatt tgcgaactaa cttagccgtc cacctcgaag   9840
ctacctactc acacccaccc cgcgcggggt aaataaggca ctaatcccag ctgagagctg   9900
gcgtagcact tagccacaag ttaattaaca gttgtctggt agtttggcgg tattaggaag   9960
atcctagaag caaggcagag ttagttctaa cctaaagcca caaataagac aggttgccaa  10020
agcccgccgg aaattaaatc ttgctcagtt cggtaacgga gtttccctcc cgcgtactta  10080
attcccaata agaaacgcgc ccaagtccta tcaggcaaaa ttcagcccct tcccgtgtta  10140
gaacgagggt aaaaatacaa gccgattgaa caagggttgg gggcttcaaa tcgtcgttta  10200
ccccacttta caacggagat taagtagttc accctatagt acgaagcaga actatttcga  10260
ggggcgtgca ataatcgaat cttctgcggt tgacttaaca cgctagggac gtgccctcga  10320
ttcaatcgaa ggtactccta ctcagactgc ctcacaccca gctagtcact gagcgataaa  10380
attgacccgc cctctaggga agcgagtacg tcccaagggg ctccggacag ggctatatag  10440
gagagtttga tctcgccccg acaactgcaa ccctcaactc ccttagataa tattgttagc  10500
cgaagttgca cgacccgccg tccacggact gctcttaggg tgtggctcct taatctgaca  10560
acgtgcaacc cctatcgaag tcgattgttt ctgcgaaagg tgttgtccta atagtcccga  10620
aatttggccc ttgtaggtgt gaaaccactt agcttcgcgc cgtagtccta aaggcccacc  10680
tattgacttt gtttcgggta gcactaggaa tcttaacaat ttgaatttgg acgtggaacg  10740
cgtacacctt aatctccgaa taattctagg gatttggaag tcctctacgt tgacacacct  10800
acactgctcg aagtaaatat acgaataacg cgggcctcgc ggagccgttc cgaatcgtca  10860
cgtgttcgtt tactgttaat tggtggcaaa taagcaatat cgtagtccgt caggcccagc  10920
cctgttatcc acggcgttat ttgtcaaatt gcgtagaact ggattgactg cctgacaata  10980
cctaattatc ggtacgaagt ccccgaatct gtcgggctat ttcactaata ctttccaaac  11040
gccccgtatc caagaagaac gaatttatcc acgctcccgt cttgggacg aataccgcta  11100 caagtggaca gaggatcggt acgggcctct aataaatcca acactctacg ccctcttcaa  11160
gagctagaag aacagggtgc agttggaaag ggaattattt cgtaaggcga gccaataccg  11220
```

```
taattaattc ggaagagtta acacgattgg aagtaggaat agtttctaac cacggttact    11280
aatcctaata acggaacgct gtctgataga ttagtgtcag cgctcggtac caaagaaaaa    11340 taaaagacg ctgaaaagcg tctttttatt tttcggtcca gtgtaactca ggcaaaagca    11400
cgtaatattc gtactttctt cctccgtaag cgtcacccac attccttaaa gagtgcatgt    11460
gcatattttg ttatcaataa aaaaggccgc gatttgcggc cttattgttc gtcttgccgg    11520
attacgcccc gccctgccac tcatcgcagt attgttgtaa ttcattaagc attctgccga    11580
catggaagcc atcacaaacg gcatgatgaa cttggatcgc cagtggcatt aacaccttgt    11640
cgccttgcgt ataatatttt cccatagtga aaacgggggc gaagaagttg tccatatttg    11700
ctacgtttaa atcaaaactg gtgaaactca cccacggatt ggcactgacg aaaaacatat    11760
tttcgataaa cccctttaggg aaatatgcta agttttcacc gtaacacgcc acatcttgac    11820
tatatatgtg tagaaactgc cggaaatcgt cgtggtattc tgaccagagc gatgaaaacg    11880
tttcagtttg ctcatggaaa acggtgtaac aagggtgaac actatcccat atcaccagct    11940
caccgtcttt cattgccata cgaaactccg gatgtgcatt catcaggcgg gcaagaatgt    12000
gaataaaggc cggataaaac ttgtgcttat ttttctttac ggttttaaaa aaggccgtaa    12060
tatccagctg aacggtttgg ttataggtgc actgagcaac tgactggaat gcctcaaaat    12120
gttctttacg atgccattga cttatatcaa ctgtagtata tccagtgatt tttttctcca    12180
ttttagcttc cttagcttgc gaaatctcga taactcaaaa aatagtagtg atcttatttc    12240
attatggtga aagttgtctt acgtgcaaca ttttcgcaaa aagttggcgc tttatcaac     12299

<210> SEQ ID NO 46
<211> LENGTH: 282
<212> TYPE: DNA
<213> ORGANISM: Artificial Sequence
<220> FEATURE:
<223> OTHER INFORMATION: primase ori from the PICI of the Escherichia
      coli strain CFT073

<400> SEQUENCE: 46
tttgttgcaa tggctgtcta ccctgtctac ctgagtaaag aaaaatacat ttaattcagt     60
acattaactt gggtagacag cctttttta ctgtctacct actatctacc ctctctacct    120
gattttacct gaatcagaca gggaggtaga tacgggtag atagtggata aaagcactct    180
accccactga aagccgcgcc attactggca tggtggccag taaggtagat aaggtagaca    240
aggggaggca caactcaaaa cttttttaaac gagggggtaa aa                      282

<210> SEQ ID NO 47
<211> LENGTH: 13
<212> TYPE: DNA
<213> ORGANISM: Artificial Sequence
<220> FEATURE:
<223> OTHER INFORMATION: restriction site
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (8)..(8)
```

<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 47
twcannnnnn tgg                                                          13

<210> SEQ ID NO 48
<211> LENGTH: 282
<212> TYPE: DNA
<213> ORGANISM: Artificial Sequence
<220> FEATURE:
<223> OTHER INFORMATION: Primase ori deltaGAAABCC

<400> SEQUENCE: 48
tttgttgcaa tggctgtcta ccctgtctac ctgagtaaag aaaaatacat ttaattcagt        60
acattaactt gggtagacag cctttttta ctgtctacct actatctacc ctctctacct        120
gattttacct gaatcagaca gggaggtaga tacggggtag atagtggata aaagcactct       180
accccactga aagcagcgcc attactggca tggtggccag taaggtagat aaggtagaca       240
aggggaggca caactcaaaa cttttaaac gaggggtaa aa                            282

<210> SEQ ID NO 49
<211> LENGTH: 282
<212> TYPE: DNA
<213> ORGANISM: Artificial Sequence
<220> FEATURE:
<223> OTHER INFORMATION: Primase ori devoid of restriction sites

<400> SEQUENCE: 49
tttgttgcaa tggctgtcta ccctgtctac ctgagtaaag aaaaatacat ttaattcagt        60
atattaactt gggtagacag ccttttttta ctgtctacct tctgtctacc ctctctacct       120
gattttacct gaatcagaca gggaggtaga cacggggtag acagtggata aaagcactct       180
accccactga aagcagtgcc attactggca tggttgccag taaggttgat aaggtagaca       240
aggggaggga caactcaaaa cttttaaac gaggggtaa aa                            282

<210> SEQ ID NO 50
<211> LENGTH: 584
<212> TYPE: PRT
<213> ORGANISM: Artificial Sequence
<220> FEATURE:
<223> OTHER INFORMATION: PICI primase-helicase

<400> SEQUENCE: 50

Met Lys Leu Ala Pro Asn Val Lys Gln Gln Ser Arg Gly Ile Lys His
1               5                   10                  15

Lys Glu Thr Glu Val Ile Ile Phe Ala Gly Ser Asp Ala Trp Ser His
            20                  25                  30

Ala Lys Gln Trp Gln Glu His Asp Ala Arg Met Ala Gly Asp Asn Glu
        35                  40                  45

Pro Pro Val Trp Leu Gly Glu Gln Gln Leu Ser Glu Leu Asp Lys Leu
    50                  55                  60

Gln Ile Val Pro Glu Gly Arg Lys Ser Val Arg Ile Phe Arg Ala Gly
65                  70                  75                  80

Tyr Leu Ala Pro Val Met Ile Lys Ala Ile Gly Gln Lys Leu Ala Ala
                        85                  90                  95

Ala Gly Val Gln Asp Ala Asn Phe Tyr Pro Asp Gly Met His Gly Gln
            100                 105                 110

Lys Val Glu Asn Trp Arg Glu Tyr Leu Ala Arg Glu Arg Gln Asn Leu
        115                 120                 125

Ser Asp Gly Leu Val Ile Glu Leu Pro Val Lys Gln Lys Ala Gln Leu
    130                 135                 140

Ser Gln Met Ala Asp Ser Glu Arg Ala Gln Leu Leu Ala Asp Arg Phe
145                 150                 155                 160

Asp Gly Val Cys Val His Pro Glu Ser Glu Ile Val His Val Trp Cys
                165                 170                 175

Gly Gly Val Trp Cys Pro Val Ser Thr Met Glu Leu Ser Arg Glu Met
            180                 185                 190

Val Ala Ile Tyr Ser Glu His Arg Ala Thr Phe Ser Lys Arg Val Ile
        195                 200                 205

Asn Asn Ala Val Glu Ala Leu Lys Val Ile Ala Glu Pro Met Gly Glu
    210                 215                 220

Pro Ser Gly Asp Leu Leu Pro Phe Ala Asn Gly Ala Leu Asp Leu Lys
225                 230                 235                 240

Thr Gly Glu Phe Ser Pro His Thr Pro Glu Asn Trp Ile Thr Thr His
                245                 250                 255

Asn Gly Ile Glu Tyr Thr Pro Pro Ala Pro Gly Glu Asn Ile Arg Asp
            260                 265                 270

Asn Ala Pro Asn Phe His Lys Trp Leu Glu His Ala Ala Gly Lys Asp
        275                 280                 285

Pro Arg Lys Met Met Arg Ile Cys Ala Ala Leu Tyr Met Ile Met Ala
    290                 295                 300

Asn Arg Tyr Asp Trp Gln Met Phe Ile Glu Ala Thr Gly Asp Gly Gly
305                 310                 315                 320

Ser Gly Lys Ser Thr Phe Thr His Ile Ala Ser Leu Leu Ala Gly Lys
                325                 330                 335

Gln Asn Thr Val Ser Ala Glu Met Thr Ser Leu Asp Asp Ala Gly Gly
            340                 345                 350

Arg Ala Gln Val Val Gly Ser Arg Leu Ile Val Leu Ala Asp Gln Pro
        355                 360                 365

Lys Tyr Thr Gly Glu Gly Thr Gly Ile Lys Lys Ile Thr Gly Gly Asp
    370                 375                 380

Pro Val Glu Ile Asn Pro Lys Tyr Glu Lys Arg Phe Thr Ala Val Ile
385                 390                 395                 400

Arg Ala Val Val Leu Ala Thr Asn Asn Asn Pro Met Ile Phe Thr Glu
                405                 410                 415

Arg Ala Gly Gly Val Ala Arg Arg Val Ile Phe Arg Phe Asp Asn
            420                 425                 430

Ile Val Ser Glu Ala Glu Lys Asp Arg Glu Leu Pro Glu Lys Ile Ala
        435                 440                 445

Ala Glu Ile Pro Val Ile Arg Arg Leu Leu Ala Asn Phe Ala Asp
    450                 455                 460

Pro Glu Lys Ala Arg Ala Leu Leu Ile Glu Gln Arg Asp Gly Asp Glu
465                 470                 475                 480

Ala Leu Ala Ile Lys Gln Gln Thr Asp Pro Val Ile Glu Phe Cys Gln
                485                 490                 495

Phe Leu Asn Phe Leu Glu Glu Ala Arg Gly Leu Met Met Gly Gly Gly

|       |       |       |       |       | 500   |       |       |       |       | 505   |       |       |       |       | 510   |       |       |
|-------|-------|-------|-------|-------|-------|-------|-------|-------|-------|-------|-------|-------|-------|-------|-------|-------|-------|

Gly Asp Ser Val Lys Tyr Thr Thr Arg Asn Ser Leu Tyr Arg Val Tyr
            515                 520                 525

Leu Ala Phe Met Ala Tyr Ala Gly Arg Ser Lys Pro Leu Asn Val Asn
        530                 535                 540

Asp Phe Gly Lys Ala Met Lys Pro Ala Ala Lys Val Tyr Gly His Glu
545                 550                 555                 560

Tyr Ile Thr Arg Lys Val Lys Gly Val Thr Gln Thr Asn Ala Ile Thr
                565                 570                 575

Thr Asp Asp Cys Asp Ala Phe Leu
            580

<210> SEQ ID NO 51
<211> LENGTH: 1752
<212> TYPE: DNA
<213> ORGANISM: Artificial Sequence
<220> FEATURE:
<223> OTHER INFORMATION: PICI primase-helicase

<400> SEQUENCE: 51

```
atgaaactgg caccgaacgt aaaacagcag tcacgcggca taaaacacaa agaaacagaa        60
gtcattattt ttgcgggtag tgatgcctgg tcacacgcaa acaatggca ggaacatgac       120
gcgcgtatgg ccggagataa tgagcctcct gtgtggcttg gggagcagca gttatccgaa       180
ctggataagc tgcaaattgt gccggaaggc agaaaatccg tgcgcatatt cagggccgga       240
tatcttgcgc cagtaatgat aaaggcgatt ggtcagaagc tggcggcggc aggcgtacag       300
gatgcaaatt tttaccctga tggtatgcac ggtcagaagg tggagaactg cgcgaatat       360
ctggcccgtg agcgccagaa tctttctgat ggtctggtca ttgagcttcc ggtaaagcaa       420
aaggcgcaac tttcgcagat ggcggacagt gagcgcgcgc agctgcttgc cgatcgcttt       480
gatggcgttt gcgtacatcc tgaaagtgaa atcgttcacg tatggtgcgg cggggtatgg       540
tgtccggtca gcacaatgga gctgagccgc gaaatggtgg cgatctattc agagcacagg       600
gccactttca gcaagcgcgt aatcaataac gccgtggaag cgttaaaagt tattgccgaa       660
ccaatgggcg agccgtccgg cgatttgctg ccgttcgcca atggtgcgct tgacctgaaa       720
acggggggaat tttccccgca cacgccggag aactggatca ccacgcacaa cggcattgag       780
tacacgccac cagcacccgg ggagaacatc cgcgataacg cgccaaactt tcataaatgg       840
cttgagcacg cagccggaaa agacccgcgc aagatgatgc gtatatgtgc cgcgctgtac       900
atgattatgc cgaaccggta cgactggcag atgtttattg aggccaccgg agacggcggg       960
agcggtaaaa gtacattcac acacatagcc agccttctgg caggaaaaca aaacacggta      1020
agcgctgaaa tgcatcgct tgatgatgct ggtgggcgtg cgcaggttgt cgggagtcgt      1080
cttatcgtcc tggcagacca gccgaaatat acaggcgaag gaacgggcat caagaaaatc      1140
acgggcggcg accccgtgga aattaacccg aaatatgaaa agcgttttac ggcggtaatc      1200
agggcggtgg tgctggcaac caataacaat ccgatgatat tcaccgaacg ggccggaggt      1260
gtggcacgtc gtcgggtgat attccggttc gataacatcg taagcgaggc agaaaaagac      1320
agggagctac cggaaaagat cgcggctgaa atccctgtca ttatccgccg cttgctggcg      1380
aactttgccg accctgaaaa ggcacgggct ttactcattg aacagcgtga cggtgatgaa      1440
gcactggcaa taaagcaaca gacgggatcc gttattgagt tttgccagtt cctgaatttt      1500
ctggaggaag cacgcggcct gatgatgggc ggcggtggcg attcagtgaa gtacacgacc      1560
```

| | | | | |
|---|---|---|---|---|
| agaaacagcc | tttaccgcgt | ctatctggcg | tttatggcgt | acgcaggcag gagcaaaccg 1620 |
| ctaaacgtaa | atgactttgg | caaggctatg | aagccagccg | cgaaagttta cggacatgaa 1680 |
| tatattacgc | ggaaagttaa | aggagtaacg | cagactaacg | caataacaac agacgattgc 1740 |
| gacgcgtttt | ta | | | 1752 |